(12) United States Patent
Oda et al.

(10) Patent No.: US 7,622,479 B2
(45) Date of Patent: Nov. 24, 2009

(54) BICYCLIC DERIVATIVE, ITS PRODUCTION AND USE

(75) Inventors: Tsuneo Oda, Ibaraki (JP); Takashi Imada, Takarazuka (JP); Kenichiro Naito, Mino (JP); Toshiya Tamura, Mino (JP); Shuichi Furuya, Kobe (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 368 days.

(21) Appl. No.: 10/498,461

(22) PCT Filed: Nov. 25, 2002

(86) PCT No.: PCT/JP02/12264

§ 371 (c)(1),
(2), (4) Date: May 26, 2004

(87) PCT Pub. No.: WO03/415929

PCT Pub. Date: Jun. 5, 2003

(65) Prior Publication Data

US 2005/0101647 A1  May 12, 2005

(30) Foreign Application Priority Data

Nov. 26, 2001  (JP) ............................ 2001-359753

(51) Int. Cl.
*A61K 31/44* (2006.01)
*C07D 513/02* (2006.01)
*C07D 471/02* (2006.01)

(52) U.S. Cl. .................. 514/300; 514/301; 514/302; 514/303; 546/114; 546/115; 546/116; 546/118

(58) Field of Classification Search ............... 514/300, 514/301, 302, 303; 546/114, 115, 116, 118
See application file for complete search history.

(56) References Cited

U.S. PATENT DOCUMENTS

| | | | |
|---|---|---|---|
| 4,659,360 | A | 4/1987 | Baum et al. |
| 5,665,737 | A | 9/1997 | Cavalla et al. |
| 6,211,215 | B1 | 4/2001 | Momose et al. |
| 2002/0107269 | A1 | 8/2002 | Bonham |
| 2002/0173526 | A1 | 11/2002 | Tasaka et al. |

FOREIGN PATENT DOCUMENTS

| | | |
|---|---|---|
| CA | 2011222 A1 | 9/1990 |
| EP | 0385850 | 9/1990 |
| GB | 1388102 | 2/1973 |
| GB | 2008108 | 5/1979 |
| JP | 2000-351769 | * 12/2000 |
| JP | 2002-179568 | * 6/2002 |
| WO | WO 99/16755 | * 4/1999 |
| WO | WO 02/22598 A1 | 3/2002 |

OTHER PUBLICATIONS

K. Soderlind, et al., "Bis-benzimidazole anticancer agents: targeting human tumour helicases", Anti-Cancer Drug Design, 14(1): 19-36 (1999).
R. Dow, et al., "Benzyloxazolidine-2,4-diones as Potent Hypoglycemic Agents", J. Med. Chem. 34(5): 1538-1544 (1991).
T. Gungor, et al., "Cardiotonic Agents. Synthesis and Cardiovascular Properties of Novel 2-Arylbenzimidazoles and Azabenzimidazoles", J. Med. Chem., (1992, 35: 4455-4463.
Y. Bathini, et al., "Molecular Recognition between Ligands and Nucleic Acids: Novel Pyridine- and Benzoxazole-Containing Agents Related to Hoechst . . . , etc.", Chem. Res. Toxicol, (1990), 3: 268-280.
R. Troschutz, et al., "Synthese von 5-Methyl-und 5-Phenyl-Sulmazol", Archiv der Pharmazie, (1992), 325(9): 617-619.
R. Gupta, et al., "Design, synthesis, DNA Sequence Preferential Alkylation and Biologivcal Evaluation of N-mustard Derivatives of Hoechst 33258 Analogues", Anti-Cancer Drug Design, (1995), 10: 25-41.

* cited by examiner

*Primary Examiner*—James O Wilson
*Assistant Examiner*—Ebenezer Sackey
(74) *Attorney, Agent, or Firm*—Hamre, Schumann, Mueller & Larson, P.C.

(57) ABSTRACT

The present invention provides a heterocyclic compound having potent tyrosine kinase-inhibiting activity represented by formula:

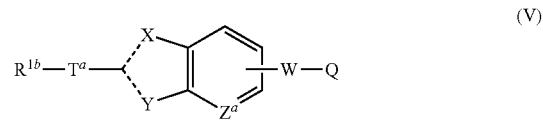

(V)

(wherein, $R^{1b}$ is a $C_{6-10}$ aryl group which has substituent(s), and the like; $T^a$ is a single bond, a $C_{1-6}$ alkyl group, —$CH_2O$—, and the like; X and Y are the same or different, and each is a nitrogen atom which may have substituent(s), and the like; the broken line is a single bond or a double bond; $Z^a$ is a nitrogen atom or CH; W is a single bond, an oxygen atom, and the like; Q is a $C_{6-10}$ aryl group which may have substituent(s) or an aromatic heterocyclic group which may have substituent(s)); or a salt thereof and a pharmaceutical composition comprising thereof.

17 Claims, No Drawings

BICYCLIC DERIVATIVE, ITS PRODUCTION AND USE

TECHNICAL FIELD

This invention relates to bicyclic derivatives showing suppression of receptor-type tyrosine kinase HER2 protein and selective inhibitory activity of HER2-expressing cancer cell proliferation as well as a method for the production and use thereof.

BACKGROUND

Receptor-type tyrosine kinase HER2 protein (Human EGF receptor-2: Akiyama et al, Science Vol. 232, Page 1644-1646, 1986) is found to have existed in normal tissue at the stage of initial development. However, it is found not to exist in normal adult tissue; it mainly exists only in cancer cells. For this reason, an antibody capable of recognizing homo- or heterodimer or homo-polymer HER2 protein is used for the treatment of high-level HER2 protein-expressing cancer for the purpose of inhibiting the proliferation of corresponding cells. Hence, HER2 antibody Herceptin ((Trademark) general term: trastuzumab) is widely used in high-level HER2-expressing breast cancer treatment.

A receptor-type tyrosine kinase HER2 protein inhibiting antibody lays question of its probability in oral absorptivity, administration style and elicitation of heart failure or allergy. On this account, a highly reliable inhibitor with the capability of oral administration and repetitive administration, which can selectively suppress the proliferation of HER2-expressing cancer cells, is strongly required.

DISCLOSURE OF INVENTION

As the result of earnest searching, the inventors have found bicyclic derivatives, which inhibit the proliferation of HER2-expressing cancer cells with a high degree of selectivity, while it has minimal effect on the proliferation of non-HER2-expressing normal cells. In addition, the inventors found that these compounds can be administered orally, have extremely low toxicity, and are satisfactory as drugs with HER2-inhibitory effects. This invention was completed on the basis of these findings.

Thus, the present invention relates to:

(1) a compound represented by formula (V):

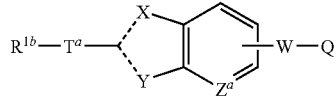

(V)

(wherein, $R^{1b}$ is a $C_{6-10}$ aryl group which has substituent(s), a $C_{3-8}$ cycloalkyl group which has substituent(s) or a heterocyclic group which may have substituent(s); $T^a$ is a single bond, a $C_{1-6}$ alkyl group, —$CH_2O$—, —$OCH_2$—, —$CH_2S$—, —$SCH_2$—, —$CH_2$—$CH_2$— or —$CH$=$CH$—; X and Y are the same or different, and each is a nitrogen atom which may have substituent(s), an oxygen atom or a sulfur atom; the broken line is a single bond or a double bond; $Z^a$ is a nitrogen atom or CH; W is a single bond, an oxygen atom, a nitrogen atom or a sulfur atom; Q is a $C_{6-10}$ aryl group which may have substituent(s) or an aromatic heterocyclic group which may have substituent(s)); or a salt thereof;

(2) a compound represented by the formula (VI):

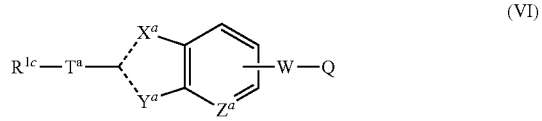

(VI)

(wherein, $R^{1c}$ is a $C_{6-10}$ aryl group which has substituent(s), a $C_{3-8}$ cycloalkyl group which has substituent(s) or a heterocyclic group which may have substituent(s); the substituent(s) in the $C_{6-10}$ aryl group which has substituent(s) and the $C_{3-8}$ cyclo alkyl group which has substituent(s) are each 1 to 5 groups optionally selected from a halogen atom, OH, CN, $NO_2$, $NH_2$, NHCOR, NHCONHR, $NHSO_2R$, $SO_2R$, COOH, COOR, CONHR, $CONH_2$, $CF_3$, $CF_3O$, a $C_{1-6}$ alkyl group which may have substituent(s), a $C_{1-6}$ alkoxy group which may have substituent(s), a $C_{1-6}$ alkoxy-carbonyl group which may have substituent(s) and a $C_{1-4}$ alkylenedioxy which may have substituent(s); R is a $C_{1-6}$ alkyl group, a $C_{3-8}$ cycloalkyl group or a $C_{6-10}$ aryl group; $T^a$ is a single bond, a $C_{1-6}$ alkyl group, —$CH_2O$—, —$OCH_2$—, —$CH_2S$—, —$SCH_2$—, —$CH_2$—$CH_2$— or —$CH$=$CH$—; $X^a$ is a nitrogen atom which may have substituent(s), an oxygen atom or a sulfur atom; $Y^a$ is a nitrogen atom, an oxygen atom or a sulfur atom with the exception of the case where $X^a$ and $Y^a$ are the same or different, and each is an oxygen atom or a sulfur atom; the broken line is a single bond or a double bond; $Z^a$ is a nitrogen atom or CH; W is a single bond, an oxygen atom, a nitrogen atom or a sulfur atom; and Q is a $C_{6-10}$ aryl group which may have substituent(s) or an aromatic heterocyclic group which may have substituent(s)); or a salt thereof;

(3) a compound as shown in (1) to (4) above, wherein X or $X^a$ is a nitrogen atom which may have substituent(s);

(4) a compound as shown in (1) to (5) above, wherein Y or $Y^a$ is a nitrogen atom;

(5) a compound as shown in (1) to (6) above, wherein Z or $Z^a$ is a nitrogen atom;

(6) a compound as shown in (1) to (7) above, wherein $R^1$, $R^{1a}$, $R^{1b}$ or $R^{1c}$ is a $C_{6-10}$ aryl group which has substituent(s);

(7) a compound represented by the formula (VII):

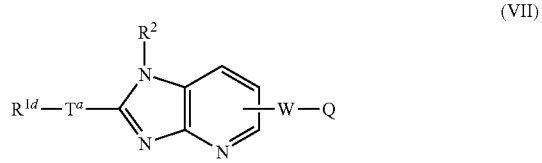

(VII)

(wherein, $R^{1d}$ is a $C_{6-10}$ aryl group which may have substituent(s), a $C_{3-8}$ cycloalkyl group which may have substituent(s) or a heterocyclic group which may have substituent(s); $T^a$ is a single bond, a $C_{1-6}$ alkyl group, —$CH_2O$—, —$OCH_2$—, —$CH_2S$—, —$SCH_2$—, —$CH_2$—$CH_2$— or —$CH$=$CH$—; $R^2$ is a hydrogen atom, a $C_{1-6}$ alkyl group which may have substituent(s), an $C_{6-10}$ aryl group which may have substituent(s) or a $C_{3-8}$ cycloalkyl group which may have substituent(s); W is a single bond, an oxygen atom, a nitrogen atom or a sulfur atom; Q is a $C_{6-10}$ aryl group which may have substituent(s) or an aromatic heterocyclic group which may have substituent(s)); or a salt thereof;

(8) a compound represented by the formula (VIII):

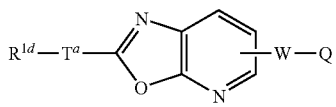

(VIII)

(wherein, $R^{1d}$ is a $C_{6-10}$ aryl group which may have substituent(s), a $C_{3-8}$ cycloalkyl group which may have substituent(s), or a heterocyclic group which may have substituent(s); $T^a$ is a single bond, a $C_{1-6}$ alkyl group, —CH$_2$O—, —OCH$_2$—, —CH$_2$S—, —SCH$_2$—, —CH$_2$—CH$_2$— or —CH=CH—; W is a single bond, an oxygen atom, a nitrogen atom or a sulfur atom; Q is a $C_{6-10}$ aryl group which may have substituent(s), or an aromatic heterocyclic group which may have substituent(s)); or a salt thereof;

(9) a compound represented by the formula (IX):

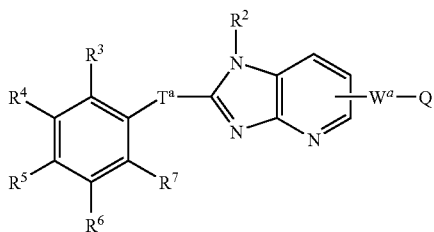

(IX)

(wherein, $R^3$, $R^4$, $R^5$, $R^6$ and $R^7$ are the same or different, and each is a hydrogen atom, a halogen atom, OH, CN, NO$_2$, NH$_2$, NHCOR, NHCONHR, NHSO$_2$R, SO$_2$R, COOH, COOR, CONHR, CONH$_2$, CF$_3$, CF$_3$O, a $C_{1-6}$ alkyl group which may have substituent(s), a $C_{1-6}$ alkoxy group which may have substituent(s), a $C_{1-6}$ alkoxycarbonyl group which may have substituent(s) or a $C_{1-4}$ alkylenedioxy group which is formed by a combination of two neighboring groups, which may have substituent(s); R is a $C_{1-6}$ alkyl group, a $C_{3-8}$ cycloalkyl group or a $C_{6-10}$ aryl group; $T^a$ is a single bond, a $C_{1-6}$ alkyl group, —CH$_2$O—, —OCH$_2$—, —CH$_2$S—, —SCH$_2$—, —CH$_2$—CH$_2$— or —CH=CH—; $R^2$ is a hydrogen atom, a $C_{1-6}$ alkyl group which may have substituent(s), a $C_{6-10}$ aryl group which may have substituent(s), or a $C_{3-8}$ cycloalkyl group which may have substituent(s); $W^a$ is a single bond or an oxygen atom; Q is a $C_{6-10}$ aryl group which may have substituent(s), or an aromatic heterocyclic group which may have substituent(s)); or a salt thereof;

(10) a compound represented by the formula (X):

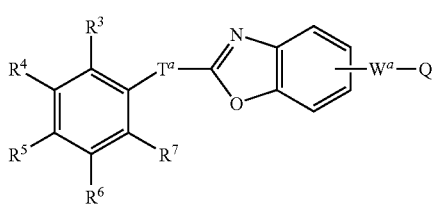

(X)

(wherein, $R^3$, $R^4$, $R^5$, $R^6$ and $R^7$ are the same or different, and each is a hydrogen atom, a halogen atom, OH, CN, NO$_2$, NH$_2$, NHCOR, NHCONHR, NHSO$_2$R, SO$_2$R, COOH, COOR, CONHR, CONH$_2$, CF$_3$, CF$_3$O, a $C_{1-6}$ alkyl group which may have substituent(s), a $C_{1-6}$ alkoxy group which may have substituent(s) or a $C_{1-6}$ alkoxycarbonyl group which may have substituent(s) or a $C_{1-4}$ alkylenedioxy group which is formed by a combination of two neighboring groups, which may have substituents; R is a $C_{1-6}$ alkyl group, a $C_{3-8}$ cycloalkyl group or a $C_{6-10}$ aryl group; $T^a$ is a single bond, a $C_{1-6}$ alkyl group, —CH$_2$O—, —OCH$_2$—, —CH$_2$S—, —SCH$_2$—, —CH$_2$—CH$_2$— or —CH=CH—; $W^a$ is a single bond or an oxygen atom; Q is a halogen atom, a $C_{6-10}$ aryl group which may have substituent(s) or an aromatic heterocyclic group which may have substituent(s), provided, $R^4$ and $R^6$ are each not a hydrogen atom when Q is a halogen atom) or a salt thereof;

(11) a compound as shown in (9) or (10) above, wherein $W^a$ is a single bond; or a salt thereof;

(12) a compound as shown in (9) or (10) above, wherein $T^a$ and $W^a$ are each a single bond; or a salt thereof;

(13) a compound as shown in (9) or (10) above, wherein $R^4$ and $R^6$ are each a group other than a hydrogen atom, or a salt thereof;

(14) a compound represented by the formula (XI):

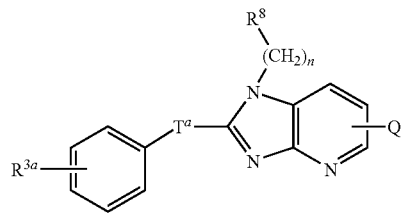

(XI)

(wherein, $R^{3a}$ is a hydrogen atom, a halogen atom, OH, CN, NO$_2$, NH$_2$, NHCOR, NHCONHR, NHSO$_2$R, SO$_2$R, COOH, COOR, CONHR, CONH$_2$, CF$_3$, CF$_3$O, a $C_{1-6}$ alkyl group which may have substituent(s), a $C_{1-6}$ alkoxy group which may have substituent(s) or a $C_{1-6}$ alkoxycarbonyl group which may have substituent(s); R is a $C_{1-6}$ alkyl group, a $C_{3-8}$ cycloalkyl group or a $C_{6-10}$ aryl group; $T^a$ is a single bond, a $C_{1-6}$ alkyl group, —CH$_2$O—, —OCH$_2$—, —CH$_2$S—, —SCH$_2$—, —CH$_2$—CH$_2$— or —CH=CH—, m is an integer from 1 to 3; $R^8$ is a $C_{6-10}$ aryl group which may have substituent(s), a $C_{3-8}$ cycloalkyl group which may have substituent(s) or a heterocyclic group which may have substituent(s); Q is a $C_{6-10}$ aryl group which may have substituent(s) or an aromatic heterocyclic group which may have substituent(s)); or a salt thereof;

(15) a compound as shown in (1) to (14) above, wherein $Q^1$, $Q^2$, $Q^3$, $Q^4$ or Q is a $C_{6-10}$ aryl group which has substituent(s), and the substituent(s) in the $C_{6-10}$ aryl group which has substituent(s) are 1 to 5 groups optionally selected from a halogen atom, a $C_{1-6}$ alkyl group which may have substituent(s) and a cyano group, or a salt thereof;

(16) a prodrug of the compound shown in (1) to (15) above;

(17) a pharmaceutical composition containing the compound shown in (1) to (16) above;

(18) a HER2 protein inhibiting agent containing a compound represented by the formula (I):

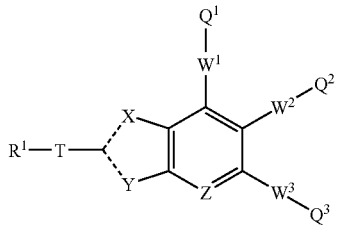

(wherein, $R^1$ is a hydrocarbon group which may have substituents or a heterocyclic group which may have substituent(s); T is a single bond or a bivalent aliphatic hydrocarbon group which may have one or more hetero atom(s), which may have substituent(s); X and Y are the same or different and each is a nitrogen atom which may have substituent(s), an oxygen atom or a sulfur atom; the broken line is a single bond or double bond;

Z is a nitrogen atom or a group represented by the formula (II):

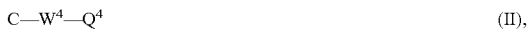

$W^1$, $W^2$, $W^3$ and $W^4$ are the same or different, and each is a single bond, a nitrogen atom which may have substituent(s), an oxygen atom, a sulfur atom or a bivalentaliphatic hydrocarbon group which may have substituent(s); $Q^1$, $Q^2$, $Q^3$ and $Q^4$ are the same or different, and each is a hydrogen atom, an alicyclic hydrocarbon group which may have substituent(s), an aromatic hydrocarbon group which may have substituent(s) or a heterocyclic group which may have substituent(s), (provided that at least one of $Q^1$, $Q^2$, $Q^3$ and $Q^4$ is not hydrogen atom); a salt thereof or a prodrug thereof;

(19) a pharmaceutical composition as shown in (17) above, which is a HER2 protein-inhibiting agent;

(20) a pharmaceutical composition as shown in (17) above, which is a preventing or treating agent for cancer;

(21) a pharmaceutical composition as shown in (20) above, wherein the cancer is breast cancer, prostate cancer, lung cancer or pancreatic carcinoma;

(22) a method for suppressing a HER2 protein which comprises administering an effective amount of a compound as shown in (1) to (16) above, to a mammal;

(23) a method for preventing or treating cancer which comprises administering an effective amount of the compound as shown in (1) to (16) above to a mammal;

(24) use of a compound as shown in (1) to (16) above, for producing a HER2 protein-inhibiting agent; and

(25) use of a compound as shown in (1) to (16) above, for producing an agent for preventing or treating cancer; and the like.

Moreover, the present invention relates to:

(26) a drug which comprises a combination of a compound as shown in (1) to (16) above and an anticancer agent;

(27) a drug which comprises a combination of a compound as shown in (1) to (16) above and kinase inhibitor;

(28) a drug which comprises a combination of a compound as shown in (1) to (16) above and a hormone therapy drug;

(29) a drug as shown in (28) above, wherein the hormonal therapeutic agent is an LH-RH modifier;

(30) a drug as shown in (29) above, wherein the LH-RH modifier is an LH-RH agonist;

(31) a drug as shown in (30) above, wherein the LH-RH agonist is leuprorelin or a salt thereof;

(32) a method for inhibiting tyrosine kinase which comprises administering an effective amount of a compound as shown in (1) to (16) above, to a mammal;

(33) a method for preventing or treating cancer which comprises administering an effective amount of a compound as shown in (1) to (16) above, in combination with an effective amount of a hormonal therapeutic agent, to a mammal;

(34) a method as shown in (33) above, wherein the hormonal therapeutic agent is an LH-RH modifier;

(35) a method as shown in (34) above, wherein the LH-RH modifier is an LH-RH agonist;

(36) a method as shown in (35) above, wherein the LH-RH agonist is leuprorelin; or a salt thereof;

(37) a method for preventing or treating cancer which comprises administering an effective amount of a compound as shown in (1) to (16) above, after administration of another anticancer drug to a mammal;

(38) a method for preventing or treating cancer which comprises administering to a mammal an effective amount of a compound as shown in (1) to (16) above, before a surgical operation, radiotherapy, gene therapy, thermotherapy, cryotherapy and/or laser cauterization therapy;

(39) a method for preventing or treating cancer by administering to a mammal an effective dose of a compound as shown in (1) to (16) above, after a surgical operation, radiotherapy, gene therapy, thermotherapy, cryotherapy and/or laser cauterization therapy;

(40) use of a compound as shown in (1) to (16) above, for producing a tyrosine kinase inhibiting agent;

(41) HER2 protein-inhibiting agent containing a compound represented by the formula (III):

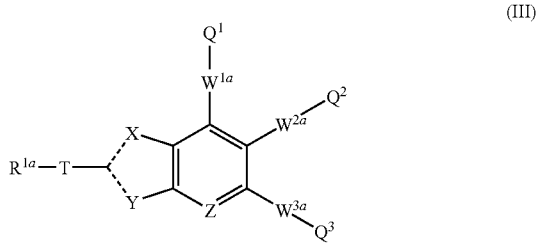

(wherein, $R^{1a}$ is an alicyclic hydrocarbon group which may have substituent(s), an aromatic hydrocarbon group which may have substituent(s), or a heterocyclic group which may have substituent(s); T is a single bond or a bivalent aliphatic hydrocarbon group having 1 or more hetero atom(s) which may have substituent(s); X and Y are the same or different, and each is a nitrogen atom which may have substituent(s), an oxygen atom or a sulfur atom; the broken line is single bond or a double bond; Z is a nitrogen atom or a group represented by the formula (IV):

$$C\!\!-\!\!W^{4a}\!\!-\!\!Q^4 \qquad \qquad (IV);$$

$W^{1a}$, $W^{2a}$, $W^{3a}$ and $W^{4a}$ are the same or different, and each is single bond or a nitrogen atom which may have substituent(s), an oxygen atom or a sulfur atom; $Q^1$, $Q^2$, $Q^3$ and $Q^4$ are the same or different, and each is a hydrogen atom, an alicyclic hydrocarbon group which may have substituent(s), an aromatic hydrocarbon group which may have substituent(s) or a heterocyclic group which may have substituent(s) (provided that at least one of $Q^1$, $Q^2$, $Q^3$ and $Q^4$ is not a hydrogen atom); (provided that (1) a compound wherein one of X or Y is a nitrogen atom and the other one is an oxygen atom, Z is CH, and T is a single bond; (2) a compound wherein T is a vinylene group; Z is CH; $W^{1a}$, $W^{2a}$, $W^{3a}$ and $W^{4a}$ are each a single bond; $Q^1$ and $Q^4$ are each a hydrogen atom; $Q^2$ or $Q^3$ is an unsubstituted phenyl group; $R^{1a}$ is biphenylyl group or N,N-diphenyl-4-amino-phenyl group; and (3) a compound wherein each of X and Y is a nitrogen atom, each of T, $W^{1a}$, $W^{2a}$, $W^{3a}$ and $W^{4a}$ is a single bond; $Q^1$, $Q^2$ and $Q^4$ are each a hydrogen atom and $Q^3$ is a 4-methylpiperazinyl group, are excluded); a salt thereof or a prodrug thereof; and the like.

DETAILED DESCRIPTION OF THIS INVENTION

The details of this invention are as follows.
Each symbol in the individual formulas of this specification is as follows.

As the hydrocarbon group in the "hydrocarbon group which may have substituent(s)" represented by $R^1$, an aliphatic chain hydrocarbon group, an alicyclic hydrocarbon group or an aryl group, etc. may be used. Among those, an aryl group, etc., are preferable.

As examples of an "aliphatic chain hydrocarbon group", which is an example of a hydrocarbon group, a straight-chain or branch-chain aliphatic hydrocarbon group such as an alkyl group, an alkenyl group or an alkynyl group, may be used.

As the alkyl group, a $C_{1-10}$ alkyl group (preferably a $C_{1-6}$ alkyl group, etc.) such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, 1-methylheptyl, 1-ethylhexyl, n-octyl, 1-methylheptyl, nonyl, etc., may be used.

As the alkenyl group, a $C_{2-6}$ alkenyl group and the like such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc., may be used.

As the alkynyl group, a $C_{2-6}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl etc., may be used.

As an example of an "alicyclic hydrocarbon group" as an example of a hydrocarbon group, a saturated or unsaturated alicyclic hydrocarbon group such as a cycloalkyl group, a cycloalkenyl group and a cycloalkanedienyl group, etc., may be used.

As the cycloalkyl group, a $C_{3-9}$ cycloalkyl group and the like such as cyclopropyl, cyclobutyl, cyclopentyl, cyclohexyl, cycloheptyl, cyclooctyl, cyclononyl, etc. may be used.

As an example of a cycloalkenyl group, a $C_{3-6}$ cycloalkenyl group and the like such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl, etc. may be used.

As the cycloalkanedienyl group, a $C_{4-6}$ cycloalkanedienyl group and the like such as 2,4-cyclopentanedien-1-yl, 2,4-cyclohexanedien-1-yl, 2,5-cyclohexandien-1-yl, etc. may be used.

As the "aryl group" as an example of a hydrocarbon group, a monocyclic or a fused polycyclic aromatic hydrocarbon group and the like may be used. While there are no restrictions, a $C_{6-22}$ aromatic hydrocarbon group is preferable, a $C_{6-18}$ aromatic hydrocarbon group is more preferable, a $C_{6-14}$ aromatic hydrocarbon group is even more preferable, a $C_{6-10}$ aromatic hydrocarbon group is still more preferable and a $C_6$ aromatic hydrocarbon group is the most preferable.

Examples of an "aromatic hydrocarbon group" include phenyl, naphthyl, anthryl, azulenyl, phenanthryl, phenalenyl, fluorenyl, indasenyl, biphenylenyl, heptalenyl, acenaphthylenyl, etc., and among these, phenyl, 1-naphthyl, 2-naphthyl, 1-anthryl, 2-anthryl, etc. are preferable.

As the aromatic hydrocarbon group in the "aromatic hydrocarbon group which may have substituent(s)" represented by $Q^1$, $Q^2$, $Q^3$, $Q^4$ and $R^{1a}$; similar to the "aryl group" above, a monocyclic or a fused polycyclic aromatic hydrocarbon group is used. While there are no restrictions, a $C_{6-22}$ aromatic hydrocarbon group is preferable, a $C_{6-18}$ aromatic hydrocarbon group is more preferable, a $C_{6-14}$ aromatic hydrocarbon group is even more preferable, a $C_{6-10}$ aromatic hydrocarbon group is still more preferable, and a $C_6$ aromatic hydrocarbon group is the most preferable. As examples, phenyl, naphthyl, anthryl, azulenyl, phenanthryl, phenalenyl, fluorenyl, indasenyl, biphenylenyl, heptalenyl, acenaphthylenyl, etc., may be used, and among these, phenyl, 1-naphthyl, 2-naphthyl, 1-anthryl, 2-anthryl, etc., are preferable.

The "$C_{6-10}$ aryl group" in the "$C_{6-10}$ aryl group which may have substituent(s)" represented by Q, $R^{1d}$, $R^2$ and $R^8$ and in the "$C_{6-10}$ aryl group which may have substituent(s)" represented by $R^{1b}$, $R^{1c}$ is a $C_{6-10}$ aromatic hydrocarbon group. Among these, a $C_6$ aromatic hydrocarbon group is preferable, and as the examples phenyl, pentalenyl, indenyl, naphthyl, etc., may be used. Among these, phenyl, 1-naphthyl, 2-naphthyl are preferable.

The alicyclic hydrocarbon group in the "alicyclic hydrocarbon group which may have substituent(s)" represented by $Q^1$, $Q^2$, $Q^3$, $Q^4$ and $R^{1a}$, has the same meaning as the alicyclic hydrocarbon group in the hydrocarbon group above and includes a saturated or an unsaturated alicyclic hydrocarbon group such as a cycloalkyl group, a cycloalkenyl group, a cycloalkanedienyl group, etc., and the same groups can be applied to each of these as the examples above.

As the $C_{3-8}$ cycloalkyl group in the "$C_{3-8}$ cycloalkyl group which may have substituent(s)" represented by $R^{1d}$, $R^2$ and $R^8$, or the "$C_{3-8}$ cycloalkyl group which has substituent(s)" represented by $R^{1b}$ and $R^{1c}$ and the $C_{3-8}$ cycloalkyl group in the "$C_{3-8}$ cycloalkyl group", represented by R, for example, cyclopropyl, cyclobutyl, cyclopentyl, cyclohexyl, cycloheptyl, and cyclooctyl, etc., may be used.

The $C_{1-6}$ alkyl group in the "$C_{1-6}$ alkyl group which may have substituent(s)" represented by $R^2$ and the "$C_{1-6}$ alkyl group" represented by R is a straight-chain or branch-chain $C_{1-6}$ alkyl group. While there are no restrictions, methyl, ethyl, n-propyl, isopropyl, n-butyl, isobutyl, sec-butyl, tert-butyl, n-pentyl, isopentyl, neopentyl, 1-methylpropyl, n-hexyl, etc., may be used. Among these, methyl, ethyl, n-propyl, isopropyl, etc., are preferable.

As the "$C_{1-4}$ alkyl group" represented by $T^a$, $R^3$, $R^4$, $R^5$, $R^6$, $R^7$ and $R^{3a}$ and which also is the substituent in the "$C_{6-10}$ aryl group which has substituent(s)" and the "$C_{3-8}$ cycloalkyl group which has the substituent(s)" represented by $R^{1c}$, a straight-chain or branch-chain $C_{1-4}$ alkyl-group, may be used. While there are no restrictions, methyl, ethyl, n-propyl, iso-propyl, n-butyl, isobutyl, sec-butyl, tert-butyl, etc., are used as examples. Among these methyl, ethyl, n-propyl, isopropyl, etc., are preferable.

The "$C_{1-4}$ alkoxy group", which is represented by $R^3$, $R^4$, $R^5$, $R^6$, $R^7$ and $R^{3a}$ and also which is the substituent(s) in the "$C_{6-10}$ aryl group which has substituent(s)" and in the "$C_{3-8}$ cycloalkyl group which has substituent(s)" represented by $R^{1c}$, is a straight-chain or a branch-chain $C_{1-4}$ alkoxy group. While there are no restrictions, examples of the "$C_{1-4}$ alkoxy group" include, for example, methoxy, ethoxy, n-propoxy, isopropoxy, n-butoxy, isobutoxy, sec-butoxy, tert-butoxy, etc., and among these methoxy, ethoxy, n-propoxy, isopropoxy are preferable.

As the "$C_{1-4}$ alkoxy-carbonyl group" which is represented by $R^3$, $R^4$, $R^5$, $R^6$, $R^7$ and $R^{3a}$ and also which is the substituent(s) in the "$C_{6-10}$ aryl group which has substituent(s)" and "$C_{3-8}$ cycloalkyl group which has substituent(s)" represented by $R^{1c}$, for example, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, etc., may be used. Among these methoxycarbonyl, ethoxycarbonyl, propoxycarbonyl, etc., are preferable.

The $C_{1-4}$ alkylenedioxy group which is represented by $R^3$, $R^4$, $R^5$, $R^6$ and $R^7$ and also which is the substituent(s) in the "$C_{6-10}$ aryl group which has substituent(s)" and the "$C_{3-8}$ cycloalkyl group which has substituent(s)" represented by $R^{1c}$, is formed by combining two neighboring groups (or neighboring atoms), and as the examples of the "$C_{1-4}$ alkylenedioxy group", methylenedioxy, ethylenedioxy, propylenedioxy, butylenedioxy, etc. may be used. Among these, methylenedioxy, ethylenedioxy, etc. are preferable.

As the "halogen atom" which is represented by $R^3$, $R^4$, $R^5$, $R^6$, $R^7$ and $R^{3a}$ and also which is the substituent(s) in the "$C_{6-10}$ aryl group which has substituent(s)" and the "$C_{3-8}$ cycloalkyl group which has substituent(s)" represented by $R^{1c}$, for example, a fluorine atom, a chlorine atom, a bromine atom, an iodine atom, etc. may be used. Among these, a chlorine atom or a bromine atom, etc. are preferable.

As the bivalent aliphatic hydrocarbon group in the "bivalent aliphatic hydrocarbon group which may have substituent(s)" represented by $W^1$, $W^2$, $W^3$ and $W^4$, a bivalent group derived by removing a hydrogen atom from a chain aliphatic hydrocarbon group and an alicyclic hydrocarbon group, etc., may be used. Specifically, for example, a bivalent group derived by removing a hydrogen atom from a straight-chain or a branched-chain aliphatic hydrocarbon group such as an alkyl group, an alkenyl group, an alkynyl group, etc. and from a saturated or an unsaturated alicyclic hydrocarbon group such as a cycloalkyl group, a cycloalkenyl group, cycloalkanedienyl, etc. may be used.

As an example, an alkylene group such as methylene, ethylene, trimethylene, tetramethylene, pentamethylene, hexamethylene, methylethylene, ethylethylene, propylene, etc., preferably a $C_{1-6}$ alkylene group; an alkenylene group such as vinylene, propenylene, butenylene, pentenylene, methylvinylene, etc., preferably, $C_{1-6}$ alkenylene group; an alkynylene group such as ethenylene, propinylene, butinylene, pentinylene, methylethenylene, etc., preferably a $C_{1-6}$ alkynylene group; a cycloalkylene group such as cyclopropylene, cyclobutylene, cyclopentilene, cyclohexylene, etc., preferably $C_{3-8}$ cycloalkylene group; a cycloalkenylene group such as cyclopropenylene, cyclobutenylene, cyclopentenylene, etc., preferably a $C_{3-8}$ cycloalkenylene group, etc., may be used. Among these, a $C_{1-6}$ alkylene group such as methylene, ethylene, trimethylene, etc., and an alkenylene group vinylene, propenylene, butenylene, etc., are particularly preferable.

As the "bivalent aliphatic hydrocarbon group which may have one or more hetero atoms" in the "bivalent aliphatic hydrocarbon group which may have one or more hetero atom(s) and which may have substituent(s), represented by T, the aforementioned "bivalent aliphatic hydrocarbon group" having 1 to 3 kinds (preferably 1 to 2 kinds) and at least one hetero atom selected from oxygen atom, sulfur atom and nitrogen atom, etc. may be used. Specifically, for example, a bivalent aliphatic hydrocarbon, which may have one or more hetero atom(s), derived by removing one hydrogen atom from an straight-chain or branched-chain aliphatic hydrocarbon group such as an alkyl group, an alkenyl group, an alkynyl group, etc., and from a saturated or an unsaturated alicyclic hydrocarbon group such as a cycloalkyl group, a cycloalkenyl group, a cycloalkanedienyl group, etc., may be used. More specifically, —CH$_2$O—, —OCH$_2$—, —CH=CHO—, —CHOCH$_2$—, —CH$_2$CH$_2$OCH$_2$—, —CH(CH$_3$)CH$_2$O—, —CH$_2$CH(CH$_3$)O—, —OCH$_2$O—, —OCH$_2$CH$_2$O—, —SCH$_2$CH$_2$O—, —OCH$_2$CH$_2$S—, —SCH$_2$CH$_2$S—, —OCH$_2$CH$_2$CH$_2$O—, —CH$_2$OCH$_2$CH$_2$—, —CH$_2$S—, —SCH$_2$—, —CH=CHS—, —CHSCH$_2$—, —CH$_2$CH$_2$SCH$_2$—, —CH(CH$_3$)CH$_2$S—, —CH$_2$CH(CH$_3$)S—, —SCH$_2$O—, —CH$_2$SCH$_2$CH$_2$—, —CH$_2$NH—, —NHCH$_2$—, —CHNHCH$_2$—, —CH$_2$CH$_2$NHCH$_2$—, —CH(CH$_3$)CH$_2$NH—, —CH$_2$CH(CH$_3$)NH—, —NHCH$_2$O—, —CH$_2$NHCH$_2$CH$_2$—, —CH$_2$N(CH$_3$)—, —CHN(CH$_3$)CH$_2$—, —CH$_2$CH$_2$N(CH$_3$)CH$_2$—, —CH(CH$_3$)CH$_2$N(CH$_3$)—, —CH$_2$CH(CH$_3$)N(CH$_3$)—, —N(CH$_3$)CH$_2$O—, —CH$_2$N(CH$_3$)CH$_2$CH$_2$—, —CH$_2$N(C$_2$H$_5$)—, —CHN(C$_2$H$_5$)CH$_2$—, —CH$_2$CH$_2$N(C$_2$H$_5$)—, —CH(CH$_3$)CH$_2$N(C$_2$H$_5$)—, —CH=CHN(C$_2$H$_5$)—, —CH$_2$CH(CH$_3$)N(C$_2$H$_5$)—, —CH=C(CH$_3$)N(C$_2$H$_5$)—, —N(C$_2$H$_5$)CH$_2$O—, —CH$_2$N(C$_2$H$_5$)CH$_2$CH$_2$—, —N(CH$_3$)CH$_2$S—, —N(C$_2$H$_5$)CH$_2$S—, etc., may be used, but there are no restrictions. Preferably —CH$_2$O—, —OCH$_2$—, —CH=CHO—, —CHOCH$_2$—, —CH$_2$CH$_2$OCH$_2$—, —CH(CH$_3$)CH$_2$O—, —CH$_2$CH(CH$_3$)O—, —OCH$_2$O—, —OCH$_2$CH$_2$O—, —SCH$_2$CH$_2$O—, —OCH$_2$CH$_2$S—, —SCH$_2$CH$_2$S—, —OCH$_2$CH$_2$O—, —CH$_2$OCH$_2$CH$_2$, etc., may be used. More preferably —CH$_2$O—, —OCH$_2$—, —CH=CHO—, —CHOCH$_2$—, —CH$_2$CH$_2$OCH$_2$—, —CH(CH$_3$)CH$_2$O—, —CH$_2$CH(CH$_3$)O—, —OCH$_2$O—, etc. may be used.

As the heterocyclic group in the "heterocyclic group which may have substituent(s)" represented by $R^1$, $Q^1$, $Q^2$, $Q^3$, $Q^4$, $R^{1a}$, $R^{1b}$, $R^{1c}$, $R^{1d}$ and $R^8$, an aromatic heterocyclic group or a saturated or an unsaturated non-aromatic heterocyclic group (aliphatic heterocyclic group), each of which contains, as ring-constituting atom(s)(ring atom(s)), 1 to 3 kinds (preferably 1 or 2 kinds) and at least 1 (preferably 1 to 4, and more preferably 1 or 2) hetero atom selected from an oxygen atom, a sulfur atom or a nitrogen atom, etc., may be used. While there are no restrictions, a 5- to 22-membered heterocyclic group is preferable, a 5- to 18-membered heterocyclic group is more preferable, a 5- to 14-membered heterocyclic group is still more preferable, 5- to 10-membered heterocyclic groups is even more preferable, and a 5- or 6-membered heterocyclic group is the most preferable.

As the "aromatic heterocyclic group", an aromatic mono-heterocyclic group such as a 5- or 6-membered aromatic mono-heterocyclic group (for example, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.), an aromatic fused heterocyclic group such as 8 to 12 membered aromatic fused heterocyclic group (for example, benzofuranyl, isobenzofuranyl, benzothienyl, indolyl, isoindolyl, 1H-indazolyl, benzindazolyl, benzoxazolyl, 1,2-benzoisoxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc., preferably a heterocyclic group formed by the condensation of the 5- or 6-membered aromatic monocyclic-heterocyclic group above and a benzene ring and a heterocyclic ring formed by the condensation of two similar or dissimilar heterocyclic rings such as the 5- or 6-membered aromatic monocyclic heterocyclic group above) may be used.

As the nonaromatic heterocyclic group", a 3- to 8-membered (preferably 5- or 6-membered) saturated or unsaturated (preferably saturated) nonaromatic heterocyclic group (aliphatic heterocyclic group) such as oxilanyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc., may be used.

As the "aromatic heterocyclic group" in the "aromatic heterocyclic group which may have substituent(s)" represented by Q, an aromatic heterocyclic group, which contains, for example, as a ring-constituting atom(s)(ring atom(s)), 1 to 3 kinds (preferably 1 or 2) and at least one (preferably 1 to 4 and more preferably 1 or 2) hetero atom selected from an oxygen atom, a sulfur atom, a nitrogen atom, etc., may be used. While there are no restrictions, a 5- to 22-membered aromatic heterocyclic group is preferable, a 5- to 18-membered aromatic heterocyclic group is even more preferable, a 5- to 14-membered aromatic heterocyclic group is still more preferable, a 5- to 10-membered aromatic heterocyclic group is even more preferable, and a 5- or 6-membered aromatic heterocyclic group is the most preferable. As an example, a group similar to the "aromatic heterocyclic group" in the explanation of the "heterocyclic group which may have substituent(s)" mentioned above, may be used.

The "substituent" in the "hydrocarbon group which may have substituent(s)" represented by $R^1$, and the "substituent" in the "heterocyclic group which may have substituent(s)" represented by $R^1$, $Q^1$, $Q^2$, $Q^3$, $Q^4$, $R^{1a}$, $R^{1b}$, $R^{1c}$, $R^{1d}$ and $R^8$ may be protected by a conventional method of organic chemosynthesis when the occasion demands. As examples, while there are no restrictions, (i), an alkyl group which may have substituent(s), (ii), an alkenyl group which may have substituent(s), (iii), an alkynyl group which may have substituent(s), (iv), an aryl group which may have substituent(s), (v), an aralkyl group which may have substituent(s), (vi), an cycloalkyl group which may have substituent(s), (vii), a cycloalkenyl group which may have substituent(s), (viii), a heterocyclic group which may have substituent(s), (ix), an amino group which may have substituent(s), (x), an imidoyl group which may have substituent(s) [for example, a group represented by the formula: —C(U')=N—U (wherein U and U' are the same or different, represent a hydrogen atom or a substituent (U is preferably a hydrogen atom))], etc., (xi), an amidino group which may have substituent(s) [for example, a group represented by the formula: —C(NE'E")=N—E (wherein E, E' and E" are the same or different, a hydrogen atom or a substituent (E preferably represents hydrogen atom))], etc., (xii), a hydroxyl group which may have substituent(s), (xiii), a thiol group which may have substituent(s), (xiv), an alkylsulfinyl group which may have substituent(s), (xv) a carboxyl group which may be esterified or amidated, (xvi), a thiocarbamoyl group which may have substituent(s), (xvii), an sulfamoyl group which may have substituent(s), (xviii) a halogen atom (e.g. fluorine, chlorine, bromine, iodine, etc.; preferably chlorine, bromine, etc.), (xix) a cyano group, (xx) an isocyano group, (xxi) a cyanate group, (xxii) an isocyanate group, (xxiii) a thiocyanate group, (xxiv) an isothiocyanate group, (xxv) a nitro group, (xxvi) a nitroso group, (xxvii) an acyl group derived from sulphonic acid, (xxviii) an acyl group derived from a carboxylic acid, (xxix) an oxo group, may be used. 1 to 5 (preferably 1 to 3) of these optional substituents may be present at the substitutable position(s).

As the "alkyl group" in the "alkyl group which may have substituent(s)", which is the substituent(s) above, a $C_{1-6}$ alkyl group and the like such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, etc. may be used. As the substituent of the alkyl group, for example, a nitro group, a carboxyl group, a lower alkoxy group (e.g., a $C_{1-6}$ alkoxy and the like such as methoxy, ethoxy, propoxy, etc.), a halogen atom (e.g., fluorine, chlorine, bromine, iodine, etc.), a lower alkyl group (e.g., a $C_{1-6}$ alkyl group and the like such as methyl, ethyl, propyl, etc.), a lower alkenyl group (e.g., a $C_{2-6}$ alkenyl group such as vinyl, allyl, etc.), or a lower alkynyl group (e.g., a $C_{2-6}$ alkynyl group and the like such as ethynyl, propargyl, etc.), an amino group which may have substituent(s), a hydroxyl group which may have substituent(s), a cyano group, an amidino group which may have substituent(s), a carboxy group, a lower alkoxycarbonyl group (e.g., a $C_{1-6}$ alkoxycarbonyl group such as methoxycaronyl, ethoxycarbonyl, etc.), etc., or a carbamoyl group which may have substituent(s) (e.g., a carbamoyl group which may be substituted by a $C_{1-6}$ alkyl group which may further be substituted by a 5- or 6-membered aromatic monocyclic heterocyclic group such as pyridinyl, etc., or a carbamoyl group which may further be substituted by an acyl group (e.g., formyl, a $C_{2-6}$ alkanoyl, benzoyl, a $C_{1-6}$ alkoxycarbonyl which may have halogen(s), $C_{1-6}$ alkylsulfonyl which may have halogen(s), benzenesulfonyl, etc.), 1-azetidinylcarbonyl, 1-pyrrolidinylcarbonyl, piperidinocarbonyl, morpholinocarbonyl, 1-piperazinocarbonyl, etc.), an alicyclic hydrocarbon group which may contain 1 or more hetero atom (s)(a nitrogen atom, a sulfur atom, an oxygen atom, etc.) as a ring-constituting atom (e.g., a morphrino group, a morpholinyl group, a piperidino group, a piperidyl group, a pyrrolidinyl group, a tetrahydrofuryl group, a pyrazolidinyl group, a piperazinyl group, quinuclidinyl group, etc.), may be used. 1 to 3 of these optional substituent(s) may be present at the substitutable position(s).

As the "amino group which may have substituent(s)", the "hydroxyl group which may have substituent(s)" and the "amidino group which may have substituent(s)", each of which is the substituent(s) of the alkyl group in the "alkyl group which may have substituent(s)" mentioned above, group(s) similar to "amino group which may have substituent(s)", the "hydroxy group which may have substituent(s)" and the "amidino group which may have substituent(s)", each of which is the substituent(s) of aromatic homo- or heterocyclic group mentioned below, may be used.

As the alkenyl group in the "alkenyl group which may have substituent(s)" which is the substituent(s) mentioned above, a $C_{2-6}$ alkenyl group and the like, such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc. may be used. As the substituent(s) of the alkenyl group, substituents similar and comparable in amount to the substituent(s) in the "alkyl group which may have substituent(s)" mentioned above, may be used.

As the alkynyl group in the "alkynyl group which may have substituent(s)" which is the substituent(s) mentioned above, a $C_{2-6}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc., may be used.

As the substituent(s) of the alkynyl group, substituents similar and comparable in amount to the substituent(s) in the "alkyl group which may have substituent(s)" which is the substituent(s) mentioned above, may be used.

As the aryl group in the "aryl group which may have substituent(s)" which is the substituent(s) mentioned above, a $C_{6-14}$ aryl group and the like such as phenyl, naphthyl, anthryl, phenanthryl, acenaphthylenyl, etc. may be used.

As the substituent(s) of the aryl group, substituents similar and comparable in amount to the substituent(s) in the "alkyl group which may have substituent(s)" which is the substituent(s) mentioned above, may be used.

As the aralkyl group in the "aralkyl group which may have substituent(s)" which is the substituent(s) mentioned above, a $C_{7-11}$ aralkyl group and the like such as benzyl, phenethyl, naphthyl methyl, etc. may be used. As the substituent(s) of the aralkyl group, substituents similar and comparable in amount to the substituent(s) in the "alkyl group which may have substituent(s)" which is the substituent(s) mentioned above, may be used.

As the cycloalkyl group in the a "cycloalkyl group which may have substituent(s)" which is the substituent(s) mentioned above, a $C_{3-7}$ cycloalkyl group and the like such as cyclopropyl, cyclobutyl, cyclopentyl, cyclohexyl, cycloheptyl, etc. may be used. As the substituent(s) of the cycloalkyl group, a substituent similar and comparable in amount to the substituent(s) in the "alkyl group which may have substituent(s)" which is the substituent(s) mentioned above, may be used.

As the cycloalkenyl group in the "cycloalkenyl group which may have substituent(s)" which is the substituent(s) mentioned above, a $C_{3-7}$ cycloalkenyl group and the like such as cyclopropenyl, cyclobutenyl, cyclopentenyl, cyclohexenyl, etc. may be used. As the substituent(s) of the cycloalkenyl group, a substituent similar and comparable in amount to the substituent(s) in the "alkyl group which may have substituent(s)" which is the substituent(s) mentioned above, may be used.

As the heterocyclic group in the "heterocyclic group which may have substituent(s)" which is the substituent(s) mentioned above, for example, as a ring-constituting atom(s) (ring atom(s)), an aromatic heterocyclic group or a saturated or an unsaturated nonaromatic heterocyclic group (aliphatic heterocyclic group), etc., containing 1 to 3 kinds (preferably 1 to 2 kinds) and at least 1 (preferably 1 to 4, more preferably 1 or 2) hetero atom selected from an oxygen atom, a sulfur atom or a nitrogen atom, may be used.

As the aromatic heterocyclic group, a 5- or 6-membered aromatic monocyclic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc., and a 8- to 12-membered aromatic fused polycyclic heterocyclic group such as benzofuranyl, isobenzofuranyl, benzo[b]thienyl, indolyl, isoindolyl, 1H-indazolyl, benzindazolyl, benzoxazolyl, 1,2-benzoxazolyl, benzothiazolyl, benzopyranyl, 1,2-benzoisothiazolyl, 1H-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc., (Preferably, a heterocyclic group formed by the condensation of the 5- or 6-membered aromatic monocyclic heterocyclic group mentioned above and benzene ring, and heterocyclic group formed by the condensation of similar or dissimilar two heterocyclic rings such as the 5- or 6-membered aromatic monocyclic heterocyclic group mentioned above), may be used. More preferably, a heterocyclic group formed by the condensation of the 5- or 6-membered monocyclic heterocyclic aromatic group mentioned above and a benzene ring, most preferably benzofuranyl, benzopyranyl, benzo[b]thienyl, etc., may be used.

As the nonaromatic heterocyclic group, a 3- to 8-membered (preferably 5- or 6-membered) saturated or an unsaturated (preferably saturated) nonaromatic heterocyclic group (aliphatic heterocyclic group) such as oxyranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc., and a nonaromatic heterocyclic group, etc., which is derived by the saturation of a double bond in part or all of an aromatic monocyclic heterocyclic group or a fused polycyclic aromatic heterocyclic group, such as 1,2,3,4-tetrahydroquinolyl, 1,2,3,4-tetrahydroisoquinolyl, etc., may be used.

As the substituent(s) in the "heterocyclic group which may have substituent(s)" which is the substituent(s) mentioned above, a lower alkyl group which may have substituent(s) (e.g., a $C_{1-6}$ alkyl group and the like such as methyl, ethyl, propyl, etc.), a lower alkenyl group (e.g., a $C_{2-6}$ alkenyl group and the like such as vinyl, allyl, etc.), a lower alkynyl group (e.g. a $C_{2-6}$ alkynyl group and the like such as ethynyl, propargyl, etc.), or an acyl group (e.g., a $C_{1-6}$ alkanoyl, benzoyl, and the like such as formyl, acetyl, propionyl, pivaloyl, etc.), an amino group, which may have substituent(s), a hydroxy group which may have substituent(s), a halogen atom (e.g., fluorine, chlorine, bromine, iodine, etc., and preferably chlorine, bromine, etc.), an imidoyl group which may have substituent(s), an amidino group which may have substituent(s), etc., may be used. 1 to 5 (preferably 1 to 3) of these optional substituent(s) can be present at the substitutable position(s).

As the "amino group which may have substituent(s)", the "hydroxy group which may have substituent(s)", the "imidoyl group which may have substituent(s)" and the "amidino group which may have substituent(s)", each of which is the substituent in the "heterocyclic group which may have the substituent(s)" which is the substituent(s) mentioned above, substituents similar to those in the "amino group which may have substituent(s)", the "hydroxy group which may have substituent(s)", "imidoyl group which may have substituent(s)" and the "amidino group which may have substituent(s)", each of which is the substituent(s) in the later-described "aromatic homo- or hetero-cyclic group which may have substituent(s) may be used.

As the substituent(s) in the "amino group which may have substituent(s)", the "imidoyl group which may have substituent(s)", the "amidino group which may have substituent(s)", the "hydroxy radical which may have substituent(s)" and the "thiol group which may have substituent(s)" each of which is the substituent(s) mentioned above, for example, a lower alkyl group (e.g., a $C_{1-6}$ alkyl group and the like such as methyl, ethyl, propyl, isopropyl, butyl, isobutyl, tert-butyl, pentyl, hexyl, etc.) which may have substituent(s) selected from the group consisting of a halogen atom (e.g., fluorine, chlorine, bromine, iodine, etc.) a $C_{1-6}$ alkoxy group which may be halogenated (e.g., methoxy, ethoxy, trifluoromethoxy, 2,2,2-trifluoroethoxy, trichloromethoxyl, 2,2,2-trichloroethoxy, etc.) and a $C_{7-11}$ alkyl-aryl group (e.g., o-tolyl, m-tolyl, p-tolyl, xylyl, mesityl, etc., preferably $C_{1-5}$ alkyl-phenyl etc.), an acyl group (e.g., a $C_{1-6}$ alkanoyl group such as formyl, acetyl, propionyl, pivaloyl, etc.), benzoyl, a $C_{1-6}$ alkylsulfonyl (e.g., methanesulfonyl, etc.), benzenesulfonyl, etc., a $C_{1-6}$ alkoxycarbonyl group which may be halogenated (e.g., methoxycarbonyl, ethoxycarbonyl, trifluoromethoxycarbonyl, 2,2,2-trifluoroethoxycarbonyl, tri chloromethoxycarbonyl, 2,2,2-trichloroethoxycarbonyl, etc.), a $C_{1-6}$ alkoxycarbonyl group which may be substituted by phenyl (e.g., benzyloxycarbonyl, etc.), an aryl group (e.g., a $C_{6-10}$ aryl group and the like such as phenyl, 1-naphthyl, 2-naphthyl, etc.), an aralkyl group (e.g., a $C_{7-10}$ aralkyl group such as benzyl, phenethyl, etc., preferably a phenyl-$C_{1-4}$ alkyl group, etc.), an arylalkenyl (e.g., a $C_{8-10}$ aryl alkenyl group such as cinnamyl, etc., and preferably phenyl-$C_{2-4}$ alkenyl, etc.), a heterocyclic group (similar to that in the "heterocyclic group which may have substituent(s)", which is the substituent(s) mentioned above, preferably pyridyl, and more preferably 4-pyridyl, etc.), etc., may be used. 1 to 3 of these optional substituent(s) may be present at the substitutable positions.

The "amino" group in the "amino group which may have substituent(s)", which is the substituent(s) mentioned above, may be substituted by an imidoyl group which may have substituent(s) (e.g., a $C_{1-6}$ alkylimidoyl (e.g., formylimidoyl, acetylimidoyl, etc.), a $C_{1-6}$ alkoxyimidoyl, a $C_{1-6}$ alkylthioimidoyl, amidino, etc.), an amino group which may be substituted by 1 or 2 $C_{1-6}$ alkyl group(s), etc. 1 or 2 of these optional substituent(s) may be present at the substitutable position(s).

2 of the substituents may combine together with a nitrogen atom to form a cyclic amino group. As the cyclic amino group in this case, for example, a 3- to 8-membered (preferably 5- to 6-membered) cyclic amino and the like such as 1-piperazinyl, 1-pyrrolyl and 1-imidazolyl, etc., which may contain 1-azetidinyl, 1-pyrrolidinyl, piperidino, thiomorpholino, morpholino, 1-piperazinyl, a 1-piperazinyl substituted at the 4-position by a lower alkyl (e.g., a $C_{1-6}$ alkyl and the like such as methyl, ethyl, propyl, isopropyl, butyl, t-butyl, pentyl, hexyl, etc.), an aralkyl (e.g., a $C_{7-10}$ aralkyl and the like such as benzyl, phenethyl, etc.), aryl (e.g., $C_{6-10}$ aryl and the like such as phenyl, 1-naphthyl, 2-naphthyl, etc.), may be used.

As the alkyl sulfinyl group, in the "alkyl sulfinyl group which may have substituent(s)" which is the substituent(s) mentioned above, a $C_{1-6}$ alkyl sulfinyl such as methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, hexylsulfinyl, etc., may be used. As the substituent(s) of the "alkylsulfinyl group", substituents similar and comparable in amount to the substituent(s) in the "alkyl group which may have substituent(s)" mentioned above, may be used.

As the "carboxyl group which may be esterified or amidated" which is the substituent(s) mentioned above, carboxyl group, an alkoxycarbonyl, an aryloxycarbonyl, an aralkyloxycarbonyl, carbamoyl, a N-mono-substituted carbamoyl and a N,N-di-substituted carbamoyl may be used.

As the alkoxycarbonyl, a $C_{1-6}$ alkoxycarbonyl (a lower alkoxycarbonyl) and the like such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, etc., may be used. Among them, a $C_{1-3}$ alkoxycarbonyl and the like such as methoxycarbonyl, ethoxycarbonyl, propoxycarbonyl, etc. is preferable. The "lower alkoxycarbonyl" may have substituent(s). As substituent, a hydroxy group, an amino group which may have substituent(s) [the amino group may have 1 or 2 of a lower alkyl group (e.g., a $C_{1-6}$ alkyl and the like such as methyl, ethyl, propyl, isopropyl, butyl, isobutyl, tert-butyl, pentyl, hexyl, etc., and preferably methyl, ethyl, etc.), which may be substituted by 1 to 5 halogen atom(s) such as fluorine, chlorine, bromine and iodine, etc., an acyl group (e.g., a $C_{1-6}$ alkanoyl such as formyl, acetyl, propionyl, pivaloyl, etc., benzoly, etc.), a carboxyl group, $C_{1-6}$ alkoxycarbonyl, etc.], a halogen atom (e.g., fluorine, chlorine, bromine and iodine, etc.), a nitro group, a cyano group, a lower alkoxy group (e.g., $C_{1-6}$ alkoxy and the like such as methoxy, ethoxy, n-propoxy, isopropoxy, n-butoxy, isobutoxy, sec-butoxy, tert-butoxy, etc., and preferably methoxy, ethoxy, etc.) which may be substituted by 1 to 5 halogen atom(s) (e.g., fluorine, chlorine, bromine, iodine, etc.), may be used. It is preferable that 1 to 3 (preferably 1 or 2) of these substituents are the same or different and may be present at the substitutable position(s).

As the aryloxcarbonyl, a $C_{6-14}$ aryloxycarbonyl and the like such as phenoxycarbonyl, 1-naphthoxycarbonyl, 2-naphthoxycarbonyl, 1-phenanthoxycarbonyl, etc. is preferable. The aryloxycarbonyl may have substituent(s), and as the substituent(s), substituent(s) similar and comparable in amount to the substituent(s) in the "aryloxycarbonyl" mentioned above may be used.

As the aralkyloxcarbonyl, a $C_{7-14}$ aralkyloxycarbonyl and the like such as benzyloxycarbonyl, phenethyloxycarbonyl (preferably $C_{6-10}$ aryl-$C_{1-4}$ alkoxy-carbonyl, etc.) is preferable.

The aralkyloxycarbonyl may have substituent(s), and as the substituent(s), substituents(s) similar and comparable in amount to the substituent(s) of the "alkoxy-carbonyl" mentioned above may be used.

The N-mono-substituted carbamoyl is a carbamoyl group which has a substituent at a nitrogen atom. As the substituent(s), for example, a lower alkyl (e.g., a $C_{1-6}$ alkyl and the like, such as methyl, ethyl, propyl, isopropyl, butyl, isobutyl, tert-butyl, pentyl, hexyl, etc.), a lower alkenyl (e.g., a $C_{2-6}$ alkenyl and the like, such as vinyl, allyl, isopropenyl, propenyl, butenyl, pentenyl, hexenyl, etc.), a cycloalkyl (e.g., a $C_{3-6}$ cycloalkyl and the like such as cyclopropyl, cyclobutyl, cyclopentyl, cyclohexyl, etc.), an aryl (e.g., a $C_{6-10}$ aryl and the like such as phenyl, 1-naphthyl, 2-naphthyl, etc.), an aralkyl (e.g., a $C_{7-10}$ aralkyl such as benzyl phenethyl, and preferably a phenyl-$C_{1-4}$ alkyl etc.), an aryl alkenyl (e.g., a $C_{8-10}$ aryl alkenyl such as cinnamyl, etc., and preferably a phenyl-$C_{2-4}$ alkenyl, etc.), a heterocyclic group (for example, a heterocyclic group similar to that in the "heterocyclic group which may have substituent(s)" which is the substituent(s) mentioned above), etc., may be used.

The "lower alkyl", the "lower alkenyl", the "cycloalkyl", the "aryl", the "aralkyl", the "aryl alkenyl" and the "heterocyclic group" may have substituent(s), and as the substituent(s), those similar and comparable in amount to the substituent(s) of the "alkoxycarbonyl" which is the substituent(s) mentioned above, may be used.

The N,N-di-substituted carbamoyl is a carbamoyl group which has 2 substituents at a nitrogen atom. As one of the substituents, for example, a group similar to the substituent of the N-mono-substituted carbamoyl which is the substituent(s) mentioned above, may be used, and as the other substituent, for example, a lower alkyl (e.g., a $C_{1-6}$ alkyl and the like such as methyl, ethyl, propyl, isopropyl, butyl tert-butyl, pentyl, hexyl, etc.), a $C_{3-7}$ cycloalkyl (e.g., cyclopropyl, cyclobutyl, cyclopentyl, cyclohexyl, etc.), a $C_{7-10}$ aralkyl (e.g., benzyl, phenethyl, etc., and preferably a phenyl-$C_{1-4}$ alkyl, etc.), may be used. Two substituents may be combined together with a nitrogen atom to form a cyclic amino group. As the cyclic aminocarbamoyl in this case, for example, a 3- to 8-membered (preferably a 5- to 6-membered) cyclic aminocarbonyl and the like such as 1-piperazinylcarbonyl and the like which may include 1-azetidinylcarbonyl, 1-pyrrolidinylcarbonyl, piperidinocarbonyl, morpholinocarbonyl, 1-piperazinylcarbonyl, a 1-piperazinylcarbonyl substituted at 4-position by a lower alkyl (e.g., a $C_{1-6}$ alkyl and the like such as methyl, ethyl, propyl, isopropyl, butyl, tert-butyl, pentyl, hexyl, etc.), an aralkyl (e.g., a $C_{7-10}$ aralkyl and the like such as benzyl, phenethyl, etc.), an aryl (e.g., $C_{6-10}$ aryl and the like such as phenyl, 1-naphthyl, 2-naphthyl, etc.), etc., may be used.

As the substituents in the "thiocarbamoyl group which may have substituent(s)" and the "sulfamoyl group which may have substituent(s)", each of which is a substituent mentioned above, substituents similar to those of an N-mono-substituted carbamoyl, N,N-di-substituted carbamoyl shown above as "carboxyl group which may be esterified or amidated", may be used.

As the "acyl derived from sulfonic acid" which is the substituent(s) mentioned above, for example, a group formed by bonding the substituent at the nitrogen atom of the "N-mono-substituted carbamoyl" mentioned above with a sulfonyl group, etc., may be used. Preferably, an acyl, for example, a $C_{1-6}$ alkyl sulfonyl and the like such as methanesulfonyl, ethane sulfonyl, etc., may be used.

As the "acyl derived from carboxylic acid" which is the substituent(s) mentioned above, a group formed by bonding a hydrogen atom or the substituent at the nitrogen atom of the "N-mono-substituted carbamoyl" mentioned above with a carbonyl group, etc., may be used. Preferably, a $C_{1-6}$ alkanoyl such as formyl, acetyl, propionyl, pivaloyl, etc., and acyl such as benzoyl, etc., may be used.

As the substituent(s) in the "aromatic hydrocarbon group which may have substituent(s)" represented by $Q^1$, $Q^2$, $Q^3$, $Q^4$ or $R^{1a}$, or the "$C_{6-10}$ aryl group which may have substituent(s) represented by Q, $R^{1d}$, $R^2$ or $R^8$, or the "$C_{6-10}$ aryl group which may have substituent(s)" represented by $R^{1b}$, $R^{1c}$, substituents similar and comparable in amount to the substituent(s) in the "alkyl group which may have substituent(s)" which is the substituent(s) mentioned above, may be used.

As the substituent(s) in the "aromatic heterocyclic group which may have substituent(s)", represented by Q, substituents similar and comparable in amount to the substituent(s) in the "heterocyclic group which may have substituent(s)" mentioned above, may be used.

As the substituent(s) in the "alicyclic hydrocarbon group which may have substituent(s)" represented by $Q^1$, $Q^2$, $Q^3$, $Q^4$, $R^{1a}$, the "$C_{3-8}$ cycloalkyl group which may have substituent(s)" represented by $R^{1d}$, $R^2$ and $R^8$ and the "$C_{3-8}$ cycloalkyl group which has substituent(s)" represented by $R^{1b}$, $R^{1c}$, substituent(s) similar and comparable in amount to the substituent(s) in the aforementioned substituent(s) in the "alkyl group which may have substituent(s)" which is the substituent(s) mentioned above, may be used.

As the substituent(s) in the "$C_{1-6}$ alkyl group which may have substituent(s)", represented by $R^2$, substituents similar and comparable in amount to the substituent(s) in the "alkyl group which may have substituent(s)" which is the substituent(s) mentioned above, may be used.

As the substituent(s) in the "nitrogen atom which may have substituent(s)" represented by X, $X^a$, Y, $W^1$, $W^2$, $W^3$ and $W^4$ substituents similar to the substituent in the "amino group which may have substituent(s)" which is the substituent(s) mentioned above, may be used.

As the substituent(s) in the "bivalent aliphatic hydrocarbon group which may have more than 1 hetero atom(s) and which may have substituent(s)" represented by T, and a bivalent aliphatic hydrocarbon group which may have substituent(s) represented by $W^1$, $W^2$, $W^3$ and $W^4$, substituents similar and comparable in amount to the substituent(s) in the "alkyl group which may have substituent(s)" which is the substituent(s) mentioned above, may be used.

As $R^1$, $R^{1a}$, $R^{1b}$, $R^{1c}$ and $R^{1d}$, an aromatic hydrocarbon group which may have substituent(s) or a heterocyclic group which may have substituent(s), etc., is preferable. A phenyl group which may have substituent(s) is more preferable.

As to $R^3$ to $R^7$, it is preferable that each of them may be the same as or different from each other and each is a hydrogen atom or a $C_{1-6}$ alkoxy group which may be substituted by halogen(s). T, $T^a$ and $T^b$ are each preferably a single bond, a methylene group, an ethylene group, a vinylene group, etc.

As X, $X^a$ and $X^b$, a nitrogen atom which may have substituent(s) is preferable.

As Y, $Y^a$ and $Y^b$, a nitrogen atom is preferable.

As Z, $Z^a$ and $Z^b$, a nitrogen atom is preferable. As W, $W^a$, $W^b$, $W^1$, $W^2$, $W^3$, $W^4$, $W^{1a}$, $W^{2a}$, $W^{3a}$ and $W^{4a}$, a single bond, a methylene group or an oxygen atom, etc., is preferable.

As Q, $Q^1$, $Q^2$, $Q^3$ and $Q^4$ a halogen atom, an aromatic hydrocarbon group which may have substituent(s) or a heterocyclic group which may have substituent(s) is preferable. A halogen atom or a phenyl group which may have substituent(s), a naphthyl group which may have substituent(s), a furyl group which may have substituent(s), a thienyl group which may have substituent(s), a benzofuryl group which may have substituent(s), etc., is more preferable. As the substituent(s), a halogen atom such as a fluorine atom, a chlorine atom, a bromine atom, etc. is preferable.

A compound wherein X is a nitrogen atom which may have substituent(s), and Y=Z=a nitrogen atom, is preferable.

A compound wherein X is a nitrogen atom which may have substituent(s), and Y=$Z^a$=a nitrogen atom, is preferable.

A compound wherein $X^a$ is a nitrogen atom which may have substituent(s), and $Y^a$=$Z^a$=a nitrogen atom, is preferable.

A compound represented by the formula (IX), wherein $W^a$ is a single bond, is a compound represented by the formula (IXa):

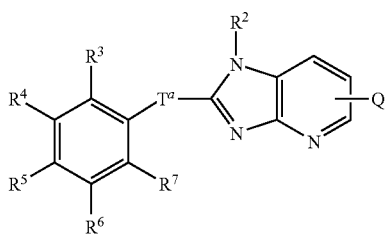

(IXa)

(wherein each symbol has the meaning given above); or a salt thereof; the compound represented by the formula (X) wherein $W^a$ is a single bond, is a compound represented by the formula (X):

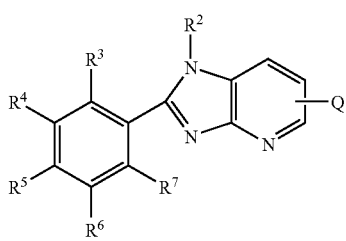

(Xa)

(wherein each symbol has the meaning given above); or a salt thereof; a compound represented by the formula (IX) wherein $T^a$ and $W^a$ are each a single bond, is a compound represented by the formula (IXb):

(IXb)

(wherein each symbol has the meaning given above); or a salt thereof; a compound represented by the formula (X) wherein $T^a$ and $W^a$ are each a single bond, is a compound represented by the formula (Xb):

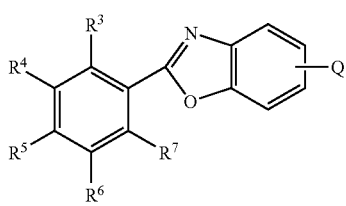

(Xb)

(wherein each symbol has the meaning given above); or a salt thereof. In the present invention, compounds represented by the formulas $(IX^a)$, $(IX^b)$, $(X^a)$ and $(X^b)$ are preferable.

As the compounds of the present invention, compounds represented by the formulas (I) to (XI) are preferable. Compounds represented by the following formulas (I'), (III'), (V') and (VI') to (XI') are more preferable.

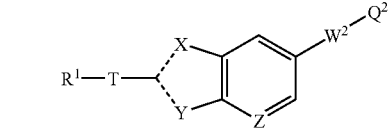

(I')

(wherein each symbol has the meaning given above); or a salt thereof;

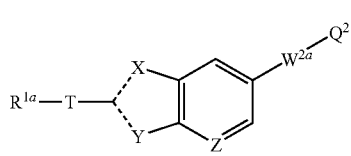

(III')

(wherein each symbol has the meaning given above); or a salt thereof;

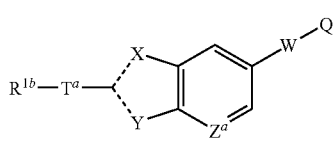

(V')

(wherein each symbol has the meaning given above); or a salt thereof;

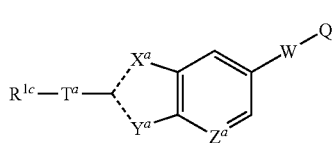

(VI')

(wherein each symbol has the meaning given above); or a salt thereof;

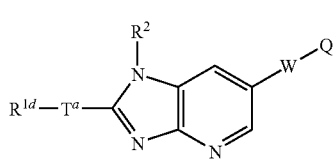

(VII')

(wherein each symbol has the meaning given above); or a salt thereof;

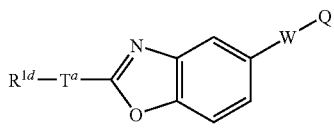

(VIII')

(wherein each symbol has the meaning given above); or a salt thereof;

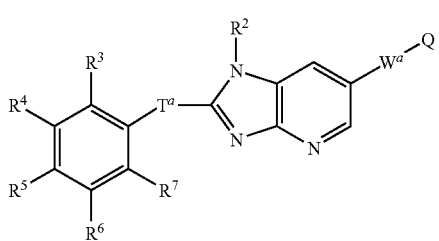

(IX')

(wherein each symbol has the meaning given above); or a salt thereof;

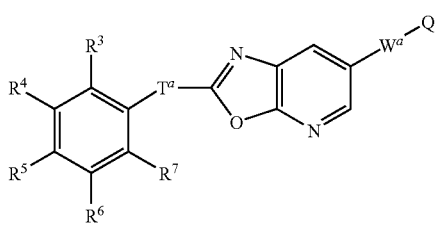

(X')

(wherein each symbol has the meaning given above); or a salt thereof;

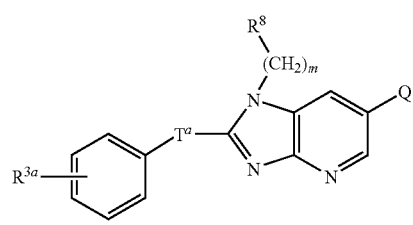

(XI')

(wherein each symbol has the meaning given above); or a salt thereof;

In the present invention, each compound represented by the formulas (I) to (XI), (I'), (III'), (V'), (VI') to (XI'), etc., may form a salt.

As the salt of compound (I) of the present invention, pharmaceutically acceptable salts are preferred, including salts with inorganic bases, salts with organic bases, salts with inorganic acids, salts with organic acids, and salts with basic or acidic amino acids. As preferable examples of salts with inorganic bases, there may be mentioned alkali metal salts such as sodium salt and potassium salt, alkaline earth metal salts such as calcium salt and magnesium salt, aluminum salt, and ammonium salt, etc. As preferable examples of salts with organic bases, there may be mentioned salts with trimethylamine, triethylamine, pyridine, picoline, ethanolamine, diethanolamine, triethanolamine, dicyclohexylamine, N,N'-dibenzylethylenediamine, etc. As preferable examples of salts with inorganic acids, there may be mentioned salts with hydrochloric acid, hydrobromic acid, nitric acid, sulfuric acid, phosphoric acid, etc. As preferable examples of salts with organic acids, there may be mentioned salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. As preferable examples of salts with basic amino acids, there may be mentioned salts with arginine, lysine, ornithine, etc. As preferable examples of salts with acidic amino acids, there may be mentioned salts with aspartic acid, glutamic acid, etc.

When compound of the present invention has asymmetric carbons, optical isomers exist; these isomers are included in the scope of the present invention, whether they are present in the form of a simple substance or a mixture.

A compound of this invention or a salt thereof can either be a hydrate or a non-hydrate.

Moreover, a compound of this invention can be labeled with an isotope (for example, $^3H$, $^{14}C$, etc.)

Compound (I), etc. of the present invention can be obtained by a known method per se. For example, the following methods may be used.

A starting compound and intermediate compound can be used not only as a free form but also as a salt similar to compound (I), etc. (As the salt, for example, a salt similar to that of compound (I), etc., may be used), and can be used for the following reaction as a reaction mixture itself or after having completed isolation by using a known method.

Compound (IVa-c) can be produced by the method shown in J. Med. Chem. (Journal of Medicinal Chemistry) volume 28, page 717-727 (1985).

Production Method 1

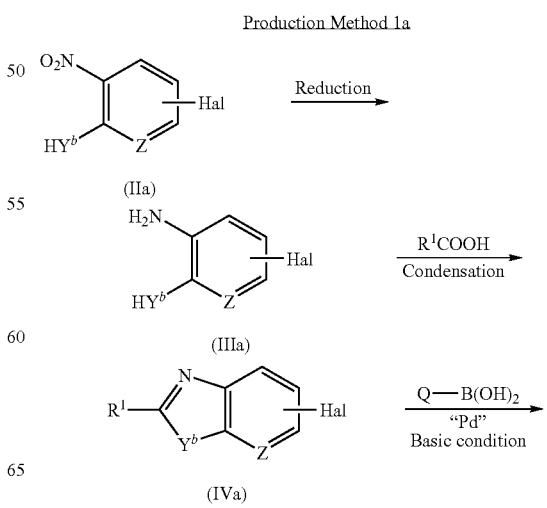

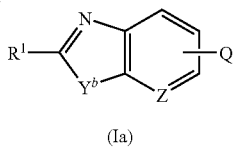

(Ia)

(wherein each symbol has the meaning given above, $Y^b$ is an oxygen atom or a sulfur atom, Hal is a halogen atom, and Pd is a palladium catalyst)

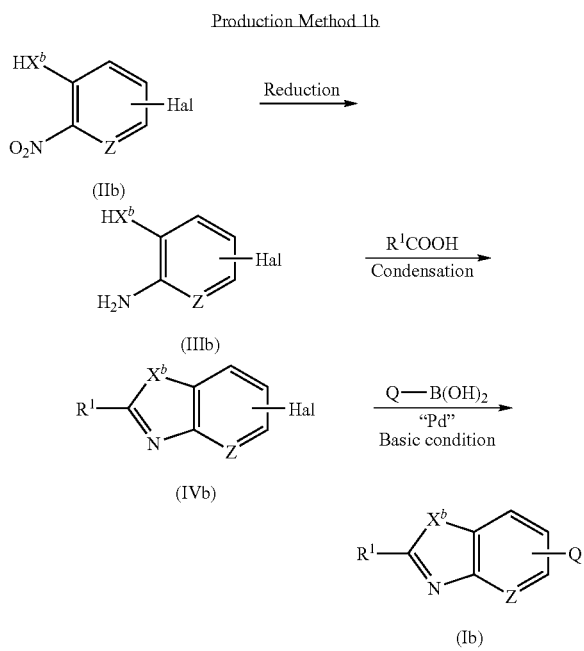

(wherein each symbol has the meaning given above, and $X^b$ is an oxygen atom or a sulfur atom)

(Production Method 1a)

The publicly available compound (IIa) is subjected to a reduction reaction under a conventional condition for the reduction of nitro group. As the reduction condition, for example, a combination of iron powder and an appropriate acid (for example, a combination with a hydrochloric acid), or use of a catalytic reduction that involves hydrogenation in the presence of a palladium catalyst, etc. may be used. Generally, the reaction can be carried out in an appropriate solvent such as ethanol. The reaction temperature may be from 0° C. to 100° C. Normally, 30 minutes to 8 hours are required for the reaction time. As the condition under which iron is used, 80° C. for several hours in ethanol is preferable.

Compound (IVa) is obtained by subjecting the obtained compound (IIIa) to dehydration condensation with a carboxylic acid compound $R^1COOH$ under appropriate condensation conditions. As the appropriate condensation conditions, for example, heating and stirring of compound (IIIa) within polyphosphoric acid ester (PPE), the addition of an appropriate amount of phosphorus pentaoxide into methanesulfonic acid while heating and stirring, or heating and stirring of compound (IIIa) within phosphorusoxychloride, may be mentioned. Reaction temperature may be from room temperature to 180° C., preferably from 100° C. to 140° C. Reaction time will be 1 to 12 hours.

Compound (Ia) can be obtained by dissolving compound (IVa) in a reaction interference free solvent (for example, toluene, tetrahydrofuran, dimethoxyethane, etc.), and by adding an appropriate catalyst (for example, a palladium catalyst such as tetrakis triphenylphosphine palladium, etc.) in the presence of an appropriate base, and then by heating and stirring compound (IVa) with an appropriate organic boron compound $Q-B(OH)_2$ under an inert gas atmosphere.

The reaction temperature ranges from room temperature to about 100° C. The reaction time will be 1 to 12 hours. The amount of the organic boron compound $Q-B(OH)_2$ used is preferably 1 equivalency or slightly more. As the "base", for example, an inorganic base such as sodium carbonate, sodium bicarbonate, potassium carbonate, potassium bicarbonate, sodium hydroxide, potassium hydroxide, thallium hydroxide, etc., and an organic base such as triethylamine, pyridine, etc., is used.

The amount of the "base" used is about 2 to 20 mol, preferably about 5 to 12 mol, per 1 mol of compound (IVa).

Production Method 1b

In a manner similar to the above, compound (Ib) can be produced from compound (IIb).

Production Method 2

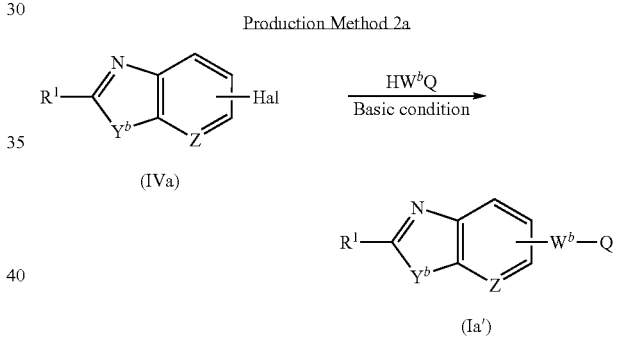

(wherein each symbol has the meaning given above. $W^b$ is NH, an oxygen atom or a sulfur atom)

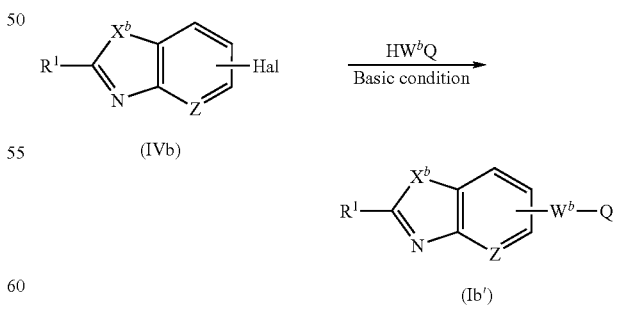

(wherein each symbol has the meaning given above)

Production Method 2a

Compound (Ia') is obtained by dissolving compound (IVa) obtained in the above Production Method 1 in a reaction interference free solvent (for example, an ether (e.g., ethyl ether, dioxane, dimethoxyethane, tetrahydrofuran, etc.), an aromatic hydrocarbon (e.g., benzene, toluene, etc.) an amide (e.g., dimethylformamide, dimethylacetamide, etc.), a halogenated hydrocarbon (e.g., chloroform, dichloromethane, etc.)), and by adding an appropriate catalyst (for example, a copper ion catalyst such as copper iodide, copper oxide, etc.), in the presence of an appropriate base, and then by heating and stirring (IVa) with a nucleophilic reagent $HW^bQ$.

The reaction temperature ranges from room temperature to about 100° C. The reaction time will be 1 to 12 hours. The amount of the nucleophilic reagent $HW^bQ$ used is preferably 1 equivalency or slightly more.

As the "base", for example, an inorganic base such as sodium carbonate, sodium bicarbonate, potassium carbonate, potassium bicarbonate, sodium hydroxide, potassium hydroxide, thallium hydroxide, etc., and an organic base such as triethylamine, pyridine, etc., is used.

The amount of the "base" used is about 2 to 20 mol, preferably about 5 to 12 mol, per 1 mol of compound (IVa). In a manner similar to the above, compound (Ib') can be produced from compound (IVb) obtained in Production Method 1b.

Production Method 3

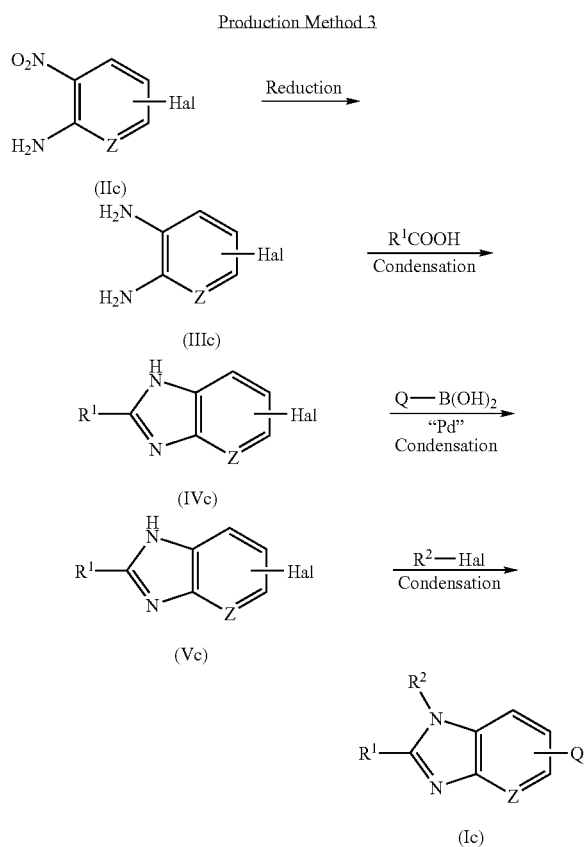

(wherein each symbol has the meaning given above.)

A publicly available compound (IIc) is subjected to the reduction reaction under a conventional condition for the reduction of nitro group. As the reduction condition, for example, a combination of iron powder and an appropriate acid (for example, a combination with a hydrochloric acid), or use of a catalytic reduction that involves hydrogenation in the presence of a palladium catalyst, etc., may be used. Generally, the reaction can be carried out in an appropriate solvent such as ethanol. The reaction temperature may be from 0° C. to 100° C. Normally, 30 minutes to 8 hours are required for the reaction time. As the condition under which iron is used, 80° C. for several hours in ethanol is preferable.

Compound (IVc) is obtained by subjecting the obtained compound (IIIc) to dehydration condensation with a carboxylic acid compound $R^1COOH$ under appropriate condensation conditions. As the appropriate condensation conditions, for example, heating and stirring of compound (IIIc) within poly phosphoric acid ester (PPE), the addition of an appropriate amount of phosphorus pentaoxide into methanesulfonic acid while heating and stirring, or heating and stirring of compound (IIIc) within phosphorusoxychloride, may be mentioned.

Reaction temperature may be from room temperature to 180° C., preferably from 100° C. to 140° C. Reaction time will be 1 to 12 hours. Compound (Vc) can be obtained by dissolving compound (IVc) in a reaction interference free solvent (for example, toluene, tetrahydrofuran, dimethoxyethane, etc.), and by adding an appropriate catalyst (for example, a palladium catalyst such as tetrakis triphenylphosphine palladium, etc.) in the presence of an appropriate base, and then by heating and stirring compound (IVa) with an appropriate organic boron compound $Q-B(OH)_2$ under an inert gas atmosphere.

The reaction temperature ranges from room temperature to about 100° C. The reaction time will be 1 to 12 hours. The amount of the compound $Q-B(OH)_2$ used is preferably 1 equivalency or slightly more. As the "base", for example, an inorganic base such as sodium carbonate, sodium bicarbonate, potassium carbonate, potassium bicarbonate, sodium hydroxide, potassium hydroxide, thallium hydroxide, etc., and an organic base such as triethylamine, pyridine, etc., is used.

The amount of the "base" used is about 2 to 20 mol, preferably about 5 to 12 mol, per 1 mol of compound (IVc).

Compound (Ic) can be obtained by dissolving compound (Vc) in a reaction interference free solvent (for example, an ether (e.g. ethyl ether, dioxane, dimethoxyethane, tetrahydrofuran, etc.), an aromatic hydrocarbon (e.g., benzene, toluene, etc.), an amide (e.g., dimethylformamide, dimethylacetamide, etc.), a halogenated hydrocarbon (e.g., chloroform, dichloromethane, etc.), in the presence of an appropriate base and then by reacting with a halide $R_2$-Hal in a basic condition. As the "base", for example, an inorganic base such as sodium carbonate, sodium bicarbonate, potassium carbonate, potassium bicarbonate, sodium hydroxide, potassium hydroxide, thallium hydroxide, sodium hydride, etc., and an organic base such as triethylamine, pyridine, 2-tert-butylimino-2-diethylamino-1,3-dimethylperhydro-1,3,2-diazaphospholin (BEMP), BEMP resin, etc., is used.

The amount of the "base" used is about 1 to 10 mol, preferably about 1 to 3 mol, per 1 mol of compound (Vc). The amount of the halide $R_2$-Hal used is about 1 to 10 mol, preferably about 1 to 2 mol, per 1 mol of compound (Vc). The reaction temperature ranges from 0° C. to about 100° C., preferably from room temperature to 50° C. The reaction time will be 1 to 24 hours.

Production Method 4

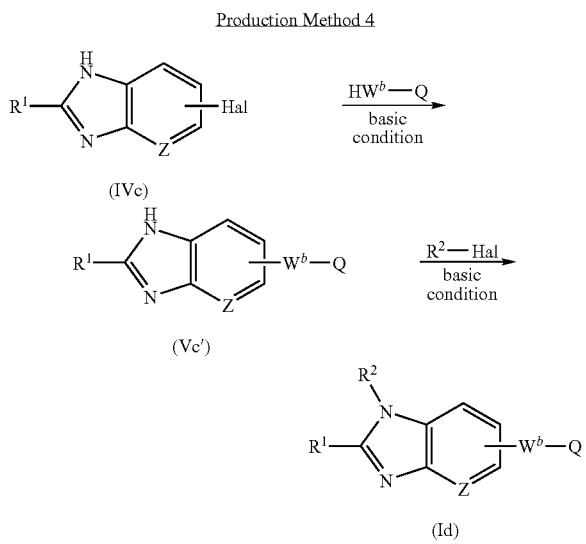

(wherein each symbol has the meaning given above.)

Compound (Vc') is obtained by dissolving compound (IVc) obtained in the above Production Method 3 in a reaction interference free solvent (for example, an ether (e.g., ethyl ether, dioxane, dimethoxyethane, tetrahydrofuran, etc.), an aromatic hydrocarbon (e.g., benzene, toluene, etc.) an amide (e.g., dimethylformamide, dimethylacetamide, etc.), a halogenated hydrocarbon (e.g., chloroform, dichloromethane, etc.)), and by adding an appropriate catalyst (for example, a copper ion catalyst such as copper iodide, copper oxide, etc.), in the presence of an appropriate base, and then by heating and stirring (IVc) with a nucleophilic reagent $HW^bQ$.

The reaction temperature ranges from room temperature to about 100° C. The reaction time will be 1 to 12 hours. The amount of the nucleophilic reagent $HW^bQ$ used is preferably 1 equivalency or slightly more. As the "base", for example, an inorganic base such as sodium carbonate, sodium bicarbonate, potassium carbonate, potassium bicarbonate, sodium hydroxide, potassium hydroxide, thallium hydroxide, etc., and an organic base such as triethylamine, pyridine, etc., is used.

The amount of the "base" used is about 2 to 20 mol, preferably about 5 to 12 mol, per 1 mol of compound (IVc).

Compound (Id) can be obtained by dissolving compound (Vc') in a reaction interference free solvent (for example, an ether (e.g. ethyl ether, dioxane, dimethoxyethane, tetrahydrofuran, etc.), an aromatic hydrocarbon (e.g., benzene, toluene, etc.), an amide (e.g., dimethylformamide, dimethylacetamide, etc.), a halogenated hydrocarbon (e.g., chloroform, dichloromethane, etc.), in the presence of an appropriate base, and then by reacting with a halide $R_2$-Hal in a basic condition. As the "base", for example, an inorganic base such as sodium carbonate, sodium bicarbonate, potassium carbonate, potassium bicarbonate, sodium hydroxide, potassium hydroxide, thallium hydroxide, sodium hydride, etc., and an organic base such as triethylamine, pyridine, 2-tert-butylimino-2-diethylamino-1,3-dimethylperhydro-1,3,2-diazaphospholin (BEMP), BEMP resin, etc., is used. The amount of the "base" used is about 1 to 10 mol, preferably about 1 to 3 mol, per 1 mol of compound (Vc'). The amount of the halide $R_2$-Hal used is about 1 to 10 mol, preferably about 1 to 2 mol, per 1 mol of compound (Vc'). The reaction temperature ranges from 0° C. to about 100° C., preferably from room temperature to 50° C. The reaction time will be 1 to 24 hours.

Production Method 5

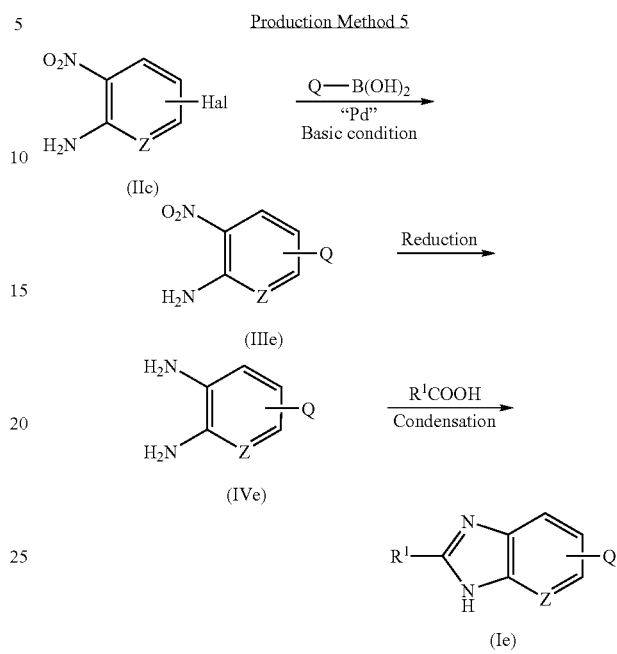

(wherein each symbol is the same as shown above.)

Compound (IIIe) can be obtained by dissolving publicly available compound (IIc) in a reaction interference free solvent (for example, toluene, tetrahydrofuran, dimethoxyethane, etc.), and by adding an appropriate catalyst (for example, a palladium catalyst such as tetrakis triphenylphosphine, a palladium, etc.) in the presence of an appropriate base, and then by heating and stirring compound (IIc) with an appropriate organic boron compound Q-B(OH)$_2$ under an inert gas atmosphere.

The reaction temperature ranges from room temperature to about 100° C. The reaction time will be 1 to 12 hours. The amount of the compound Q-B(OH)$_2$ used is preferably 1 equivalency or slightly more. As the "base", for example, an inorganic base such as sodium carbonate, sodium bicarbonate, potassium carbonate, potassium bicarbonate, sodium hydroxide, potassium hydroxide, thallium hydroxide, etc., and an organic base such as triethylamine, pyridine, etc., is used.

The amount of the "base" used is about 2 to 20 mol, preferably about 5 to 12 mol, per 1 mol of compound (IIc).

The obtained compound (IIIe) is subjected to the reduction reaction under a conventional condition for the reduction of nitro group. As the reduction condition, for example, a combination of iron powder and an appropriate acid (for example, a combination with a hydrochloric acid), or use of a catalytic reduction that involves hydrogenation in the presence of a palladium catalyst, etc., may be used.

Generally, the reaction can be carried out in an appropriate solvent such as ethanol. The reaction temperature may be from 0° C. to 100° C. Normally, 30 minutes to 8 hours are required for the reaction time. As the condition under which iron is used, 80° C. for several hours in ethanol is preferable.

Compound (Ie) is obtained by subjecting the obtained compound (IVe) to dehydration condensation with a carboxylic acid compound $R^1COOH$ under appropriate condensation conditions. As the appropriate condensation conditions, for example, heating and stirring of compound (IVe) within poly phosphoric acid ester (PPE), the addition of an appropriate amount of phosphorus pentaoxide into methanesulfonic acid while heating and stirring, or heating and stirring of compound (IVe) within phosphorusoxychloride, may be mentioned. Reaction temperature may be from room temperature to 180° C., preferably from 100° C. to 140° C. Reaction time will be 1 to 12 hours.

Production Method 6

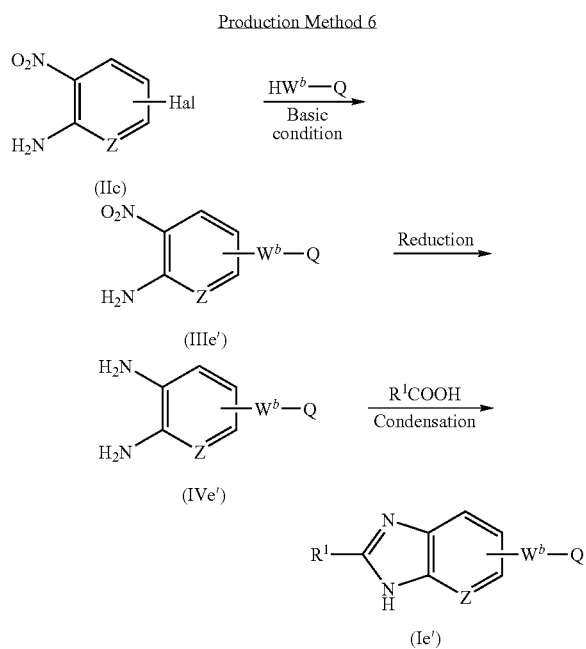

(wherein each symbol has the meaning given above Condensation

Compound (IIIe') is obtained by dissolving publicly available compound (IIc) in a reaction interference free solvent (for example, an ether (e.g., ethyl ether, dioxane, dimethoxyethane, tetrahydrofuran, etc.), an aromatic hydrocarbon (e.g., benzene, toluene, etc.) an amide (e.g., dimethylformamide, dimethylacetamide, etc.), a halogenated hydrocarbon (e.g., chloroform, dichloromethane, etc.)), and by adding an appropriate catalyst (for example, a copper ion catalyst such as copper iodide, copper oxide, etc.), in the presence of an appropriate base, and then by heating and stirring (IIc) with a nucleophilic reagent $HW^bQ$.

The reaction temperature ranges from room temperature to about 100° C. The reaction time will be 1 to 12 hours. The amount of the nucleophilic reagent $HW^bQ$ used is preferably 1 equivalency or slightly more. As the "base", for example, an inorganic base such as sodium carbonate, sodium bicarbonate, potassium carbonate, potassium bicarbonate, sodium hydroxide, potassium hydroxide, thallium hydroxide, etc., and an organic base such as triethylamine, pyridine, etc., is used.

The amount of the "base" used is about 2 to 20 mol, preferably about 5 to 12 mol, per 1 mol of compound (IIc).

The obtained compound (IIIe') is subjected to the reduction reaction under a conventional condition for the reduction of nitro group. As the reduction condition, for example, a combination of iron powder and an appropriate acid (for example, a combination with a hydrochloric acid), or use of a catalytic reduction that involves hydrogenation in the presence of a palladium catalyst, etc., may be used. Generally, the reaction can be carried out in an appropriate solvent such as ethanol. The reaction temperature may be from 0° C. to about 100° C. Normally, 30 minutes to 8 hours are required for the reaction time. As the condition under which iron is used, 80° C. for several hours in ethanol is preferable.

Compound (Ie') is obtained by subjecting the obtained compound (IVe') to dehydration condensation with a carboxylic acid compound $R^1COOH$ under appropriate condensation conditions. As the appropriate condensation conditions, for example, heating and stirring of compound (IVe') within poly phosphoric acid ester (PPE), the addition of an appropriate amount of phosphorus pentaoxide into methanesulfonic acid while heating and stirring, or heating and stirring of compound (IVe') within phosphorusoxychloride, may be mentioned. Reaction temperature may be from room temperature to 180° C., preferably from 100° C. to 140° C. Reaction time will be 1 to 12 hours.

When the target compound mentioned above is obtained as a mixture of optical isomers, the desired (R)-configuration or (S)-configuration can be separated by a commonly known means of optical resolution. Specifically, optical resolution can be efficiently carried out by using an optically active column (e.g., Chiralpak AD, produced by Daicel Chemical Industries, Ltd.), and also, optical isomers can be divided by forming a salt of diastereomer with an optically active acid and utilizing the difference of solubility.

When the compound of the present invention is obtained as a free form, it can be converted to a salt by a conventional manner, and when it is obtained as a salt, it can be converted to a free form or another salt by a conventional manner.

The compound and optical isomers thereof thus obtained can be isolated and purified by commonly known means for separation, e.g., phasic transfer, concentration, solvent extraction, fractionating, crystallization, recrystallization, chromatography, and the like.

In the above reactions, when the compound or a salt thereof obtained by the reactions has an amino group, a carboxyl group or a hydroxy group which does not take part the reaction, these groups each may be protected by a protective group. Protection and de-protection can be conducted by a known method.

As the deprotection method, a known method or a method similar to a known method can be used. For example, a method using acid, base, reduction, ultraviolet ray, hydrazine, phenyl hydrazine, sodium N-methyldithiocarbamate, tetra butyl ammonium fluoride, palladium acetate, etc., is used.

A pro-drug of the compound (I), etc. or a salt thereof (hereinafter referred to as the compound (I), etc.) means a compound which is converted to the compound (I), etc. of the present invention under the physiological condition or with a reaction due to an enzyme, a gastric acid, etc. in vivo, that is, a compound which is converted to the compound (I), etc. of the present invention with oxidation, reduction, hydrolysis, etc. according to an enzyme; a compound which is converted to the compound (I), etc. of the present invention with gastric acid, etc. A prodrug for compound (I), etc. may for example be a compound obtained by subjecting an amino group (nitrogen) in compound (I), etc. to an acylation, alkylation or phosphorylation (e.g., a compound obtained by subjecting an amino group (nitrogen) in compound (I), etc. to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I), etc. to an acylation, alkylation, phosphorylation or boration (e.g., a compound obtained by subjecting a hydroxy in compound (I), etc. to an acetylation, palmitoylation, propanoylation, pivaloylation, succinylation, fumarylation, alanylation, dimethylaminomethylcarbonylation, etc.); a compound obtained by subjecting a carboxyl group in compound (I), etc. to an esterification or amidation (e.g., a compound obtained by subjecting a carboxyl group in compound (I), etc. to an ethylesterification, phenylesterification, carboxymethylesterification, dimethylaminomethylesterification, pivaloyloxymethylesterification, ethoxycarbonyloxyethylesterification, phthalidylesterification, (5-methyl-2-oxo-1,3-dioxolen-4-yl) methylesterification, cyclohexyloxycarbonylethylesterification and methylamidation, etc.) and the like. Any of these compounds can be produced from compound (I), etc. by a known method per se.

A prodrug for compound (I) and the like may also be one which is converted into compound (I) and the like under a physiological condition, such as that described in "IYAKUHIN no KAIHATSU (Development of Pharmaceuticals)", Vol. 7, Design of molecules, p. 163-198, Published by HIROKAWA SHOTEN (1990).

The prodrug such as Compound (I) and the like may be a hydrate or a non-hydrate. Further, the prodrug has 1 or more asymmetric carbon(s) in the molecule. The compound of the present invention may have R-configuration or S-configuration for the asymmetric carbons.

The compound (I) and the like of the present invention, or a salt thereof or a pro-drug thereof (hereinafter referred to as the compound of the present invention) possesses tyrosine kinase-inhibiting activity and can be used to prevent or treat tyrosine kinase-dependent diseases in mammals. Tyrosine kinase-dependent diseases include diseases characterized by increased cell proliferation due to abnormal tyrosine kinase activity. Furthermore, the compound of the present invention specifically inhibits HER2 tyrosine kinase and is therefore also useful as a therapeutic agent for suppressing the growth of HER2-expressing cancer, or a preventive agent for preventing the transition of hormone-dependent cancer to hormone-independent cancer. In the present invention, the meaning of the "inhibition of tyrosine kinase" includes that the compound directly acts as an antagonist to an enzyme to inhibit the activity of the enzyme and that the compound indirectly inhibits tyrosine kinase by reducing the amount of protein of tyrosine kinase or by reducing the enzyme activity.

Accordingly, the compound of the present invention can be used as a safe preventive or therapeutic agent for diseases due to abnormal cell proliferation such as various cancers (particularly breast cancer, prostate cancer, pancreatic cancer, gastric cancer, lung cancer, colon cancer, rectal cancer, esophagus cancer, duodenal cancer, cancer of the tongue, cancer of pharynx, cerebral cancer, neurilemoma, non-small cell lung-cancer, small cell lung cancer, liver cancer, kidney cancer, cancer of the bile duct, cancer of the uterine body, cancer of the uterine cervix, ovarian cancer, bladder cancer, skin cancer, hemangioma, malignant lymphoma, malignant melanoma, thyroid cancer, bone tumors, vascular fibroma, retinoblastoma, penile cancer, tumor in childhood, Kaposi's sarcoma, Kaposi's sarcoma-derived from AIDS, maxillary tumor, fibrous histiocytoma, leiomyosarcoma, rhabdomyosarcoma, leukemia, etc.), atheroma arteriosclerosis, angiogenesis (e.g., angiogenesis associated with growth of solid cancer and sarcoma, angiogenesis associated with tumor metastasis, and angiogenesis associated with diabetic nephropathy, etc.), and viral diseases (HIV infection etc.).

Tyrosine kinase-dependent diseases further include cardiovascular diseases associated with abnormal tyrosine kinase activity. The compound of the present invention can therefore be used as a preventive or therapeutic agent for cardiovascular diseases such as re-stenosis.

The compound of the present invention is useful as an anticancer agent for preventing or treating cancers, especially e.g., breast cancer, prostate cancer, pancreatic cancer, gastric cancer, lung cancer, colonic cancer, carcinoma of the colon and rectum.

The compound of the present invention is of low toxicity and can be used as a pharmaceutical composition as-is, or in a mixture with a commonly known pharmaceutically acceptable carrier etc. in mammals (e.g., humans, horses, bovines, dogs, cats, rats, mice, rabbits, pigs, monkeys, and the like).

In addition to the compound of the present invention, said pharmaceutical composition may contain other active ingredients, e.g., the following hormone therapy agents, anti-cancer agent (e.g., chemotherapy agents, immunotherapy agents, or drugs which inhibit the activity of cell growth factors and receptors thereof), and the like.

As a pharmaceutical for mammals such as humans, the compound of the present invention can be administered orally in the form of, for example, tablets, capsules (including soft capsules and microcapsules), powders, and granules, or non-orally in the form of injections, suppositories, and pellets. Examples of the "parenteral administration route" include intravenous, intramuscular, subcutaneous, intra-tissue, intranasal, intradermal, instillation, intracerebral, intrarectal, intravaginal, intraperitoneal, intratumoral, juxtaposition of tumor and administration directly to the lesion.

The dose of the compound varies depending on the route of administration, symptoms, etc. For example, when it is administered orally as an anticancer agent to a patient (body weight 40 to 80 kg) with breast cancer or prostate cancer, its dose is, for example, 0.5 to 100 mg/kg body weight per day, preferably 1 to 50 mg/kg body weight per day, and more preferably 1 to 25 mg/kg body weight per day. This amount may be administered once or in 2 to 3 divided portions daily.

The compound of the present invention can be formulated with a pharmaceutically acceptable carrier and administered orally or non-orally in the form of solid preparations such as tablets, capsules, granules and powders, etc.; or liquid preparations such as syrups and injectable preparations, etc.

As pharmaceutically acceptable carriers, there may be used various organic or inorganic carrier substances in common use for pharmaceutical preparations, including excipients, lubricants, binders, and disintegrating agents in solid preparations; solvents, dissolution aids, suspending agents, isotonizing agents, buffers, and soothing agents in liquid preparations. Such pharmaceutical additives as antiseptics, antioxidants, coloring agents, and sweetening agents can also be used as necessary.

As examples of preferable excipients, there may be mentioned, lactose, sucrose, D-mannitol, starch, crystalline cellulose, light silicic anhydride, and the like.

As examples of preferable lubricants, there may be mentioned, for example, magnesium stearate, calcium stearate, talc, colloidal silica, and the like.

As examples of preferable binders, there may be mentioned, for example, crystalline cellulose, sucrose, D-mannitol, dextrin, hydroxypropyl cellulose, hydroxypropylmethyl cellulose, polyvinylpyrrolidone, and the like.

As examples of preferable disintegrating agents, there may be mentioned, for example, starch, carboxymethyl cellulose, carboxymethyl cellulose calcium, crosslinked carmellose sodium, carboxymethyl starch sodium, and the like.

As examples of preferable solvents, there may be mentioned, for example, water for injection, alcohol, propylene glycol, macrogol, sesame oil, corn oil, and the like.

As examples of preferable dissolution aids, there may be mentioned, for example, polyethylene glycol, propylene glycol, D-mannitol, benzyl benzoate, ethanol, trisaminomethane, cholesterol, triethanolamine, sodium carbonate, sodium citrate, and the like.

As examples of preferable suspending agents, there may be mentioned, for example, surfactants such as stearyltriethanolamine, sodium lauryl sulfate, laurylaminopropionic acid, lecithin, benzalkonium chloride, benzetonium chloride, monostearic glycerol, and the like; and hydrophilic polymers such as polyvinyl alcohol, polyvinylpyrrolidone, carboxymethyl cellulose sodium, methyl cellulose, hydroxymethyl cellulose, hydroxyethyl cellulose, hydroxypropyl cellulose, and the like.

As examples of preferable isotonizing agents, there may be mentioned, for example, sodium chloride, glycerol, D-mannitol, and the like.

As examples of preferable buffers, there may be mentioned, for example, buffer solutions of phosphates, acetates, carbonates, citrates, and the like.

As examples of preferable soothing agents, there may be mentioned, benzyl alcohol, and the like.

As examples of preferable antiseptics, there may be mentioned, a para-oxybenzoate, chlorobutanol, benzyl alcohol, phenethyl alcohol, dehydroacetic acid, sorbic acid, and the like.

As examples of preferable antioxidants, there may be mentioned, for example, sulfites, ascorbic acid, and the like.

A pharmaceutical composition can be produced by a conventional method by containing the compound of the present invention in a ratio of normally 0.1 to 95% (w/w) to the total amount of the preparation, although the ratio varies depending on dosage form, method of administration, carrier, etc.

And a combination of (1) administering an effective amount of a compound of the present invention and (2) 1 to 3 selected from the group consisting of (i) administering an effective amount of other anti-cancer agents, (ii) administering an effective amount of hormonal therapeutic agents and (iii) non-drug therapy can prevent and/or treat cancer more effectively. As the non-drug therapy, for example, surgery, radiotherapy, gene therapy, thermotherapy, cryotherapy, laser cauterization, and the like are exemplified and two or more of these may be combined.

For example, the compound of the present invention can be administered to the same subject simultaneously with hormonal therapeutic agents, anticancer agents (e.g., chemotherapeutic agents, immunotherapeutic agents, or drugs that inhibit the activity of growth factors or growth factor receptors) (hereafter, these are referred to as a combination drug).

Although the compound of the present invention exhibits excellent anticancer action even when used as a simple agent, its effect can be enhanced by using it in combination with one or more of the concomitant drug(s) mentioned above (multi-agent co-administration).

As examples of said "hormonal therapeutic agents," there may be mentioned fosfestrol, diethylstylbestrol, chlorotrianiserin, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate, and the like), pill preparations, mepitiostane, testrolactone, aminoglutethimide, LH-RH agonists (e.g., goserelin acetate, buserelin, leuprorelin, and the like), droloxifene, epitiostanol, ethinylestradiol sulfonate, aromatase inhibitors (e.g., fadrozole hydrochloride, anastrozole, retrozole, exemestane, vorozole, formestane, and the like), anti-androgens (e.g., flutamide, bicartamide, nilutamide), 5α-reductase inhibitors (e.g., finasteride, epristeride, and the like), adrenocorticohormone drugs (e.g., dexamethasone, prednisolone, betamethasone, triamcinolone, and the like), androgen synthesis inhibitors (e.g., abiraterone and the like), retinoid and drugs that retard retinoid metabolism (e.g., liarozole, and the like), etc. and LH-RH agonists (e.g., goserelin acetate, buserelin, leuprorelin) are preferable.

As examples of said "chemotherapeutic agents", there may be mentioned alkylating agents, antimetabolites, anticancer antibiotics, plant-derived anticancer agents, and the like.

As examples of "alkylating agents", there may be mentioned nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, carboquone, adozelesin, cystemustine, bizelesin and the like.

As examples of "antimetabolites", there may be mentioned mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emmitefur, and the like), aminopterine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, and ambamustine, etc.

As examples of "anticancer antibiotics", there may be mentioned actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, and the like.

As examples of "plant-derived anticancer agents", there may be mentioned etoposide, etoposide phosphate, vinblastine sulfate, vincristine sulfate, vindesine sulfate, teniposide, paclitaxel, docetaxel, vinorelbine, and the like.

As examples of said "immunotherapeutic agents (BRM)", there may be mentioned picibanil, krestin, sizofiran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, and the like.

The "growth factor" in said "drugs that inhibit the activity of growth factors or growth factor receptors", there may be mentioned any substances that promote cell proliferation, which are normally peptides having a molecular weight of not more than 20,000 that are capable of exhibiting their activity at low concentrations by binding to a receptor, including (1) EGF (epidermal growth factor) or substances possessing substantially the same activity as it [e.g., EGF, heregulin (HER2 ligand), and the like], (2) insulin or substances possessing substantially the same activity as it [e.g., insulin, IGF (insulin-like growth factor)-1, IGF-2, and the like], (3) FGF (fibroblast growth factor) or substances possessing substantially the same activity as it [e.g., acidic FGF, basic FGF, KGF (keratinocyte growth factor), FGF-10, and the like], (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), and the like], and the like.

As examples of said "growth factor receptors", there may be mentioned any receptors capable of binding to the aforementioned growth factors, including EGF receptor, heregulin receptor (HER2), insulin receptor, IGF receptor, FGF receptor-1 or FGF receptor-2, and the like.

As examples of said "drugs that inhibit the activity of cell growth factor", there may be mentioned various kinase inhibitors, trastuzumab (Herceptin (trade mark): (HER2 antibody)), imatinib mesilate (Gleevec (trade mark), Iressa (trade mark): ZD1839), Cetuximab, and the like.

In addition to the aforementioned drugs, L-asparaginase, aceglatone, procarbazine hydrochloride, protoporphyrin-cobalt complex salt, mercuric hematoporphyrin-sodium, topoisomerase II inhibitors (e.g., irinotecan, topotecan, and the like), topoisomerase II inhibitors (e.g., sobuzoxane, and the like), differentiation inducers (e.g., retinoid, vitamin D, and the like), angiogenesis inhibitors, α-blockers (e.g., tamsulosin hydrochloride), etc., may be used.

Among those mentioned above, LH-RH agonists (e.g., goserelin acetate, buserelin, leuprorelin, and the like), Herceptin (Trademark: HER2 antibody), etc. are preferable as a combination drug.

In combination of the compound of the present invention and the combination agent of the present invention, the administration time of the compound of the present invention and the combination agent is not restricted, and the compound of the present invention or the combination agent can be administered to the administration subject simultaneously, or may be administered at different times. The dosage of the combination agent may be determined according to the administration amount clinically used, and can be appropriately selected depending on the administration subject, administration route, disease, combination and the like.

The administration mode of the compound of the present invention and the combination agent of the present invention is not particularly restricted, and it is sufficient that the compound of the present invention and the combination agent are combined in administration. Examples of such administration mode include the following methods:

(1) The compound of the present invention and the combination agent are simultaneously produced to give a single preparation which is administered. (2) The compound of the present invention and the combination agent are separately produced to give two kinds of preparations which are administered simultaneously by the same administration route. (3) The compound of the present invention and the combination agent are separately produced to give two kinds of preparations which are administered by the same administration route only at the different times. (4) The compound of the present invention and the combination agent are separately produced to give two kinds of preparations which are administered simultaneously by different administration routes. (5) The compound of the present invention and the combination agent are separately produced to give two kinds of preparations which are administered by different administration routes at different times (for example, the compound of the present invention and the combination agent are administered in this order, or in the reverse order). Hereafter, these administration modes are referred to as the combination agent of the present invention.

The combination agent of the present invention has low toxicity, and for example, the compound of the present invention or (and) the above-mentioned combination drug can be mixed, according to a known method per se, with a pharmacologically acceptable carrier to give pharmaceutical compositions, for example, tablets (including a sugar-coated tablet, film-coated tablet), powders, granules, capsules (including a soft capsule), solutions, injections, suppositories, sustained release agents and the like which can be safely administered orally or parenterally (e.g., local, rectum, vein, and the like). An injection can be administered by intravenous, intramuscular, subcutaneous, intra-tissue, intranasal, intradermal, instillation, intracerebral, intrarectal, intravaginal, intraperitoneal, intratumoral, juxtaposition of tumor and administration directly to the lesion.

As the pharmacologically acceptable carrier which may be used in production of the combination agent of the present invention, the same as those for the above mentioned pharmaceutical composition of the present invention, may be used.

The compounding ratio of the compound of the present invention to the combination drug in the combination agent of the present invention can be appropriately selected depending on the administration subject, administration route, diseases and the like.

For example, the content of the compound of the present invention in the combination agent of the present invention differs depending on the form of preparation, and is usually from about 0.01 to 100% by weight, preferably from about 0.1 to 50% by weight, more preferably from about 0.5 to 20% by weight, based on the preparation.

The content of the combination drug in the combination agent of the present invention differs depending on the form of preparation, and is usually from about 0.0 to 100% by weight, preferably from about 0.1 to 50% by weight, more preferably from about 0.5 to 20% by weight, based on the preparation.

The content of additives such as a carrier and the like in the combination agent of the present invention differs depending on the form of preparation, and is usually from about 1 to 99.99% by weight, preferably from about 10 to 90% by weight, based on the preparation.

If the compound of the present invention and the combination drug are prepared separately, the same contents may be adopted.

These preparations can be produced by a known method per se commonly used in a preparation process.

For example, the compound of the present invention and the combination drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin and the like), a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, mannitol, sorbitol, glucose and the like), a pH regulator (e.g., hydrochloric acid, sodium hydroxide and the like), a preservative (e.g., ethyl p-oxybenzoate, benzoic acid, methylparaben, propylparaben, benzyl alcohol and the like), a dissolving agent (e.g., conc. glycerin, meglumine and the like), a dissolution aid (e.g., propylene glycol, sucrose and the like), a soothing agent (e.g., glucose, benzyl alcohol and the like), and the like, or can be dissolved, suspended or emulsified in a vegetable oil such as olive oil, sesame oil, cotton seed oil, corn oil and the like or a dissolution aid such as propylene glycol and molded into an oily injection.

In the case of a preparation for oral administration, an excipient (e.g., lactose, sucrose, starch and the like), a disintegrating agent (e.g., starch, calcium carbonate and the like), a binder (e.g., starch, gum Arabic, carboxymethylcellulose, polyvinylpyrrolidone, hydroxypropylcellulose and the like), a lubricant (e.g., talc, magnesium stearate, polyethylene glycol 6000 and the like) and the like, for example, can be added to the compound of the present invention or the combination drug, according to a known method per se, and the mixture can be compression-molded, then if desirable, the mol der product can be coated by a known method per se for the purpose of masking of taste, enteric property or durability, to obtain a preparation for oral administration. As this coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudoragit (methacrylic acid acrylic acid copolymer, manufactured by Rohm, DE), pigment (e.g., iron oxide red, titanium-dioxide, etc.) and the like, may be used. The preparation for oral administration may be either a quick release preparation or a sustained release preparation.

For example, in the case of a suppository, the compound of the present invention and the combination drug can be made into an oily or aqueous solid, semisolid or liquid suppository according to a known method per se. As the oily substrate used in the above-mentioned composition, for example, glycerides of higher fatty acids [e.g., cacao butter, Witebsols (manufactured by Dynamite Novel, DE), etc.], intermediate grade fatty acids [e.g., Myglyols (manufactured by Dynamite Novel, DE), etc.], or vegetable oils (e.g., sesame oil, soy bean oil, cotton seed oil and the like), and the like are listed. Further, as the aqueous substrate, for example, polyethylene glycols, propylene glycol are listed, and as the aqueous gel substrate, for example, natural gums, cellulose derivatives, vinyl polymers, acrylic acid polymers and the like are listed.

As the above-mentioned sustained release agent, sustained release microcapsules and the like are listed.

For obtaining a sustained release microcapsule, a known method per se can be adopted.

A compound of the present invention is preferably molded into an oral administration preparation such as a solid preparation (e.g., powder, granule, tablet, capsule, etc.) and the like, or molded into a rectum administration preparation such as a suppository. Particularly, an oral administration preparation is preferable.

The combination drug can be made into the above-mentioned drug form depending on the kind of drug.

An injectable preparation containing the present compound and combination drug is specifically shown in the followings.

Injection and Preparation Thereof

An injection prepared by dissolving the compound of the present invention or the combination drug into water is preferable. This injection may be allowed to contain a benzoate and/or salicylate.

The injection is obtained by dissolving the compound of the present invention or the combination drug, and if desirable, a benzoate and/or salicylate, into water.

As the above-mentioned salts of benzoic acid and salicylic acid, for example, salts of alkali metals such as sodium, potassium and the like, salts of alkaline earth metals such as calcium, magnesium and the like, ammonium salts, meglumine salts, organic acid salts such as tromethamol and the like, etc. are listed.

The concentration of the compound of the present invention or the combination drug in an injection is from 0.5 to 50 w/v %, preferably from about 3 to 20 w/v %. The concentration of a benzoate or/and a salicylate is from 0.5 to 50 w/v %, preferably from 3 to 20 w/v %.

Into a preparation of the present invention, additives usually used in an injection, for example, a stabilizer (e.g. ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, and the like), a dispersing agent (e.g., hydroxypropylmethylcellulose, dextrin), a pH regulator (e.g., hydrochloric acid, sodium hydroxide and the like), a preservative (e.g., ethyl p-oxybenzoate, benzoic acid and the like), a dissolving agent (e.g., conc. glycerin, meglumine and the like), a dissolution aid (e.g., propylene glycol, sucrose and the like), a soothing agent (e.g., glucose, benzyl alcohol and the like), and the like, can be appropriately blended. These additives are generally blended in a proportion usually used in an injection.

It is advantageous that the pH of the injection is controlled from 2 to 12, preferably from 2.5 to 8.0 by addition of a pH regulator.

An injection is obtained by dissolving the compound of the present invention or the combination drug and if desirable, a benzoate and/or a salicylate, and if necessary, the above-mentioned additives into water. These may be dissolved in any order, and can be appropriately dissolved in the same manner as in a conventional method of producing an injection.

An aqueous solution for injection may be advantageously heated, alternatively, for example, filter sterilization, high pressure heat sterilization and the like can be conducted in the same manner as for a usual injection, to provide an injection.

It may be advantageous that an aqueous solution for injection is subjected to high pressure heat sterilization, for example, at 100 to 121° C. for 5 to 30 minutes.

Further, a preparation endowed with the antibacterial property of a solution may also be produced so that it can be used as a preparation which is divided and administered multiple-times.

The composition may contain secondary components such as a preservative, antioxidant, surfactant, thickening agent, coloring agent, pH controlling agent, flavoring agent, sweetening agent, food taste masking agent and the like. As a suitable coloring agent, there are listed red, black and yellow iron oxides, and FD & C dyes such as FD & C Blue 2, FD & C Red 40 and the like manufactured by Elis and Eberald. Examples of a suitable flavoring agent include mint, raspberry, licorice, orange, lemon, grapefruit, caramel, vanilla, cherry, grape flavor and combinations thereof. Examples of a suitable pH controlling agent include citric acid, tartaric acid, phosphoric acid, hydrochloric acid and maleic acid. Examples of a suitable sweetening agent include aspartame, acesulfame K and thaumatin and the like. Examples of a suitable food taste masking agent include sodium bicarbonate, ion exchange resin, cyclodextrin-containing compounds, adsorbent substances and microcapsulated apomorphine.

The preparation contains the compound of the present invention or the combination drug in an amount usually from about 0.1 to 50% by weight, preferably from about 0.1 to 30% by weight, and preferable are preparations (such as the above-mentioned sublingual agent, buccal and the like) which can dissolve 90% or more the compound of the present invention or the combination drug (into water) within the time range of about 1 to 60 minutes, preferably of about 1 to 15 minutes, more preferably of about 2 to 5 minutes, and intraoral quick disintegrating preparations which are disintegrated within the range of 1 to 60 seconds, preferably of 1 to 30 seconds, more preferably of 1 to 10 seconds after placement in an oral cavity.

The content of the above-mentioned excipient in the whole preparation is from about 10 to 99% by weight, preferably from about 30 to 90% by weight. The content of β-cyclodextrin or β-cyclodextrin derivative in the whole preparation is from 0 to about 30% by weight. The content of the lubricant in the whole preparation is from about 0.01 to 10% by weight, preferably from about 1 to 5% by weight. The content of the isotonizing agent in the whole preparation is from about 0.1 to 90% by weight, preferably from about 10 to 70% by weight. The content of the hydrophilic carrier agent in the whole preparation is from about 0.1 to 50% by weight, preferably from about 10 to 30% by weight. The content of the water-dispersible polymer in the whole preparation is from about 0.1 to 30% by weight, preferably from about 10 to 25% by weight. The content of the stabilizer in the whole preparation is from about 0.1 to 10% by weight, preferably from about 1 to 5% by weight. The above-mentioned preparation may further contain additives such as a coloring agent, sweetening agent, preservative and the like, if necessary.

The dosage of the combination agent of the present invention differs depending on the kind of the compound of the present invention, age, body weight, condition, drug form, administration method, administration period and the like, and for example, for one breast cancer patient (adult, body weight: about 60 kg), the combination agent is administered intravenously, at a dose of about 0.01 to 1000 mg/kg/day, preferably about 0.01 to 100 mg/kg/day, more preferably about 0.1 to 100 mg/kg/day, particularly about 0.1 to 50 mg/kg/day, especially about 1.5 to 30 mg/kg/day, in terms of the compound of the present invention or the combination drug, once or several times in each day. Of course, since the dose as described above varies depending on various conditions, amounts smaller than the above-mentioned dosage may sometimes be sufficient. Further, amounts over that range sometimes have to be administered.

The amount of the combination drug can be set at any value unless side effects are problematical. The daily dosage of the combination drug differs depending on the severity, age, sex, body weight, sensitivity difference of the subject, administration period, interval, and nature, pharmacy, the kind of pharmaceutical preparation, kind of effective ingredient, and the like, and not particularly restricted, and the amount of drug is, in the case of oral administration for example, usually from about 0.001 to 2000 mg, preferably from about 0.01 to 500 mg, further preferably from about 0.1 to 100 mg, per 1 kg of a mammal and this is usually administered once to 4-times each day.

In administration of a medicine of the present invention, the compound of the present invention may be administered after administration of the combination drug or the combination drug may be administered after administration of the compound of the present invention, though they may be administered simultaneously. When administered at a time interval, the interval differs depending on the effective ingredient, drug form and administration method, and for example, when the combination drug is administered first, the method in which the compound of the present invention is administered within time range of from 1 minute to 3 days, preferably from 10 minutes to 1 day, more preferably from 15 minutes to 1 hour after administration of the combination drug is exemplified. When the compound of the present invention is administered first, a method in which the combination drug is administered within time range of from 1 minute to 1 day, preferably from 10 minutes to 6 hours, more preferably from 15 minutes to 1 hour after administration of the compound of the present invention is exemplified.

In a preferable administration method, for example, the combination drug which has been formed into an oral administration preparation is administered orally at a daily dose of about 0.001 to 200 mg/kg, and 15 minutes later, the compound of the present invention which has been formed into an oral administration preparation is administered orally at a daily dose of about 0.005 to 100 mg/kg.

In addition, the pharmaceutical composition of the present invention or the combined agent of the present invention can be combined with a non-drug therapy such as (1) surgery, (2) hypertensive chemotherapy using angiotensin II etc., (3) gene therapy, (4) thermotherapy, (5) cryotherapy, (6) laser cauterization, (7) radiotherapy, etc.

For example, the pharmaceutical composition of the present invention or the combined agent of the present invention inhibit an expression of resistance, extend disease-free survival, suppress cancer metastasis or recurrence, prolong survival and provide other benefits when used before or after surgery, etc., or a combination treatment comprising 2 or 3 of these therapies.

Also, treatment with the pharmaceutical composition of the present invention or the combined agent of the present invention can be combined with supportive therapies [e.g., (i) administration of antibiotics (e.g., β-lactams such as pansporin, and the like, macrolides such as clarytheromycin, and the like) to a combined expression of various infectious diseases, (ii) administration of intravenous hyperalimentations, amino acid preparations and general vitamin preparations for improvement of malnutrition, (iii) morphine administration for pain mitigation, (iv) administration of drugs which mitigate adverse reactions such as nausea, vomiting, anorexia, diarrhea, leukopenia, thrombocytopenia, hemoglobin concentration reduction, hair loss, hepatopathy, renopathy, DIC, fever, and the like, (v) administration of drugs for inhibition of multiple drug resistance in cancer, and the like].

Preferably, the pharmaceutical composition of the present invention or the combined agent of the present invention is administered orally (including sustained-release preparations), intravenously (including boluses, infusions and clathrates), subcutaneously and intramuscularly (including boluses, infusions and sustained-release preparations), transdermally, intratumorally or proximally before or after the above-described treatment is conducted.

As a period for administering the pharmaceutical composition of the present invention or the combined agent of the present invention before surgery, etc., for example, it can be administrated 1 time about 30 minutes to 24 hours before surgery, etc., or in 1 to 3 cycles about 3 months to 6 months before surgery, etc. In this way, surgery, etc. can be conducted easily because, for example, cancer tissue would be reduced by administering the pharmaceutical composition of the present invention or the combined agent of the present invention before surgery, etc.

As a period for administering the pharmaceutical composition of the present invention or the combined agent of the present invention after surgery, etc., for example, it can be administrated repeatedly a few weeks to 3 months, about 30 minutes to 24 hours after surgery, etc. In this way, it increases the effect of the surgery, etc. by administering the pharmaceutical composition of the present invention or the combined agent of the present invention after the surgery, etc.

EXAMPLES

The present invention is hereinafter described in detail by means of the following reference examples, examples, preparation examples and test examples, but is not limited to these. The embodiment of the present invention may be varied within the extent of the present invention.

In the reference examples and examples, column chromatography was conducted with observation by TLC (thin layer chromatography). In TLC observation, the TLC plate used was the Merck Kieselgel 60F$_{254}$ plate, the developing solvent used was the solvent used as the eluent for column chromatography, and the means of detection used was a UV detector. The silica gel for the column chromatography was also Merck Kieselgel 60F$_{254}$ (70-230 mesh). NMR spectra ($^1$H-NMR) are measured with tetramethylsilane as the internal standard, by using the JMTCO400/54 (400 MHz) type spectrometer produced by NDK Incorporated, (or the Gemini-200 (200 MHz) type spectrometer, produced by Varian Medical Systems, Inc.); δ values are expressed in ppm.

The abbreviations used in the reference examples and examples are defined as follows:

s: Singlet br: Broad d: Doublet t: Triplet q: Quartet dd: Double doublet dt: Double triplet m: Multiplet J: Coupling constant Hz: Hertz DMF: N,N-dimethylformamide THF: Tetrahydrofuran The chemical formulas produced in Reference Examples and Examples are as shown in Tables 1 to 5. In the Tables, "Ref." means "Reference Example" and "Ex." means "Example".

Reference Example 1

A suspension of 2-amino-5-bromo-3-nitropyridine (21.0 g), iron filings (26.9 g) and ethanol (150 ml) was cooled with ice, and to the suspension was added dropwise concentrated hydrochloric acid (20 ml). After the dropwise addition, the mixture was stirred at room temperature for 10 minutes and at 80° C. for 50 minutes. The reaction mixture was poured onto ice, neutralized with 8 N sodium hydroxide, and extracted with ethyl acetate-tetrahydrofuran (3:1, v/v) (at that time, insolubles were filtered off by using celite). The organic layer was dried over MgSO$_4$, the solvent was distilled off under reduced pressure, and crystals were collected by filtration to obtain 2,3-diamino-5-bromopyridine (15.8 g, 87%).

$^1$H NMR (CDCl$_3$) δ 3.38 (2H, broad s), 4.21 (2H, broad s), 7.01 (1H, d, J=2.2 Hz), 7.69 (1H, d, J=2.2 Hz) ppm IR (KBr) ν 3179, 1632, 1476 cm$^{-1}$ Reference Example 2

Phosphorus pentaoxide (23.8 g) was added to methanesulfonic acid (85 ml), the mixture was stirred at 100° C. for 1 hour to give a solution. To the solution were added 2,3-diamino-5-bromopyridine (Compound of Reference Example 1) (15.8 g) and 3-methoxybenzoic acid (12.7 g), and the mixture was stirred at 100° C. for 1 hour. The reaction mixture was poured onto ice, neutralized with 8 N sodium hydroxide, and extracted with ethyl acetate-tetrahydrofuran (3:1, v/v). The organic layer was washed with water and dried over MgSO$_4$. The solvent was distilled off under reduced pressure, and crystals were collected by filtration to obtain 6-bromo-2-(3-methoxyphenyl)-1H-imidazo[4,5-b]pyridine (21.3 g, 84%).

$^1$H NMR (DMSO-d$_6$) δ 3.87 (3H, s), 7.13 (1H, d, J=8.6 Hz), 7.49 (1H, t, J=7.8 Hz), 7.80 (1H, s), 7.82 (1H, d, J=7.4 Hz), 8.28 (1H, s), 8.42 (1H, s) ppm IR (KBr) ν 3103, 1489, 1264, 1233 cm$^{-1}$ HPLC (220 nm) Purity 89% (Retention time 2.92 minutes)

MS (APCI+, m/e) 304 (M+1)

HPLC was carried out under the following conditions.

Column: CAPCELLPAKCC18UG120, S-3 μm, 2.0×50 mm

Solvent: Solution A (0.1% solution of trifluoroacetic acid in water), Solution B (0.1% solution of trifluoroacetic acid in acetonitrile).

Gradient cycle: 0.00 minute (Solution A/Solution B=90/10), 4.00 minutes (Solution A/Solution B=5/95), 5.50 minutes (Solution A/Solution B=5/95), 5.51 minutes (Solution A/Solution B=90/10), 8.00 minutes (Solution A/Solution B=90/10).

Flow rate: 0.5 ml/minute

By using the compound obtained in Reference Example 1 and various carboxylic acids as starting materials, the compounds of the following Reference Examples 3 to 8 were synthesized in a manner similar to Reference Example 2.

Reference Example 3

6-bromo-2-phenyl-1H-imidazo[4,5-b]pyridine

HPLC (220 nm) Purity 99% (Retention time 2.68 minutes)

MS (ESI+, m/e) 274 (M+1)

Reference Example 4

6-bromo-2-(2-methoxyphenyl)-1H-imidazo[4,5-b]pyridine

HPLC (220 nm) Purity 99% (Retention time 2.67 minutes)

MS (ESI+, m/e) 304 (M+1)

Reference Example 5

6-bromo-2-(4-methoxyphenyl)-1H-imidazo[4,5-b]pyridine

HPLC (220 nm) Purity 98% (Retention time 2.66 minutes)

MS (ESI+, m/e) 304 (M+1)

Reference Example 6

2-(1,3-benzodioxol-5-yl)-6-bromo-1H-imidazo[4,5-b]pyridine

HPLC (220 nm) Purity 95% (Retention time 2.74 minutes)
MS (ESI+, m/e) 318 (M+1)

Reference Example 7

6-bromo-2-[4-(trifluoromethoxy)phenyl]-1H-imidazo[4,5-b]pyridine

HPLC (220 nm) Purity 98% (Retention time 3.64 minutes)
MS (ESI+, m/e) 358 (M+1)

Reference Example 8

6-bromo-2-(5-methyl-2-thienyl)-1H-imidazo[4,5-b]pyridine

HPLC (220 nm) Purity 95% (Retention time 2.95 minutes)
MS (ESI+, m/e) 294 (M+1)

Reference Example 9

A mixture of 2,3-diamino-5-bromopyridine (Compound of Reference Example 1) (1.32 g), 3-chlorobenzoic acid (1.10 g) and polyphosphoric acid (30 g) was stirred at 170° C. for 2 hours. The mixture was poured onto ice, neutralized with 8N-sodium hydroxide and extracted with ethyl acetate-tetrahydrofuran (3:1, v/v). The organic layer was washed with water and dried with MgSO$_4$. The solvent was distilled off under reduced pressure, and resulting crystals were collected by filtration to obtain 6-bromo-2-(3-chlorophenyl)-1H-imidazo[4,5-b]pyridine (1.50 g, 69%).

$^1$H NMR (DMSO-d$_6$) δ 7.59-7.62 (2H, m), 8.19-8.28 (2H, m), 8.35 (1H, s), 8.43 (1H, s) ppm
IR (KBr) ν 3096, 1466, 1427, 957 cm$^{-1}$
HPLC (220 nm) Purity 99% (Retention time 3.42 minutes)
MS (APCI+, m/e) 308 (M+1)

By using the compound obtained in Reference Example 1 and various carboxylic acids as starting materials, the compounds of the following Reference Examples 10 to 13 were synthesized in a manner similar to Reference Example 9.

Reference Example 10

6-bromo-2-[(E)-2-phenylethenyl]-1H-imidazo[4,5-b]pyridine

HPLC (220 nm) Purity 99% (Retention time 3.64 minutes)
MS (APCI+, m/e) 300 (M+1)

Reference Example 11

6-bromo-2-(2-naphthyl)-1H-imidazo[4,5-b]pyridine

HPLC (220 nm) Purity 100% (Retention time 4.10 minutes)
MS (APCI+, m/e) 324 (M+1)

Reference Example 12

6-bromo-2-(3-phenoxyphenyl)-1H-imidazo[4,5-b]pyridine

HPLC (220 nm) Purity 85% (Retention time 4.50 minutes)
MS (APCI+, m/e) 366 (M+1)

Reference Example 13

2-(4-benzoylphenyl)-6-bromo-1H-imidazo[4,5-b]pyridine

HPLC (220 nm) Purity 99% (Retention time 4.31 minutes)
MS (APCI+, m/e) 378 (M+1)

Reference Example 14

A mixture of 2,3-diamino-5-bromopyridine (Compound of Reference Example 1) (1.32 g) and 4-methoxyphenylacetyl chloride (1.29 g) was stirred in the absence of solvent at 170° C. for 1.5 hour. The mixture was distributed with ethyl acetate-tetrahydrofuran (3:1, v/v) and water (at that time, the water layer was neutralized with 1 N sodium hydroxide). The organic layer was washed with water, dried over MgSO$_4$, and the solvent was distilled off under reduced pressure. The resulting crystals were collected by filtration to obtain 6-bromo-2-(4-methoxybenzyl)-1H-imidazo[4,5-b]pyridine (1.22 g, 55%).

$^1$H NMR (CDCl$_3$) δ 3.82 (3H, s), 4.30 (2H, s), 6.90 (2H, d, J=8.8 Hz), 7.24 (2H, d, J=9.2 Hz), 7.82 (1H, s), 8.10 (1H, s), 12.14 (1H, broad s) ppm
IR (KBr) ν 3007, 1512, 1433, 1254 cm$^{-1}$
HPLC (220 nm) Purity 100% (Retention time 2.57 minutes)
MS (APCI+, m/e) 318 (M+1)

By using the compound obtained in Reference Example 1 and various carboxylic acid chlorides as starting materials, the compounds of the following Reference Examples 15 to 25 were synthesized in a manner similar to Reference Example 14.

Reference Example 15

6-bromo-2-(phenoxymethyl)-1H-imidazo[4,5-b]pyridine

HPLC (220 nm) Purity 99% (Retention time 3.02 minutes)
MS (ESI+, m/e) 304 (M+1)

Reference Example 16

6-bromo-2-cyclohexyl-1H-imidazo[4,5-b]pyridine

HPLC (220 nm) Purity 96% (Retention time 2.29 minutes)
MS (ESI+, m/e) 280 (M+1)

Reference Example 17

6-bromo-2-(2-cyclopentylethyl)-1H-imidazo[4,5-b]pyridine

HPLC (220 nm) Purity 100% (Retention time 2.78 minutes)
MS (ESI+, m/e) 294 (M+1)

Reference Example 18

6-bromo-2-[(phenylthio)methyl]-1H-imidazo[4,5-b]pyridine

HPLC (220 nm) Purity 99% (Retention time 2.95 minutes)
MS (APCI+, m/e) 320 (M+1)

Reference Example 19

6-bromo-2-(2-phenylethyl)-1H-imidazo[4,5-b]pyridine

HPLC (220 nm) Purity 100% (Retention time 2.62 minutes)
MS (APCI+, m/e) 302 (M+1)

Reference Example 20

2-benzyl-6-bromo-1H-imidazo[4,5-b]pyridine

HPLC (220 nm) Purity 99% (Retention time 2.51 minutes)
MS (APCI+, m/e) 288 (M+1)

Reference Example 21

6-bromo-2-(3-methoxybenzyl)-1H-imidazo[4,5-b]pyridine

HPLC (220 nm) Purity 97% (Retention time 2.63 minutes)
MS (APCI+, m/e) 318 (M+1)

Reference Example 22

6-bromo-2-(2,5-dimethoxybenzyl)-1H-imidazo[4,5-b]pyridine

HPLC (220 nm) Purity 97% (Retention time 2.62 minutes)
MS (APCI+, m/e) 348 (M+1)

Reference Example 23

6-bromo-2-(3,4-dimethoxybenzyl)-1H-imidazo[4,5-b]pyridine

HPLC (220 nm) Purity 95% (Retention time 2.41 minutes)
MS (APCI+, m/e) 348 (M+1)

Reference Example 24

6-bromo-2-(4-chlorobenzyl)-1H-imidazo[4,5-b]pyridine

HPLC (220 nm) Purity 95% (Retention time 2.96 minutes)
MS (APCI+, m/e) 322 (M+1)

Reference Example 25

6-bromo-2-[(4-chlorophenoxy)methyl]-1H-imidazo[4,5-b]pyridine

HPLC (220 nm) Purity 100% (Retention time 3.47 minutes)
MS (APCI+, m/e) 338 (M+1)

Reference Example 26

4-Fluorophenyl acetate (678 mg) was dissolved in tetrahydrofuran (15 ml), and to the solution were added oxalyl chloride (0.67 g) and N,N-dimethyl formamide (10 µl) successively. The mixture was stirred at room temperature for 1.5 hour, and the solvent and surplus oxalyl chloride were distilled off under reduced pressure. To the residue was added toluene (2 ml) and the solvent was distilled off again under reduced pressure to remove oxalyl chloride entirely. To the residue was added 2,3-diamino-5-bromopyridine (Compound of Reference Example 1) (752 mg), and the mixture was stirred at 170° C. for 1.5 hour in the absence of solvent. The mixture was distributed to ethyl acetate-tetrahydrofuran (3:1, v/v) and water (At that time, the aqueous layer was neutralized with 1 N sodium hydroxide). The organic layer was washed with water and dried over $MgSO_4$. The solvent was distilled off under reduced pressure and the resulting crystals were collected by filtration to obtain 6-bromo-2-(4-fluorobenzyl)-1H-imidazo[4,5-b]pyridine (722 mg, 59%).

$^1$H NMR (DMSO-$d_6$) δ 4.20 (2H, s), 7.14 (2H, t, J=9.0 Hz), 7.38 (2H, dd, J=8.8, 6.0 Hz), 8.15 (1H, d, J=2.2 Hz), 8.34 (1H, d, J=2.2 Hz) ppm
IR (KBr) ν 3083, 1508, 1429, 1235 cm$^{-1}$
HPLC (220 nm) Purity 100% (Retention time 2.67 minutes)
MS (APCI+, m/e) 306 (M+1)

By using the compound obtained in Reference Example 1 and various carboxylic acids as starting materials, the compounds of the following Reference Examples 27 to 42 were synthesized in a manner similar to Reference Example 26.

Reference Example 27

6-bromo-2-(3-chlorobenzyl)-1H-imidazo[4,5-b]pyridine

HPLC (220 nm) Purity 100% (Retention time 2.97 minutes)
MS (APCI+, m/e) 322 (M+1)

Reference Example 28

6-bromo-2-(2-chlorobenzyl)-1H-imidazo[4,5-b]pyridine

HPLC (220 nm) Purity 100% (Retention time 2.77 minutes)
MS (APCI+, m/e) 322 (M+1)

Reference Example 29

6-bromo-2-(2,4-difluorobenzyl)-1H-imidazo[4,5-b]pyridine

HPLC (220 nm) Purity 99% (Retention time 2.76 minutes)
MS (APCI+, m/e) 324 (M+1)

Reference Example 30

6-bromo-2-(3,4-dichlorobenzyl)-1H-imidazo[4,5-b]pyridine

HPLC (220 nm) Purity 99% (Retention time 3.32 minutes)
MS (APCI+, m/e) 358 (M+1)

Reference Example 31

6-bromo-2-[4-(trifluoromethyl)benzyl]-1H-imidazo[4,5-b]pyridine

HPLC (220 nm) Purity 98% (Retention time 3.23 minutes)
MS (APCI+, m/e) 356 (M+1)

Reference Example 32

6-bromo-2-[4-(trifluoromethoxy)benzyl]-1H-imidazo[4,5-b]pyridine

HPLC (220 nm) Purity 99% (Retention time 3.27 minutes)
MS (APCI+, m/e) 372 (M+1)

Reference Example 33

6-bromo-2-(4-nitrobenzyl)-1H-imidazo[4,5-b]pyridine

HPLC (220 nm) Purity 99% (Retention time 2.86 minutes)
MS (APCI+, m/e) 333 (M+1)

Reference Example 34

6-bromo-2-(4-methylbenzyl)-1H-imidazo[4,5-b]pyridine

HPLC (220 nm) Purity 100% (Retention time 2.84 minutes)
MS (APCI+, m/e) 302 (M+1)

Reference Example 35

2-[(1,1'-biphenyl)-4-ylmethyl]-6-bromo-1H-imidazo[4,5-b]pyridine

HPLC (220 nm) Purity 97% (Retention time 3.38 minutes)
MS (APCI+, m/e) 364 (M+1)

Reference Example 36

6-bromo-2-(2-naphthylmethyl)-1H-imidazo[4,5-b]pyridine

HPLC (220 nm) Purity 99% (Retention time 3.17 minutes)
MS (APCI+, m/e) 338 (M+1)

Reference Example 37

2-(1,3-benzodioxol-5-ylmethyl)-6-bromo-1H-imidazo[4,5-b]pyridine

HPLC (220 nm) Purity 99% (Retention time 2.66 minutes)
MS (APCI+, m/e) 332 (M+1)

Reference Example 38

6-bromo-2-(3,4,5-trimethoxybenzyl)-1H-imidazo[4,5-b]pyridine

HPLC (220 nm) Purity 84% (Retention time 2.67 minutes)
MS (APCI+, m/e) 378 (M+1)

Reference Example 39

6-bromo-2-(2-thienylmethyl)-1H-imidazo[4,5-b]pyridine

HPLC (220 nm) Purity 100% (Retention time 2.58 minutes)
MS (APCI+, m/e) 294 (M+1)

Reference Example 40

6-bromo-2-[(1-methyl-1H-indol-3-yl)methyl]-1H-imidazo[4,5-b]pyridine

HPLC (220 nm) Purity 99% (Retention time 2.93 minutes)
MS (APCI+, m/e) 341 (M+1)

Reference Example 41

6-bromo-2-[2-(3,4-dimethoxyphenyl)ethyl]-1H-imidazo[4,5-b]pyridine

HPLC (220 nm) Purity 100% (Retention time 2.58 minutes)
MS (APCI+, m/e) 362 (M+1)

Reference Example 42

6-bromo-2-[4-(methylthio)benzyl]-1H-imidazo[4,5-b]pyridine

HPLC (220 nm) Purity 100% (Retention time 3.00 minutes)
MS (APCI+, m/e) 334 (M+1)

Reference Example 43

Phosphorus pentaoxide (2.84 g) was added to methanesulfonic acid (10 ml) and the mixture was stirred at 100° C. for 1 hour to give a solution. To the solution were added 2-amino-4-bromophenol (1.88 g) and trans-cinnamic acid (1.48 g), and the mixture was stirred at 100° C. for 1.5 hours. The reaction mixture was poured onto ice, neutralized with an 8 N sodium hydroxide and extracted with ethyl acetate-tetrahydrofuran (3:1, v/v). The organic layer was washed with water and dried over $MgSO_4$. The solvent was distilled off under reduced pressure. The residue was subjected to silica gel column chromatography. The fraction eluted with ethyl acetate-hexane (1:3, v/v) was concentrated under reduced pressure. The resulting crystals were collected by filtration to obtain 5-bromo-2-[(E)-2-phenylethenyl]benzoxazole (966 mg, 32%).

$^1$H NMR ($CDCl_3$) δ 7.05 (1H, d, J=16.4 Hz), 7.37-7.48 (5H, m), 7.58-7.62 (2H, m), 7.81 (1H, d, J=16.4 Hz), 7.84-7.85 (1H, m) ppm IR (KBr) ν 1535, 1260, 974, 756 $cm^{-1}$ HPLC (220 nm) Purity 100% (Retention time 4.92 minutes)
MS (APCI+, m/e) 300 (M+1)

By using various carboxylic acids as one of the starting materials, the compounds of the following Reference Examples 44 to 45 were synthesized in a manner similar to Reference Example 43.

Reference Example 44

5-bromo-2-[(E)-2-[4-(trifluoromethyl)phenyl]ethenyl]benzoxazole

HPLC (220 nm) Purity 99% (Retention time 5.17 minutes)
MS (APCI+, m/e) 368 (M+1)

Reference Example 45

5-bromo-2-[(E)-2-(2,4-difluorophenyl)ethenyl]benzoxazole

HPLC (220 nm) Purity 97% (Retention time 5.04 minutes)
MS (APCI+, m/e) 336 (M+1)

By using the compound obtained in Reference Example 1 and 3-methylbenzoic acid as starting materials, the compound of the following Reference Example 46 was synthesized in a manner similar to Reference Example 2.

Reference Example 46

6-bromo-2-(3-methylphenyl)-1H-imidazo[4,5-b]pyridine

HPLC (220 nm) Purity 100% (Retention time 3.20 minutes)
MS (ESI+, m/e) 288 (M+1)

Reference Example 47

A mixture of 2,3-diamino-5-bromopyridine (Compound of Reference Example 1) (1.13 g), 3-ethoxybenzoic acid (997 mg) and phosphorus oxychloride (24 ml) was stirred at 120° C. for 2 hours and poured onto ice. The mixture was neutralized with 8 N sodium hydroxide, stirred for 20 minutes and extracted with ethyl acetate-tetrahydrofuran (3:1, v/v). The organic layer was washed with water, dried over $MgSO_4$. The solvent was distilled off under reduced pressure and the resulting crystals were collected by filtration to obtain 6-bromo-2-(3-ethoxyphenyl)-1H-imidazo[4,5-b]pyridine (978 mg, 51%).

$^1$H NMR (DMSO-$d_6$) δ 1.39 (3H, t, J=7.0 Hz), 4.14 (2H, q, J=7.0 Hz), 7.08-7.12 (1H, m), 7.47 (1H, t, J=8.2 Hz), 7.78-7.82 (2H, m), 8.26 (1H, s), 8.41 (1H, d, J=1.8 Hz) ppm
IR (KBr) ν 2973, 1491, 1262 $cm^{-1}$
HPLC (220 nm) Purity 100% (Retention time 3.42 minutes)
MS (ESI+, m/e) 318 (M+1)

By using the compound obtained in Reference Example 1 and various carboxylic acids as starting materials, the compounds of the following Reference Examples 48 to 50 were synthesized in a manner similar to Reference Example 47.

Reference Example 48

6-bromo-2-(3-propoxyphenyl)-1H-imidazo[4,5-b]pyridine

HPLC (220 nm) Purity 100% (Retention time 3.71 minutes)
MS (ESI+, m/e) 332 (M+1)

Reference Example 49

6-bromo-2-(3-isopropoxyphenyl)-1H-imidazo[4,5-b]pyridine

HPLC (220 nm) Purity 100% (Retention time 3.59 minutes)
MS (ESI+, m/e) 332 (M+1)

Reference Example 50

6-bromo-2-(3-butoxyphenyl)-1H-imidazo[4,5-b]pyridine

HPLC (220 nm) Purity 100% (Retention time 3.98 minutes)
MS (ESI+, m/e) 346 (M+1)

By using the compound obtained in Reference Example 1 and a carboxylic acid as starting materials, the compound of the following Reference Example 51 was synthesized in a manner similar to Reference Example 26.

Reference Example 51

6-bromo-2-(4-methoxy-3-methylbenzyl)-1H-imidazo[4,5-b]pyridine

HPLC (220 nm) Purity 98% (Retention time 3.03 minutes)
MS (APCI+, m/e) 332 (M+1)

By using the compound obtained in Reference Example 1 and various carboxylic acids as starting materials, the compounds of the following Reference Examples 52 to 58 were synthesized in a manner similar to Reference Example 47.

Reference Example 52

6-bromo-2-[3-(hexyloxy)phenyl]-1H-imidazo[4,5-b]pyridine

HPLC (220 nm) Purity 100% (Retention time 4.46 minutes)
MS (APCI+, m/e) 374 (M+1)

Reference Example 53

6-bromo-2-[3-(3-buthenyloxy)phenyl]-1H-imidazo[4,5-b]pyridine

HPLC (220 nm) Purity 100% (Retention time 3.78 minutes)
MS (APCI+, m/e) 344 (M+1)

Reference Example 54

6-bromo-2-[3-(3-methylbuthoxy)phenyl]-1H-imidazo[4,5-b]pyridine

HPLC (220 nm) Purity 100% (Retention time 4.48 minutes)
MS (APCI+, m/e) 360 (M+1)

Reference Example 55

6-bromo-2-[3-(neopentyloxy)phenyl]-1H-imidazo[4,5-b]pyridine

HPLC (220 nm) Purity 99% (Retention time 4.24 minutes)
MS (APCI+, m/e) 360 (M+1)

Reference Example 56

6-bromo-2-[3-(cyclohexylmethoxy)phenyl]-1H-imidazo[4,5-b]pyridine

HPLC (220 nm) Purity 100% (Retention time 4.50 minutes)
MS (APCI+, m/e) 386 (M+1)

Reference Example 57

6-bromo-2-[3-(cyclopentyloxy)phenyl]-1H-imidazo[4,5-b]pyridine

HPLC (220 nm) Purity 99% (Retention time 3.96 minutes)
MS (APCI+, m/e) 358 (M+1)

Reference Example 58

6-bromo-2-[3-(2-phenylehoxy)phenyl]-1H-imidazo[4,5-b]pyridine

HPLC (220 nm) Purity 97% (Retention time 4.11 minutes)
MS (APCI+, m/e) 394 (M+1)

By using the compound obtained in Reference Example 1 and a carboxylic acid as starting materials, the compound of the following Reference Example 59 was synthesized in a manner similar to Reference Example 2.

Reference Example 59

6-bromo-2-(3-ethylphenyl)-1H-imidazo[4,5-b]pyridine

HPLC (220 nm) Purity 95% (Retention time 3.47 minutes)
MS (APCI+, m/e) 302 (M+1)

By using the compound obtained in Reference Example 1 and various carboxylic acids as starting materials, the compounds of the following Reference Examples 60 to 66 were synthesized in a manner similar to Reference Example 43.

Reference Example 60

5-bromo-2-(3-methoxyphenyl)benzoxazole

HPLC (220 nm) Purity 98% (Retention time 4.82 minutes)
MS (ESI+, m/e) 304 (M+1)

Reference Example 61

5-bromo-2-[(E)-2-(4-chlorophenyl)ethenyl]benzoxazole

HPLC (220 nm) Purity 100% (Retention time 5.21 minutes)
MS (ESI+, m/e) 334 (M+1)

Reference Example 62

5-bromo-2-[(E)-2-(3-fluorophenyl)ethenyl]benzoxazole

HPLC (220 nm) Purity 100% (Retention time 4.95 minutes)
MS (ESI+, m/e) 318 (M+1)

Reference Example 63

5-bromo-2-[(E)-2-(2-fluorophenyl)ethenyl]benzoxazole

HPLC (220 nm) Purity 99% (Retention time 5.04 minutes)
MS (ESI+, m/e) 318 (M+1)

Reference Example 64

5-bromo-2-[(E)-2-(3,4-dichlorophenyl)ethenyl]benzoxazole

HPLC (220 nm) Purity 98% (Retention time 5.45 minutes)
MS (ESI+, m/e) 370 (M+1)

Reference Example 65

5-bromo-2-[(E)-2-(4-methylphenyl)ethenyl]benzoxazole

HPLC (220 nm) Purity 99% (Retention time 5.19 minutes)
MS (ESI+, m/e) 314 (M+1)

Reference Example 66

5-bromo-2-[(E)-2-[3-(trifluoromethoxy)phenyl]ethenyl]benzoxazole

HPLC (220 nm) Purity 100% (Retention time 5.24 minutes)
MS (ESI+, m/e) 384 (M+1)

Reference Example 67

Phosphorus pentachloride (2.27 g) was added to methanesulfonic acid (8 ml), and the mixture was stirred at 120° C. for 1 hour. To the solution were added 2-amino-5-bromophenol (1.50 g) and 4-chlorophenylacetic acid (1.36 g) and the mixture was stirred at 100° C. for 1 hour. The mixture was poured onto ice, neutralized with 8 N sodium hydroxide and extracted with ethyl acetate-tetrahydrofuran (3:1, v/v). The organic layer was washed with water and dried over MgSO$_4$. The solvent was distilled off under reduced pressure. The residue was subjected to silica gel column chromatography and the fraction eluted with ethyl acetate-hexane (1:4, v/v) was concentrated under reduced pressure. The resulting crystals were collected by filtration to obtain 6-bromo-2-(4-chlorobenzyl)benzoxazole (1.83 g, 71%).

$^1$H NMR (CDCl$_3$) δ 4.22 (2H, s), 7.32 (4H, s), 7.43 (1H, dd, J=8.4, 1.4 Hz), 7.55 (1H, d, J=8.4 Hz), 7.64 (1H, d, J=1.8 Hz) ppm IR (KBr) ν 1564, 1493, 1424 cm$^{-1}$ HPLC (220 nm) Purity 99% (Retention time 4.76 minutes)
MS (APCI+, m/e) 322 (M+1)

By using various carboxylic acids as starting materials, the compounds of the following Reference Examples 68 to 72 were synthesized in a manner similar to Reference Example 67.

Reference Example 68

6-bromo-2-[(E)-2-phenylethenyl]benzoxazole

HPLC (220 nm) Purity 100% (Retention time 4.97 minutes)
MS (APCI+, m/e) 300 (M+1)

Reference Example 69

6-bromo-2-[(E)-2-(2,4-difluorophenyl)ethenyl]benzoxazole

HPLC (220 nm) Purity 99% (Retention time 5.10 minutes)
MS (APCI+, m/e) 336 (M+1)

Reference Example 70

6-bromo-2-[(E)-2-(2-fluorophenyl)ethenyl]benzoxazole

HPLC (220 nm) Purity 99% (Retention time 5.07 minutes)
MS (APCI+, m/e) 318 (M+1)

Reference Example 71

6-bromo-2-[(E)-2-[4-(trifluoromethyl)phenyl]ethenyl]benzoxazole

HPLC (220 nm) Purity 100% (Retention time 5.22 minutes)
MS (APCI+, m/e) 368 (M+1)

Reference Example 72

6-bromo-2-(2-phenylethyl)benzoxazole

HPLC (220 nm) Purity 97% (Retention time 4.70 minutes)
MS (APCI+, m/e) 302 (M+1)

By using the compound obtained in Reference Example 1 and various carboxylic acids as starting materials, the compounds of the following Reference Examples 73 to 82 were synthesized in a manner similar to Reference Example 2.

Reference Example 73

6-bromo-2-(2,3-dihydro-1,4-benzodioxin-6-yl)-1H-imidazo[4,5-b]pyridine

HPLC (220 nm) Purity 100% (Retention time 2.92 minutes)
MS (APCI+, m/e) 332 (M+1)

Reference Example 74

6-bromo-2-(2-pyridinyl)-1H-imidazo[4,5-b]pyridine

HPLC (220 nm) Purity 83% (Retention time 3.05 minutes)
MS (APCI+, m/e) 275 (M+1)

Reference Example 75

6-bromo-2-(3-fluorophenyl)-1H-imidazo[4,5-b]pyridine

HPLC (220 nm) Purity 99% (Retention time 3.34 minutes)
MS (APCI+, m/e) 292 (M+1)

Reference Example 76

6-bromo-2-(2-fluorophenyl)-1H-imidazo[4,5-b]pyridine

HPLC (220 nm) Purity 94% (Retention time 3.12 minutes)
MS (APCI+, m/e) 292 (M+1)

Reference Example 77

6-bromo-2-(4-fluorophenyl)-1H-imidazo[4,5-b]pyridine

HPLC (220 nm) Purity 89% (Retention time 3.15 minutes)
MS (APCI+, m/e) 292 (M+1)

Reference Example 78

3-(6-bromo-1H-imidazo[4,5-b]pyridin-2-yl)benzonitrile

HPLC (220 nm) Purity 83% (Retention time 3.29 minutes)
MS (APCI+, m/e) 299 (M+1)

Reference Example 79

6-bromo-2-(3-fluoro-4-methoxyphenyl)-1H-imidazo[4,5-b]pyridine

HPLC (220 nm) Purity 82% (Retention time 3.23 minutes)
MS (APCI+, m/e) 322 (M+1)

Reference Example 80

N-(3-(6-bromo-1H-imidazo[4,5-b]pyridin-2-yl)phenyl)-N,N-dimethylamine

HPLC (220 nm) Purity 99% (Retention time 2.59 minutes)
MS (APCI+, m/e) 317 (M+1)

Reference Example 81

6-bromo-2-(3-(1-pyrrolidinyl)phenyl)-1H-imidazo[4,5-b]pyridine

HPLC (220 nm) Purity 96% (Retention time 3.35 minutes)
MS (APCI+, m/e) 343 (M+1)

Reference Example 82

6-bromo-2-(3-morpholinophenyl)-1H-imidazo[4,5-b]pyridine

HPLC (220 nm) Purity 97% (Retention time 2.96 minutes)
MS (APCI+, m/e) 359 (M+1)

By using the compound obtained in Reference Example 1 and various carboxylic acids as starting materials, the compounds of the following Reference Examples 83 to 85 were synthesized in a manner similar to Reference Example 14.

Reference Example 83

6-bromo-2-(2-(3-methoxyphenyl)ethyl)-1H-imidazo[4,5-b]pyridine

HPLC (220 nm) Purity 97% (Retention time 2.90 minutes)
MS (ACPI+, m/e) 332 (M+1)

Reference Example 84

6-bromo-2-(2-(2-methoxyphenyl)ethyl)-1H-imidazo[4,5-b]pyridine

HPLC (220 nm) Purity 100% (Retention time 2.89 minutes)
MS (ACPI+, m/e) 332 (M+1)

Reference Example 85

6-bromo-2-(2-(4-methoxyphenyl)ethyl)-1H-imidazo[4,5-b]pyridine

HPLC (220 nm) Purity 98% (Retention time 2.87 minutes)
MS (ACPI+, m/e) 332 (M+1)

By using the compound obtained in Reference Example 1 and various carboxylic acids as starting materials, the compounds of the following Reference Examples 86 to 111 were synthesized in a manner similar to Reference Example 47.

Reference Example 86

6-bromo-2-(3-(2-methoxyethoxy)phenyl)-1H-imidazo[4,5-b]pyridine

HPLC (220 nm) Purity 83% (Retention time 3.10 minutes)
MS (ACPI+, m/e) 348 (M+1)

Reference Example 87

6-bromo-2-(4-(2-methoxyethoxy)phenyl)-1H-imidazo[4,5-b]pyridine

HPLC (220 nm) Purity 93% (Retention time 2.87 minutes)
MS (ACPI+, m/e) 348 (M+1)

Reference Example 88

6-bromo-2-(3-(trifluoromethyl)phenyl)-1H-imidazo[4,5-b]pyridine

HPLC (220 nm) Purity 100% (Retention time 3.86 minutes)
MS (ACPI+, m/e) 342 (M+1)

Reference Example 89

6-bromo-2-(3-(methylsulfonyl)phenyl)-1H-imidazo[4,5-b]pyridine

HPLC (220 nm) Purity 99% (Retention time 3.01 minutes)
MS (ACPI+, m/e) 352 (M+1)

Reference Example 90

6-bromo-2-(5-methyl-3-phenyl-4-isoxazolyl)-1H-imidazo[4,5-b]pyridine

HPLC (220 nm) Purity 100% (Retention time 3.52 minutes)
MS (ACPI+, m/e) 355 (M+1)

Reference Example 91

6-bromo-2-(2-(4-chlorophenyl)ethyl)-1H-imidazo[4,5-b]pyridine

HPLC (220 nm)-Purity 97% (Retention time 3.19 minutes)
MS (ACPI+, m/e) 336 (M+1)

Reference Example 92

6-bromo-2-(2-(2-chlorophenyl)ethyl)-1H-imidazo[4,5-b]pyridine

HPLC (220 nm) Purity 100% (Retention time 3.19 minutes)
MS (ACPI+, m/e) 336 (M+1)

Reference Example 93

6-bromo-2-(2-(4-methylphenyl)ethyl)-1H-imidazo[4,5-b]pyridine

HPLC (220 nm) Purity 99% (Retention time 3.07 minutes)
MS (ACPI+, m/e) 316 (M+1)

Reference Example 94

6-bromo-2-(2-(3,4-dichlorophenyl)ethyl)-1H-imidazo[4,5-b]pyridine

HPLC (220 nm) Purity 88% (Retention time 3.43 minutes)
MS (ACPI+, m/e) 371 (M+1)

Reference Example 95

4-(2-(6-bromo-1H-imidazo[4,5-b]pyridin-2-yl)ethyl)benzonitrile

HPLC (220 nm) Purity 97% (Retention time 2.83 minutes)
MS (ACPI+, m/e) 327 (M+1)

Reference Example 96

6-bromo-2-(2-(4-(trifluoromethyl)phenyl)ethyl)-1H-imidazo[4,5-b]pyridine

HPLC (220 nm) Purity 100% (Retention time 3.38 minutes)
MS (ACPI+, m/e) 370 (M+1)

Reference Example 97

6-bromo-2-(2-phenylcyclopropyl)-1H-imidazo[4,5-b]pyridine

HPLC (220 nm) Purity 9.8% (Retention time 3.05 minutes)
MS (ACPI+, m/e) 314 (M+1)

Reference Example 98

6-bromo-2-(2-(4-fluorophenyl)ethyl)-1H-imidazo[4,5-b]pyridine

HPLC (220 nm) Purity 100% (Retention time 2.95 minutes)
MS (ACPI+, m/e) 320 (M+1)

Reference Example 99

6-bromo-2-(2-(4-isopropylphenyl)ethyl)-1H-imidazo[4,5-b]pyridine

HPLC (220 nm) Purity 100% (Retention time 3.46 minutes)
MS (ACPI+, m/e) 344 (M+1)

Reference Example 100

6-bromo-2-(2-(2-thienyl)ethyl)-1H-imidazo[4,5-b]pyridine

HPLC (220 nm) Purity 100% (Retention time 2.77 minutes)
MS (ACPI+, m/e) 308 (M+1)

Reference Example 101

6-bromo-2-(2-(4-nitrophenyl)ethyl)-1H-imidazo[4,5-b]pyridine

HPLC (220 nm) Purity 99% (Retention time 3.00 minutes)
MS (ACPI+, m/e) 347 (M+1)

Reference Example 102

6-bromo-2-(2-(4-ethoxyphenyl)ethyl)-1H-imidazo[4,5-b]pyridine

HPLC (220 nm) Purity 100% (Retention time 3.07 minutes)
MS (ACPI+, m/e) 346 (M+1)

Reference Example 103

6-bromo-2-(2-phenylpropyl)-1H-imidazo[4,5-b]pyridine

HPLC (220 nm) Purity 100% (Retention time 2.96 minutes)
MS (ACPI+, m/e) 316 (M+1)

Reference Example 104

6-bromo-2-(5-phenylpentyl)-1H-imidazo[4,5-b]pyridine

HPLC (220 nm) Purity 100% (Retention time 3.37 minutes)
MS (ACPI+, m/e) 344 (M+1)

Reference Example 105

2-((1S)-1-(6-bromo-1H-imidazo[4,5-b]pyridin-2-yl)-2-phenylethyl)-1H-isoindol-1,3(2H)-dione HPLC (220 nm) Purity 96% (Retention time 3.87 minutes)
MS (ACPI+, m/e) 447 (M+1)

Reference Example 106

6-bromo-2-(2-(4-butoxyphenyl)ethyl)-1H-imidazo[4,5-b]pyridine

HPLC (220 nm) Purity 99% (Retention time 3.53 minutes)
MS (ACPI+, m/e) 374 (M+1)

Reference Example 107

6-bromo-2-(2-(3,4,5-trimethoxyphenyl)ethyl)-1H-imidazo[4,5-b]pyridine

HPLC (220 nm) Purity 97% (Retention time 2.74 minutes)
MS (ACPI+, m/e) 392 (M+1)

Reference Example 108

6-bromo-2-(2-(3-chlorophenyl)ethyl)-1H-imidazo[4,5-b]pyridine

HPLC (220 nm) Purity 100% (Retention time 3.19 minutes)
MS (ACPI+, m/e) 336 (M+1)

Reference Example 109

6-bromo-2-(3-(2,2,2-trifluoroethoxy)phenyl)-1H-imidazo[4,5-b]pyridine

HPLC (220 nm) Purity 92% (Retention time 3.77 minutes)
MS (ACPI+, m/e) 372 (M+1)

Reference Example 110

6-bromo-2-(3-isopropoxy-2-methylphenyl)-1H-imidazo[4,5-b]pyridine

HPLC (220-nm) Purity 99% (Retention time 3.53 minutes)
MS (ACPI+, m/e) 346 (M+1)

Reference Example 111

6-bromo-2-(2-(4-isopropoxyphenyl)ethyl)-1H-imidazo[4,5-b]pyridine

HPLC (220 nm) Purity 99% (Retention time 3.22 minutes)
MS (ACPI+, m/e) 360 (M+1)

Reference Example 112

Under an argon stream, a mixture of 6-chloro-3-nitro-2-pyridine amine (2.0 g), phenylboric acid (2.1 g), tetrakis(triphenylphosphine)palladium(0) (1.3 g), 2 M sodium carbonate (35 ml), toluene (40 ml) and tetrahydrofuran (20 ml) was stirred at 90° C. for 12 hours. The mixture was distributed into ethyl acetate-tetrahydrofuran (3:1, v/v) and water. The organic layer was washed with water and dried over MgSO$_4$. The solvent was distilled off under reduced pressure and the resulting crystals were collected by filtration to obtain 3-nitro-6-phenyl-2-pyridine amine (1.3 g, 53%).

$^1$H NMR (CDCl$_3$) δ 7.20 (1H, d, J=8.4 Hz), 7.49-7.54 (3H, m), 8.00-8.05 (2H, m), 8.49 (1H, d, J=8.4 Hz) ppm.

IR (KBr) ν 3501, 3382, 1617, 1586, 1578, 1271, 1244 cm$^{-1}$
HPLC (220 nm) Purity 97% (Retention time 3.86 minutes)
MS (ESI, m/e) 216 (M+1)

Reference Example 113

A suspension of 3-nitro-6-phenyl-2-pyridine amine (Compound of Reference Example 112) (0.8 g), iron filings (1.3 g) and methanol (7 ml) was cooled with ice and to the suspension was added dropwise concentrated hydrochloric acid (3 ml). After the dropwise addition, the mixture was stirred at room temperature for 10 minutes and at 80° C. for 50 minutes. The reaction mixture was poured onto ice, neutralized with an aqueous solution of 8 N sodium hydroxide and extracted with ethyl acetate-tetrahydrofuran (3:1, v/v) (At that time, insolubles were filtered off by means of celite). The organic layer was dried over MgSO$_4$, and the solvent was distilled off under reduced pressure. The resulting crystals were collected by filtration to obtain 6-phenyl-2,3-pyridine diamine (0.7 g, 99%).

$^1$H NMR (CDCl$_3$) δ 3.00-3.60 (2H, broad s), 4.00-4.60 (2H, broad s), 6.95 (1H, d, J=8.0 Hz), 7.09 (1H, d, J=8.0 Hz), 7.22-7.41 (3H, m), 7.87 (2H, d, J=7.2 Hz) ppm IR (KBr) ν 3337, 1622, 1470, 754, 696 cm$^{-1}$
HPLC (220 nm) Purity 99% (Retention time 2.31 minutes)
MS (ESI, m/e) 186 (M+1)

Reference Example 114

6-Chloro-3-nitro-2-pyridine amine (1.2 g), phenol (3.1 g) and sodium methoxide (0.4 g) were dissolved in acetonitrile (20 ml), and the solution was heated for 12 hours under reflux. After the completion of the reaction, the solvent was distilled off under reduced pressure. The residue was distributed into ethyl acetate and a saturated aqueous solution of sodium bicarbonate. The organic layer was washed with water and dried over MgSO$_4$. The solvent was distilled off under reduced pressure, and the residue was subjected to silica gel column chromatography. The fraction eluted with ethyl acetate-hexane (1:10, v/v) was concentrated under reduced pressure. The resulting crystals were collected by filtration to obtain 3-nitro-6-phenoxy-2-pyridine amine (1.1 g, 66%).

$^1$H NMR (CDCl$_3$) δ 6.27 (1H, d, J=9.0 Hz), 7.10-7.46 (7H, m), 8.41 (2H, d, J=9.0 Hz) ppm IR (KBr) ν 3372, 1620, 1447, 1250 cm$^{-1}$
HPLC (220 nm) Purity 98% (Retention time 3.84 minutes)
MS (ESI, m/e) 232 (M+1)

Reference Example 115

Under a hydrogen stream, a suspension of 3-nitro-6-phenoxy-2-pyridine amine (Compound of Reference Example 114) (0.1 g), palladium-carbon (10 mg) and methanol (2 ml) were stirred at room temperature for 10 hours. The reaction mixture was filtered, and the filtrate was concentrated under reduced pressure. The residue was subjected to silica gel chromatography and the fraction eluted with ethyl acetate-hexane (1:1, v/v) was concentrated under reduced pressure to obtain 6-phenoxy-2,3-pyridine diamine (0.06 g, 59%).

$^1$H NMR (CDCl$_3$) δ 2.50-3.00 (2H, broad s), 4.00-4.50 (2H, broad s), 6.12 (1H, d, J=8.1 Hz), 6.93 (1H, d, J=8.1 Hz), 7.02-7.20 (3H, m), 7.29-7.36 (2H, m) ppm IR (KBr) ν 3328, 1622, 1591, 1464, 1238, 693 cm$^{-1}$
HPLC (220 nm) Purity 90% (Retention time 2.31 minutes)
MS (ESI, m/e) 202 (M+1)

Example 1

Under an argon stream, a mixture of 6-bromo-2-(3-methoxyphenyl)-1H-imidazo[4,5-b]pyridine (Compound of Reference Example 2) (21.3 g), phenylboric acid (22.2 g), tetrakis(triphenylphosphine)palladium(0) (7.60 g), 2 M sodium carbonate (175 ml), toluene (525 ml) and tetrahydrofuran (175 ml) was stirred at 90° C. for 24 hours. The reaction mixture was distributed into ethyl acetate-tetrahydrofuran (3:1, v/v) and water. The organic layer was washed with water, dried over MgSO$_4$. The solvent was distilled off under reduced pressure, and the resulting crystals were collected by filtration to obtain 2-(3-methoxyphenyl)-6-phenyl-1H-imidazo[4,5-b]pyridine (14.0 g, 66%). The crystals were recrystallized from chloroform-methanol.

$^1$H NMR (DMSO-d$_6$) δ 3.89 (3H, s), 7.09-7.14 (1H, m), 7.36-7.56 (4H, m), 7.75-7.88 (4H, m), 8.30 (1H, s), 8.66 (1H, s) ppm IR (KBr) ν 3098, 1489, 1267, 1055 cm$^{-1}$
HPLC (220 nm) Purity 100% (Retention time 3.05 minutes)
MS (APCI+, m/e) 302 (M+1)

By using the compounds obtained in Reference Examples 2 to 42 and various boron acids as starting materials, the compounds of the following Examples 2 to 96 were synthesized in a manner similar to Example 1. At that time, purification by means of recrystallization or silica gel column chromatography was carried out as required.

Example 2

2-(1,3-benzodioxol-5-yl)-6-phenyl-1H-imidazo[4,5-b]pyridine

HPLC (220 nm) Purity 99% (Retention time 2.82 minutes)
MS (ESI+, m/e) 316 (M+1)

Example 3

2-(3-chlorophenyl)-6-phenyl-1H-imidazo[4,5-b]pyridine

HPLC (220 nm) Purity 94% (Retention time 3.20 minutes)
MS (ESI+, m/e) 306 (M+1)

Example 4

6-phenyl-2-[4-(trifluoromethoxy)phenyl]-1H-imidazo[4,5-b]pyridine

HPLC (220 nm) Purity 93% (Retention time 3.39 minutes)
MS (ESI+, m/e) 356 (M+1)

Example 5

2-(5-methyl-2-thienyl)-6-phenyl-1H-imidazo[4,5-b]pyridine

HPLC (220 nm) Purity 93% (Retention time 3.33 minutes)
MS (ESI+, m/e) 292 (M+1)

Example 6

2-(4-methoxybenzyl)-6-phenyl-1H-imidazo[4,5-b]pyridine

HPLC (220 nm) Purity 86% (Retention time 2.82 minutes)
MS (ESI+, m/e) 316 (M+1)

Example 7

2-(2-cyclopentylethyl)-6-phenyl-1H-imidazo[4,5-b]pyridine

HPLC (220 nm) Purity 94% (Retention time 3.03 minutes)
MS (ESI+, m/e) 292 (M+1)

Example 8

6-(2-fluorophenyl)-2-(2-methoxyphenyl)-1H-imidazo[4,5-b]pyridine

HPLC (220 nm) Purity 96% (Retention time 2.95 minutes)
MS (APCI+, m/e) 320 (M+1)

Example 9

6-(2-fluorophenyl)-2-(4-methoxyphenyl)-1H-imidazo[4,5-b]pyridine

HPLC (220 nm) Purity 100% (Retention time 2.89 minutes)
MS (APCI+, m/e) 320 (M+1)

Example 10

2-(1,3-benzodioxol-5-yl)-6-(2-fluorophenyl)-1H-imidazo[4,5-b]pyridine

HPLC (220 nm) Purity 99% (Retention time 2.89 minutes)
MS (APCI+, m/e) 334 (M+1)

Example 11

2-(3-chlorophenyl)-6-(2-fluorophenyl)-1H-imidazo[4,5-b]pyridine

HPLC (220 nm) Purity 99% (Retention time 3.35 minutes)
MS (APCI+, m/e) 324 (M+1)

Example 12

6-(2-fluorophenyl)-2-[4-(trifluoromethoxy)phenyl]-1H-imidazo[4,5-b]pyridine

HPLC (220 nm) Purity 100% (Retention time 3.52 minutes)
MS (APCI+, m/e) 374 (M+1)

Example 13

6-(2-fluorophenyl)-2-(5-methyl-2-thienyl)-1H-imidazo[4,5-b]pyridine

HPLC (220 nm) Purity 99% (Retention time 2.95 minutes)
MS (APCI+, m/e) 310 (M+1)

Example 14

6-(2-fluorophenyl)-2-(4-methoxybenzyl)-1H-imidazo[4,5-b]pyridine

HPLC (220 nm) Purity 99% (Retention time 2.87 minutes)
MS (APCI+, m/e) 334 (M+1)

Example 15

2-(2-cyclopentylethyl)-6-(2-fluorophenyl)-1H-imidazo[4,5-b]pyridine

HPLC (220 nm) Purity 99% (Retention time 3.08 minutes)
MS (APCI+, m/e) 310 (M+1)

Example 16

6-(2-fluorophenyl)-2-(phenoxymethyl)-1H-imidazo[4,5-b]pyridine

HPLC (220 nm) Purity 100% (Retention time 3.11 minutes)
MS (APCI+, m/e) 320 (M+1)

Example 17

2-(2-methoxyphenyl)-6-(1-naphthyl)-1H-imidazo[4,5-b]pyridine

HPLC (220 nm) Purity 98% (Retention time 3.23 minutes)
MS (APCI+, m/e) 352 (M+1)

Example 18

2-(3-methoxyphenyl)-6-(1-naphthyl)-1H-imidazo[4,5-b]pyridine

HPLC (220 nm) Purity 100% (Retention time 3.30 minutes)
MS (APCI+, m/e) 352 (M+1)

Example 19

2-(4-methoxyphenyl)-6-(1-naphthyl)-1H-imidazo[4,5-b]pyridine

HPLC (220 nm) Purity 99% (Retention time 3.17 minutes)
MS (APCI+, m/e) 352 (M+1)

Example 20

2-(1,3-benzodioxol-5-yl)-6-(1-naphthyl)-1H-imidazo[4,5-b]pyridine

HPLC (220 nm) Purity 100% (Retention time 3.18 minutes)
MS (APCI+, m/e) 366 (M+1)

Example 21

2-(3-chlorophenyl)-6-(1-naphthyl)-1H-imidazo[4,5-b]pyridine

HPLC (220 nm) Purity 91% (Retention time 3.60 minutes)
MS (APCI+, m/e) 356 (M+1)

Example 22

6-(1-naphthyl)-2-[4-(trifluoromethoxy)phenyl]-1H-imidazo[4,5-b]pyridine

HPLC (220 nm) Purity 99% (Retention time 3.73 minutes)
MS (APCI+, m/e) 406 (M+1)

Example 23

2-(5-methyl-2-thienyl)-6-(1-naphthyl)-1H-imidazo[4,5-b]pyridine

HPLC (220 nm) Purity 97% (Retention time 3.24 minutes)
MS (APCI+, m/e) 342 (M+1)

Example 24

2-(4-methoxybenzyl)-6-(1-naphthyl)-1H-imidazo[4,5-b]pyridine

HPLC (220 nm) Purity 98% (Retention time 3.16 minutes)
MS (APCI+, m/e) 366 (M+1)

Example 25

2-(2-cyclopentylethyl)-6-(1-naphthyl)-1H-imidazo[4,5-b]pyridine

HPLC (220 nm) Purity 99% (Retention time 3.33 minutes)
MS (APCI+, m/e) 342 (M+1)

Example 26

2-(2-methoxyphenyl)-6-(3-methoxyphenyl)-1H-imidazo[4,5-b]pyridine

HPLC (220 nm) Purity 100% (Retention time 2.96 minutes)
MS (APCI+, m/e) 332 (M+1)

Example 27

6-(3-methoxyphenyl)-2-(4-methoxyphenyl)-1H-imidazo[4,5-b]pyridine

HPLC (220 nm) Purity 90% (Retention time 2.91 minutes)
MS (APCI+, m/e) 332 (M+1)

Example 28

2-(3-chlorophenyl)-6-(3-methoxyphenyl)-1H-imidazo[4,5-b]pyridine

HPLC (220 nm) Purity 91% (Retention time 3.28 minutes)
MS (APCI+, m/e) 336 (M+1)

Example 29

2-(4-methoxybenzyl)-6-(3-methoxyphenyl)-1H-imidazo[4,5-b]pyridine

HPLC (220 nm) Purity 94% (Retention time 2.90 minutes)
MS (APCI+, m/e) 346 (M+1)

Example 30

2,6-bis(3-methoxyphenyl)-1H-imidazo[4,5-b]pyridine

HPLC (220 nm) Purity 100% (Retention time 3.01 minutes)
MS (APCI+, m/e) 332 (M+1)

Example 31

2-(1,3-benzodioxol-5-yl)-6-(3-methoxyphenyl)-1H-imidazo[4,5-b]pyridine

HPLC (220 nm) Purity 80% (Retention time 2.91 minutes)
MS (APCI+, m/e) 346 (M+1)

Example 32

6-(3-methoxyphenyl)-2-[4-(trifluoromethoxy)phenyl]-1H-imidazo[4,5-b]pyridine

HPLC (220 nm) Purity 81% (Retention time 3.45 minutes)
MS (APCI+, m/e) 386 (M+1)

Example 33

2-(2-methoxyphenyl)-6-[3-(trifluoromethyl)phenyl]-1H-imidazo[4,5-b]pyridine

HPLC (220 nm) Purity 99% (Retention time 3.29 minutes)
MS (APCI+, m/e) 370 (M+1)

Example 34

2-(3-methoxyphenyl)-6-[3-(trifluoromethyl)phenyl]-1H-imidazo[4,5-b]pyridine

HPLC (220 nm) Purity 100% (Retention time 3.39 minutes)
MS (APCI+, m/e) 370 (M+1)

Example 35

2-(4-methoxyphenyl)-6-[3-(trifluoromethyl)phenyl]-1H-imidazo[4,5-b]pyridine

HPLC (220 nm) Purity 96% (Retention time 3.25 minutes)
MS (APCI+, m/e) 370 (M+1)

Example 36

2-(1,3-benzodioxol-5-yl)-6-[3-(trifluoromethyl)phenyl]-1H-imidazo[4,5-b]pyridine HPLC (220 nm) Purity 85% (Retention time 3.27 minutes)
MS (APCI+, m/e) 384 (M+1)

Example 37

2-(3-chlorophenyl)-6-[3-(trifluoromethyl)phenyl]-1H-imidazo[4,5-b]pyridine

HPLC (220 nm) Purity 92% (Retention time 3.73 minutes)
MS (APCI+, m/e) 374 (M+1)

Example 38

2-[4-(trifluoromethoxy)phenyl]-6-[3-(trifluoromethyl)phenyl]-1H-imidazo[4,5-b]pyridine HPLC (220 nm) Purity 92% (Retention time 3.85 minutes)
MS (APCI+, m/e) 424 (M+1)

Example 39

2-(5-methyl-2-thienyl)-6-[3-(trifluoromethyl)phenyl]-1H-imidazo[4,5-b]pyridine

HPLC (220 nm) Purity 93% (Retention time 3.35 minutes)
MS (APCI+, m/e) 360 (M+1)

Example 40

2-(4-methoxybenzyl)-6-[3-(trifluoromethyl)phenyl]-1H-imidazo[4,5-b]pyridine

HPLC (220 nm) Purity 96% (Retention time 3.22 minutes)
MS (APCI+, m/e) 384 (M+1)

Example 41

2-(2-cyclopentylethyl)-6-[3-(trifluoromethyl)phenyl]-1H-imidazo[4,5-b]pyridine

HPLC (220 nm) Purity 100% (Retention time 3.37 minutes)
MS (APCI+, m/e) 360 (M+1)

Example 42

4-[2-(2-methoxyphenyl)-1H-imidazo[4,5-b]pyridin-6-yl]benzonitrile

HPLC (220 nm) Purity 100% (Retention time 2.90 minutes)
MS (APCI+, m/e) 327 (M+1)

Example 43

4-[2-(3-methoxyphenyl)-1H-imidazo[4,5-b]pyridin-6-yl]benzonitrile

HPLC (220 nm) Purity 98% (Retention time 3.02 minutes)
MS (APCI+, m/e) 327 (M+1)

Example 44

4-[2-(4-methoxyphenyl)-1H-imidazo[4,5-b]pyridin-6-yl]benzonitrile

HPLC (220 nm) Purity 100% (Retention time 2.86 minutes)
MS (APCI+, m/e) 327 (M+1)

Example 45

4-[2-(1,3-benzodioxol-5-yl)-1H-imidazo[4,5-b]pyridin-6-yl]benzonitrile

HPLC (220 nm) Purity 98% (Retention time 2.88 minutes)
MS (APCI+, m/e) 341 (M+1)

Example 46

4-[2-(3-chlorophenyl)-1H-imidazo[4,5-b]pyridin-6-yl]benzonitrile

HPLC (220 nm) Purity 82% (Retention time 3.33 minutes)
MS (APCI+, m/e) 331 (M+1)

Example 47

4-[2-[4-(trifluoromethoxy)phenyl]-1H-imidazo[4,5-b]pyridin-6-yl]benzonitrile

HPLC (220 nm) Purity 98% (Retention time 3.52 minutes)
MS (APCI+, m/e) 381 (M+1)

Example 48

4-[2-(4-methoxybenzyl)-1H-imidazo[4,5-b]pyridin-6-yl]benzonitrile

HPLC (220 nm) Purity 98% (Retention time 2.82 minutes)
MS (APCI+, m/e) 341 (M+1)

Example 49

4-[2-(2-cyclopentylethyl)-1H-imidazo[4,5-b]pyridin-6-yl]benzonitrile

HPLC (220 nm) Purity 99% (Retention time 3.01 minutes)
MS (APCI+, m/e) 317 (M+1)

Example 50

2-(2-methoxyphenyl)-6-[4-(methylsulfonyl)phenyl]-1H-imidazo[4,5-b]pyridine

HPLC (220 nm) Purity 100% (Retention time 2.65 minutes)
MS-(APCI+, m/e) 380 (M+1)

Example 51

2-(3-methoxyphenyl)-6-[4-(methylsulfonyl)phenyl]-1H-imidazo[4,5-b]pyridine

HPLC (220 nm) Purity 88% (Retention time 2.74 minutes)
MS (APCI+, m/e) 380 (M+1)

Example 52

2-(4-methoxyphenyl)-6-[4-(methylsulfonyl)phenyl]-1H-imidazo[4,5-b]pyridine

HPLC (220 nm) Purity 100% (Retention time 2.63 minutes)
MS (APCI+, m/e) 380 (M+1)

Example 53

2-(1,3-benzodioxol-5-yl)-6-[4-(methylsulfonyl)phenyl]-1H-imidazo[4,5-b]pyridine

HPLC (220 nm) Purity 93% (Retention time 2.62 minutes)
MS (APCI+, m/e) 394 (M+1)

Example 54

2-(3-chlorophenyl)-6-[4-(methylsulfonyl)phenyl]-1H-imidazo[4,5-b]pyridine

HPLC (220 nm) Purity 90% (Retention time 3.03 minutes)
MS (APCI+, m/e) 384 (M+1)

Example 55

6-[4-(methylsulfonyl)phenyl]-2-[4-(trifluoromethoxy)phenyl]-1H-imidazo[4,5-b]pyridine HPLC (220 nm) Purity 98% (Retention time 3.25 minutes)
MS (APCI+, m/e) 434 (M+1)

Example 56

2-(4-methoxybenzyl)-6-[4-(methylsulfonyl)phenyl]-1H-imidazo[4,5-b]pyridine

HPLC (220 nm) Purity 99% (Retention time 2.57 minutes)
MS (APCI+, m/e) 394 (M+1)

Example 57

2-(2-cyclopentylethyl)-6-[4-(methylsulfonyl)phenyl]-1H-imidazo[4,5-b]pyridine

HPLC (220 nm) Purity 94% (Retention time 2.80 minutes)
MS (APCI+, m/e) 370 (M+1)

Example 58

6-(2-fluorophenyl)-2-[(phenylthio)methyl]-1H-imidazo[4,5-b]pyridine

HPLC (220 nm) Purity 99% (Retention time 3.04 minutes)
MS (APCI+, m/e) 336 (M+1)

Example 59

6-(2-fluorophenyl)-2-(2-phenylethyl)-1H-imidazo[4,5-b]pyridine

HPLC (220 nm) Purity 99% (Retention time 2.91 minutes)
MS (APCI+, m/e) 318 (M+1)

Example 60

2-benzyl-6-(2-fluorophenyl)-1H-imidazo[4,5-b]pyridine

HPLC (220 nm) Purity 99% (Retention time 2.81 minutes)
MS (APCI+, m/e) 304 (M+1)

Example 61

6-(2-fluorophenyl)-2-(3-methoxybenzyl)-1H-imidazo[4,5-b]pyridine

HPLC (220 nm) Purity 99% (Retention time 2.90 minutes)
MS (APCI+, m/e) 334 (M+1)

Example 62

2-(2,5-dimethoxybenzyl)-6-(2-fluorophenyl)-1H-imidazo[4,5-b]pyridine

HPLC (220 nm) Purity 96% (Retention time 2.93 minutes)
MS (APCI+, m/e) 364 (M+1)

Example 63

2-(3,4-dimethoxybenzyl)-6-(2-fluorophenyl)-1H-imidazo[4,5-b]pyridine

HPLC (220 nm) Purity 89% (Retention time 2.76 minutes)
MS (APCI+, m/e) 364 (M+1)

Example 64

2-(4-chlorobenzyl)-6-(2-fluorophenyl)-1H-imidazo[4,5-b]pyridine

HPLC (220 nm) Purity 99% (Retention time 3.11 minutes)
MS (APCI+, m/e) 338 (M+1)

Example 65

6-(2-fluorophenyl)-2-[(E)-2-phenylethenyl]-1H-imidazo[4,5-b]pyridine

HPLC (220 nm) Purity 98% (Retention time 3.06 minutes)
MS (APCI+, m/e) 316 (M+1)

Example 66

6-(2-fluorophenyl)-2-(3-phenoxyphenyl)-1H-imidazo[4,5-b]pyridine

HPLC (220 nm) Purity 87% (Retention time 3.62 minutes)
MS (APCI+, m/e) 382 (M+1)

Example 67

2-(4-benzoylphenyl)-6-(2-fluorophenyl)-1H-imidazo[4,5-b]pyridine

HPLC (220 nm) Purity 98% (Retention time 3.54 minutes)
MS (APCI+, m/e) 394 (M+1)

Example 68

2-(phenoxymethyl)-6-phenyl-1H-imidazo[4,5-b]pyridine

HPLC (220 nm) Purity 97% (Retention time 2.98 minutes)
MS (APCI+, m/e) 302 (M+1)

Example 69

6-phenyl-2-[(phenylthio)methyl]-1H-imidazo[4,5-b]pyridine

HPLC (220 nm) Purity 99% (Retention time 2.95 minutes)
MS (APCI+, m/e) 318 (M+1)

Example 70

6-phenyl-2-(2-phenylethyl)-1H-imidazo[4,5-b]pyridine

HPLC (220 nm) Purity 97% (Retention time 2.88 minutes)
MS (APCI+, m/e) 300 (M+1)

Example 71

2-benzyl-6-phenyl-1H-imidazo[4,5-b]pyridine

HPLC (220 nm) Purity 99% (Retention time 2.76 minutes)
MS (APCI+, m/e) 286 (M+1)

Example 72

2-(3-methoxybenzyl)-6-phenyl-1H-imidazo[4,5-b]pyridine

HPLC (220 nm) Purity 99% (Retention time 2.84 minutes)
MS (APCI+, m/e) 316 (M+1)

Example 73

2-(2,5-dimethoxybenzyl)-6-phenyl-1H-imidazo[4,5-b]pyridine

HPLC (220 nm) Purity 99% (Retention time 2.88 minutes)
MS (APCI+, m/e) 346 (M+1)

Example 74

2-(3,4-dimethoxybenzyl)-6-phenyl-1H-imidazo[4,5-b]pyridine

HPLC (220 nm) Purity 92% (Retention time 2.68 minutes)
MS (APCI+, m/e) 346 (M+1)

Example 75

2-(4-chlorobenzyl)-6-phenyl-1H-imidazo[4,5-b]pyridine

HPLC (220 nm) Purity 99% (Retention time 3.02 minutes)
MS (APCI+, m/e) 320 (M+1)

Example 76

6-phenyl-2-[(E)-2-phenylethenyl]-1H-imidazo[4,5-b]pyridine

HPLC (220 nm) Purity 99% (Retention time 2.97 minutes)
MS (APCI+, m/e) 298 (M+1)

Example 77

2-(3-phenoxyphenyl)-6-phenyl-1H-imidazo[4,5-b]pyridine

HPLC (220 nm) Purity 94% (Retention time 3.48 minutes)
MS (APCI+, m/e) 364 (M+1)

Example 78

2-(4-benzoylphenyl)-6-phenyl-1H-imidazo[4,5-b]pyridine

HPLC (220 nm) Purity 100% (Retention time 3.38 minutes)
MS (APCI+, m/e) 37.6 (M+1)

Example 79

6-(1-benzofuran-2-yl)-2-(4-fluorobenzyl)-1H-imidazo[4,5-b]pyridine

HPLC (220 nm) Purity 100% (Retention time 3.25 minutes)
MS (APCI+, m/e) 344 (M+1)

Example 80

6-(1-benzofuran-2-yl)-2-(3-chlorobenzyl)-1H-imidazo[4,5-b]pyridine

HPLC (220 nm) Purity 100% (Retention time 3.44 minutes)
MS (APCI+, m/e) 360 (M+1)

Example 81

6-(1-benzofuran-2-yl)-2-(2-chlorobenzyl)-1H-imidazo[4,5-b]pyridine

HPLC (220 nm) Purity 100% (Retention time 3.31 minutes)
MS (APCI+, m/e) 360 (M+1)

Example 82

6-(1-benzofuran-2-yl)-2-(2,4-difluorobenzyl)-1H-imidazo[4,5-b]pyridine

HPLC (220 nm). Purity 100% (Retention time 3.30 minutes)
MS (APCI+, m/e) 362 (M+1)

Example 83

6-(1-benzofuran-2-yl)-2-(3,4-dichlorobenzyl)-1H-imidazo[4,5-b]pyridine

HPLC (220 nm) Purity 99% (Retention time 3.66 minutes)
MS (APCI+, m/e) 394 (M+1)

Example 84

6-(1-benzofuran-2-yl)-2-[4-(trifluoromethyl)benzyl]-1H-imidazo[4,5-b]pyridine

HPLC (220 nm) Purity 100% (Retention time 3.58 minutes)
MS (APCI+, m/e) 394 (M+1)

Example 85

6-(1-benzofuran-2-yl)-2-[4-(trifluoromethoxy)benzyl]-1H-imidazo[4,5-b]pyridine

HPLC (220 nm) Purity 100% (Retention time 3.74 minutes)
MS (APCI+, m/e) 410 (M+1)

Example 86

6-(1-benzofuran-2-yl)-2-(4-nitrobenzyl)-1H-imidazo[4,5-b]pyridine

HPLC (220 nm) Purity 98% (Retention time 3.47 minutes)
MS (APCI+, m/e) 371 (M+1)

Example 87

6-(1-benzofuran-2-yl)-2-(4-methylbenzyl)-1H-imidazo[4,5-b]pyridine

HPLC (220 nm) Purity 100% (Retention time 3.42 minutes)
MS (APCI+, m/e) 340 (M+1)

Example 88

6-(1-benzofuran-2-yl)-2-[(1,1'-biphenyl)-4-ylmethyl]-1H-imidazo[4,5-b]pyridine

HPLC (220 nm) Purity 100% (Retention time 3.79 minutes)
MS (APCI+, m/e) 402 (M+1)

Example 89

6-(1-benzofuran-2-yl)-2-(2-naphthylmethyl)-1H-imidazo[4,5-b]pyridine

HPLC (220 nm) Purity 100% (Retention time 3.62 minutes)
MS (APCI+, m/e) 376 (M+1)

Example 90

2-(1,3-benzodioxol-5-ylmethyl)-6-(1-benzofuran-2-yl)-1H-imidazo[4,5-b]pyridine

HPLC (220 nm) Purity 100% (Retention time 3.29 minutes)
MS (APCI+, m/e) 370 (M+1)

Example 91

6-(1-benzofuran-2-yl)-2-(3,4,5-trimethoxybenzyl)-1H-imidazo[4,5-b]pyridine

HPLC (220 nm) Purity 99% (Retention time 3.25 minutes)
MS (APCI+, m/e) 416 (M+1)

Example 92

6-(1-benzofuran-2-yl)-2-(2-thienylmethyl)-1H-imidazo[4,5-b]pyridine

HPLC (220 nm) Purity 100% (Retention time 3.27 minutes)
MS (APCI+, m/e) 332 (M+1)

Example 93

6-(1-benzofuran-2-yl)-2-[(1-methyl-1H-indol-3-yl)methyl]-1H-imidazo[4,5-b]pyridine HPLC (220 nm) Purity 98% (Retention time 3.44 minutes)
MS (APCI+, m/e) 379 (M+1)

Example 94

6-(1-benzofuran-2-yl)-2-[(4-chlorophenoxy)methyl]-1H-imidazo[4,5-b]pyridine

HPLC (220 nm) Purity 100% (Retention time 3.90 minutes)
MS (APCI+, m/e) 376 (M+1)

Example 95

6-(1-benzofuran-2-yl)-2-[4-(methylthio)benzyl]-1H-imidazo[4,5-b]pyridine

HPLC (220 nm) Purity 100% (Retention time 3.49 minutes)
MS (APCI+, m/e) 372 (M+1)

Example 96

6-(1-benzofuran-2-yl)-2-[2-(3,4-dimethoxyphenyl)ethyl]-1H-imidazo[4,5-b]pyridine HPLC (220 nm) Purity 100% (Retention time 3.19 minutes)
MS (APCI+, m/e) 400 (M+1)

Example 97

Under an argon stream, a mixture of 6-bromo-2-(3,4-dimethoxybenzyl)-1H-imidazo[4,5-b]pyridine (Compound of Reference Example 23) (140 mg), 2-(tributylstanyl)furan (185 mg), dichlorobis(triphenylphosphine)palladium(II) (14 mg) and N,N-dimethyl formamide (4 ml) was stirred at 80° C. for 24 hours. The reaction mixture was poured into water and extracted with ethyl acetate-tetrahydrofuran (3:1, v/v). The organic layer was washed with water and dried over $MgSO_4$ and the solvent was distilled off under reduced pressure. The residue was subjected to silica gel column chromatography, and the fraction eluted with ethyl acetate-chloroform (1:1, v/v) was concentrated under reduced pressure. The resulting crystals were collected by filtration to obtain 2-(3,4-dimethoxybenzyl)-6-(2-furyl)-1H-imidazo[4,5-b]pyridine (55 mg, 41%).

$^1$H NMR (CDCl$_3$) δ 3.80 (3H, s), 3.82 (3H, s), 4.33 (2H, s), 6.53 (1H, dd, J=3.4, 1.8 Hz), 6.69 (1H, d, J=3.4 Hz), 7.54 (1H, d, J=1.8 Hz), 8.24 (1H, s), 8.36 (1H, s) ppm IR (KBr) ν 2928, 1516, 1263, 1236 cm$^{-1}$
HPLC (220 nm) Purity 100% (Retention time 2.66 minutes)
MS (APCI+, m/e) 336 (M+1)

By using the compounds obtained in Reference Examples 2 to 42 and various tributyltin compounds as starting materials, the compounds of the following Examples 98 to 145 were synthesized in a manner similar to Example 97. At that time, purification by means of recrystallization or silica gel column chromatography was carried out as required.

Example 98

6-(2-furyl)-2-(2-methoxyphenyl)-1H-imidazo[4,5-b]pyridine

HPLC (220 nm) Purity 99% (Retention time 2.74 minutes)
MS (APCI+, m/e) 292 (M+1)

Example 99

6-(2-furyl)-2-(3-methoxyphenyl)-1H-imidazo[4,5-b]pyridine

HPLC (220 nm) Purity 100% (Retention time 2.83 minutes)
MS (APCI+, m/e) 292 (M+1)

Example 100

6-(2-furyl)-2-(4-methoxyphenyl)-1H-imidazo[4,5-b]pyridine

HPLC (220 nm) Purity 100% (Retention time 2.70 minutes)
MS (APCI+, m/e) 292 (M+1)

Example 101

2-(1,3-benzodioxol-5-yl)-6-(2-furyl)-1H-imidazo[4,5-b]pyridine

HPLC (220 nm) Purity 99% (Retention time 2.70 minutes)
MS (APCI+, m/e) 306 (M+1)

Example 102

2-(3-chlorophenyl)-6-(2-furyl)-1H-imidazo[4,5-b]pyridine

HPLC (220 nm) Purity 100% (Retention time 3.16 minutes)
MS (APCI+, m/e) 296 (M+1)

Example 103

6-(2-furyl)-2-[4-(trifluoromethoxy)phenyl]-1H-imidazo[4,5-b]pyridine

HPLC (220 nm) Purity 100% (Retention time 3.37 minutes)
MS (APCI+, m/e) 346 (M+1)

Example 104

6-(2-furyl)-2-(5-methyl-2-thienyl)-1H-imidazo[4,5-b]pyridine

HPLC (220 nm) Purity 100% (Retention time 2.76 minutes)
MS (APCI+, m/e) 282 (M+1)

Example 105

6-(2-furyl)-2-(4-methoxybenzyl)-1H-imidazo[4,5-b]pyridine

HPLC (220 nm) Purity 98% (Retention time 2.68 minutes)
MS (APCI+, m/e) 306 (M+1)

Example 106

6-(2-furyl)-2-(phenoxymethyl)-1H-imidazo[4,5-b]pyridine

HPLC (220 nm) Purity 100% (Retention time 2.91 minutes)
MS (APCI+, m/e) 292 (M+1)

Example 107

2-(2-cyclopentylethyl)-6-(2-furyl)-1H-imidazo[4,5-b]pyridine

HPLC (220 nm) Purity 100% (Retention time 2.91 minutes)
MS (APCI+, m/e) 282 (M+1)

Example 108

6-(2-furyl)-2-[(phenylthio)methyl]-1H-imidazo[4,5-b]pyridine

HPLC (220 nm) Purity 95% (Retention time 3.61 minutes)
MS (APCI+, m/e) 308 (M+1)

Example 109

6-(2-furyl)-2-(2-phenylethyl)-1H-imidazo[4,5-b]pyridine

HPLC (220 nm) Purity 92% (Retention time 2.74 minutes)
MS (APCI+, m/e) 290 (M+1)

Example 110

2-benzyl-6-(2-furyl)-1H-imidazo[4,5-b]pyridine

HPLC (220 nm) Purity 100% (Retention time 2.61 minutes)
MS (APCI+, m/e) 276 (M+1)

Example 111

6-(2-furyl)-2-(3-methoxybenzyl)-1H-imidazo[4,5-b]pyridine

HPLC (220 nm) Purity 98% (Retention time 2.70 minutes)
MS (APCI+, m/e) 306 (M+1)

Example 112

2-(2,5-dimethoxybenzyl)-6-(2-furyl)-1H-imidazo[4,5-b]pyridine

HPLC (220 nm). Purity 83% (Retention time 2.74 minutes)
MS (APCI+, m/e) 336 (M+1)

Example 113

2-(4-chlorobenzyl)-6-(2-furyl)-1H-imidazo[4,5-b]pyridine

HPLC (220 nm) Purity 100% (Retention time 2.93 minutes)
MS (APCI+, m/e) 310 (M+1)

Example 114

6-(2-furyl)-2-[(E)-2-phenylethenyl]-1H-imidazo[4,5-b]pyridine

HPLC (220 nm) Purity 96% (Retention time 2.89 minutes)
MS (APCI+, m/e) 288 (M+1)

Example 115

6-(2-furyl)-2-(3-phenoxyphenyl)-1H-imidazo[4,5-b]pyridine

HPLC (220 nm) Purity 85% (Retention time 3.49 minutes)
MS (APCI+, m/e) 354 (M+1)

Example 116

2-(4-benzoylphenyl)-6-(2-furyl)-1H-imidazo[4,5-b]pyridine

HPLC (220 nm) Purity 90% (Retention time 3.39 minutes)
MS (APCI+, m/e) 366 (M+1)

Example 117

2-(phenoxymethyl)-6-(2-thienyl)-1H-imidazo[4,5-b]pyridine

HPLC (220 nm) Purity 99% (Retention time 3.05 minutes)
MS (APCI+, m/e) 308 (M+1)

Example 118

2-[(phenylthio)methyl]-6-(2-thienyl)-1H-imidazo[4,5-b]pyridine

HPLC (220 nm) Purity 95% (Retention time 2.99 minutes)
MS (APCI+, m/e) 324 (M+1)

Example 119

2-(2-phenylethyl)-6-(2-thienyl)-1H-imidazo[4,5-b]pyridine

HPLC (220 nm) Purity 94% (Retention time 2.84 minutes)
MS (APCI+, m/e) 306 (M+1)

Example 120

2-benzyl-6-(2-thienyl)-1H-imidazo[4,5-b]pyridine

HPLC (220 nm) Purity 99% (Retention time 2.73 minutes)
MS (APCI+, m/e) 292 (M+1)

Example 121

2-(2,5-dimethoxybenzyl)-6-(2-thienyl)-1H-imidazo[4,5-b]pyridine

HPLC (220 m) Purity 97% (Retention time 2.84 minutes)
MS (APCI+, m/e) 352 (M+1)

Example 122

2-(3,4-dimethoxybenzyl)-6-(2-thienyl)-1H-imidazo[4,5-b]pyridine

HPLC (220 nm) Purity 88% (Retention time 2.66 minutes)
MS (APCI+, m/e) 352 (M+1)

Example 123

2-(4-chlorobenzyl)-6-(2-thienyl)-1H-imidazo[4,5-b]pyridine

HPLC (220 nm) Purity 98% (Retention time 3.04 minutes)
MS (APCI+, m/e) 326 (M+1)

Example 124

2-(3-phenoxyphenyl)-6-(2-thienyl)-1H-imidazo[4,5-b]pyridine

HPLC (220 nm) Purity 95% (Retention time 3.62 minutes)
MS (APCI+, m/e) 370 (M+1)

Example 125

2-(3-methoxybenzyl)-6-(2-thienyl)-1H-imidazo[4,5-b]pyridine

HPLC (220 nm) Purity 98% (Retention time 2.82 minutes)
MS (APCI+, m/e) 322 (M+1)

Example 126

2-[(E)-2-phenylethenyl]-6-(2-thienyl)-1H-imidazo[4,5-b]pyridine

HPLC (220 nm) Purity 98% (Retention time 3.00 minutes)
MS (APCI+, m/e) 304 (M+1)

Example 127

2-(4-benzoylphenyl)-6-(2-thienyl)-1H-imidazo[4,5-b]pyridine

HPLC (220 nm) Purity 92% (Retention time 3.52 minutes)
MS (APCI+, nm) 382 (M+1)

Example 128

2-(4-fluorobenzyl)-6-(2-furyl)-1H-imidazo[4,5-b]pyridine

HPLC (220 nm) Purity 83% (Retention time 2.82 minutes)
MS (APCI+, m/e) 294 (M+1)

Example 129

2-(3-chlorobenzyl)-6-(2-furyl)-1H-imidazo[4,5-b]pyridine

HPLC (220 nm) Purity 100% (Retention time 2.99 minutes)
MS (APCI+, m/e) 310 (M+1)

Example 130

2-(2,4-difluorobenzyl)-6-(2-furyl)-1H-imidazo[4,5-b]pyridine

HPLC (220 nm) Purity 84% (Retention time 2.85 minutes)
MS (APCI+, m/e) 312 (M+1)

Example 131

2-(3,4-dichlorobenzyl)-6-(2-furyl)-1H-imidazo[4,5-b]pyridine

HPLC (220 nm) Purity 100% (Retention time 3.25 minutes)
MS (APCI+, m/e) 344 (M+1)

Example 132

6-(2-furyl)-2-[4-(trifluoromethyl)benzyl]-1H-imidazo[4,5-b]pyridine

HPLC (220 nm) Purity 100% (Retention time 3.20 minutes)
MS (APCI+, m/e) 344 (M+1)

Example 133

6-(2-furyl)-2-[4-(trifluoromethoxy)benzyl]-1H-imidazo[4,5-b]pyridine

HPLC (220 nm) Purity 100% (Retention time 3.24 minutes)
MS (APCI+, m/e) 360 (M+1)

Example 134

6-(2-furyl)-2-(4-nitrobenzyl)-1H-imidazo[4,5-b]pyridine

HPLC (220 nm) Purity 97% (Retention time 2.89 minutes)
MS (APCI+, m/e) 321 (M+1)

Example 135

6-(2-furyl)-2-(4-methylbenzyl)-1H-imidazo[4,5-b]pyridine

HPLC (220 nm) Purity 84% (Retention time 2.91 minutes)
MS (APCI+, m/e) 290 (M+1)

Example 136

6-(2-furyl)-2-(2-naphthylmethyl)-1H-imidazo[4,5-b]pyridine

HPLC (220 nm) Purity 100% (Retention time 3.15 minutes)
MS (APCI+, m/e) 326 (M+1)

Example 137

2-(1,3-benzodioxol-5-ylmethyl)-6-(2-furyl)-1H-imidazo[4,5-b]pyridine

HPLC (220 nm) Purity 86% (Retention time 2.75 minutes)
MS (APCI+, m/e) 320 (M+1)

Example 138

6-(2-furyl)-2-(3,4,5-trimethoxybenzyl)-1H-imidazo[4,5-b]pyridine

HPLC (220 nm) Purity 98% (Retention time 2.66 minutes)
MS (APCI+, m/e) 366 (M+1)

Example 139

6-(2-furyl)-2-(2-thienylmethyl)-1H-imidazo[4,5-b]pyridine

HPLC (220 nm) Purity 100% (Retention time 2.54 minutes)
MS (APCI+, m/e) 282 (M+1)

Example 140

6-(2-furyl)-2-[(1-methyl-1H-indol-3-yl)methyl]-1H-imidazo[4,5-b]pyridine

HPLC (220 nm) Purity 100% (Retention time 2.93 minutes)
MS (APCI+, m/e) 329 (M+1)

Example 141

2-[(4-chlorophenoxy)methyl]-6-(2-furyl)-1H-imidazo[4,5-b]pyridine

HPLC (220 nm) Purity 99% (Retention time 3.19 minutes)
MS (APCI+, m/e) 326 (M+1)

Example 142

2-[2-(3,4-dimethoxyphenyl)ethyl]-6-(2-furyl)-1H-imidazo[4,5-b]pyridine

HPLC (220 nm) Purity 98% (Retention time 2.65 minutes)
MS (APCI+, m/e) 350 (M+1)

Example 143

6-(2-furyl)-2-[4-(methylthio)benzyl]-1H-imidazo[4,5-b]pyridine

HPLC (220 nm) Purity 100% (Retention time 2.93 minutes)
MS (APCI+, m/e) 322 (M+1)

Example 144

2-(2-chlorobenzyl)-6-(2-furyl)-1H-imidazo[4,5-b]pyridine

HPLC (220 nm) Purity 100% (Retention time 2.85 minutes)
MS (APCI+, m/e) 310 (M+1)

Example 145

2-[(1,1'-biphenyl)-4-ylmethyl]-6-(2-furyl)-1H-imidazo[4,5-b]pyridine

HPLC (220 nm) Purity 94% (Retention time 3.34 minutes)
MS (APCI+, m/e) 352 (M+1)

Example 146

A mixture of 2-(3-methoxyphenyl)-6-phenyl-1H-imidazo[4,5-b]pyridine (Compound of Example 1) (50 mg), 2-tert-butylimino-2-diethylamino-1,3-dimethylperhydro-1,3,2-diazaphosphorine resin (PS-BEMP, 2.2 mmol/g) (113 mg) and N,N-dimethyl formamide (2 ml) was shaken at room temperature for 30 minutes. To the mixture was added iodomethane (28 mg), and the mixture was further shaken for 1 hour. After the resin was filtered off, the filtrate was poured into water and extracted with ethyl acetate. The organic layer was washed with water and dried over MgSO$_4$ and the solvent was distilled off under reduced pressure. The residue was subjected to silica gel column chromatography, and the fraction eluted with ethyl acetate-chloroform-hexane (1:1:4 to 1:1:0, v/v) was concentrated under reduced pressure. The resulting crystals were collected by filtration to isolate 2-(3-methoxyphenyl)-1-methyl-6-phenyl-1H-imidazo[4,5-b]pyridine (22 mg, 41%) (As a result of this reaction, a mixture of two isomers was obtained, and the isomer having higher polarity is the desired compound.)

$^1$H NMR (CDCl$_3$) δ 3.95 (3H, s), 4.43 (3H, s), 7.00-7.05 (1H, m), 7.37-7.61 (6H, m), 7.81 (1H, d, J=1.6 Hz), 8.06-8.15 (2H, m), 8.40 (1H, d, J=1.4 Hz) ppm IR (KBr) ν 1472, 1397, 1292, 1252 cm$^{-1}$
HPLC (220 nm) Purity 100% (Retention time 2.87 minutes)
MS (APCI+, m/e) 316 (M+1)

By using the compound obtained in Example 1 and various alkyl halides as starting materials, the compounds of the following Examples 147 to 153 were synthesized in a manner similar to Example 146. (The reaction time was 15 hours.)

Example 147

1-(2-methoxyethyl)-2-(3-methoxyphenyl)-6-phenyl-1H-imidazo[4,5-b]pyridine

HPLC (220 nm) Purity 86% (Retention time 3.06 minutes)
MS (APCI+, m/e) 360 (M+1)

Example 148

1-(cyclohexylmethyl)-2-(3-methoxyphenyl)-6-phenyl-1H-imidazo[4,5-b]pyridine

HPLC (220 nm) Purity 97% (Retention time 3.70 minutes)
MS (APCI+, m/e) 398 (M+1)

Example 149

2-(3-methoxyphenyl)-6-phenyl-1-(2-phenylethyl)-1H-imidazo[4,5-b]pyridine

HPLC (220 nm) Purity 98% (Retention time 3.50 minutes)
MS (APCI+, m/e) 406 (M+1)

Example 150

2-(3-methoxyphenyl)-1-(3-phenoxypropyl)-6-phenyl-1H-imidazo[4,5-b]pyridine

HPLC (220 nm) Purity 99% (Retention time 3.50 minutes)
MS (APCI+, m/e) 436 (M+1)

Example 151

N-[3-[2-(3-methoxyphenyl)-6-phenyl-1H-imidazo[4,5-b]pyridin-1-yl]propyl]phthalimide HPLC (220 nm) Purity 99% (Retention time 3.31 minutes)
MS (APCI+, m/e) 489 (M+1)

Example 152

1-decyl-2-(3-methoxyphenyl)-6-phenyl-1H-imidazo[4,5-b]pyridine

HPLC (220 nm) Purity 99% (Retention time 4.32 minutes)
MS (APCI+, m/e) 442 (M+1)

Example 153

2-[[2-(3-methoxyphenyl)-6-phenyl-1H-imidazo[4,5-b]pyridin-1-yl]methyl]phenyl acetate HPLC (220 nm) Purity 97% (Retention time 3.36 minutes)
MS (APCI+, m/e) 450 (M+1)

Example 154

A mixture of 2-(3-methoxyphenyl)-6-phenyl-1H-imidazo[4,5-b]pyridine (Compound of Example 1) (250 mg), 2-tert-butylimino-2-diethylamino-1,3-dimethylperhydro-1,3,2-diazaphosphorine resin (PS-BEMP, 2.2 mmol/g) (566 mg) and N,N-dimethyl formamide (10 ml) was shaken at room temperature for 30 minutes. To the mixture was added bromo tert-butyl acetate (194 mg), and the mixture was further shaken at room temperature for 1 hour. After the resin was filtered off, the filtrate was poured into water and the mixture was extracted with ethyl acetate. The organic layer was washed with water and dried over MgSO$_4$. The solvent was distilled off under reduced pressure, and the residue was subjected to silica gel column chromatography. The fraction eluted with ethyl acetate-hexane (1:2 to 1:1:1.5, v/v) was concentrated to isolate tert-butyl [2-(3-methoxyphenyl)-6-phenyl-1H-imidazo[4,5-b]pyridin-1-yl]acetate.

To tert-butyl [2-(3-methoxyphenyl)-6-phenyl-1H-imidazo[4,5-b]pyridin-1-yl]acetate (209 mg) was added a solution of 4 N hydrogen chloride in ethyl acetate (8.0 ml), and the mixture was stirred at room temperature for 5 hours to hydrolyze. The reaction mixture was poured into water and extracted with ethyl acetate. The organic layer was washed with water and dried over $MgSO_4$, and the solvent was distilled off under reduced pressure. The resulting crystals were collected by filtration to obtain [2-(3-methoxyphenyl)-6-phenyl-1H-imidazo[4,5-b]pyridin-1-yl]acetic acid (129 mg, 43%).

$^1$H NMR (DMSO-$d_6$) δ 3.86 (3H, s), 5.56 (2H, s), 7.02-7.07 (1H, m), 7.45-7.55 (4H, m), 7.79-7.92 (4H, m), 8.63 (1H, s), 8.72 (1H, s) ppm IR (KBr) ν 3368, 1634, 1478, 1362 $cm^{-1}$ HPLC (220 nm) Purity 100% (Retention time 2.73 minutes)

MS (APCI+, m/e) 360 (M+1)

Example 155

A mixture of [2-(3-methoxyphenyl)-6-phenyl-1H-imidazo[4,5-b]pyridin-1-yl]acetic acid (Compound of Example 154) (100 mg), glycinetert-butyl hydrochloride (56 mg), 1-ethyl-3-(3-dimethylaminopropyl)carbodiimide hydrochloride (WSC.HCl) (80 mg), 1-hydroxybenzotriazole (HOBt) (56 mg), N,N-diisopropylethylamine (108 mg) and N,N-dimethyl formamide (5 ml) was stirred at room temperature for 3 days. The reaction mixture was poured into water and extracted with ethyl acetate. The organic layer was washed with water and dried over $MgSO_4$. The solvent was distilled off under reduced pressure and the resulting crystals were collected by filtration to obtain tert-butyl [[[2-(3-methoxyphenyl)-6-phenyl-1H-imidazo[4,5-b]pyridin-1-yl]acetyl]amino]acetate (78 mg, 60%).

$^1$H NMR (CDCl$_3$) δ 1.41 (9H, s), 3.95 (3H, s), 3.95 (2H, d, J=5.0 Hz), 5.38 (2H, s), 7.00-7.05 (1H, m), 7.36-7.58 (6H, m), 7.95 (1H, d, J=1.6 Hz), 8.05-8.12 (3H, m), 8.40 (1H, d, J=1.4 Hz) ppm IR (KBr) ν 2980, 1748, 1667, 1292 $cm^{-1}$ HPLC (220 nm) Purity 100% (Retention time 3.24 minutes)

MS (APCI+, m/e) 473 (M+1)

Example 156

To tert-butyl [[[2-(3-methoxyphenyl)-6-phenyl-1H-imidazo[4,5-b]pyridin-1-yl]acetyl]amino] acetate (Compound of Example 155) (50 mg) was added a solution of 4 N hydrogen chloride in ethyl acetate (10.0 ml), and the mixture was stirred at room temperature for 5 hours to hydrolyze. The reaction mixture was poured into water and extracted with ethyl acetate. The organic layer was washed with water and dried over $MgSO_4$. The solvent was distilled off under reduced pressure, and the resulting crystals were collected by filtration to obtain [[[2-(3-methoxyphenyl)-6-phenyl-1H-imidazo[4,5-b]pyridin-1-yl]acetyl]amino]acetic acid (19 mg, 42%).

$^1$H NMR (DMSO-$d_6$) δ 3.87 (3H, s), 3.91 (2H, d, J=5.6 Hz), 5.58 (2H, s), 7.04-7.09 (1H, m), 7.39-7.59 (4H, m), 7.79-7.97 (4H, m), 8.65 (1H, s), 8.66 (1H, s), 8.97 (1H, t, J=5.6 Hz) ppm IR (KBr) ν 3015, 1688, 1591, 1478 $cm^{-1}$ HPLC (220 nm) Purity 93% (Retention time 2.59 minutes)

MS (APCI+, m/e) 417 (M+1)

Example 157

2-[[2-(3-methoxyphenyl)-6-phenyl-1H-imidazo[4,5-b]pyridin-1-yl]methyl]phenyl acetate (Compound of Example 153) (177 mg) was dissolved in tetrahydrofuran-methanol (1:1, v/v, 20 ml). To the solution was added 2 N lithium hydroxide (6.8 ml). The mixture was stirred at room temperature for 1.5 hour. The reaction mixture was poured into water and extracted with ethyl acetate-tetrahydrofuran (3:1, v/v). The organic layer was washed with water and dried over $MgSO_4$. The solvent was distilled off under reduced pressure, and the resulting crystals were collected by filtration to obtain 2-[[2-(3-methoxyphenyl)-6-phenyl-1H-imidazo[4,5-b]pyridin-1-yl]methyl]phenol (133 mg, 83%). The crystals were recrystallized from tetrahydrofuran-ethyl acetate.

$^1$H NMR (DMSO-$d_6$) δ 3.88 (3H, s), 5.89 (2H, s), 6.79-6.92 (2H, m), 7.03-7.08 (1H, m), 7.15-7.23 (1H, m), 7.41-7.58 (5H, m), 7.76-7.80 (2H, m), 7.93-8.00 (2H, m), 8.59 (1H, d, J=1.4 Hz), 8.75 (1H, d, J=1.4 Hz), 10.96 (1H, s) ppm IR (KBr) ν 3063, 1468, 1404, 1238 $cm^{-1}$ HPLC (220 nm) Purity 100% (Retention time 3.30 minutes)

MS (ESI+, m/e) 408 (M+1)

Example 158

To a solution consisting of 2-[[2-(3-methoxyphenyl)-6-phenyl-1H-imidazo[4,5-b]pyridin-1-yl]methyl]phenol (Compound of Example 157) (41 mg), bromoethyl acetate (18 mg), N,N-dimethyl formamide (1 ml) was added potassium carbonate (19 mg), and the mixture was stirred at room temperature for 2 hours. The reaction mixture was poured into water and extracted with ethyl acetate. The organic layer was washed with water and dried over $MgSO_4$. The solvent was distilled off under reduced pressure, and the resulting crystals were collected by filtration to obtain [2-[[2-(3-methoxyphenyl)-6-phenyl-1H-imidazo[4,5-b]pyridin-1-yl]methyl]phenoxy]ethyl acetate (37 mg, 74%).

HPLC (220 nm) Purity 100% (Retention time 3.59 minutes)

MS (APCI+, m/e) 494 (M+1)

Example 159

[2-[[2-(3-methoxyphenyl)-6-phenyl-1H-imidazo[4,5-b]pyridin-1-yl]methyl]phenoxy]ethyl acetate (Compound of Example 158) (28 mg) was dissolved in tetrahydrofuran-ethanol (1:1, v/v, 3.6 ml), and to the solution was added 2 N lithium hydroxide (1.2 ml). The mixture was stirred at room temperature for 2 hours. The reaction mixture was poured into water, and to the mixture was added 2 N hydrochloric acid to adjust the pH to 3. The mixture was extracted with ethyl acetate-tetrahydrofuran (3:1, v/v). The organic layer was washed with water and dried over $MgSO_4$. The solvent was distilled off under reduced pressure and the resulting crystals were collected by filtration to obtain [2-[[2-(3-methoxyphenyl)-6-phenyl-1H-imidazo[4,5-b]pyridin-1-yl]methyl]phenoxy]acetic acid (15 mg, 55%).

$^1$H NMR (DMSO-$d_6$) δ 3.87 (3H, s), 4.85 (2H, s), 5.98 (2H, s), 6.94-7.05 (3H, m), 7.28-7.55 (6H, m), 7.74-7.78 (2H, m), 7.96-8.03 (2H, m), 8.54 (1H, s), 8.66 (1H, s) ppm IR (KBr) ν 3403, 1605, 1474, 1235 $cm^{-1}$ HPLC (220 nm) Purity 98% (Retention time 3.27 minutes)

MS (APCI+, m/e) 466 (M+1)

Example 160

By using the compound obtained in Example 157 and 4-bromoethyl butyrate as starting materials, 4-[2-[[2-(3-methoxyphenyl)-6-phenyl-1H-imidazo[4,5-b]pyridin-1-yl]methyl]phenoxy]butyric acid was synthesized in a manner similar to Examples 158 to 159.

$^1$H NMR (DMSO-$d_6$) δ 1.95 (2H, quintet, J=6.7 Hz), 2.39 (2H, t, J=6.8 Hz), 3.86 (3H, s), 4.07 (2H, t, J=6.1 Hz), 5.96 (2H, s), 6.89-7.07 (3H, m), 7.27-7.56 (6H, m), 7.75-7.79 (2H, m), 7.93-8.01 (2H, m), 8.52 (1H, s), 8.56 (1H, s) ppm IR (KBr) ν 2940, 1713, 1470, 1244 cm$^{-1}$ HPLC (220 nm) Purity 95% (Retention time 3.34 minutes)
MS (APCI+, m/e) 494 (M+1)

Example 161

A mixture of 2-(3-methoxyphenyl)-6-phenyl-1H-imidazo[4,5-b]pyridine (Compound of Example 1) (80 mg), 2-tert-butylimino-2-diethylamino-1,3-dimethylperhydro-1,3,2-diazaphosphorine resin (PS-BEMP, 2.2 mmol/g) (181 mg) and N,N-dimethyl formamide (3.2 ml) was shaken at room temperature for 1 hour. To the mixture was added 4-fluorobenzyl chloride (46 mg), and the mixture was further shaken at room temperature for 15 hours. The resin was filtered off, and the filtrate was concentrated under reduced pressure. The residue was subjected to a preparative HPLC, and the desired fraction was concentrated. The concentrate was distributed into dichloromethane and a saturated aqueous solution of sodium bicarbonate. The organic layer was filtered by means of a PTFE filter tube, and concentrated under reduced pressure to obtain 1-(4-fluorobenzyl)-2-(3-methoxyphenyl)-6-phenyl-1H-imidazo[4,5-b]pyridine (84 mg, 78%).

$^1$H NMR (CDCl$_3$) δ 3.96 (3H, s), 5.91 (2H, s), 7.01-7.12 (3H, m), 7.39-7.57 (8H, m), 7.76 (1H, d, J=1.8 Hz), 8.09-8.18 (2H, m), 8.37 (1H, d, J=1.8 Hz) ppm HPLC (220 nm) Purity 100% (Retention time 3.72 minutes)
MS (APCI+, m/e) 410 (M+1)

By using the compound obtained in Example 1 and various alkyl halides as starting materials, the compounds of the following Examples 162 to 206 were synthesized in a manner similar to Example 161.

Example 162

1-(2-fluorobenzyl)-2-(3-methoxyphenyl)-6-phenyl-1H-imidazo[4,5-b]pyridine

HPLC (220 nm) Purity 99% (Retention time 3.52 minutes)
MS (APCI+, m/e) 410 (M+1)

Example 163

1-(3-fluorobenzyl)-2-(3-methoxyphenyl)-6-phenyl-1H-imidazo[4,5-b]pyridine

HPLC (220 nm) Purity 99% (Retention time 3.56 minutes)
MS (APCI+, m/e) 410 (M+1)

Example 164

1-(2,4-difluorobenzyl)-2-(3-methoxyphenyl)-6-phenyl-1H-imidazo[4,5-b]pyridine

HPLC (220 nm) Purity 98% (Retention time 3.59 minutes)
MS (APCI+, m/e) 428 (M+1)

Example 165

1-(3,5-difluorobenzyl)-2-(3-methoxyphenyl)-6-phenyl-1H-imidazo[4,5-b]pyridine

HPLC (220 nm) Purity 98% (Retention time 3.62 minutes)
MS (APCI+, m/e) 428 (M+1)

Example 166

1-(2,6-difluorobenzyl)-2-(3-methoxyphenyl)-6-phenyl-1H-imidazo[4,5-b]pyridine

HPLC (220 nm) Purity 99% (Retention time 3.65 minutes)
MS (APCI+, m/e) 428 (M+1)

Example 167

1-(2-chlorobenzyl)-2-(3-methoxyphenyl)-6-phenyl-1H-imidazo[4,5-b]pyridine

HPLC (220 nm) Purity 96% (Retention time 3.66 minutes)
MS (APCI+, m/e) 426 (M+1)

Example 168

1-(3,4-dichlorobenzyl)-2-(3-methoxyphenyl)-6-phenyl-1H-imidazo[4,5-b]pyridine

HPLC (220 nm) Purity 99% (Retention time 4.01 minutes)
MS (APCI+, m/e) 460 (M+1)

Example 169

1-(3-bromobenzyl)-2-(3-methoxyphenyl)-6-phenyl-1H-imidazo[4,5-b]pyridine

HPLC (220 nm) Purity 97% (Retention time 3.74 minutes)
MS (APCI+, m/e) 470 (M+1)

Example 170

2-(3-methoxyphenyl)-6-phenyl-1-[2-(trifluoromethyl)benzyl]-1H-imidazo[4,5-b]pyridine HPLC (220 nm) Purity 97% (Retention time 3.71 minutes)
MS (APCI+, m/e) 460 (M+1)

Example 171

2-(3-methoxyphenyl)-6-phenyl-1-[3-(trifluoromethyl)benzyl]-1H-imidazo[4,5-b]pyridine HPLC (220 nm) Purity 97% (Retention time 3.75 minutes)
MS (APCI+, m/e) 460 (M+1)

Example 172

2-(3-methoxyphenyl)-6-phenyl-1-[4-(trifluoromethyl)benzyl]-1H-imidazo[4,5-b]pyridine HPLC (220 nm) Purity 98% (Retention time 3.78 minutes)
MS (APCI+, m/e) 460 (M+1)

Example 173

2-(3-methoxyphenyl)-6-phenyl-1-[4-(trifluoromethoxy)benzyl]-1H-imidazo[4,5-b]pyridine HPLC (220 nm) Purity 98% (Retention time 3.84 minutes)
MS (APCI+, m/e) 476 (M+1)

Example 174

2-(3-methoxyphenyl)-1-(2-methylbenzyl)-6-phenyl-1H-imidazo[4,5-b]pyridine

HPLC (220 nm) Purity 98% (Retention time 3.65 minutes)
MS (APCI+, m/e) 406 (M+1)

Example 175

2-(3-methoxyphenyl)-1-(4-methylbenzyl)-6-phenyl-1H-imidazo[4,5-b]pyridine

HPLC (220 nm) Purity 97% (Retention time 3.72 minutes)
MS (APCI+, m/e) 406 (M+1)

Example 176

1-(3,4-dimethylbenzyl)-2-(3-methoxyphenyl)-6-phenyl-1H-imidazo[4,5-b]pyridine

HPLC (220 nm) Purity 99% (Retention time 3.95 minutes)
MS (APCI+, m/e) 420 (M+1)

Example 177

1-(4-tert-butylbenzyl)-2-(3-methoxyphenyl)-6-phenyl-1H-imidazo[4,5-b]pyridine

HPLC (220 nm) Purity 100% (Retention time 4.20 minutes)
MS (APCI+, m/e) 448 (M+1)

Example 178

1-(3-methoxybenzyl)-2-(3-methoxyphenyl)-6-phenyl-1H-imidazo[4,5-b]pyridine

HPLC (220 nm) Purity 99% (Retention time 3.71 minutes)
MS (APCI+, m/e) 422 (M+1)

Example 179

1-(4-methoxybenzyl)-2-(3-methoxyphenyl)-6-phenyl-1H-imidazo[4,5-b]pyridine

HPLC (220 nm) Purity 97% (Retention time 3.71 minutes)
MS (APCI+, m/e) 422 (M+1)

Example 180

1-(3,5-dimethoxybenzyl)-2-(3-methoxyphenyl)-6-phenyl-1H-imidazo[4,5-b]pyridine

HPLC (220 nm) Purity 98% (Retention time 3.62 minutes)
MS (APCI+, m/e) 452 (M+1)

Example 181

2-(3-methoxyphenyl)-1-(2-nitrobenzyl)-6-phenyl-1H-imidazo[4,5-b]pyridine

HPLC (220 nm) Purity 99% (Retention time 3.62 minutes)
MS (APCI+, m/e) 437 (M+1)

Example 182

2-(3-methoxyphenyl)-1-(3-nitrobenzyl)-6-phenyl-1H-imidazo[4,5-b]pyridine

HPLC (220 nm) Purity 95% (Retention time 3.52 minutes)
MS (APCI+, m/e) 437 (M+1)

Example 183

2-(3-methoxyphenyl)-1-(4-nitrobenzyl)-6-phenyl-1H-imidazo[4,5-b]pyridine

HPLC (220 nm) Purity 99% (Retention time 3.64 minutes)
MS (APCI+, m/e) 437 (M+1)

Example 184

4-[[2-(3-methoxyphenyl)-6-phenyl-1H-imidazo[4,5-b]pyridin-1-yl]methyl]benzonitrile HPLC (220 nm) Purity 93% (Retention time 3.53 minutes)
MS (APCI+, m/e) 417 (M+1)

Example 185

1-[(1,1'-biphenyl)-2-ylmethyl]-2-(3-methoxyphenyl)-6-phenyl-1H-imidazo[4,5-b]pyridine HPLC (220 nm) Purity 96% (Retention time 4.00 minutes)
MS (APCI+, m/e) 468 (M+1)

Example 186

1-[(1,1'-biphenyl)-4-ylmethyl]-2-(3-methoxyphenyl)-6-phenyl-1H-imidazo[4,5-b]pyridine HPLC (220 nm) Purity 99% (Retention time 4.10 minutes)
MS (APCI+, m/e) 468 (M+1)

Example 187

2-(3-methoxyphenyl)-1-(1-naphthylmethyl)-6-phenyl-1H-imidazo[4,5-b]pyridine

HPLC (220 nm) Purity 99% (Retention time 3.94 minutes)
MS (APCI+, m/e) 442 (M+1)

Example 188

2-(3-methoxyphenyl)-1-(2-naphthylmethyl)-6-phenyl-1H-imidazo[4,5-b]pyridine

HPLC (220 nm) Purity 100% (Retention time 3.95 minutes)
MS (APCI+, m/e) 442 (M+1)

Example 189

1-benzhydryl-2-(3-methoxyphenyl)-6-phenyl-1H-imidazo[4,5-b]pyridine

HPLC (220 nm) Purity 99% (Retention time 4.04 minutes)
MS (APCI+, m/e) 468 (M+1)

Example 190

1-(9H-fluoren-9-yl)-2-(3-methoxyphenyl)-6-phenyl-1H-imidazo[4,5-b]pyridine

HPLC (220 nm) Purity 91% (Retention time 4.06 minutes)
MS (APCI+, m/e) 466 (M+1)

Example 191

2-(3-methoxyphenyl)-1-(3-phenoxybenzyl)-6-phenyl-1H-imidazo[4,5-b]pyridine

HPLC (220 nm) Purity 99% (Retention time 4.07 minutes)
MS (APCI+, m/e) 484 (M+1)

Example 192

1-(4-benzoylbenzyl)-2-(3-methoxyphenyl)-6-phenyl-1H-imidazo[4,5-b]pyridine

HPLC (220 nm) Purity 97% (Retention time 3.88 minutes)
MS (APCI+, m/e) 496 (M+1)

Example 193

Methyl 4-[[2-(3-methoxyphenyl)-6-phenyl-1H-imidazo[4,5-b]pyridin-1-yl]methyl]benzoate HPLC (220 nm) Purity 90% (Retention time 3.62 minutes)
MS (APCI+, m/e) 450 (M+1)

Example 194

Methyl [2-(3-methoxyphenyl)-6-phenyl-1H-imidazo[4,5-b]pyridin-1-yl](phenyl)acetate HPLC (220 nm) Purity 97% (Retention time 3.71 minutes)
MS (APCI+, m/e) 450 (M+1)

Example 195

2-(3-methoxyphenyl)-1-phenacyl-6-phenyl-1H-imidazo[4,5-b]pyridine

HPLC (220 nm) Purity 90% (Retention time 3.62 minutes)
MS (APCI+, m/e) 420 (M+1)

Example 196

1-(4-chlorophenacyl)-2-(3-methoxyphenyl)-6-phenyl-1H-imidazo[4,5-b]pyridine

HPLC (220 nm) Purity 100% (Retention time 3.82 minutes)
MS (APCI+, m/e) 454 (M+1)

Example 197

1-(4-methoxyphenacyl)-2-(3-methoxyphenyl)-6-phenyl-1H-imidazo[4,5-b]pyridine

HPLC (220 nm) Purity 99% (Retention time 3.65 minutes)
MS (APCI+, m/e) 450 (M+1)

Example 198

4-[[2-(3-methoxyphenyl)-6-phenyl-1H-imidazo[4,5-b]pyridin-1-yl]acetyl]benzonitrile HPLC (220 nm) Purity 100% (Retention time 3.55 minutes)
MS (APCI+, m/e) 445 (M+1)

Example 199

2-(3-methoxyphenyl)-6-phenyl-1-[(E)-3-phenyl-2-propenyl]-1H-imidazo[4,5-b]pyridine HPLC (220 nm) Purity 99% (Retention time 3.87 minutes)
MS (APCI+, m/e) 418 (M+1)

Example 200

1-[(3,5-dimethyl-4-isoxazolyl)methyl]-2-(3-methoxyphenyl)-6-phenyl-1H-imidazo[4,5-b]pyridine HPLC (220 nm) Purity 100% (Retention time 3.38 minutes)
MS (APCI+, m/e) 411 (M+1)

Example 201

1-ethyl-2-(3-methoxyphenyl)-6-phenyl-1H-imidazo[4,5-b]pyridine

HPLC (220 nm) Purity 100% (Retention time 3.27 minutes)
MS (APCI+, m/e) 330 (M+1)

Example 202

1-(cyclopropylmethyl)-2-(3-methoxyphenyl)-6-phenyl-1H-imidazo[4,5-b]pyridine

HPLC (220 nm) Purity 97% (Retention time 3.54 minutes)
MS (APCI+, m/e) 356 (M+1)

Example 203

1-(2-cyclohexylethyl)-2-(3-methoxyphenyl)-6-phenyl-1H-imidazo[4,5-b]pyridine

HPLC (220 nm) Purity 100% (Retention time 4.15 minutes)
MS (APCI+, m/e) 412 (M+1)

Example 204

1-isobutyl-2-(3-methoxyphenyl)-6-phenyl-1H-imidazo[4,5-b]pyridine

HPLC (220 nm) Purity 94% (Retention time 3.61 minutes)
MS (APCI+, m/e) 358 (M+1)

Example 205

2-(3-methoxyphenyl)-1-(4-pentenyl)-6-phenyl-1H-imidazo[4,5-b]pyridine

HPLC (220 nm) Purity 99% (Retention time 3.68 minutes)
MS (APCI+, m/e) 370 (M+1)

Example 206

4-[2-(3-methoxyphenyl)-6-phenyl-1H-imidazo[4,5-b]pyridin-1-yl]butanenitrile

HPLC (220 nm) Purity 100% (Retention time 3.19 minutes)
MS (APCI+, m/e) 369 (M+1)

Example 207

A mixture of 2-(3-methoxyphenyl)-6-phenyl-1H-imidazo[4,5-b]pyridine (Compound of Example 1) (80 mg), 2-tert-butylimino-2-diethylamino-1,3-dimethylperhydro-1,3,2-diazaphosphorine resin (PS-BEMP, 2.2 mmol/g) (326 mg) and N,N-dimethyl formamide (4.5 ml) was shaken at room temperature for 1 hour. To the mixture was added 3-pyridylmethylchloride hydrochloride (52 mg), and the mixture was further shaken at room temperature for 15 hours. Purification was carried out in a manner similar to Example 222 to obtain 2-(3-methoxyphenyl)-6-phenyl-1-(3-pyridylmethyl)-1H-imidazo[4,5-b]pyridine (67 mg, 65%).

HPLC (220 nm) Purity 98% (Retention time 2.68 minutes)
MS (APCI+, m/e) 393 (M+1)

By using the compound obtained in Example 1 and various alkyl halides hydrochloric acid salt (or alkyl halide hydrobromic acid salts) as starting materials, the compounds of the following Examples 208 to 213 were synthesized in a manner similar to Example 207.

Example 208

2-(3-methoxyphenyl)-6-phenyl-1-(4-pyridylmethyl)-1H-imidazo[4,5-b]pyridine

HPLC (220 nm) Purity 97% (Retention time 2.60 minutes)
MS (APCI+, m/e) 393 (M+1)

Example 209

2-[[2-(3-methoxyphenyl)-6-phenyl-1H-imidazo[4,5-b]pyridin-1-yl]methyl]quinoline

HPLC (220 nm) Purity 97% (Retention time 3.67 minutes)
MS (APCI+, m/e) 443 (M+1)

Example 210

2-(3-methoxyphenyl)-6-phenyl-1-(thiazol-4-ylmethyl)-1H-imidazo[4,5-b]pyridine

HPLC (220 nm) Purity 81% (Retention time 3.28 minutes)
MS (APCI+, m/e) 399 (M+1)

Example 211

N,N-diethyl-N-[2-[2-(3-methoxyphenyl)-6-phenyl-1H-imidazo[4,5-b]pyridin-1-yl]ethyl]amine HPLC (220 nm) Purity 96% (Retention time 2.64 minutes)
MS (APCI+, m/e) 401 (M+1)

Example 212

2-(3-methoxyphenyl)-6-phenyl-1-(2-piperidinoethyl)-1H-imidazo[4,5-b]pyridine

HPLC (220 nm) Purity 96% (Retention time 2.67 minutes)
MS (APCI+, m/e) 413 (M+1)

Example 213

2-(3-methoxyphenyl)-1-(2-morpholinoethyl)-6-phenyl-1H-imidazo[4,5-b]pyridine

HPLC (220 nm) Purity 97% (Retention time 2.59 minutes)
MS (APCI+, m/e) 415 (M+1)

Example 214

Under an argon stream, a mixture of 5-bromo-2-[(E)-2-[4-(trifluoromethyl)phenyl]ethenyl]benzoxazole (Compound of Reference Example 44) (129 mg), phenylboric acid (171 mg), tetrakis(triphenylphosphine)palladium(0) (61 mg), 2 M sodium carbonate (1.05 ml), toluene (3.15 ml) and tetrahydrofuran (1.05 ml) was stirred at 90° C. for 24 hours. The reaction mixture was subjected to distribution into ethyl acetate-tetrahydrofuran (3:1, v/v) and water. The organic layer was washed with water and dried over $MgSO_4$, and the solvent was distilled off under reduced pressure. The residue was subjected silica gel column chromatography and the fraction eluted with ethyl acetate-hexane (1:6, v/v) was concentrated under reduced pressure. The resulting crystals were collected by filtration to obtain 5-phenyl-2-[(E)-2-[4-(trifluoromethyl)phenyl]ethenyl]benzoxazole (70 mg, 55%). The compound was recrystallized from ethyl acetate-hexane.

$^1$H NMR (CDCl$_3$) δ 7.18 (1H, d, J=16.6 Hz), 7.34-7.52 (3H, m), 7.60-7.75 (8H, m), 7.83 (1H, d, J=16.4 Hz), 7.93 (1H, t, J=1.3 Hz) ppm IR (KBr) ν 1337, 1121, 1073, 829 cm$^{-1}$ HPLC (220 nm) Purity 97% (Retention time 5.37 minutes)
MS (APCI+, m/e) 366 (M+1)

By using the compounds obtained in Reference Examples 43 to 45 and various boron acids as starting materials, the compounds of the following Examples 215 to 219 were synthesized in a manner similar to Example 214.

Example 215

5-phenyl-2-[(E)-2-phenylethenyl]benzoxazole

HPLC (220 nm) Purity 93% (Retention time 5.14 minutes)
MS (APCI+, m/e) 298 (M+1)

Example 216

2-[(E)-2-(2,4-difluorophenyl)ethenyl]-5-phenylbenzoxazole

HPLC (220 nm) Purity 100% (Retention time 5.26 minutes)
MS (APCI+, m/e) 334 (M+1)

Example 217

5-(2-furyl)-2-[(E)-2-phenylethenyl]benzoxazole

HPLC (220 nm) Purity 97% (Retention time 4.94 minutes)
MS (APCI+, m/e) 288 (M+1)

Example 218

5-(2-furyl)-2-[(E)-2-[4-(trifluoromethyl)phenyl]ethenyl]benzoxazole

HPLC (220 nm) Purity 92% (Retention time 5.19 minutes)
MS (APCI+, m/e) 356 (M+1)

Example 219

2-[(E)-2-(2,4-difluorophenyl)ethenyl]-5-(2-furyl)benzoxazole

HPLC (220 nm) Purity 100% (Retention time 5.06 minutes)
MS (APCI+, m/e) 324 (M+1)

Example 220

Under an argon stream, a mixture of 5-bromo-2-[(E)-2-phenylethenyl]benzoxazole (Compound of Reference Example 43) (105 mg), p-cresol (45 mg), potassium carbonate (97 mg), copper oxide(II) (70 mg) and pyridine (1.5 ml) was stirred at 130° C. for 24 hours. The reaction mixture was poured into water and the mixture was extracted with ethyl acetate. The organic layer was washed with a 5% aqueous solution of potassium hydrogen sulfate and water and dried over $MgSO_4$. The solvent was distilled off under reduced pressure, and the residue was subjected to silica gel column chromatography. The fraction eluted with ethyl acetate-hexane (1:6, v/v) was concentrated under reduced pressure, and the resulting crystals were collected by filtration to obtain 5-(4-methylphenoxy)-2-[(E)-2-phenylethenyl]benzoxazole (69 mg, 60%). The compound was recrystallized from ethyl acetate-hexane.

$^1$H NMR (CDCl$_3$) δ 2.34 (3H, S), 6.92 (2H, d, J=8.8 Hz), 7.03 (1H, dd, J=8.6, 2.2 Hz), 7.06 (1H, d, J=16.4 Hz), 7.14 (2H, d, J=8.4 Hz), 7.32 (1H, d, J=2.6 Hz), 7.38-7.48 (4H, m), 7.58-7.63 (2H, m), 7.79 (1H, d, J=16.6 Hz) ppm IR (KBr) ν 1532, 1507, 1472, 1223 cm$^{-1}$ HPLC (220 nm) Purity 95% (Retention time 5.30 minutes)
MS (APCI+, m/e) 328 (M+1)

By using the compounds obtained in Reference Examples 43 to 44 and various substituted phenols as starting materials, the compounds of the following Examples 221 to 222 were synthesized in a manner similar to Example 220.

Example 221

2-[(E)-2-phenylethenyl]-5-[4-[4-(1H-1,2,3-triazol-1-yl)butyl]phenoxy]benzoxazole HPLC (220 nm) Purity 97% (Retention time 4.76 minutes)
MS (APCI+, m/e) 437 (M+1)

Example 222

5-[4-[4-(1H-1,2,3-triazol-1-yl)butyl]phenoxy]-2-[(E)-2-[4-(trifluoromethyl)phenyl]ethenyl]benzoxazole HPLC (220 nm) Purity 100% (Retention time 5.00 minutes)
MS (APCI+, m/e) 505 (M+1)

Example 223

Under an argon stream, a mixture of 6-bromo-2-phenyl-1H-imidazo[4,5-b]pyridine (Compound of Reference Example 3) (90 mg), phenylboric acid (104 mg), tetrakis(triphenylphosphine)palladium(0) (38 mg), 2 M sodium carbonate (0.82 ml) and tetrahydrofuran (3.3 ml) was stirred at 85° C. for 24 hours. The mixture was distributed into ethyl acetate-tetrahydrofuran (3:1, v/v) and water. The organic layer was washed with water and dried over $MgSO_4$, and the solvent was distilled off under reduced pressure. The residue was subjected to silica gel column chromatography, and the fraction eluted with ethyl acetate-chloroform-hexane (1:1:4, v/v) was concentrated under reduced pressure. The resulting crystals were collected by filtration to obtain 2,6-diphenyl-1H-imidazo[4,5-b]pyridine (20 mg, 22%). The crystals were recrystallized from chloroform-methanol.

HPLC (220 nm) Purity 97% (Retention time 2.78 minutes)
MS (ESI+, m/e) 272 (M+1)

By using the compounds obtained in Reference Examples 3, 11 and 16 and various boron acids as starting materials, the compounds of the following Examples 224 to 237 were synthesized in a manner similar to Example 223. At that time, purification by means of recrystallization or silica gel column chromatography was carried out as required.

Example 224

2-cyclohexyl-6-phenyl-1H-imidazo[4,5-b]pyridine

HPLC (220 nm) Purity 85% (Retention time 2.74 minutes)
MS (ESI+, m/e) 278 (M+1)

Example 225

6-(2-fluorophenyl)-2-phenyl-1H-imidazo[4,5-b]pyridine

HPLC (220 nm) Purity 99% (Retention time 2.88 minutes)
MS (APCI+, m/e) 290 (M+1)

Example 226

2-cyclohexyl-6-(2-fluorophenyl)-1H-imidazo[4,5-b]pyridine

HPLC (220 nm) Purity 99% (Retention time 2.79 minutes)
MS (APCI+, m/e) 296 (M+1)

Example 227

6-(1-naphthyl)-2-phenyl-1H-imidazo[4,5-b]pyridine

HPLC (220 nm) Purity 100% (Retention time 3.18 minutes)
MS (APCI+, m/e) 322 (M+1)

Example 228

2-cyclohexyl-6-(1-naphthyl)-1H-imidazo[4,5-b]pyridine

HPLC (220 nm) Purity 96% (Retention time 3.11 minutes)
MS (APCI+, m/e) 328 (M+1)

Example 229

2-cyclohexyl-6-(3-methoxyphenyl)-1H-imidazo[4,5-b]pyridine

HPLC (220 nm) Purity 100% (Retention time 2.83 minutes)
MS (APCI+, m/e) 308 (M+1)

Example 230

6-(3-methoxyphenyl)-2-phenyl-1H-imidazo[4,5-b]pyridine

HPLC (220 nm) Purity 100% (Retention time 2.87 minutes)
MS (APCI+, m/e) 302 (M+1)

Example 231

2-cyclohexyl-6-[3-(trifluoromethyl)phenyl]-1H-imidazo[4,5-b]pyridine

HPLC (220 nm) Purity 97% (Retention time 3.13 minutes)
MS (APCI+, m/e) 346 (M+1)

Example 232

4-(2-phenyl-1H-imidazo[4,5-b]pyridin-6-yl)benzonitrile

HPLC (220 nm) Purity 100% (Retention time 2.87 minutes)
MS (APCI+, m/e) 297 (M+1)

Example 233

4-(2-cyclohexyl-1H-imidazo[4,5-b]pyridin-6-yl)benzonitrile

HPLC (220 nm) Purity 99% (Retention time 2.71 minutes)
MS (APCI+, m/e) 303 (M+1)

Example 234

6-[4-(methylsulfonyl)phenyl]-2-phenyl-1H-imidazo[4,5-b]pyridine

HPLC (220 nm) Purity 80% (Retention time 2.58 minutes)
MS (APCI+, m/e) 350 (M+1)

Example 235

2-cyclohexyl-6-[4-(methylsulfonyl)phenyl]-1H-imidazo[4,5-b]pyridine

HPLC (220 nm) Purity 96% (Retention time 2.48 minutes)
MS (APCI+, m/e) 356 (M+1)

Example 236

6-(2-fluorophenyl)-2-(2-naphthyl)-1H-imidazo[4,5-b]pyridine

HPLC (220 nm) Purity 98% (Retention time 3.34 minutes)
MS (APCI+, m/e) 340 (M+1)

Example 237

2-(2-naphthyl)-6-phenyl-1H-imidazo[4,5-b]pyridine

HPLC (220 nm) Purity 100% (Retention time 3.21 minutes)
MS (APCI+, m/e) 322 (M+1)

Example 238

Under an argon stream, a mixture of 6-bromo-2-phenyl-1H-imidazo[4,5-b]pyridine (Compound of Reference Example 3) (90 mg), 2-(tributylstanyl)furan (305 mg), dichlorobis(triphenylphosphine)palladium(II) (23 mg) and N,N-dimethyl formamide (4 ml) was stirred at 80° C. for 24 hours. The reaction mixture was poured into water and extracted with ethyl acetate-tetrahydrofuran (3:1, v/v). The organic layer was washed with water and dried over MgSO$_4$, and the solvent was distilled off under reduced pressure. The residue was subjected to silica gel column chromatography, and the fraction eluted with ethyl acetate-chloroform-hexane (1:1:4, v/v) were concentrated under reduced pressure. The resulting crystals were collected by filtration to obtain 6-(2-furyl)-2-phenyl-1H-imidazo[4,5-b]pyridine (49 mg, 57%).

HPLC (220 nm) Purity 100% (Retention time 2.66 minutes)
MS (APCI+, m/e) 262 (M+1)

By using the compounds obtained in Reference Examples 3, 11 and 16 and various tributyl tin compounds as starting materials, the compounds of the following Examples 239 to 241 were synthesized in a manner similar to Example 238. At that time, purification by means of recrystallization or silica gel column chromatography was carried out as required.

Example 239

2-cyclohexyl-6-(2-furyl)-1H-imidazo[4,5-b]pyridine

HPLC (220 nm) Purity 99% (Retention time 2.57 minutes)
MS (APCI+, m/e) 268 (M+1)

Example 240

6-(2-furyl)-2-(2-naphthyl)-1H-imidazo[4,5-b]pyridine

HPLC (220 nm) Purity 98% (Retention time 3.18 minutes)
MS (APCI+, m/e) 312 (M+1)

Example 241

2-(2-naphthyl)-6-(2-thienyl)-1H-imidazo[4,5-b]pyridine

HPLC (220 nm) Purity 99% (Retention time 3.31 minutes)
MS (APCI+, m/e) 328 (M+1)

By using various carboxylic acids as one of the starting materials, the compounds of the following Examples 242 to 254 were synthesized in a manner similar to Reference Example 67.

Example 242

6-bromo-2-(3-methoxyphenyl)benzoxazole

HPLC (220 nm) Purity 97% (Retention time 4.85 minutes)
MS (APCI+, m/e) 304 (M+1)

Example 243

6-bromo-2-(2-naphthyl)benzoxazole

HPLC (220 nm) Purity 95% (Retention time 5.41 minutes)
MS (APCI+, m/e) 324 (M+1)

Example 244

6-bromo-2-phenylbenzoxazole

HPLC (220 nm) Purity 99% (Retention time 4.83 minutes)
MS (APCI+, m/e) 274 (M+1)

Example 245

6-bromo-2-(3-methylphenyl)benzoxazole

HPLC (220 nm) Purity 97% (Retention time 5.12 minutes)
MS (APCI+, m/e) 288 (M+1)

Example 246

6-bromo-2-(4-methoxyphenyl)benzoxazole

HPLC (220 nm) Purity 98% (Retention time 4.81 minutes)
MS (APCI+, m/e) 304 (M+1)

Example 247

6-bromo-2-(3,4-dimethoxyphenyl)benzoxazole

HPLC (220 nm) Purity 95% (Retention time 4.50 minutes)
MS (APCI+, m/e) 334 (M+1)

Example 248

6-bromo-2-(2-methoxyphenyl)benzoxazole

HPLC (220 nm) Purity 99% (Retention time 4.41 minutes)
MS (APCI+, m/e) 304 (M+1)

Example 249

6-bromo-2-(3,4,5-trimethoxyphenyl)benzoxazole

HPLC (220 nm) Purity 99% (Retention time 4.57 minutes)
MS (APCI+, m/e) 364 (M+1)

Example 250

6-bromo-2-(3-fluorophenyl)benzoxazole

HPLC (220 nm) Purity 96% (Retention time 4.95 minutes)
MS (APCI+, m/e) 292 (M+1)

Example 251

6-bromo-2-[3-(trifluoromethyl)phenyl]benzoxazole

HPLC (220 nm) Purity 99% (Retention time 5.23 minutes)
MS (APCI+, m/e) 342 (M+1)

Example 252

6-bromo-2-[3-(trifluoromethoxy)phenyl]benzoxazole

HPLC (220 nm) Purity 100% (Retention time 5.30 minutes)
MS (APCI+, m/e) 358 (M+1)

Example 253

3-(6-bromobenzoxazol-2-yl)benzamide

HPLC (220 nm) Purity 98% (Retention time 3.65 minutes)
MS (APCI+, m/e) 317 (M+1)

Example 254

6-bromo-2-(3-butoxyphenyl)benzoxazole

HPLC (220 nm) Purity 99% (Retention time 5.71 minutes)
MS (APCI+, m/e) 346 (M+1)

Example 255

To a mixture of 3-(6-bromobenzoxazol-2-yl)benzamide (Compound of Example 253) (1.09 g), pyridine (0.41 g) and N,N-dimethyl formamide (20 ml) was added dropwise oxalyl chloride (0.52 g) at 0° C., and the mixture was stirred at 0° C. for 50 minutes. The reaction mixture was poured into water, and the mixture was extracted with ethyl acetate. The organic layer was washed with 1 N hydrochloric acid, water, a saturated aqueous solution of sodium bicarbonate and water, successively, and dried over $MgSO_4$. The solvent was distilled off under reduced pressure, and the resulting crystals were collected by filtration to obtain 3-(6-bromobenzoxazol-2-yl)benzonitrile (949 mg, 92%).

$^1$H NMR ($CDCl_3$) δ 7.53 (1H, dd, J=8.7, 1.7 Hz), 7.64-7.72 (2H, m), 7.80 (1H, d, J=1.8 Hz), 7.84 (1H, dt, J=7.7, 1.5 Hz), 8.45-8.53 (2H, m) ppm IR (KBr) ν 2232, 1333, 804 cm$^{-1}$
HPLC (220 nm) Purity 98% (Retention time 4.57 minutes)
MS (ESI+, m/e) 299 (M+1)

By using various carboxylic acids as starting materials, the compounds of the following Examples 256 to 266 were synthesized in a manner similar to Reference Example 67.

Example 256

6-bromo-2-[3-[(trifluoromethyl)thio]phenyl]benzoxazole

HPLC (220 nm) Purity 98% (Retention time 5.42 minutes)
MS (APCI+, m/e) 374 (M+1)

Example 257

6-bromo-2-[3-fluoro-5-(trifluoromethyl)phenyl]benzoxazole

HPLC (220 nm) Purity 100% (Retention time 5.28 minutes)
MS (APCI+, m/e) 360 (M+1)

Example 258

6-bromo-2-(3-ethoxyphenyl)benzoxazole

HPLC (220 nm) Purity 100% (Retention time 5.13 minutes)
MS (APCI+, m/e) 318 (M+1)

Example 259

2-[3,5-bis(trifluoromethyl)phenyl]-6-bromobenzoxazole

HPLC (220 nm) Purity 100% (Retention time 5.48 minutes)
MS (APCI+, m/e) 410 (M+1)

Example 260

6-bromo-2-(3,5-difluorophenyl)benzoxazole

HPLC (220 nm) Purity 100% (Retention time 5.07 minutes)
MS (APCI+, m/e) 310 (M+1)

Example 261

6-bromo-2-(3-phenoxyphenyl)benzoxazole

HPLC (220 nm) Purity 100% (Retention time 5.46 minutes)
MS (APCI+, m/e) 366 (M+1)

Example 262

6-bromo-2-(5-methyl-2-thienyl)benzoxazole

HPLC (220 nm) Purity 99% (Retention time 4.91 minutes)
MS (APCI+, m/e) 294 (M+1)

Example 263

2-(1-benzofuran-2-yl)-6-bromobenzoxazole

HPLC (220 nm) Purity 99% (Retention time 4.92 minutes)
MS (APCI+, m/e) 314 (M+1)

Example 264

2-(1-benzothiophen-2-yl)-6-bromobenzoxazole

HPLC (220 nm) Purity 97% (Retention time 5.31 minutes)
MS (APCI+, m/e) 330 (M+1)

Example 265

6-(6-bromobenzoxazol-2-yl)quinoline

HPLC (220 nm) Purity 97% (Retention time 3.40 minutes)
MS (APCI+, m/e) 325 (M+1)

Example 266

6-bromo-2-(3-nitrophenyl)benzoxazole

HPLC (220 nm) Purity 99% (Retention time 4.70 minutes)
MS (APCI+, m/e) 319 (M+1)

Example 267

To a mixture of 6-bromo-2-(3-nitrophenyl)benzoxazole (Compound of Example 266) (5.96 g), nickel bromide(II) (204 mg), methanol (100 ml), tetrahydrofuran (100 ml) was added sodium borohydride (2.12 g) little by little at 0° C. The mixture was stirred at 0° C. for 10 minutes and at room temperature for 1 hour. The reaction mixture was poured into a saturated aqueous solution of sodium bicarbonate and extracted with ethyl acetate. The organic layer was washed with water, dried over MgSO$_4$ and treated with activated carbon. The solvent was distilled off under reduced pressure, and resulting crystals were collected by filtration to obtain 3-(6-bromobenzoxazol-2-yl)aniline (4.46 g, 83%).

$^1$H NMR (CDCl$_3$) δ 3.86 (2H, s), 6.86 (1H, ddd, J=7.8, 2.3, 0.8 Hz), 7.26-7.37 (2H, m), 7.47 (1H, dd, J=8.5, 1.9 Hz), 7.54-7.64 (2H, m), 7.74 (1H, d, J=1.8 Hz) ppm
IR (KBr) ν 3206, 1456, 1335 cm$^{-1}$
HPLC (220 nm) Purity 85% (Retention time 3.28 minutes)
MS (APCI+, m/e) 289 (M+1)

Example 268

To a solution of 3-(6-bromobenzoxazol-2-yl)aniline (Compound of Example 267) (925 mg), triethylamine (390 mg) and tetrahydrofuran (35 ml) was added acetyl chloride (276 mg) at room temperature. The mixture was stirred at room temperature for 1 hour. The reaction mixture was poured into water, and extracted with ethyl acetate-tetrahydrofuran (3:1, v/v). The organic layer was washed with 1 N hydrochloric acid, water, a saturated aqueous solution of sodium bicarbonate and water, successively and dried over MgSO$_4$. The solvent was distilled off under reduced pressure, and the resulting crystals were collected by filtration to obtain N-[3-(6-bromobenzoxazol-2-yl)phenyl]acetamide (923 mg, 87%).

$^1$H NMR (CDCl$_3$) δ 2.24 (3H, s), 7.34-7.39 (1H, m), 7.45-7.53 (2H, m), 7.62 (1H, d, J=8.0 Hz), 7.74 (1H, d, J=1.8 Hz), 7.79-7.84 (1H, m), 7.96-8.00 (1H, m), 8.28 (1H, s) ppm IR (KBr) ν 3274, 1663, 1564 cm$^{-1}$
HPLC (220 nm) Purity 86% (Retention time 4.00 minutes)
MS (ESI+, m/e) 331 (M+1)

By using the compound obtained in Example 267 and benzoyl chloride as starting materials, the compound of the following Example 269 was synthesized in a manner similar to Example 268.

Example 269

N-[3-(6-bromobenzoxazol-2-yl)phenyl]benzamide

HPLC (220 nm) Purity 89% (Retention time 4.72 minutes)
MS (ESI+, m/e) 393 (M+1)

Example 270

To a solution of 3-(6-bromobenzoxazol-2-yl)aniline (Compound of Example 267) (925 mg), triethylamine (490 mg), 4-dimethylaminopyridine (39 mg) and tetrahydrofuran (35 ml) was added methanesulfonyl chloride (440 mg) at room temperature, and the mixture was stirred at room temperature for 2 hours. The reaction mixture was poured into water and extracted with ethyl acetate. The organic layer was washed with 1 N hydrochloric acid, water, a saturated aqueous solution of sodium bicarbonate and water, successively, and dried over MgSO$_4$. The solvent was distilled off under reduced pressure, and the resulting crystals were collected by filtration to obtain N-[3-(6-bromobenzoxazol-2-yl)phenyl] methane sulfonamide (686 mg, 58%). The crystals were recrystallized from ethyl acetate-hexane.

$^1$H NMR (DMSO-d$_6$) δ 3.07 (3H, s), 7.44-7.48 (1H, m), 7.55-7.63 (2H, m), 7.79 (1H, d, J=8.8 Hz), 7.90-7.94 (1H, m), 8.08-8.15 (2H, m), 10.13 (1H, s) ppm
IR (KBr) ν 3270, 1321, 1159 cm$^{-1}$
HPLC (220 nm) Purity 93% (Retention time 4.10 minutes)
MS (ESI+, m/e) 367 (M+1)

Example 271

To a solution of 3-(6-bromobenzoxazol-2-yl)aniline (Compound of Example 267) (925 mg) in pyridine (15 ml) was added ethyl isocyanate (680 mg) at room temperature, and the mixture was stirred at room temperature for 3 hours. The reaction mixture was poured into water and extracted with ethyl acetate-tetrahydrofuran (3:1, v/v). The organic layer was washed with 1 N hydrochloric acid, water, a saturated aqueous solution of sodium bicarbonate and water, successively, and dried over MgSO$_4$. The solvent was distilled off under reduced pressure, and the resulting crystals were collected by filtration to obtain N-[3-(6-bromobenzoxazol-2-yl)phenyl]-N'-ethylurea (986 mg, 86%).

$^1$H NMR (DMSO-d$_6$) δ 1.09 (3H, t, J=7.2 Hz), 3.15 (2H, quintet, J=6.7 Hz), 6.20 (1H, t, J=5.5 Hz), 7.40-7.60 (3H, m), 7.70-7.78 (2H, m), 8.12 (1H, d, J=1.4 Hz), 8.46 (1H, s), 8.78 (1H, s) ppm
IR (KBr) ν 3281, 1645, 1570 cm$^{-1}$
HPLC (220 nm) Purity 92% (Retention time 4.10 minutes)
MS (ESI+, m/e) 360 (M+1)

Example 272

To a solution of 6-bromo-2-(3-methoxyphenyl)benzoxazole (Compound of Example 242) (19.45 g) in chloroform (800 ml) was added dropwise boron tribromide (100.05 g) at 0° C., and the mixture was stirred at room temperature for 4 hours and 65° C. for 9 hours. The reaction mixture was poured into water, and the mixture was stirred at room temperature for 30 minutes and extracted with chloroform-tetrahydrofuran (4:1, v/v). The organic layer was washed with water and dried over MgSO$_4$, and the solvent was distilled off under reduced pressure. The resulting crystals were collected by filtration to obtain 3-(6-bromobenzoxazol-2-yl)phenol (16.46 g, 89%).

$^1$H NMR (DMSO-d$_6$) δ 7.03 (1H, ddd, J=8.2, 2.4, 0.9 Hz), 7.41 (1H, t, J=7.9 Hz), 7.54-7.65 (3H, m), 7.75 (1H, d, J=8.4 Hz), 8.09 (1H, d, J=1.8 Hz), 9.95 (1H, s) ppm
IR (KBr) ν 3094, 1460, 1300 cm$^{-1}$
HPLC (220 nm) Purity 97% (Retention time 4.14 minutes)
MS (APCI+, m/e) 290 (M+1)

Example 273

To a solution of 3-(6-bromobenzoxazol-2-yl)phenol (Compound of Example 272) (1.02 g) in N,N-dimethyl formamide (6 ml) were added 2-iodopropane (0.68 g) and potassium carbonate (0.63 g) at 50° C., and the mixture was stirred at 50° C. for 1.5 hour. To the mixture were further added 2-iodopropane (0.34 g) and potassium carbonate (0.31 g), and the mixture was further stirred at 50° C. for 1 hour. The reaction mixture was poured into water and extracted with ethyl acetate-tetrahydrofuran (3:1, v/v). The organic layer was washed with water and dried over MgSO$_4$. The solvent was distilled off under reduced pressure, and the residue was subjected to silica gel column chromatography. The fraction eluted with ethyl acetate-hexane (1:20 to 1:6, v/v) was concentrated under reduced pressure to isolate 6-bromo-2-(3-isopropoxyphenyl)benzoxazole (896 mg, 77%).

$^1$H NMR (CDCl$_3$) δ 1.39 (6H, d, J=6.2 Hz), 4.69 (1H, sevenplet, J=6.0 Hz), 7.08 (1H, ddd, J=8.4, 2.6, 1.0 Hz), 7.38-7.50 (2H, m), 7.63 (1H, d, J=8.8 Hz), 7.73-7.82 (3H, m) ppm
IR (KBr) ν 2975, 1557, 1265 cm$^{-1}$
HPLC (220 nm) Purity 100% (Retention time 5.30 minutes)
MS (APCI+, m/e) 332 (M+1)

By using the compound obtained in Example 272 and various alkyl halides as starting materials, the compounds of the following Examples 274 to 279 were synthesized in a manner similar to Example 273.

Example 274

6-bromo-2-[3-(hexyloxy)phenyl]benzoxazole

HPLC (220 nm) Purity 99% (Retention time 6.33 minutes)
MS (APCI+, m/e) 374 (M+1)

Example 275

6-bromo-2-[3-(3-methylbuthoxy)phenyl]benzoxazole

HPLC (220 nm) Purity 98% (Retention time 5.90 minutes)
MS (APCI+, m/e) 360 (M+1)

Example 276

6-bromo-2-[3-(cyclopentyloxy)phenyl]benzoxazole

HPLC (220 nm) Purity 100% (Retention time 5.75 minutes)
MS (APCI+, m/e) 358 (M+1)

Example 277

6-bromo-2-[3-(cyclopropylmethoxy)phenyl]benzoxazole

HPLC (220 nm) Purity 99% (Retention time 5.29 minutes)
MS (APCI+, m/e) 344 (M+1)

Example 278

2-[3-(benzyloxy)phenyl]-6-bromobenzoxazole

HPLC (220 nm) Purity 100% (Retention time 5.41 minutes)
MS (APCI+, m/e) 380 (M+1)

Example 279 tert-butyl [3-(6-bromobenzoxazol-2-yl)phenoxy]acetate

HPLC (220 nm) Purity 100% (Retention time 5.12 minutes)
MS (APCI+, m/e) 404 (M+1)

Example 280

To a solution of tert-butyl [3-(6-bromobenzoxazol-2-yl)phenoxy]acetate (Compound of Example 279) (2.22 g) in tetrahydrofuran (10 ml) was added 4 N hydrochloric acid-ethyl acetate (50 ml), and the mixture was stirred at room temperature for 2 hours. The reaction mixture was poured into water and extracted with ethyl acetate-tetrahydrofuran (3:1, v/v). The organic layer was washed with water and dried over MgSO$_4$. The solvent was distilled off under reduced pressure, and the resulting crystals were collected by filtration to obtain [3-(6-bromobenzoxazol-2-yl)phenoxy]acetic acid (1.27 g, 66%). The crystals were recrystallized from tetrahydrofuran-ethyl acetate.

$^1$H NMR (DMSO-d$_6$) δ 4.83 (2H, s), 7.19-7.25 (1H, m), 7.50-7.64 (3H, m), 7.76-7.80 (2H, m), 8.12 (1H, d, J=1.8 Hz) ppm
IR (KBr) ν 2913, 1717, 1327 cm$^{-1}$
HPLC (220 nm) Purity 99% (Retention time 4.06 minutes)
MS (APCI+, m/e) 348 (M+1)

Example 281

[3-(6-Bromobenxoxazol-2-yl)phenoxy]acetic acid (Compound of Example 280) (1.17 g) was dissolved in tetrahydrofuran (35 ml) and to the mixture were added oxalyl chloride (0.51 g) and N,N-dimethyl formamide (15 μl), successively. The mixture was stirred at room temperature for 2 hours, and the solvent and excessive oxalyl chloride were distilled off under reduced pressure. The residue was dissolved in tetrahydrofuran (11 ml), and to the solution was added a 40% aqueous solution of methylamine (9 ml) at 0° C. The mixture was stirred at room temperature for 1 hour. The reaction mixture was poured into water and extracted with ethyl acetate-tetrahydrofuran (3:1, v/v). The organic layer was washed with water and dried over MgSO$_4$. The solvent was distilled off under reduced pressure, and the resulting crystals were collected by filtration to obtain 2-[3-(6-bromobenzoxazol-2-yl)phenoxy]-N-methylacetamide (1.16 g, 96%).

$^1$H NMR (CDCl$_3$) δ 2.95 (3H, d, J=5.0 Hz), 4.61 (2H, s), 6.64 (1H, broad s), 7.11 (1H, ddd, J=8.4, 2.8, 1.2 Hz), 7.45-7.53 (2H, m), 7.64 (1H, d, J=8.0 Hz), 7.76-7.80 (2H, m), 7.91 (1H, ddd, J=8.0, 1.4, 0.7 Hz) ppm
IR (KBr) ν 3330, 167.8, 1055 cm$^{-1}$
HPLC (220 nm) Purity 100% (Retention time 3.98 minutes)
MS (APCI+, m/e) 361 (M+1)

By using the compound obtained in Example 272 and various alkyl halides as starting materials, the compounds of the following Examples 282 to 284 were synthesized in a manner similar to Example 273.

Example 282

6-bromo-2-(3-(2-methoxyethoxy)phenyl)benzoxazole

HPLC (220 nm) Purity 98% (Retention time 4.65 minutes)
MS (ACPI+, m/e) 348 (M+1)

Example 283

4-(3-(6-bromobenzoxazol-2-yl)phenoxy)butanenitrile

HPLC (220 nm) Purity 98% (Retention time 4.65 minutes)
MS (ACPI+, m/e) 357 (M+1)

Example 284

6-bromo-2-(3-(2-morpholinoehoxy)phenyl)benzoxazole

HPLC (220 nm) Purity 99% (Retention time 3.30 minutes)
MS (ACPI+, m/e) 403 (M+1)

By using the compounds obtained in Reference Examples 46 to 51 and various boron acids as starting materials, the compounds of the following Examples 285 to 302 were synthesized in a manner similar to Example 1. At that time, purification by means of recrystallization or silica gel column chromatography was carried out as required.

Example 285

2-(3-methylphenyl)-6-phenyl-1H-imidazo[4,5-b]pyridine

HPLC (220 nm) Purity 100% (Retention time 3.14 minutes)
MS (APCI+, m/e) 286 (M+1)

Example 286

2-(3-ethoxyphenyl)-6-phenyl-1H-imidazo[4,5-b]pyridine

HPLC (220 nm) Purity 96% (Retention time 3.27 minutes)
MS (APCI+, m/e) 316 (M+1)

Example 287

6-phenyl-2-(3-propoxyphenyl)-1H-imidazo[4,5-b]pyridine

HPLC (220 nm) Purity 97% (Retention time 3.49 minutes)
MS (APCI+, m/e) 330 (M+1)

Example 288

2-(3-isopropoxyphenyl)-6-phenyl-1H-imidazo[4,5-b]pyridine

HPLC (220 nm) Purity 98% (Retention time 3.40 minutes)
MS (APCI+, m/e) 330 (M+1)

Example 289

2-(3-butoxyphenyl)-6-phenyl-1H-imidazo[4,5-b]pyridine

HPLC (220 nm) Purity 98% (Retention time 3.68 minutes)
MS (APCI+, m/e) 344 (M+1)

Example 290

2-(4-methoxy-3-methylbenzyl)-6-phenyl-1H-imidazo[4,5-b]pyridine

HPLC (220 nm) Purity 99% (Retention time 3.19 minutes)
MS (APCI+, m/e) 330 (M+1)

Example 291

6-(2-fluorophenyl)-2-(3-methylphenyl)-1H-imidazo[4,5-b]pyridine

HPLC (220 nm) Purity 99% (Retention time 3.24 minutes)
MS (APCI+, m/e) 304 (M+1)

Example 292

2-(3-ethoxyphenyl)-6-(2-fluorophenyl)-1H-imidazo[4,5-b]pyridine

HPLC (220 nm) Purity 100% (Retention time 3.38 minutes)
MS (APCI+, m/e) 334 (M+1)

Example 293

6-(2-fluorophenyl)-2-(3-propoxyphenyl)-1H-imidazo[4,5-b]pyridine

HPLC (220 nm) Purity 99% (Retention time 3.60 minutes)
MS (APCI+, m/e) 348 (M+1)

Example 294

6-(2-fluorophenyl)-2-(3-isopropoxyphenyl)-1H-imidazo[4,5-b]pyridine

HPLC (220 nm) Purity 98% (Retention time 3.50 minutes)
MS (APCI+, m/e) 348 (M+1)

Example 295

2-(3-butoxyphenyl)-6-(2-fluorophenyl)-1H-imidazo[4,5-b]pyridine

HPLC (220 nm) Purity 99% (Retention time 3.79 minutes)
MS (APCI+, m/e) 362 (M+1)

Example 296

6-(2-fluorophenyl)-2-(4-methoxy-3-methylbenzyl)-1H-imidazo[4,5-b]pyridine

HPLC (220 nm) Purity 98% (Retention time 3.25 minutes)
MS (APCI+, m/e) 348 (M+1)

Example 297

6-(2-furyl)-2-(3-methylphenyl)-1H-imidazo[4,5-b]pyridine

HPLC (220 nm) Purity 99% (Retention time 3.03 minutes)
MS (APCI+, m/e) 276 (M+1)

Example 298

2-(3-ethoxyphenyl)-6-(2-furyl)-1H-imidazo[4,5-b]pyridine

HPLC (220 nm) Purity 94% (Retention time 3.20 minutes)
MS (APCI+, m/e) 306 (M+1)

Example 299

6-(2-furyl)-2-(3-propoxyphenyl)-1H-imidazo[4,5-b]pyridine

HPLC (220 nm) Purity 95% (Retention time 3.43 minutes)
MS (APCI+, m/e) 320 (M+1)

Example 300

6-(2-furyl)-2-(3-isopropoxyphenyl)-1H-imidazo[4,5-b]pyridine

HPLC (220 nm) Purity 95% (Retention time 3.34 minutes)
MS (APCI+, m/e) 320 (M+1)

Example 301

2-(3-butoxyphenyl)-6-(2-furyl)-1H-imidazo[4,5-b]pyridine

HPLC (220 nm) Purity 96% (Retention time 3.66 minutes)
MS (APCI+, m/e) 334 (M+1)

Example 302

6-(2-furyl)-2-(4-methoxy-3-methylbenzyl)-1H-imidazo[4,5-b]pyridine

HPLC (220 nm) Purity 96% (Retention time 3.06 minutes)
MS (APCI+, m/e) 320 (M+1)

By using the compounds obtained in Reference Examples 2, 10, 15 and 23 and various boron acids as starting materials, the compounds of the following Examples 303 to 311 were synthesized in a manner similar to Example 1. At that time, purification by means of recrystallization or silica gel column chromatography was carried out as required.

Example 303

2-(3,4-dimethoxybenzyl)-6-[(E)-2-phenylethenyl]-1H-imidazo[4,5-b]pyridine

HPLC (220 nm) Purity 100% (Retention time 3.17 minutes)
MS (APCI+, m/e) 372 (M+1)

Example 304

2-(phenoxymethyl)-6-[(E)-2-phenylethenyl]-1H-imidazo[4,5-b]pyridine

HPLC (220 nm) Purity 99% (Retention time 3.46 minutes)
MS (APCI+, m/e) 328 (M+1)

Example 305

2,6-bis[(E)-2-phenylethenyl]-1H-imidazo[4,5-b]pyridine

HPLC (220 nm) Purity 98% (Retention time 3.45 minutes)
MS (APCI+, m/e) 324 (M+1)

Example 306

6-(2-acetylphenyl)-2-(3-methoxyphenyl)-1H-imidazo[4,5-b]pyridine

HPLC (220 nm) Purity 93% (Retention time 2.97 minutes)
MS (APCI+, m/e) 344 (M+1)

Example 307

6-(2-acetylphenyl)-2-(3,4-dimethoxybenzyl)-1H-imidazo[4,5-b]pyridine

HPLC (220 nm) Purity 91% (Retention time 2.76 minutes)
MS (APCI+, m/e) 388 (M+1)

Example 308

6-(2-acetylphenyl)-2-(phenoxymethyl)-1H-imidazo[4,5-b]pyridine

HPLC (220 nm). Purity 98% (Retention time 3.05 minutes)
MS (APCI+, m/e) 344 (M+1)

Example 309

6-(2-acetylphenyl)-2-[(E)-2-phenylethenyl]-1H-imidazo[4,5-b]pyridine

HPLC (220 nm) Purity 90% (Retention time 3.04 minutes)
MS (APCI+, m/e) 340 (M+1)

Example 310

2-(3-methoxyphenyl)-6-(3-pyridyl)-1H-imidazo[4,5-b]pyridine

HPLC (220 nm) Purity 92% (Retention time 2.20 minutes)
MS (APCI+, m/e) 303 (M+1)

Example 311

2-(3,4-dimethoxybenzyl)-6-(3-pyridyl)-1H-imidazo[4,5-b]pyridine

HPLC (220 nm) Purity 95% (Retention time 2.01 minutes)
MS (APCI+, m/e) 347 (M+1)

By using the compounds obtained in Reference Examples 52 to 59 and various boron acids as starting materials, the compounds of the following Examples 312 to 335 were synthesized in a manner similar to Example 1. At that time, purification by means of recrystallization or silica gel column chromatography was carried out as required.

Example 312

2-[3-(hexyloxy)phenyl]-6-phenyl-1H-imidazo[4,5-b]pyridine

HPLC (220 nm) Purity 99% (Retention time 4.07 minutes)
MS (APCI+, m/e) 372 (M+1)

Example 313

2-[3-(3-buthenyloxy)phenyl]-6-phenyl-1H-imidazo[4,5-b]pyridine

HPLC (220 nm) Purity 99% (Retention time 3.56 minutes)
MS (APCI+, m/e) 342 (M+1)

Example 314

2-[3-(3-methylbuthoxy)phenyl]-6-phenyl-1H-imidazo[4,5-b]pyridine

HPLC (220 nm) Purity 97% (Retention time 3.86 minutes)
MS (APCI+, m/e) 358 (M+1)

Example 315

2-[3-(neopentyloxy)phenyl]-6-phenyl-1H-imidazo[4,5-b]pyridine

HPLC (220 nm) Purity 99% (Retention time 3.89 minutes)
MS (APCI+, m/e) 358 (M+1)

Example 316

2-[3-(cyclohexylmethoxy)phenyl]-6-phenyl-1H-imidazo[4,5-b]pyridine

HPLC (220 nm) Purity 97% (Retention time 4.11 minutes)
MS (APCI+, m/e) 384 (M+1)

Example 317

2-[3-(cyclopentyloxy)phenyl]-6-phenyl-1H-imidazo[4,5-b]pyridine

HPLC (220 nm) Purity 99% (Retention time 3.69 minutes)
MS (APCI+, m/e) 356 (M+1)

Example 318

6-phenyl-2-[3-(2-phenylehoxy)phenyl]-1H-imidazo[4,5-b]pyridine

HPLC (220 nm) Purity 98% (Retention time 3.81 minutes)
MS (APCI+, m/e) 392 (M+1)

Example 319

2-(3-ethoxyphenyl)-6-phenyl-1H-imidazo[4,5-b]pyridine

HPLC (220 nm) Purity 96% (Retention time 3.33 minutes)
MS (APCI+, m/e) 300 (M+1)

Example 320

6-(2-fluorophenyl)-2-[3-(hexyloxy)phenyl]-1H-imidazo[4,5-b]pyridine

HPLC (220 nm) Purity 98% (Retention time 4.18 minutes)
MS (APCI+, m/e) 390 (M+1)

Example 321

2-[3-(3-buthenyloxy)phenyl]-6-(2-fluorophenyl)-1H-imidazo[4,5-b]pyridine

HPLC (220 nm) Purity 100% (Retention time 3.66 minutes)
MS (APCI+, m/e) 360 (M+1)

Example 322

6-(2-fluorophenyl)-2-[3-(3-methylbuthoxy)phenyl]-1H-imidazo[4,5-b]pyridine

HPLC (220 nm) Purity 98% (Retention time 3.97 minutes)
MS (APCI+, m/e) 376 (M+1)

Example 323

6-(2-fluorophenyl)-2-[3-(neopentyloxy)phenyl]-1H-imidazo[4,5-b]pyridine

HPLC (220 nm) Purity 97% (Retention time 4.02 minutes)
MS (APCI+, m/e) 376 (M+1)

Example 324

2-[3-(cyclohexylmethoxy)phenyl]-6-(2-fluorophenyl)-1H-imidazo[4,5-b]pyridine

HPLC (220 nm) Purity 98% (Retention time 4.20 minutes)
MS (APCI+, m/e) 402 (M+1)

Example 325

2-[3-(cyclopentyloxy)phenyl]-6-(2-fluorophenyl)-1H-imidazo[4,5-b]pyridine

HPLC (220 nm) Purity 98% (Retention time 3.79 minutes)
MS (APCI+, m/e) 374 (M+1)

Example 326

6-(2-fluorophenyl)-2-[3-(2-phenylehoxy)phenyl]-1H-imidazo[4,5-b]pyridine

HPLC (220 nm) Purity 99% (Retention time 3.91 minutes)
MS (APCI+, m/e) 410 (M+1)

Example 327

2-(3-ethylphenyl)-6-(2-fluorophenyl)-1H-imidazo[4,5-b]pyridine

HPLC (220 nm) Purity 99% (Retention time 3.41 minutes)
MS (APCI+, m/e) 318 (M+1)

Example 328

6-(2-furyl)-2-[3-(hexyloxy)phenyl]-1H-imidazo[4,5-b]pyridine

HPLC (220 nm) Purity 97% (Retention time 4.07 minutes)
MS (APCI+, m/e) 362 (M+1)

Example 329

2-[3-(3-buthenyloxy)phenyl]-6-(2-furyl)-1H-imidazo[4,5-b]pyridine

HPLC (220 nm) Purity 96% (Retention time 3.52 minutes)
MS (APCI+, m/e) 332 (M+1)

Example 330

6-(2-furyl)-2-[3-(3-methylbuthoxy)phenyl]-1H-imidazo[4,5-b]pyridine

HPLC (220 nm) Purity 96% (Retention time 3.84 minutes)
MS (APCI+, m/e) 348 (M+1)

Example 331

6-(2-furyl)-2-[3-(neopentyloxy)phenyl]-1H-imidazo[4,5-b]pyridine

HPLC (220 nm) Purity 99% (Retention time 3.89 minutes)
MS (APCI+, m/e) 348 (M+1)

Example 332

2-[3-(cyclohexylmethoxy)phenyl]-6-(2-furyl)-1H-imidazo[4,5-b]pyridine

HPLC (220 nm) Purity 97% (Retention time 4.10 minutes)
MS (APCI+, m/e) 374 (M+1)

Example 333

2-[3-(cyclopentyloxy)phenyl]-6-(2-furyl)-1H-imidazo[4,5-b]pyridine

HPLC (220 nm) Purity 96% (Retention time 3.65 minutes)
MS (APCI+, m/e), 346 (M+1)

Example 334

6-(2-furyl)-2-[3-(2-phenylehoxy)phenyl]-1H-imidazo[4,5-b]pyridine

HPLC (220 nm) Purity 96% (Retention time 3.81 minutes)
MS (APCI+, m/e) 382 (M+1)

Example 335

2-(3-ethylphenyl)-6-(2-furyl)-1H-imidazo[4,5-b]pyridine

HPLC (220 nm) Purity 94% (Retention time 3.26 minutes)
MS (APCI+, m/e) 290 (M+1)

By using the compound obtained in Reference Example 49 and various boron acids as starting materials, the compounds of the following Examples 336 to 351 were synthesized in a manner similar to Example 1. At that time, purification by means of recrystallization or silica gel column chromatography was carried out as required.

Example 336

6-(3-fluorophenyl)-2-(3-isopropoxyphenyl)-1H-imidazo[4,5-b]pyridine

HPLC (220 nm) Purity 99% (Retention time 3.58 minutes)
MS (APCI+, m/e) 348 (M+1)

Example 337

6-(4-fluorophenyl)-2-(3-isopropoxyphenyl)-1H-imidazo[4,5-b]pyridine

HPLC (220 nm) Purity 100% (Retention time 3.51 minutes)
MS (APCI+, m/e) 348 (M+1)

Example 338

6-(2,4-difluorophenyl)-2-(3-isopropoxyphenyl)-1H-imidazo[4,5-b]pyridine

HPLC (220 nm) Purity 99% (Retention time 3.63 minutes)
MS (APCI+, m/e) 366 (M+1)

Example 339

6-(3,4-difluorophenyl)-2-(3-isopropoxyphenyl)-1H-imidazo[4,5-b]pyridine

HPLC (220 nm) Purity 100% (Retention time 3.68 minutes)
MS (APCI+, m/e) 366 (M+1)

Example 340

6-(2-chlorophenyl)-2-(3-isopropoxyphenyl)-1H-imidazo[4,5-b]pyridine

HPLC (220 nm) Purity 99% (Retention time 3.66 minutes)
MS (APCI+, m/e) 364 (M+1)

Example 341

2-(3-isopropoxyphenyl)-6-[2-(trifluoromethyl)phenyl]-1H-imidazo[4,5-b]pyridine

HPLC (220 nm) Purity 98% (Retention time 3.76 minutes)
MS (APCI+, m/e) 398 (M+1)

Example 342

2-(3-isopropoxyphenyl)-6-[3-(trifluoromethyl)phenyl]-1H-imidazo[4,5-b]pyridine

HPLC (220 nm) Purity 99% (Retention time 3.87 minutes)
MS (APCI+, m/e) 398 (M+1)

Example 343

2-(3-isopropoxyphenyl)-6-[4-(trifluoromethoxy)phenyl]-1H-imidazo[4,5-b]pyridine

HPLC (220 nm) Purity 99% (Retention time 3.91 minutes)
MS (APCI+, m/e) 414 (M+1)

Example 344

2-(3-isopropoxyphenyl)-6-(2-methoxyphenyl)-1H-imidazo[4,5-b]pyridine

HPLC (220 nm) Purity 100% (Retention time 3.41 minutes)
MS (APCI+, m/e) 360 (M+1)

Example 345

2-(3-isopropoxyphenyl)-6-(3-methoxyphenyl)-1H-imidazo[4,5-b]pyridine

HPLC (220 nm) Purity 100% (Retention time 3.50 minutes)
MS (APCI+, m/e) 360 (M+1)

Example 346

6-(1,3-benzodioxol-5-yl)-2-(3-isopropoxyphenyl)-1H-imidazo[4,5-b]pyridine

HPLC (220 nm) Purity 99% (Retention time 3.43 minutes)
MS (APCI+, m/e) 374 (M+1)

Example 347

2-(3-isopropoxyphenyl)-6-(4-phenoxyphenyl)-1H-imidazo[4,5-b]pyridine

HPLC (220 nm) Purity 100% (Retention time 3.96 minutes)
MS (APCI+, m/e) 422 (M+1)

Example 348

2-(3-isopropoxyphenyl)-6-[4-(methylthio)phenyl]-1H-imidazo[4,5-b]pyridine

HPLC (220 nm) Purity 100% (Retention time 3.65 minutes)
MS (APCI+, m/e) 376 (M+1)

Example 349

3-[2-(3-isopropoxyphenyl)-1H-imidazo[4,5-b]pyridin-6-yl]benzonitrile

HPLC (220 nm) Purity 98% (Retention time 3.51 minutes)
MS (APCI+, m/e) 355 (M+1)

Example 350

N-[3-[2-(3-isopropoxyphenyl)-1H-imidazo[4,5-b]pyridin-6-yl]phenyl]acetamide

HPLC (220 nm) Purity 97% (Retention time 3.12 minutes)
MS (APCI+, m/e) 387 (M+1)

Example 351

6-(1-benzofuran-2-yl)-2-(3-isopropoxyphenyl)-1H-imidazo[4,5-b]pyridine

HPLC (220 nm) Purity 100% (Retention time 3.98 minutes)
MS (APCI+, m/e) 370 (M+1)

By using the compound obtained in Example 97 and various alkyl halides as starting materials, the compounds of the following Examples 352 to 359 were synthesized in a manner similar to Example 161.

Example 352

2-(3,4-dimethoxybenzyl)-6-(2-furyl)-1-methyl-1H-imidazo[4,5-b]pyridine

HPLC (220 nm) Purity 100% (Retention time 2.93 minutes)
MS (ESI+, m/e) 350 (M+1)

Example 353

2-(3,4-dimethoxybenzyl)-6-(2-furyl)-1-(2-methoxyethyl)-1H-imidazo[4,5-b]pyridine HPLC (220 nm) Purity 98% (Retention time 3.10 minutes)
MS (ESI+, m/e) 394 (M+1)

Example 354

1-(cyclopropylmethyl)-2-(3,4-dimethoxybenzyl)-6-(2-furyl)-1H-imidazo[4,5-b]pyridine HPLC (220 nm) Purity 100% (Retention time 3.35 minutes)
MS (ESI+, m/e) 390 (M+1)

Example 355

2-(3,4-dimethoxybenzyl)-6-(2-furyl)-1-isobutyl-1H-imidazo[4,5-b]pyridine

HPLC (220 nm) Purity 100% (Retention time 3.44 minutes)
MS (ESI+, m/e) 392 (M+1)

Example 356

2-(3,4-dimethoxybenzyl)-6-(2-furyl)-1-(4-pentenyl)-1H-imidazo[4,5-b]pyridine

HPLC (220 nm) Purity 100% (Retention time 3.50 minutes)
MS (ESI+, m/e) 404 (M+1)

Example 357

4-[2-(3,4-dimethoxybenzyl)-6-(2-furyl)-1H-imidazo[4,5-b]pyridin-1-yl]butanenitrile HPLC (220 nm) Purity 100% (Retention time 3.11 minutes)
MS (ESI+, m/e) 403 (M+1)

Example 358

2-(3,4-dimethoxybenzyl)-6-(2-furyl)-1-(2-phenylethyl)-1H-imidazo[4,5-b]pyridine

HPLC (220 nm) Purity 99% (Retention time 3.62 minutes)
MS (ESI+, m/e) 440 (M+1)

Example 359

2-[[2-(3,4-dimethoxybenzyl)-6-(2-furyl)-1H-imidazo[4,5-b]pyridin-1-yl]methyl]phenyl acetate HPLC (220 nm) Purity 100% (Retention time 3.43 minutes)
MS (ESI+, m/e) 484 (M+1)

By using the compound obtained in Example 359 as a starting material, compound of the following Example 360 was synthesized in a manner similar to Example 157.

Example 360

2-[[2-(3,4-dimethoxybenzyl)-6-(2-furyl)-1H-imidazo[4,5-b]pyridin-1-yl]methyl]phenol HPLC (220 nm) Purity 100% (Retention time 3.21 minutes)
MS (ESI+, m/e) 442 (M+1)

By using the compound obtained in Example 301 and various alkyl halides as starting materials, the compounds of the following Examples 361 to 366 were synthesized in a manner similar to Example 161.

Example 361

2-(3-butoxyphenyl)-6-(2-furyl)-1-methyl-1H-imidazo[4,5-b]pyridine

HPLC (220 nm) Purity 100% (Retention time 3.48 minutes)
MS (APCI+, m/e) 348 (M+1)

Example 362

2-(3-butoxyphenyl)-6-(2-furyl)-1-(2-methoxyethyl)-1H-imidazo[4,5-b]pyridine

HPLC (220 nm) Purity 97% (Retention time 3.63 minutes)
MS (APCI+, m/e) 392 (M+1)

Example 363

2-(3-butoxyphenyl)-1-(cyclopropylmethyl)-6-(2-furyl)-1H-imidazo[4,5-b]pyridine

HPLC (220 nm) Purity 98% (Retention time 3.90 minutes)
MS (APCI+, m/e) 388 (M+1)

Example 364

2-(3-butoxyphenyl)-6-(2-furyl)-1-(4-pentenyl)-1H-imidazo[4,5-b]pyridine

HPLC (220 nm) Purity 96% (Retention time 4.02 minutes)
MS (APCI+, m/e) 402 (M+1)

Example 365

4-[2-(3-butoxyphenyl)-6-(2-furyl)-1H-imidazo[4,5-b]pyridin-1-yl]butanenitrile

HPLC (220 nm) Purity 99% (Retention time 3.59 minutes)
MS (APCI+, m/e) 401 (M+1)

Example 366

2-[[2-(3-butoxyphenyl)-6-(2-furyl)-1H-imidazo[4,5-b]pyridin-1-yl]methyl]phenyl acetate HPLC (220 nm) Purity 91% (Retention time 3.93 minutes)
MS (APCI+, m/e) 482 (M+1)

By using the compound obtained in Example 366 as starting material, compound of the following Examples 367 was synthesized in a manner similar to Example 157.

Example 367

2-[[2-(3-butoxyphenyl)-6-(2-furyl)-1H-imidazo[4,5-b]pyridin-1-yl]methyl]phenol

HPLC (220 nm) Purity 97% (Retention time 3.85 minutes)
MS (ESI+, m/e) 440 (M+1)

By using the compounds obtained in Reference Examples 60 to 66 and various boron acids as starting materials, the compounds of the following Examples 368 to 380 were synthesized in a manner similar to Example 214. At that time, purification by means of recrystallization or silica gel column chromatography was carried out as required.

Example 368

2-(3-methoxyphenyl)-5-phenylbenzoxazole

HPLC (220 nm) Purity 98% (Retention time 5.04 minutes)
MS (ESI+, m/e) 302 (M+1)

Example 369

2-[(E)-2-(3-fluorophenyl)ethenyl]-5-phenylbenzoxazole

HPLC (220 nm) Purity 98% (Retention time 5.15 minutes)
MS (ESI+, m/e) 316 (M+1)

Example 370

2-[(E)-2-(2-fluorophenyl)ethenyl]-5-phenylbenzoxazole

HPLC (220 nm) Purity 97% (Retention time 5.24 minutes)
MS (ESI+, m/e) 316 (M+1)

Example 371

2-[(E)-2-(3,4-dichlorophenyl)ethenyl]-5-phenylbenzoxazole

HPLC (220 nm) Purity 91% (Retention time 5.44 minutes)
MS (ESI+, m/e) 366 (M+1)

Example 372

2-[(E)-2-(4-methylphenyl)ethenyl]-5-phenylbenzoxazole

HPLC (220 nm) Purity 100% (Retention time 5.37 minutes)
MS (ESI+, m/e) 321 (M+1)

Example 373

5-phenyl-2-[(E)-2-[3-(trifluoromethoxy)phenyl]ethenyl]benzoxazole

HPLC (220 nm) Purity 99% (Retention time 5.42 minutes)
MS (ESI+, m/e) 382 (M+1)

Example 374

5-(2-furyl)-2-(3-methoxyphenyl)benzoxazole

HPLC (220 nm) Purity 99% (Retention time 4.82 minutes)
MS (ESI+, m/e) 292 (M+1)

Example 375

2-[(E)-2-(4-chlorophenyl)ethenyl]-5-(2-furyl)benzoxazole

HPLC (220 nm) Purity 99% (Retention time 5.21 minutes)
MS (ESI+, m/e) 322 (M+1)

Example 376

2-[(E)-2-(3-fluorophenyl)ethenyl]-5-(2-furyl)benzoxazole

HPLC (220 nm) Purity 90% (Retention time 4.96 minutes)
MS (ESI+, m/e) 306 (M+1)

Example 377

2-[(E)-2-(2-fluorophenyl)ethenyl]-5-(2-furyl)benzoxazole

HPLC (220 nm) Purity 100% (Retention time 5.03 minutes)
MS (ESI+, m/e) 306 (M+1)

Example 378

2-[(E)-2-(3,4-dichlorophenyl)ethenyl]-5-(2-furyl)benzoxazole

HPLC (220 nm) Purity 95% (Retention time 5.46 minutes)
MS (ESI+, m/e) 356 (M+1)

Example 379

5-(2-furyl)-2-[(E)-2-(4-methylphenyl)ethenyl]benzoxazole

HPLC (220 nm) Purity 99% (Retention time 5.17 minutes)
MS (ESI+, m/e) 302 (M+1)

Example 380

5-(2-furyl)-2-[(E)-2-[3-(trifluoromethoxy)phenyl]ethenyl]benzoxazole

HPLC (220 nm) Purity 99% (Retention time 5.24 minutes)
MS (ESI+, m/e) 372 (M+1)

By using the compound obtained in Reference Examples 43, 45 and 60 and various boron acids as starting materials, the compounds of the following Examples 381 to 389 were synthesized in a manner similar to Example 214. At that time, purification by means of recrystallization or silica gel column chromatography was carried out as required.

Example 381

2-(3-methoxyphenyl)-5-[(E)-2-phenylethenyl]benzoxazole

HPLC (220 nm) Purity 99% (Retention time 5.30 minutes)
MS (APCI+, m/e) 328 (M+1)

Example 382

2,5-bis[(E)-2-phenylethenyl]benzoxazole

HPLC (220 nm) Purity 93% (Retention time 5.38 minutes)
MS (APCI+, m/e) 324 (M+1)

Example 383

2-[(E)-2-(2,4-difluorophenyl)ethenyl]-5-[(E)-2-phenylethenyl]benzoxazole

HPLC (220 nm) Purity 99% (Retention time 5.21 minutes)
MS (APCI+, m/e) 360 (M+1)

Example 384

5-(2-acetylphenyl)-2-(3-methoxyphenyl)benzoxazole

HPLC (220 nm) Purity 93% (Retention time 4.61 minutes)
MS (APCI+, m/e) 344 (M+1)

Example 385

5-(2-acetylphenyl)-2-[(E)-2-phenylethenyl]benzoxazole

HPLC (220 nm) Purity 92% (Retention time 4.73 minutes)
MS (APCI+, m/e) 340 (M+1)

Example 386

5-(2-acetylphenyl)-2-[(E)-2-(2,4-difluorophenyl)ethenyl]benzoxazole

HPLC (220 nm) Purity 86% (Retention time 4.86 minutes)
MS (APCI+, m/e) 376 (M+1)

Example 387

2-(3-methoxyphenyl)-5-(3-pyridyl)benzoxazole

HPLC (220 nm) Purity 97% (Retention time 3.04 minutes)
MS (APCI+, m/e) 303 (M+1)

Example 388

2-[(E)-2-phenylethenyl]-5-(3-pyridyl)benzoxazole

HPLC (220 nm) Purity 99% (Retention time 3.21 minutes)
MS (APCI+, m/e) 299 (M+1)

Example 389

2-[(E)-2-(2,4-difluorophenyl)ethenyl]-5-(3-pyridyl)benzoxazole

HPLC (220 nm) Purity 98% (Retention time 3.32 minutes)
MS (APCI+, m/e) 335 (M+1)

By using the compounds obtained in Reference Examples 67 to 72, Examples 242 to 243 and phenyl boron acid as starting materials, the compounds of the following Examples 390 to 397 were synthesized in a manner similar to Example 214. At that time, purification by means of recrystallization or silica gel column chromatography was carried out as required.

Example 390

2-(3-methoxyphenyl)-6-phenylbenzoxazole

HPLC (220 nm) Purity 99% (Retention time 5.06 minutes)
MS (APCI+, m/e) 302 (M+1)

Example 391

2-(4-chlorobenzyl)-6-phenylbenzoxazole

HPLC (220 nm) Purity 98% (Retention time 4.98 minutes)
MS (APCI+, m/e) 320 (M+1)

Example 392

6-phenyl-2-[(E)-2-phenylethenyl]-benzoxazole

HPLC (220 nm) Purity 98% (Retention time 5.16 minutes)
MS (APCI+, m/e) 298 (M+1)

Example 393

2-[(E)-2-(2,4-difluorophenyl)ethenyl]-6-phenylbenzoxazole

HPLC (220 nm) Purity 99% (Retention time 5.28 minutes)
MS (APCI+, m/e) 334 (M+1)

Example 394

2-[(E)-2-(2-fluorophenyl)ethenyl]-6-phenylbenzoxazole

HPLC (220 nm) Purity 97% (Retention time 5.26 minutes)
MS (APCI+, m/e) 316 (M+1)

Example 395

6-phenyl-2-[(E)-2-[4-(trifluoromethyl)phenyl]ethenyl]benzoxazole

HPLC (220 nm) Purity 90% (Retention time 5.42 minutes)
MS (APCI+, m/e) 366 (M+1)

Example 396

6-phenyl-2-(2-phenylethyl)benzoxazole

HPLC (220 nm) Purity 99% (Retention time 4.92 minutes)
MS (APCI+, m/e) 300 (M+1)

Example 397

2-(2-naphthyl)-6-phenylbenzoxazole

HPLC (220 nm) Purity 97% (Retention time 5.58 minutes)
MS (APCI+, m/e) 322 (M+1)

Example 398

Under an argon stream, a mixture of 6-bromo-2-(3-methoxyphenyl)benzoxazole (Compound of Example 242) (137 mg), 2-(tributylstanyl)furan (321 mg), dichlorobis(triphenylphosphine)palladium(II) (24 mg) and N,N-dimethyl formamide (4.5 ml) was stirred at 80° C. for 24 hours. The mixture was poured into water and extracted with ethyl acetate. The organic layer was washed with water and dried over MgSO$_4$, and the solvent was distilled off under reduced pressure. The residue was subjected to silica gel column chromatography, and the fraction eluted with ethyl acetate-hexane (1:9, v/v) was concentrated under reduced pressure. The resulting crystals were collected by filtration to 6-(2-furyl)-2-(3-methoxyphenyl)benzoxazole (76 mg, 58%).

$^1$H NMR (CDCl$_3$) δ 3.93 (3H, s), 6.52 (1H, dd, J=3.2, 1.8 Hz), 6.72 (1H, dd, J=3.4, 0.8 Hz), 7.10 (1H, ddd, J=8.3, 2.5, 0.6 Hz), 7.45 (1H, t, J=7.8 Hz), 7.52 (1H, dd, J=1.8, 0.8 Hz), 7.66-7.89 (5H, m) ppm HPLC (220 nm) Purity 99% (Retention time 4.86 minutes)
MS (APCI+, m/e) 292 (M+1)

By using the compounds obtained in Reference Examples 67 to 72, Examples 243 to 255 and 2-(tributylstanyl)furan as starting materials, the compounds of the following Examples 399 to 416 were synthesized in a manner similar to Example 398. At that time, purification by means of recrystallization or silica gel column chromatography was carried out as required.

Example 399

2-(4-chlorobenzyl)-6-(2-furyl)benzoxazole

HPLC (220 nm) Purity 100% (Retention time 4.78 minutes)
MS (APCI+, m/e) 310 (M+1)

Example 400

6-(2-furyl)-2-[(E)-2-phenylethenyl]-benzoxazole

HPLC (220 nm) Purity 99% (Retention time 4.97 minutes)
MS (APCI+, m/e) 288 (M+1)

Example 401

2-[(E)-2-(2,4-difluorophenyl)ethenyl]-6-(2-furyl)benzoxazole

HPLC (220 nm) Purity 99% (Retention time 5.09 minutes)
MS (APCI+, m/e) 324 (M+1)

Example 402

2-[(E)-2-(2-fluorophenyl)ethenyl]-6-(2-furyl)benzoxazole

HPLC (220 nm) Purity 99% (Retention time 5.06 minutes)
MS (APCI+, m/e) 306 (M+1)

Example 403

6-(2-furyl)-2-[(E)-2-[4-(trifluoromethyl)phenyl]ethenyl]benzoxazole

HPLC (220 nm) Purity 100% (Retention time 5.23 minutes)
MS (APCI+, m/e) 356 (M+1)

Example 404

6-(2-furyl)-2-(2-phenylethyl)benzoxazole

HPLC (220 nm) Purity 99% (Retention time 4.72 minutes)
MS (APCI+, m/e) 290 (M+1)

Example 405

6-(2-furyl)-2-(2-naphthyl)benzoxazole

HPLC (220 nm) Purity 100% (Retention time 5.37 minutes)
MS (APCI+, m/e) 312 (M+1)

Example 406

6-(2-furyl)-2-phenylbenzoxazole

HPLC (220 nm) Purity 100% (Retention time 4.81 minutes)
MS (APCI+, m/e) 262 (M+1)

Example 407

6-(2-furyl)-2-(3-methylphenyl)benzoxazole

HPLC (220 nm) Purity 99% (Retention time 5.07 minutes)
MS (APCI+, m/e) 276 (M+1)

Example 408

6-(2-furyl)-2-(4-methoxyphenyl)benzoxazole

HPLC (220 nm) Purity 98% (Retention time 4.78 minutes)
MS (APCI+, m/e) 292 (M+1)

Example 409

2-(3,4-dimethoxyphenyl)-6-(2-furyl)benzoxazole

HPLC (220 nm) Purity 98% (Retention time 4.50 minutes)
MS (APCI+, m/e) 322 (M+1)

Example 410

6-(2-furyl)-2-(2-methoxyphenyl)benzoxazole

HPLC (220 nm) Purity 99% (Retention time 4.42 minutes)
MS (APCI+, m/e) 292 (M+1)

Example 411

6-(2-furyl)-2-(3,4,5-trimethoxyphenyl)benzoxazole

HPLC (220 nm) Purity 99% (Retention time 4.58 minutes)
MS (APCI+, m/e) 352 (M+1)

Example 412

2-(3-fluorophenyl)-6-(2-furyl)benzoxazole

HPLC (220 nm) Purity 98% (Retention time 4.96 minutes)
MS (APCI+, m/e) 280 (M+1)

Example 413

6-(2-furyl)-2-[3-(trifluoromethyl)phenyl]benzoxazole

HPLC (220 nm) Purity 98% (Retention time 5.21 minutes)
MS (APCI+, m/e) 330 (M+1)

Example 414

6-(2-furyl)-2-[3-(trifluoromethoxy)phenyl]benzoxazole

HPLC (220 nm) Purity 99% (Retention time 5.28 minutes)
MS (APCI+, m/e) 346 (M+1)

Example 415

3-[6-(2-furyl)benzoxazol-2-yl]benzonitrile

HPLC (220 nm) Purity 98% (Retention time 4.63 minutes)
MS (APCI+, m/e) 287 (M+1)

Example 416

2-(3-butoxyphenyl)-6-(2-furyl)benzoxazole

HPLC (220 nm) Purity 99% (Retention time 5.60 minutes)
MS (APCI+, m/e) 334 (M+1)

By using the compounds obtained in Examples 242, 244 to 255 and various boron acids as starting materials, the compounds of the following Examples 417 to 448 were synthesized in a manner similar to Example 214. At that time, purification by means of recrystallization or silica gel column chromatography was carried out as required.

Example 417

6-(2-fluorophenyl)-2-(3-methoxyphenyl)benzoxazole

HPLC (220 nm) Purity 95% (Retention time 5.01 minutes)
MS (APCI+, m/e) 320 (M+1)

Example 418

6-(2-fluorophenyl)-2-phenylbenzoxazole

HPLC (220 nm) Purity 100% (Retention time 5.02 minutes)
MS (APCI+, m/e) 290 (M+1)

Example 419

6-(2-fluorophenyl)-2-(3-methylphenyl)benzoxazole

HPLC (220 nm) Purity 99% (Retention time 5.26 minutes)
MS (APCI+, m/e) 304 (M+1)

Example 420

6-(2-fluorophenyl)-2-(4-methoxyphenyl)benzoxazole

HPLC (220 nm) Purity 97% (Retention time 4.97 minutes)
MS (APCI+, m/e) 320 (M+1)

Example 421

2-(3,4-dimethoxyphenyl)-6-(2-fluorophenyl)benzoxazole

HPLC (220 nm) Purity 97% (Retention time 4.71 minutes)
MS (APCI+, m/e) 350 (M+1)

Example 422

6-(2-fluorophenyl)-2-(2-methoxyphenyl)benzoxazole

HPLC (220 nm) Purity 100% (Retention time 4.63 minutes)
MS (APCI+, m/e) 320 (M+1)

Example 423

6-(2-fluorophenyl)-2-(3,4,5-trimethoxyphenyl)benzoxazole

HPLC (220 nm) Purity 100% (Retention time 4.79 minutes)
MS (APCI+, m/e) 380 (M+1)

Example 424

6-(2-fluorophenyl)-2-(3-fluorophenyl)benzoxazole

HPLC (220 nm) Purity 99% (Retention time 5.13 minutes)
MS (APCI+, m/e) 308 (M+1)

Example 425

6-(2-fluorophenyl)-2-[3-(trifluoromethyl)phenyl]benzoxazole

HPLC (220 nm) Purity 99% (Retention time 5.37 minutes)
MS (APCI+, m/e) 358 (M+1)

Example 426

6-(2-fluorophenyl)-2-[3-(trifluoromethoxy)phenyl]benzoxazole

HPLC (220 nm) Purity 100% (Retention time 5.43 minutes)
MS (APCI+, m/e) 374 (M+1)

Example 427

3-[6-(2-fluorophenyl)benzoxazol-2-yl]benzonitrile

HPLC (220 nm) Purity 99% (Retention time 4.81 minutes)
MS (APCI+, m/e) 315 (M+1)

Example 428

2-(3-methoxyphenyl)-6-[2-(trifluoromethyl)phenyl]benzoxazole

HPLC (220 nm) Purity 100% (Retention time 5.09 minutes)
MS (APCI+, m/e) 370 (M+1)

Example 429

2-phenyl-6-[2-(trifluoromethyl)phenyl]benzoxazole

HPLC (220 nm) Purity 100% (Retention time 5.08 minutes)
MS (APCI+, m/e) 340 (M+1)

Example 430

2-(3-methylphenyl)-6-[2-(trifluoromethyl)phenyl]benzoxazole

HPLC (220 nm) Purity 100% (Retention time 5.32 minutes)
MS (APCI+, m/e) 354 (M+1)

Example 431

2-(4-methoxyphenyl)-6-[2-(trifluoromethyl)phenyl]benzoxazole

HPLC (220 nm) Purity 99% (Retention time 5.08 minutes)
MS (APCI+, m/e) 370 (M+1)

Example 432

2-(3,4-dimethoxyphenyl)-6-[2-(trifluoromethyl)phenyl]benzoxazole

HPLC (220 nm) Purity 100% (Retention time 4.83 minutes)
MS (APCI+, m/e) 400 (M+1)

Example 433

2-(2-methoxyphenyl)-6-[2-(trifluoromethyl)phenyl]benzoxazole

HPLC (220 nm) Purity 100% (Retention time 4.78 minutes)
MS (APCI+, m/e) 370 (M+1)

Example 434

6-[2-(trifluoromethyl)phenyl]-2-(3,4,5-trimethoxyphenyl)benzoxazole

HPLC (220 nm) Purity 99% (Retention time 4.91 minutes)
MS (APCI+, m/e) 430 (M+1)

Example 435

2-(3-fluorophenyl)-6-[2-(trifluoromethyl)phenyl]benzoxazole

HPLC (220 nm) Purity 100% (Retention time 5.22 minutes)
MS (APCI+, m/e) 358 (M+1)

Example 436

6-[2-(trifluoromethyl)phenyl]-2-[3-(trifluoromethyl)phenyl]benzoxazole

HPLC (220 nm) Purity 99% (Retention time 5.43 minutes)
MS (APCI+, m/e) 408 (M+1)

Example 437

2-[3-(trifluoromethoxy)phenyl]-6-[2-(trifluoromethyl)phenyl]benzoxazole

HPLC (220 nm) Purity 100% (Retention time 5.49 minutes)
MS (APCI+, m/e) 424 (M+1)

Example 438

3-[6-[2-(trifluoromethyl)phenyl]benzoxazol-2-yl]benzonitrile

HPLC (220 nm) Purity 99% (Retention time 4.92 minutes)
MS (APCI+, m/e) 365 (M+1)

Example 439

2,6-bis(3-methoxyphenyl)benzoxazole

HPLC (220 nm) Purity 93% (Retention time 4.97 minutes)
MS (APCI+, m/e) 332 (M+1)

Example 440

6-(3-methoxyphenyl)-2-phenylbenzoxazole

HPLC (220 nm) Purity 98% (Retention time 4.95 minutes)
MS (APCI+, m/e) 302 (M+1)

Example 441

6-(3-methoxyphenyl)-2-(3-methylphenyl)benzoxazole

HPLC (220 nm) Purity 99% (Retention time 5.20 minutes)
MS (APCI+, m/e) 316 (M+1)

Example 442

6-(3-methoxyphenyl)-2-(4-methoxyphenyl)benzoxazole

HPLC (220 nm) Purity 98% (Retention time 4.94 minutes)
MS (APCI+, m/e) 332 (M+1)

Example 443

2-(3,4-dimethoxyphenyl)-6-(3-methoxyphenyl)benzoxazole

HPLC (220 nm) Purity 91% (Retention time 4.67 minutes)
MS (APCI+, m/e) 362 (M+1)

Example 444

2-(2-methoxyphenyl)-6-(3-methoxyphenyl)benzoxazole

HPLC (220 nm) Purity 93% (Retention time 4.59 minutes)
MS (APCI+, m/e) 332 (M+1)

Example 445

2-(3-fluorophenyl)-6-(3-methoxyphenyl)benzoxazole

HPLC (220 nm) Purity 97% (Retention time 5.08 minutes)
MS (APCI+, m/e) 320 (M+1)

Example 446

6-(3-methoxyphenyl)-2-[3-(trifluoromethyl)phenyl]benzoxazole

HPLC (220 nm) Purity 100% (Retention time 5.34 minutes)
MS (APCI+, m/e) 370 (M+1)

Example 447

6-(3-methoxyphenyl)-2-[3-(trifluoromethoxy)phenyl]benzoxazole

HPLC (220 nm) Purity 99% (Retention time 5.40 minutes)
MS (APCI+, m/e) 386 (M+1)

Example 448

3-[6-(3-methoxyphenyl)benzoxazol-2-yl]benzonitrile

HPLC (220 nm) Purity 100% (Retention time 4.80 minutes)
MS (APCI+, m/e) 327 (M+1)

By using the compounds obtained in Examples 256 to 271 and 2-(tributylstanyl)furan as starting materials, the compounds of the following Examples 449 to 464 were synthesized in a manner similar to Example 398. At that time, purification by means of recrystallization or silica gel column chromatography was carried out as required.

Example 449

6-(2-furyl)-2-[3-[(trifluoromethyl)thio]phenyl]benzoxazole

HPLC (220 nm) Purity 96% (Retention time 5.41 minutes)
MS (APCI+, m/e) 362 (M+1)

Example 450

2-[3-fluoro-5-(trifluoromethyl)phenyl]-6-(2-furyl)benzoxazole

HPLC (220 nm) Purity 93% (Retention time 5.32 minutes)
MS (APCI+, m/e) 348 (M+1)

Example 451

2-(3-ethoxyphenyl)-6-(2-furyl)benzoxazole

HPLC (220 nm) Purity 98% (Retention time 5.06 minutes)
MS (APCI+, m/e) 306 (M+1)

Example 452

2-[3,5-bis(trifluoromethyl)phenyl]-6-(2-furyl)benzoxazole

HPLC (220 nm) Purity 93% (Retention time 5.55 minutes)
MS (APCI+, m/e) 398 (M+1)

Example 453

2-(3,5-difluorophenyl)-6-(2-furyl)benzoxazole

HPLC (220 nm) Purity 95% (Retention time 5.14 minutes)
MS (APCI+, m/e) 298 (M+1)

Example 454

6-(2-furyl)-2-(3-phenoxyphenyl)benzoxazole

HPLC (220 nm) Purity 100% (Retention time 5.43 minutes)
MS (APCI+, m/e) 354 (M+1)

Example 455

6-(2-furyl)-2-(5-methyl-2-thienyl)benzoxazole

HPLC (220 nm) Purity 100% (Retention time 4.91 minutes)
MS (APCI+, m/e) 282 (M+1)

Example 456

2-(1-benzofuran-2-yl)-6-(2-furyl)benzoxazole

HPLC (220 nm) Purity 99% (Retention time 4.95 minutes)
MS (APCI+, m/e) 302 (M+1)

Example 457

2-(1-benzothiophen-2-yl)-6-(2-furyl)benzoxazole

HPLC (220 nm) Purity 100% (Retention time 5.30 minutes)
MS (APCI+, m/e) 318 (M+1)

Example 458

6-[6-(2-furyl)benzoxazol-2-yl]quinoline

HPLC (220 nm) Purity 100% (Retention time 3.51 minutes)
MS (APCI+, m/e) 313 (M+1)

Example 459

6-(2-furyl)-2-(3-nitrophenyl)benzoxazole

HPLC (220 nm) Purity 100% (Retention time 4.82 minutes)
MS (APCI+, m/e) 307 (M+1)

Example 460

3-[6-(2-furyl)benzoxazol-2-yl]aniline

HPLC (220 nm) Purity 92% (Retention time 3.37 minutes)
MS (APCI+, m/e) 277 (M+1)

Example 461

N-[3-[6-(2-furyl)benzoxazol-2-yl]phenyl]acetamide

HPLC (220 nm) Purity 83% (Retention time 4.08 minutes)
MS (APCI+, m/e) 319 (M+1)

Example 462

N-[3-[6-(2-furyl)benzoxazol-2-yl]phenyl]benzamide

HPLC (220 nm) Purity 86% (Retention time 4.72 minutes)
MS (APCI+, m/e) 381 (M+1)

Example 463

N-[3-[6-(2-furyl)benzoxazol-2-yl]phenyl]methane sulfonamide

HPLC (220 nm) Purity 92% (Retention time 4.16 minutes)
MS (APCI+, m/e) 355 (M+1)

Example 464

N-ethyl-N'-[3-[6-(2-furyl)benzoxazol-2-yl]phenyl] urea

HPLC (220 nm) Purity 95% (Retention time 4.16 minutes)
MS (APCI+, m/e) 348 (M+1)

By using the compounds obtained in Examples 256 to 271 and 2-fluorophenyl boron acids as starting materials, the compounds of the following Examples 465 to 480 were synthesized in a manner similar to Example 214. At that time, purification by means of recrystallization or silica gel column chromatography was carried out as required.

Example 465

6-(2-fluorophenyl)-2-[3-[(trifluoromethyl)thio]phenyl]benzoxazole

HPLC (220 nm) Purity 99% (Retention time 5.56 minutes)
MS (APCI+, m/e) 390 (M+1)

Example 466

6-(2-fluorophenyl)-2-[3-fluoro-5-(trifluoromethyl) phenyl]benzoxazole

HPLC (220 nm) Purity 97% (Retention time 5.46 minutes)
MS (APCI+, m/e) 376 (M+1)

Example 467

2-(3-ethoxyphenyl)-6-(2-fluorophenyl)benzoxazole

HPLC (220 nm) Purity 96% (Retention time 5.23 minutes)
MS (APCI+, m/e) 334 (M+1)

Example 468

2-[3,5-bis(trifluoromethyl)phenyl]-6-(2-fluorophenyl)benzoxazole

HPLC (220 nm) Purity 99% (Retention time 5.68 minutes)
MS (APCI+, m/e) 426 (M+1)

Example 469

2-(3,5-difluorophenyl)-6-(2-fluorophenyl)benzoxazole

HPLC (220 nm) Purity 100% (Retention time 5.29 minutes)
MS (APCI+, m/e) 326 (M+1)

Example 470

6-(2-fluorophenyl)-2-(3-phenoxyphenyl)benzoxazole

HPLC (220 nm) Purity 100% (Retention time 5.57 minutes)
MS (APCI+, m/e) 382 (M+1)

Example 471

6-(2-fluorophenyl)-2-(5-methyl-2-thienyl)benzoxazole

HPLC (220 nm) Purity 99% (Retention time 5.08 minutes)
MS (APCI+, m/e) 310 (M+1)

Example 472

2-(1-benzofuran-2-yl)-6-(2-fluorophenyl)benzoxazole

HPLC (220 nm) Purity 97% (Retention time 5.12 minutes)
MS (APCI+, m/e) 330 (M+1)

Example 473

2-(1-benzothiophen-2-yl)-6-(2-fluorophenyl)benzoxazole

HPLC (220 nm) Purity 100% (Retention time 5.44 minutes)
MS (APCI+, m/e) 346 (M+1)

Example 474

6-[6-(2-fluorophenyl)benzoxazol-2-yl]quinoline

HPLC (220 nm) Purity 99% (Retention time 3.74 minutes)
MS (APCI+, m/e) 341 (M+1)

Example 475

6-(2-fluorophenyl)-2-(3-nitrophenyl)benzoxazole

HPLC (220 nm) Purity 100% (Retention time 4.99 minutes)
MS (APCI+, m/e) 335 (M+1)

Example 476

3-[6-(2-fluorophenyl)benzoxazol-2-yl]aniline

HPLC (220 nm) Purity 97% (Retention time 3.62 minutes)
MS (APCI+, m/e) 305 (M+1)

Example 477

N-[3-[6-(2-fluorophenyl)benzoxazol-2-yl]phenyl]acetamide

HPLC (220 nm) Purity 90% (Retention time 4.28 minutes)
MS (APCI+, m/e) 347 (M+1)

Example 478

N-[3-[6-(2-fluorophenyl)benzoxazol-2-yl]phenyl]benzamide

HPLC (220 nm) Purity 87% (Retention time 4.88 minutes)
MS (APCI+, m/e) 409 (M+1)

Example 479

N-[3-[6-(2-fluorophenyl)benzoxazol-2-yl]phenyl]methane sulfonamide

HPLC (220 nm) Purity 95% (Retention time 4.35 minutes)
MS (APCI+, m/e) 383 (M+1)

Example 480

N-ethyl-N'-[3-[6-(2-fluorophenyl)benzoxazol-2-yl]phenyl]urea

HPLC (220 nm) Purity 96% (Retention time 4.36 minutes)
MS (APCI+, m/e) 376 (M+1)

By using the compounds obtained in Examples 273 to 281 and 2-(tributylstanyl)furan as starting materials, the compounds of the following Examples 481 to 488 were synthesized in a manner similar to Example 398. At that time, purification by means of recrystallization or silica gel column chromatography was carried out as required.

Example 481

6-(2-furyl)-2-(3-isopropoxyphenyl)benzoxazole

HPLC (220 nm) Purity 95% (Retention time 5.25 minutes)
MS (APCI+, m/e) 320 (M+1)

Example 482

6-(2-furyl)-2-[3-(hexyloxy)phenyl]benzoxazole

HPLC (220 nm) Purity 100% (Retention time 6.20 minutes)
MS (APCI+, m/e) 362 (M+1)

Example 483

6-(2-furyl)-2-[3-(3-methylbuthoxy)phenyl]benzoxazole

HPLC (220 nm) Purity 100% (Retention time 5.83 minutes)
MS (APCI+, m/e) 348 (M+1)

Example 484

2-[3-(cyclopentyloxy)phenyl]-6-(2-furyl)benzoxazole

HPLC (220 nm) Purity 99% (Retention time 5.66 minutes)
MS (APCI+, m/e) 346 (M+1)

Example 485

2-[3-(cyclopropylmethoxy)phenyl]-6-(2-furyl)benzoxazole

HPLC (220 nm) Purity 100% (Retention time 5.25 minutes)
MS (APCI+, m/e) 332 (M+1)

Example 486

2-[3-(benzyloxy)phenyl]-6-(2-furyl)benzoxazole

HPLC (220 nm) Purity 100% (Retention time 5.36 minutes)
MS (APCI+, m/e) 368 (M+1)

Example 487

Tert-butyl [3-[6-(2-furyl)benzoxazol-2-yl]phenoxy]acetate

HPLC (220 nm) Purity 99% (Retention time 5.10 minutes)
MS (APCI+, m/e) 392 (M+1)

Example 488

2-[3-[6-(2-furyl)benzoxazol-2-yl]phenoxy]-N-methylacetamide

HPLC (220 nm) Purity 97% (Retention time 4.06 minutes)
MS (APCI+, m/e) 349 (M+1)

By using the compounds obtained in Examples 273 to 281 and various boron acids as starting materials, the compounds of the following Examples 489 to 504 were synthesized in a manner similar to Example 214. At that time, purification by means of recrystallization or silica gel column chromatography was carried out as required.

Example 489

6-(2-fluorophenyl)-2-(3-isopropoxyphenyl)benzoxazole

HPLC (220 nm) Purity 100% (Retention time 5.47 minutes)
MS (APCI+, m/e) 348 (M+1)

Example 490

6-(2-fluorophenyl)-2-[3-(hexyloxy)phenyl]benzoxazole

HPLC (220 nm) Purity 100% (Retention time 6.52 minutes)
MS (APCI+, m/e) 390 (M+1)

Example 491

6-(2-fluorophenyl)-2-[3-(3-methylbuthoxy)phenyl]benzoxazole

HPLC (220 nm) Purity 100% (Retention time 6.10 minutes)
MS (APCI+, m/e) 376 (M+1)

Example 492

2-[3-(cyclopentyloxy)phenyl]-6-(2-fluorophenyl)benzoxazole

HPLC (220 nm) Purity 100% (Retention time 5.93 minutes)
MS (APCI+, m/e) 374 (M+1)

Example 493

2-[3-(cyclopropylmethoxy)phenyl]-6-(2-fluorophenyl)benzoxazole

HPLC (220 nm) Purity 100% (Retention time 5.46 minutes)
MS (APCI+, m/e) 360 (M+1)

Example 494

2-[3-(benzyloxy)phenyl]-6-(2-fluorophenyl)benzoxazole

HPLC (220 nm) Purity 100% (Retention time 5.57 minutes)
MS (APCI+, m/e) 396 (M+1)

Example 495

Tert-butyl [3-[6-(2-fluorophenyl)benzoxazol-2-yl]phenoxy]acetate

HPLC (220 nm) Purity 100% (Retention time 5.30 minutes)
MS (APCI+, m/e) 420 (M+1)

Example 496

2-[3-[6-(2-fluorophenyl)benzoxazol-2-yl]phenoxy]-N-methylacetamide

HPLC (220 nm) Purity 97% (Retention time 4.23 minutes)
MS (APCI+, m/e) 377 (M+1)

Example 497

6-(2,4-difluorophenyl)-2-(3-isopropoxyphenyl)benzoxazole

HPLC (220 nm) Purity 100% (Retention time 5.48 minutes)
MS (APCI+, m/e) 366 (M+1)

Example 498

6-(2,4-difluorophenyl)-2-[3-(hexyloxy)phenyl]benzoxazole

HPLC (220 nm) Purity 100% (Retention time 6.49 minutes)
MS (APCI+, m/e) 408 (M+1)

Example 499

6-(2,4-difluorophenyl)-2-[3-(3-methylbuthoxy)phenyl]benzoxazole

HPLC (220 nm) Purity 99% (Retention time 6.10 minutes)
MS (APCI+, m/e) 394 (M+1)

Example 500

2-[3-(cyclopentyloxy)phenyl]-6-(2,4-difluorophenyl)benzoxazole

HPLC (220 nm) Purity 100% (Retention time 5.92 minutes)
MS (APCI+, m/e) 392 (M+1)

Example 501

2-[3-(cyclopropylmethoxy)phenyl]-6-(2,4-difluorophenyl)benzoxazole

HPLC (220 nm) Purity 100% (Retention time 5.47 minutes)
MS (APCI+, m/e) 378 (M+1)

Example 502

2-[3-(benzyloxy)phenyl]-6-(2,4-difluorophenyl)benzoxazole

HPLC (220 nm) Purity 100% (Retention time 5.58 minutes)
MS (APCI+, m/e) 414 (M+1)

Example 503

Tert-butyl [3-[6-(2,4-difluorophenyl)benzoxazol-2-yl]phenoxy]acetate

HPLC (220 nm) Purity 100% (Retention time 5.32 minutes)
MS (APCI+, m/e) 438 (M+1)

Example 504

2-[3-[6-(2,4-difluorophenyl)benzoxazol-2-yl]phenoxy]-N-methylacetamide

HPLC (220 nm) Purity 100% (Retention time 4.30 minutes)
MS (APCI+, m/e) 395 (M+1)

By using the compounds obtained in Reference Examples 73 to 111 and various boron acids as starting materials, the compounds of the following Examples 505 to 588 were synthesized in a manner similar to Example 1. At that time, purification by means of recrystallization or silica gel column chromatography was carried out as required.

Example 505

2-(2-methoxyphenyl)-6-phenyl-1H-imidazo[4,5-b]pyridine

HPLC (220 nm) Purity 94% (Retention time 3.07 minutes)
MS (APCI+, m/e) 302 (M+1)

Example 506

2-(2-(2-methoxyethoxy)phenyl)-6-phenyl-1H-imidazo[4,5-b]pyridine

HPLC (220 nm) Purity 99% (Retention time 3.24 minutes)
MS (APCI+, m/e) 346 (M+1)

Example 507

2-(2,3-dihydro-1,4-benzodioxin-6-yl)-6-phenyl-1H-imidazo[4,5-b]pyridine

HPLC (220 nm) Purity 83% (Retention time 3.05 minutes)
MS (APCI+, m/e) 330 (M+1)

Example 508

2-(3-fluorophenyl)-6-phenyl-1H-imidazo[4,5-b]pyridine

HPLC (220 nm) Purity 96% (Retention time 3.23 minutes)
MS (APCI+, m/e) 290 (M+1)

Example 509

2-(3-fluorophenyl)-6-(2-furyl)-1H-imidazo[4,5-b]pyridine

HPLC (220 nm) Purity 95% (Retention time 3.13 minutes)
MS (APCI+, m/e) 280 (M+1)

Example 510

2-(2-fluorophenyl)-6-phenyl-1H-imidazo[4,5-b]pyridine

HPLC (220 nm) Purity 100% (Retention time 3.09 minutes)
MS (APCI+, m/e) 290 (M+1)

Example 511

2-(2-fluorophenyl)-6-(2-furyl)-1H-imidazo[4,5-b]pyridine

HPLC (220 nm) Purity 100% (Retention time 2.98 minutes)
MS (APCI+, m/e) 280 (M+1)

Example 512

2-(4-fluorophenyl)-6-phenyl-1H-imidazo[4,5-b]pyridine

HPLC (220 nm) Purity 99% (Retention time 3.13 minutes)
MS (APCI+, m/e) 290 (M+1)

Example 513

2-(4-fluorophenyl)-6-(2-furyl)-1H-imidazo[4,5-b]pyridine

HPLC (220 nm) Purity 92% (Retention time 3.01 minutes)
MS (APCI+, m/e) 280 (M+1)

Example 514

N-(3-(6-(2-methoxyphenyl)-1H-imidazo[4,5-b]pyridin-2-yl)phenyl)-N,N-dimethylamine HPLC (220 nm) Purity 99% (Retention time 2.81 minutes)
MS (APCI+, m/e) 345 (M+1)

Example 515

2-(2-fluorophenyl)-6-(2-methoxyphenyl)-1H-imidazo[4,5-b]pyridine

HPLC (220 nm) Purity 99% (Retention time 3.20 minutes)
MS (APCI+, m/e) 320 (M+1)

Example 516

2-(3-fluorophenyl)-6-(2-methoxyphenyl)-1H-imidazo[4,5-b]pyridine

HPLC (220 nm) Purity 99% (Retention time 3.20 minutes)
MS (APCI+, m/e) 320 (M+1)

Example 517

2-(4-fluorophenyl)-6-(2-methoxyphenyl)-1H-imidazo[4,5-b]pyridine

HPLC (220 nm) Purity 95% (Retention time 3.08 minutes)
MS (APCI+, m/e) 320 (M+1)

Example 518

N,N-dimethyl-N-(3-(6-phenyl-1H-imidazo[4,5-b]pyridin-2-yl)phenyl)amine

HPLC (220 nm) Purity 100% (Retention time 2.80 minutes)
MS (APCI+, m/e) 315 (M+1)

Example 519

N-(3-(6-(2-furyl)-1H-imidazo[4,5-b]pyridin-2-yl)phenyl)-N,N-dimethylamine

HPLC (220 nm) Purity 98% (Retention time 2.58 minutes)
MS (APCI+, m/e) 305 (M+1)

Example 520

3-(6-phenyl-1H-imidazo[4,5-b]pyridin-2-yl)benzonitrile

HPLC (220 nm) Purity 98% (Retention time 3.21 minutes)
MS (APCI+, m/e) 297 (M+1)

Example 521

3-(6-(2-methoxyphenyl)-1H-imidazo[4,5-b]pyridin-2-yl)benzonitrile

HPLC (220 nm) Purity 99% (Retention time 3.20 minutes)
MS (APCI+, m/e) 327 (M+1)

Example 522

2-(2-fluorophenyl)-6-(3-methoxyphenyl)-1H-imidazo[4,5-b]pyridine

HPLC (220 nm) Purity 100% (Retention time 3.15 minutes)
MS (APCI+, m/e) 320 (M+1)

Example 523

2-(3-fluorophenyl)-6-(3-methoxyphenyl)-1H-imidazo[4,5-b]pyridine

HPLC (220 nm) Purity 100% (Retention time 3.28 minutes)
MS (APCI+, m/e) 320 (M+1)

Example 524

2-(4-fluorophenyl)-6-(3-methoxyphenyl)-1H-imidazo[4,5-b]pyridine

HPLC (220 nm) Purity 99% (Retention time 3.17 minutes)
MS (APCI+, m/e) 320 (M+1)

Example 525

6-phenyl-2-(3-(trifluoromethyl)phenyl)-1H-imidazo[4,5-b]pyridine

HPLC (220 nm) Purity 93% (Retention time 3.61 minutes)
MS (APCI+, m/e) 340 (M+1)

Example 526

6-(2-furyl)-2-(3-(trifluoromethyl)phenyl)-1H-imidazo[4,5-b]pyridine

HPLC (220 nm) Purity 85% (Retention time 3.58 minutes)
MS (APCI+, m/e) 330 (M+1)

Example 527

6-(2-methoxyphenyl)-2-(3-(trifluoromethyl)phenyl)-1H-imidazo[4,5-b]pyridine

HPLC (220 nm) Purity 100% (Retention time 3.54 minutes)
MS (APCI+, m/e) 370 (M+1)

Example 528

2-(3-(methylsulfonyl)phenyl)-6-phenyl-1H-imidazo[4,5-b]pyridine

HPLC (220 nm) Purity 94% (Retention time 2.98 minutes)
MS (APCI+, m/e) 350 (M+1)

Example 529

6-(2-methoxyphenyl)-2-(3-(methylsulfonyl)phenyl)-1H-imidazo[4,5-b]pyridine

HPLC (220 nm) Purity 99% (Retention time 2.96 minutes)
MS (APCI+, m/e) 380 (M+1)

Example 530

6-(2-furyl)-2-(3-(methylsulfonyl)phenyl)-1H-imidazo[4,5-b]pyridine

HPLC (220 nm) Purity 99% (Retention time 2.89 minutes)
MS (APCI+, m/e) 340 (M+1)

Example 531

6-(2-furyl)-2-(3-(2-methoxyethoxy)phenyl)-1H-imidazo[4,5-b]pyridine

HPLC (220 nm) Purity 89% (Retention time 3.00 minutes)
MS (APCI+, m/e) 336 (M+1)

Example 532

6-(2-furyl)-2-(4-(2-methoxyethoxy)phenyl)-1H-imidazo[4,5-b]pyridine

HPLC (220 nm) Purity 90% (Retention time 3.53 minutes)
MS (APCI+, m/e) 336 (M+1)

Example 533

2-(3-morpholinophenyl)-6-phenyl-1H-imidazo[4,5-b]pyridine

HPLC (220 nm) Purity 100% (Retention time 3.03 minutes)
MS (APCI+, m/e) 357 (M+1)

Example 534

6-(2-furyl)-2-(3-morpholinophenyl)-1H-imidazo[4,5-b]pyridine

HPLC (220 nm) Purity 100% (Retention time 2.92 minutes)
MS (APCI+, m/e) 347 (M+1)

Example 535

6-(2-fluorophenyl)-2-(3-morpholinophenyl)-1H-imidazo[4,5-b]pyridine

HPLC (220 nm) Purity 100% (Retention time 3.11 minutes)
MS (APCI+, m/e) 375 (M+1)

Example 536

6-(2-furyl)-2-(3-(1-pyrrolidinyl)phenyl)-1H-imidazo[4,5-b]pyridine

HPLC (220 nm) Purity 99% (Retention time 3.31 minutes)
MS (APCI+, m/e) 331 (M+1)

Example 537

6-(3-furyl)-2-(3-methoxyphenyl)-1H-imidazo[4,5-b]pyridine

HPLC (220 nm) Purity 93% (Retention time 2.91 minutes)
MS (APCI+, m/e) 292 (M+1)

Example 538

2-(5-methyl-3-phenyl-4-isoxazolyl)-6-phenyl-1H-imidazo[4,5-b]pyridine

HPLC (220 nm) Purity 100% (Retention time 3.38 minutes)
MS (APCI+, m/e) 353 (M+1)

Example 539

6-(2-furyl)-2-(5-methyl-3-phenyl-4-isoxazolyl)-1H-imidazo[4,5-b]pyridine

HPLC (220 nm) Purity 100% (Retention time 3.32 minutes)
MS (APCI+, m/e) 343 (M+1)

Example 540

6-phenyl-2-(3-(2,2,2-trifluoroehoxy)phenyl)-1H-imidazo[4,5-b]pyridine

HPLC (220 nm) Purity 86% (Retention time 3.53 minutes)
MS (APCI+, m/e) 370 (M+1)

Example 541

6-(2-furyl)-2-(3-(2,2,2-trifluoroehoxy)phenyl)-1H-imidazo[4,5-b]pyridine

HPLC (220 nm) Purity 92% (Retention time 3.53 minutes)
MS (APCI+, m/e) 360 (M+1)

Example 542

6-(2-fluorophenyl)-2-(3-(2,2,2-trifluoroehoxy)phenyl)-1H-imidazo[4,5-b]pyridine

HPLC (220 nm) Purity 87% (Retention time 3.65 minutes)
MS (APCI+, m/e) 388 (M+1)

Example 543

2-(3-isopropoxy-2-methylphenyl)-6-phenyl-1H-imidazo[4,5-b]pyridine

HPLC (220 nm) Purity 99% (Retention time 3.45 minutes)
MS (APCI+, m/e) 344 (M+1)

Example 544

6-(2-furyl)-2-(3-isopropoxy-2-methylphenyl)-1H-imidazo[4,5-b]pyridine

HPLC (220 nm) Purity 95% (Retention time 3.37 minutes)
MS (APCI+, m/e) 334 (M+1)

Example 545

6-(2-fluorophenyl)-2-(3-isopropoxy-2-methylphenyl)-1H-imidazo[4,5-b]pyridine

HPLC (220 nm) Purity 99% (Retention time 3.54 minutes)
MS (APCI+, m/e) 362 (M+1)

Example 546

6-(2,4-difluorophenyl)-2-(3-isopropoxy-2-methylphenyl)-1H-imidazo[4,5-b]pyridine HPLC (220 nm) Purity 96% (Retention time 3.62 minutes)
MS (APCI+, m/e) 380 (M+1)

Example 547

2-(2-(2-methoxyphenyl)ethyl)-6-phenyl-1H-imidazo[4,5-b]pyridine

HPLC (220 nm) Purity 98% (Retention time 3.17 minutes)
MS (APCI+, m/e) 330 (M+1)

Example 548

6-(2-furyl)-2-(2-(2-methoxyphenyl)ethyl)-1H-imidazo[4,5-b]pyridine

HPLC (220 nm) Purity 97% (Retention time 3.01 minutes)
MS (APCI+, m/e) 320 (M+1)

Example 549

2-(2-(4-methoxyphenyl)ethyl)-6-phenyl-1H-imidazo[4,5-b]pyridine

HPLC (220 nm) Purity 94% (Retention time 3.13 minutes)
MS (APCI+, m/e) 330 (M+1)

Example 550

6-(2-furyl)-2-(2-(4-methoxyphenyl)ethyl)-1H-imidazo[4,5-b]pyridine

HPLC (220 nm) Purity 99% (Retention time 2.97 minutes)
MS (APCI+, m/e) 320 (M+1)

Example 551

2-(2-(3-methoxyphenyl)ethyl)-6-phenyl-1H-imidazo[4,5-b]pyridine

HPLC (220 nm) Purity 89% (Retention time 3.14 minutes)
MS (APCI+, m/e) 330 (M+1)

Example 552

6-(2-furyl)-2-(2-(3-methoxyphenyl)ethyl)-1H-imidazo[4,5-b]pyridine

HPLC (220 nm) Purity 99% (Retention time 2.98 minutes)
MS (APCI+, m/e) 320 (M+1)

Example 553

2-(2-(4-chlorophenyl)ethyl)-6-phenyl-1H-imidazo[4,5-b]pyridine

HPLC (220 nm) Purity 96% (Retention time 3.33 minutes)
MS (APCI+, m/e) 334 (M+1)

Example 554

2-(2-(4-chlorophenyl)ethyl)-6-(2-furyl)-1H-imidazo[4,5-b]pyridine

HPLC (220 nm) Purity 100% (Retention time 3.20 minutes)
MS (APCI+, m/e) 324 (M+1)

Example 555

2-(2-(2-chlorophenyl)ethyl)-6-phenyl-1H-imidazo[4,5-b]pyridine

HPLC (220 nm) Purity 100% (Retention time 3.24 minutes)
MS (APCI+, m/e) 334 (M+1)

Example 556

2-(2-(2-chlorophenyl)ethyl)-6-(2-furyl)-1H-imidazo[4,5-b]pyridine

HPLC (220 nm) Purity 100% (Retention time 3.10 minutes)
MS (APCI+, m/e) 324 (M+1)

Example 557

2-(2-(3-chlorophenyl)ethyl)-6-phenyl-1H-imidazo[4,5-b]pyridine

HPLC (220 nm) Purity 96% (Retention time 3.31 minutes)
MS (APCI+, m/e) 334 (M+1)

Example 558

2-(2-(3-chlorophenyl)ethyl)-6-(2-furyl)-1H-imidazo[4,5-b]pyridine

HPLC (220 nm) Purity 96% (Retention time 3.19 minutes)
MS (APCI+, m/e) 324 (M+1)

Example 559

2-(2-(4-methylphenyl)ethyl)-6-phenyl-1H-imidazo[4,5-b]pyridine

HPLC (220 nm) Purity 99% (Retention time 3.26 minutes)
MS (APCI+, m/e) 314 (M+1)

Example 560

6-(2-furyl)-2-(2-(4-methylphenyl)ethyl)-1H-imidazo[4,5-b]pyridine

HPLC (220 nm) Purity 99% (Retention time 3.13 minutes)
MS (APCI+, m/e) 304 (M+1)

Example 561

2-(2-(3,4-dichlorophenyl)ethyl)-6-phenyl-1H-imidazo[4,5-b]pyridine

HPLC (220 nm) Purity 87% (Retention time 3.47 minutes)
MS (APCI+, m/e) 368 (M+1)

Example 562

2-(2-(3,4-dichlorophenyl)ethyl)-6-(2-furyl)-1H-imidazo[4,5-b]pyridine

HPLC (220 nm) Purity 94% (Retention time 3.38 minutes)
MS (APCI+, m/e) 358 (M+1)

Example 563

4-(2-(6-phenyl-1H-imidazo[4,5-b]pyridin-2-yl)ethyl)benzonitrile

HPLC (220 nm) Purity 98% (Retention time 3.03 minutes)
MS (APCI+, m/e) 325 (M+1)

Example 564

4-(2-(6-(2-furyl)-1H-imidazo[4,5-b]pyridin-2-yl)ethyl)benzonitrile

HPLC (220 nm) Purity 100% (Retention time 2.88 minutes)
MS (APCI+, m/e) 315 (M+1)

Example 565

2-(2-(4-fluorophenyl)ethyl)-6-phenyl-1H-imidazo[4,5-b]pyridine

HPLC (220 nm) Purity 94% (Retention time 3.17 minutes)
MS (APCI+, m/e) 318 (M+1)

Example 566

2-(2-(4-fluorophenyl)ethyl)-6-(2-furyl)-1H-imidazo[4,5-b]pyridine

HPLC (220 nm) Purity 100% (Retention time 3.03 minutes)
MS (APCI+, m/e) 308 (M+1)

Example 567

6-phenyl-2-(2-(4-(trifluoromethyl)phenyl)ethyl)-1H-imidazo[4,5-b]pyridine

HPLC (220 nm) Purity 100% (Retention time 3.45 minutes)
MS (APCI+, m/e) 368 (M+1)

Example 568

6-(2-furyl)-2-(2-(4-(trifluoromethyl)phenyl)ethyl)-1H-imidazo[4,5-b]pyridine

HPLC (220 nm) Purity 90% (Retention time 3.34 minutes)
MS (APCI+, m/e) 358 (M+1)

Example 569

6-phenyl-2-(2-phenylcyclopropyl)-1H-imidazo[4,5-b]pyridine

HPLC (220 nm) Purity 100% (Retention time 3.20 minutes)
MS (APCI+, m/e) 312 (M+1)

Example 570

6-(2-furyl)-2-(2-phenylcyclopropyl)-1H-imidazo[4,5-b]pyridine

HPLC (220 nm) Purity 100% (Retention time 3.07 minutes)
MS (APCI+, m/e) 302 (M+1)

Example 571

2-(2-(4-isopropylphenyl)ethyl)-6-phenyl-1H-imidazo[4,5-b]pyridine

HPLC (220 nm) Purity 96% (Retention time 3.57 minutes)
MS (APCI+, m/e) 342 (M+1)

Example 572

6-(2-furyl)-2-(2-(4-isopropylphenyl)ethyl)-1H-imidazo[4,5-b]pyridine

HPLC (220 nm) Purity 80% (Retention time 3.47 minutes)
MS (APCI+, m/e) 332 (M+1)

Example 573

6-phenyl-2-(2-(2-thienyl)ethyl)-1H-imidazo[4,5-b]pyridine

HPLC (220 nm) Purity 100% (Retention time 3.03 minutes)
MS (APCI+, m/e) 306 (M+1)

Example 574

6-(2-furyl)-2-(2-(2-thienyl)ethyl)-1H-imidazo[4,5-b]pyridine

HPLC (220 nm) Purity 99% (Retention time 2.88 minutes)
MS (APCI+, m/e) 296 (M+1)

Example 575

2-(2-(4-ethoxyphenyl)ethyl)-6-phenyl-1H-imidazo[4,5-b]pyridine

HPLC (220 nm) Purity 100% (Retention time 3.27 minutes)
MS (APCI+, m/e) 344 (M+1)

Example 576

2-(2-(4-ethoxyphenyl)ethyl)-6-(2-furyl)-1H-imidazo[4,5-b]pyridine

HPLC (220 nm) Purity 100% (Retention time 3.15 minutes)
MS (APCI+, m/e) 334 (M+1)

Example 577

2-(2-(4-nitrophenyl)ethyl)-5-phenyl-1H-benzoimidazole

HPLC (220 nm) Purity 100% (Retention time 3.16 minutes)
MS (APCI+, m/e) 344 (M+1)

Example 578

6-phenyl-2-(2-phenylpropyl)-1H-imidazo[4,5-b]pyridine

HPLC (220 nm) Purity 100% (Retention time 3.20 minutes)
MS (APCI+, m/e) 314 (M+1)

Example 579

6-(2-furyl)-2-(2-phenylpropyl)-1H-imidazo[4,5-b]pyridine

HPLC (220 nm) Purity 100% (Retention time 3.05 minutes)
MS (APCI+, m/e) 304 (M+1)

Example 580

6-phenyl-2-(5-phenylpentyl)-1H-imidazo[4,5-b]pyridine

HPLC (220 nm) Purity 100% (Retention time 3.53 minutes)
MS (APCI+, m/e) 342 (M+1)

Example 581

6-(2-furyl)-2-(5-phenylpentyl)-1H-imidazo[4,5-b]pyridine

HPLC (220 nm) Purity 100% (Retention time 3.41 minutes)
MS (APCI+, m/e) 332 (M+1)

Example 582

2-(2-(4-butoxyphenyl)ethyl)-6-phenyl-1H-imidazo[4,5-b]pyridine

HPLC (220 nm) Purity 99% (Retention time 3.62 minutes)
MS (APCI+, m/e) 372 (M+1)

Example 583

2-(2-(4-butoxyphenyl)ethyl)-6-(2-furyl)-1H-imidazo[4,5-b]pyridine

HPLC (220 nm) Purity 100% (Retention time 3.52 minutes)
MS (APCI+, m/e) 362 (M+1)

Example 584

6-phenyl-2-(2-(3,4,5-trimethoxyphenyl)ethyl)-1H-imidazo[4,5-b]pyridine

HPLC (220 nm) Purity 100% (Retention time 3.01 minutes)
MS (APCI+, m/e) 390 (M+1)

Example 585

6-(2-furyl)-2-(2-(3,4,5-trimethoxyphenyl)ethyl)-1H-imidazo[4,5-b]pyridine

HPLC (220 nm) Purity 100% (Retention time 2.86 minutes)
MS (APCI+, m/e) 380 (M+1)

Example 586

2-(2-(4-isopropoxyphenyl)ethyl)-6-phenyl-1H-imidazo[4,5-b]pyridine

HPLC (220 nm) Purity 92% (Retention time 3.38 minutes)
MS (APCI+, m/e) 358 (M+1)

Example 587

6-(2-furyl)-2-(2-(4-isopropoxyphenyl)ethyl)-1H-imidazo[4,5-b]pyridine

HPLC (220 nm) Purity 88% (Retention time 3.26 minutes)
MS (APCI+, m/e) 348 (M+1)

Example 588

6-(2-fluorophenyl)-2-(2-(4-isopropoxyphenyl)ethyl)-1H-imidazo[4,5-b]pyridine

HPLC (220 nm) Purity 88% (Retention time 3.40 minutes)
MS (APCI+, m/e) 376 (M+1)

Example 589

2-(2-(4-Nitrophenyl)ethyl)-5-phenyl-1H-benzoimidazole (Compound of Example 577) (0.5 g) was dissolved in acetic acid (50 ml). To the solution was added palladium-carbon (0.1 g), and under a hydrogen stream, the mixture was stirred at room temperature for 16 hours. After the catalyst was removed, the solvent was distilled off under reduced pressure. The resulting crystals were collected by filtration to obtain 4-(2-(6-phenyl-1H-imidazo[4,5-b]pyridin-2-yl)ethyl)aniline (0.44 g, 95%).

$^1$H NMR (DMSO-$d_6$) δ 2.96-3.12 (4H, m), 4.74 (2H, s), 6.49 (2H, d, J=8.4 Hz), 6.90 (1H, d, J=8.4 Hz), 7.34-7.70 (5H, m), 7.95-8.10 (1H, broad s), 8.24 (1H, s), 8.42-8.60 (1H, broad s) ppm IR (KBr) ν 3032, 1622, 1518, 1424, 1393, 764, 700 cm$^{-1}$
HPLC (220 nm) Purity 94% (Retention time 2.39 minutes)
MS (APCI+, m/e) 315 (M+1)

Example 590

A solution of 4-(2-(6-phenyl-1H-imidazo[4,5-b]pyridin-2-yl)ethyl)aniline (Compound of Example 589) (25 mg) and acetic anhydride (0.01 ml) in pyridine was stirred at room temperature for 6 hours, and the reaction mixture was poured onto ice. The mixture was neutralized with a 5% aqueous solution of ammonium acetate and extracted with ethyl acetate. The organic layer was washed with water and dried over Na$_2$SO$_4$. The solvent was distilled off and the resulting crystals were collected by filtration to obtain N-(4-(2-(6-phenyl-1H-imidazo[4,5-b]pyridin-2-yl)ethyl)phenyl)acetamide (22 mg, 78%).

$^1$H NMR (DMSO-d$_6$) δ 2.02 (3H, s), 3.12 (4H, s), 7.16 (2H, d, J=8.7 Hz), 7.34-7.49 (5H, m), 7.70 (2H, d, J=8.7 Hz), 7.79-8.57 (2H, m), 9.80 (1H, s), 12.9 (1H, s) ppm IR (KBr) ν 3293, 3032, 1659, 1539, 1387, 764 cm$^{-1}$
HPLC (220 nm) Purity 99% (Retention time 2.75 minutes)
MS (APCI+, m/e) 357 (M+1)

Example 591

Phosphorus pentachloride (0.5 g) was added to methanesulfonic acid (2 ml), and the mixture was stirred at 120° C. for 1 hour to make a solution. To the solution were added 2,3-diamino-6-phenylpyridine (Compound of Reference Example 113) (0.2 g) and 3-methoxybenzoic acid (0.17 g), and the mixture was stirred at 120° C. for 1 hour. The reaction mixture was poured onto ice, neutralized with 8 N sodium hydroxide solution and extracted with ethyl acetate-tetrahydrofuran (3:1, v/v). The organic layer was washed with water and dried over MgSO$_4$. The solvent was distilled off under reduced pressure, and the resulting crystals were collected by filtration to obtain 5-phenyl-2-(3-methoxyphenyl)-1H-imidazo[4,5-b]pyridine (0.18 g, 55%).

$^1$H NMR (CDCl$_3$) δ 3.88 (3H, s), 6.97-7.02 (1H, m), 7.30-7.78 (8H, m), 7.95-8.20 (3H, m) ppm IR (KBr) ν 3005, 2938, 1590, 1466, 1227, 762 cm$^{-1}$
HPLC (220 nm) Purity 89% (Retention time 2.92 minutes)
MS (APCI+, m/e) 304 (M+1)

Example 592

6-Phenoxy-2,3-pyridine diamine (Compound of Reference Example 115) (0.2 g) and 3-methoxybenzoic acid (0.08 g) were dissolved in phosphorus oxychloride (5 ml) and the solution was stirred at 140° C. for 4 hours. The reaction mixture was poured onto ice, neutralized with 8 N sodium hydroxide solution and extracted with ethyl acetate-tetrahydrofuran (3:1, v/v). The organic layer was washed with water and dried over MgSO$_4$. The solvent was distilled off under reduced pressure, and the resulting crystals were collected by filtration to obtain 5-phenoxy-2-(3-methoxyphenyl)-1H-imidazo[4,5-b]pyridine (0.04 g, 23%).

$^1$H NMR (CDCl$_3$) δ 3.87 (3H, s), 6.84 (1H, d, J=8.8 Hz), 7.00 (1H, dd, J=8.4, 2.4 Hz), 7.10-7.26 (3H, m), 7.30-7.44 (3H, m), 7.53-7.73 (3H, m), 8.08 (1H, d, J=8.8 Hz) ppm IR (KBr) ν 3009, 1590, 1490, 1227, 762 cm$^{-1}$
HPLC (220 nm) Purity 80% (Retention time 3.29 minutes)
MS (APCI+, m/e) 318 (M+1)

By using the compounds obtained in Examples 282 to 284 and various boron acids as starting materials, the compounds of the following Examples 593 to 601 were synthesized in a manner similar to Example 214. At that time, purification by means of recrystallization or silica gel column chromatography was carried out as required.

Example 593

2-(3-(2-methoxyethoxy)phenyl)-6-phenylbenzoxazole

HPLC (220 nm) Purity 99% (Retention time 4.93 minutes)
MS (APCI+, m/e) 346 (M+1)

Example 594

6-(2-furyl)-2-(3-(2-methoxyethoxy)phenyl)benzoxazole

HPLC (220 nm) Purity 87% (Retention time 4.71 minutes)
MS (APCI+, m/e) 336 (M+1)

Example 595

6-(2-fluorophenyl)-2-(3-(2-methoxyethoxy)phenyl)benzoxazole

HPLC (220 nm) Purity 97% (Retention time 4.91 minutes)
MS (APCI+, m/e) 364 (M+1)

Example 596

4-(3-(6-phenylbenzoxazol-2-yl)phenoxy)butanenitrile

HPLC (220 nm) Purity 99% (Retention time 4.90 minutes)
MS (APCI+, m/e) 355 (M+1)

Example 597

4-(3-(6-(2-furyl)benzoxazol-2-yl)phenoxy)butanenitrile

HPLC (220 nm) Purity 95% (Retention time 4.69 minutes)
MS (APCI+, m/e) 345 (M+1)

Example 598

4-(3-(6-(2-fluorophenyl)benzoxazol-2-yl)phenoxy)butanenitrile

HPLC (220 nm) Purity 98% (Retention time 4.87 minutes)
MS (APCI+, m/e) 373 (M+1)

Example 599

2-(3-(3-(2-morpholinoehoxy)phenyl)-6-phenylbenzoxazole

HPLC (220 nm) Purity 95% (Retention time 3.69 minutes)
MS (APCI+, m/e) 401 (M+1)

Example 600

6-(2-furyl)-2-(3-(2-morpholinoehoxy)phenyl)benzoxazole

HPLC (220 nm) Purity 99% (Retention time 3.40 minutes)
MS (APCI+, m/e) 391 (M+1)

Example 601

6-(2-fluorophenyl)-2-(3-(2-morpholinoehoxy)phenyl)benzoxazole

HPLC (220 nm) Purity 92% (Retention time 3.69 minutes)
MS (APCI+, m/e) 419 (M+1)

TABLE 1

| Ref. 1 | 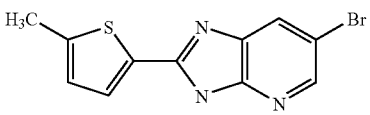 |
| --- | --- |
| Ref. 2 | 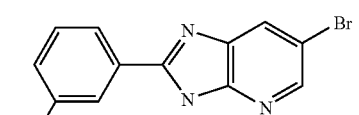 |
| Ref. 3 | 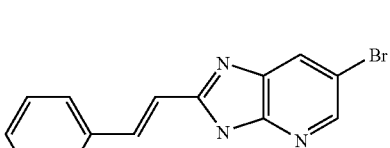 |
| Ref. 4 | 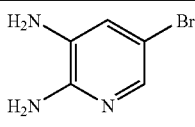 |
| Ref. 5 | 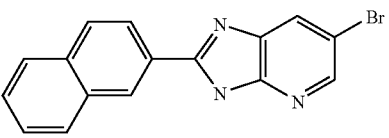 |
| Ref. 6 | 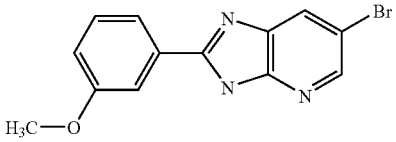 |
| Ref. 7 | 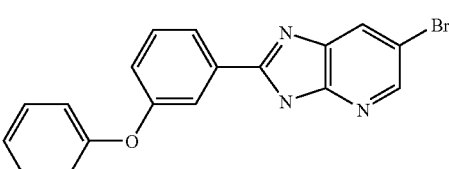 |

TABLE 1-continued

| Ref. 8 | 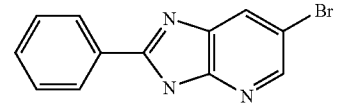 |
| --- | --- |
| Ref. 9 | 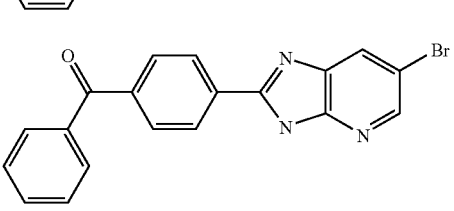 |
| Ref. 10 | 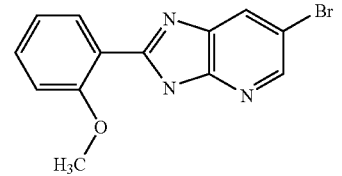 |

TABLE 2

| Ref. 11 | 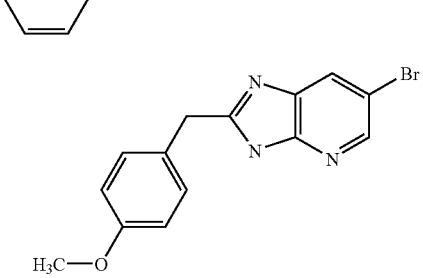 |
| --- | --- |
| Ref. 12 | 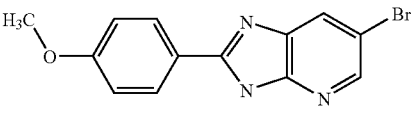 |
| Ref. 13 | 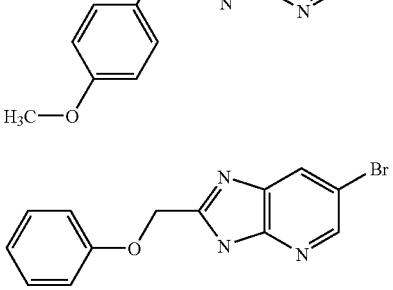 |
| Ref. 14 | 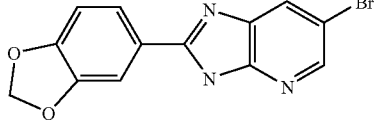 |
| Ref. 15 | 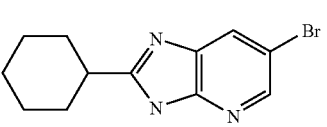 |
| Ref. 16 | 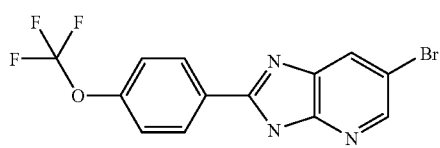 |

TABLE 2-continued
| Ref. 17 | 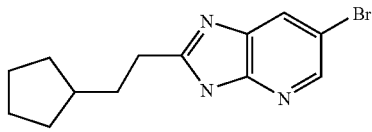 |
|---|---|
| Ref. 18 | 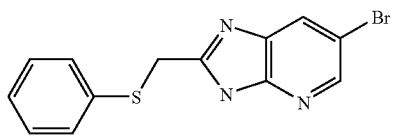 |
| Ref. 19 | 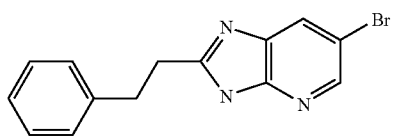 |
| Ref. 20 | 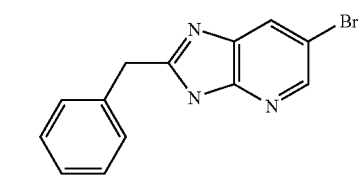 |
TABLE 3
| Ref. 21 | 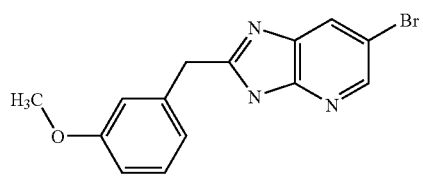 |
|---|---|
| Ref. 22 | 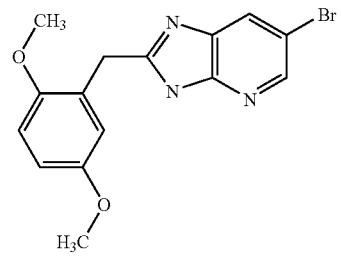 |
| Ref. 23 | 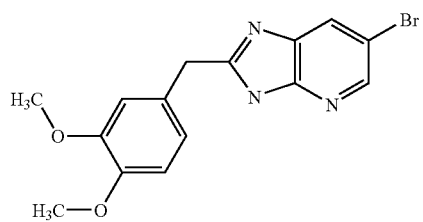 |
| Ref. 24 | 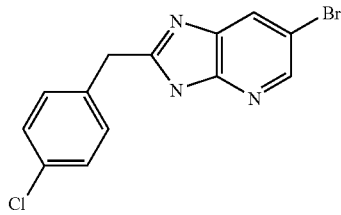 |
TABLE 3-continued
| Ref. 25 | 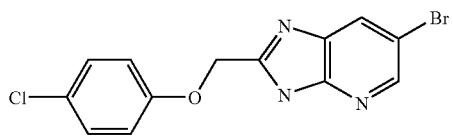 |
|---|---|
| Ref. 26 | 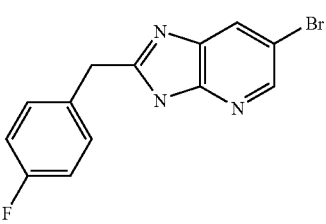 |
| Ref. 27 | 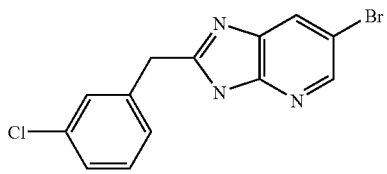 |
| Ref. 28 | 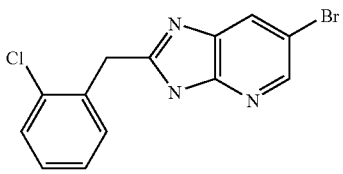 |
| Ref. 29 | 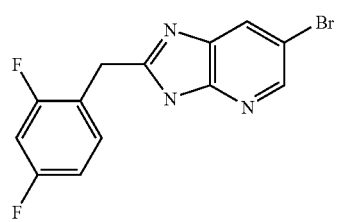 |
| Ref. 30 | 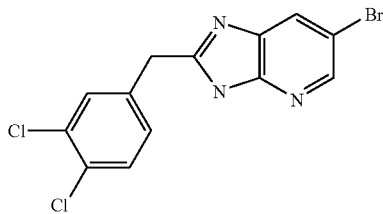 |
TABLE 4
| Ref. 31 | 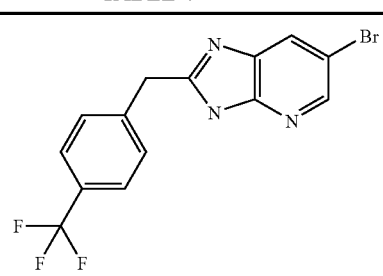 |
|---|---|

TABLE 4-continued
| Ref. 32 | 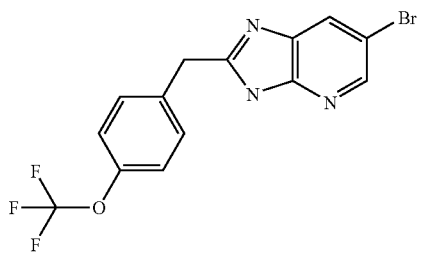 |
| --- | --- |
| Ref. 33 | 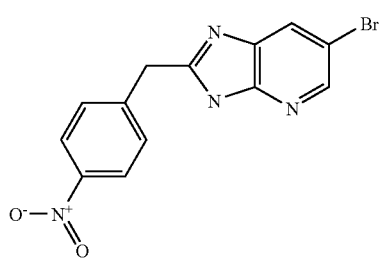 |
| Ref. 34 | 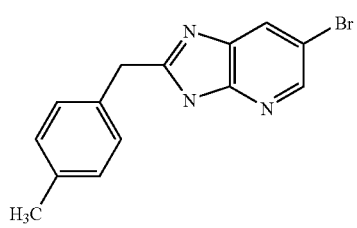 |
| Ref. 35 | 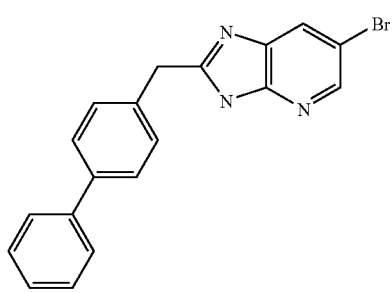 |
| Ref. 36 | 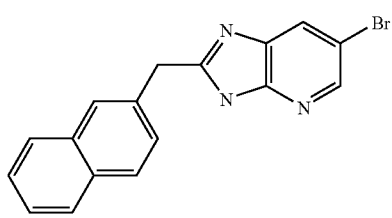 |
| Ref. 37 | 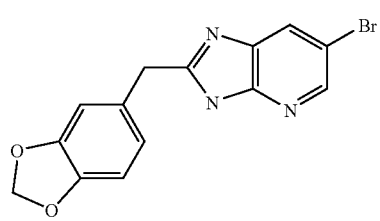 |
TABLE 4-continued
| Ref. 38 | 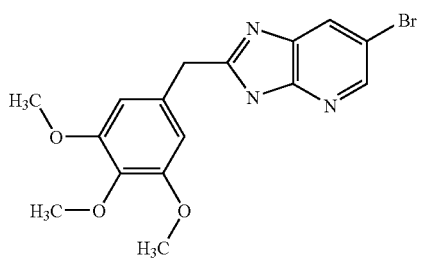 |
| --- | --- |
| Ref. 39 | 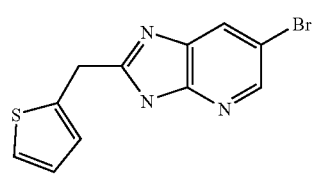 |
| Ref. 40 | 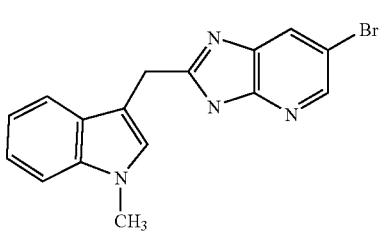 |
TABLE 5
| Ref. 41 | 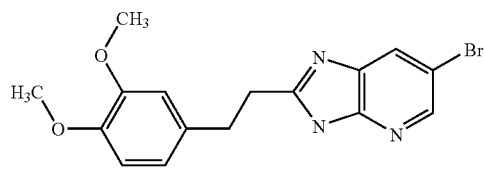 |
| --- | --- |
| Ref. 42 | 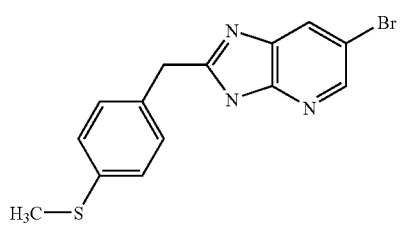 |
| Ref. 43 | 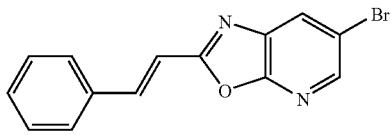 |
| Ref. 44 | 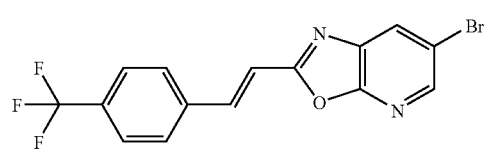 |
| Ref. 45 | 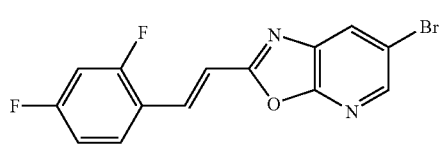 |

TABLE 5-continued
| Ref. 46 | 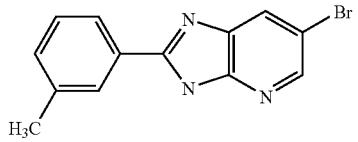 |
| Ref. 47 | 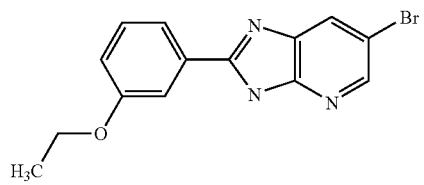 |
| Ref. 48 | 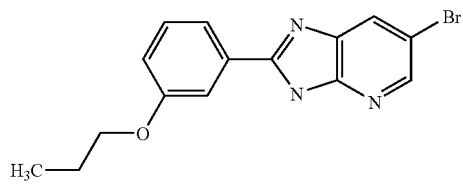 |
| Ref. 49 | 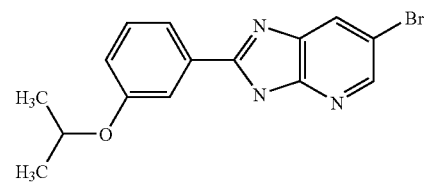 |
| Ref. 50 | 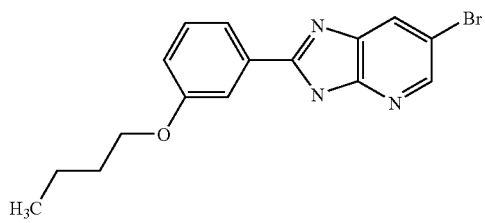 |
TABLE 6
| Ref. 51 | 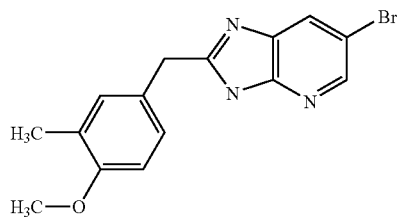 |
| Ref. 52 | 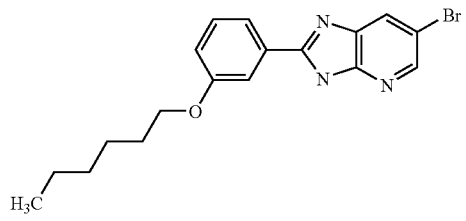 |
TABLE 6-continued
| Ref. 53 | 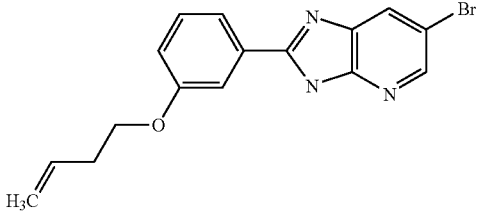 |
| Ref. 54 | 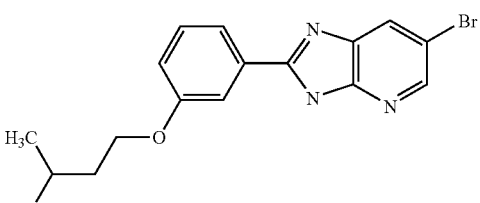 |
| Ref. 55 | 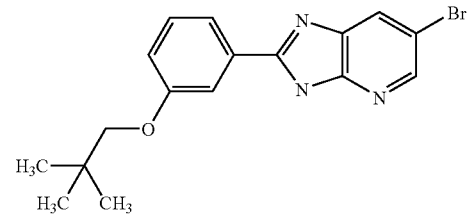 |
| Ref. 56 | 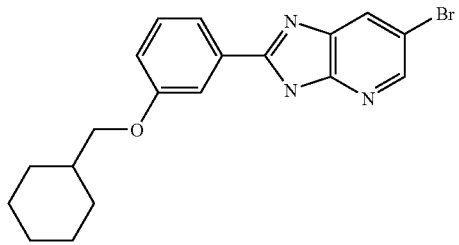 |
| Ref. 57 | 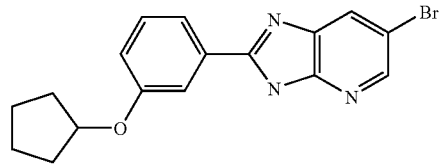 |
| Ref. 58 | 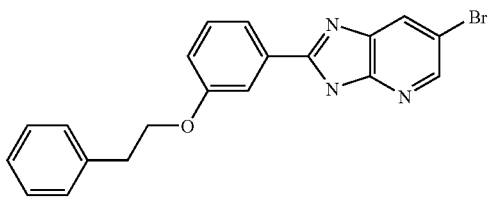 |
| Ref. 59 | 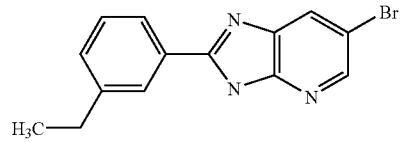 |

TABLE 6-continued
Ref. 60 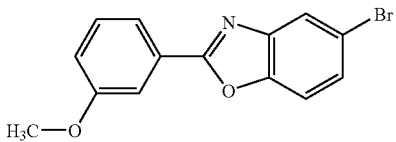
TABLE 7
Ref. 61 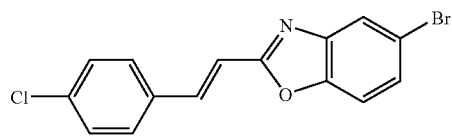
Ref. 62 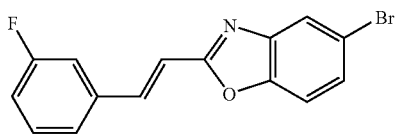
Ref. 63 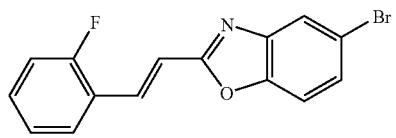
Ref. 64 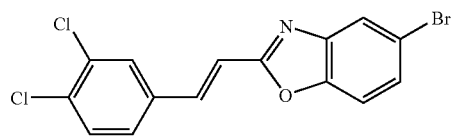
Ref. 65 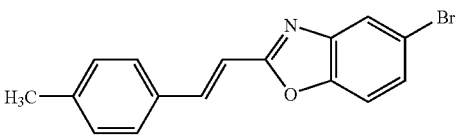
Ref. 66 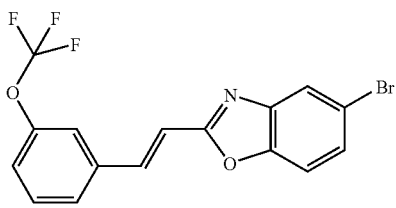
Ref. 67 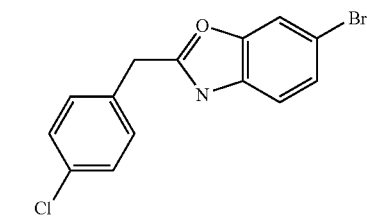
Ref. 68 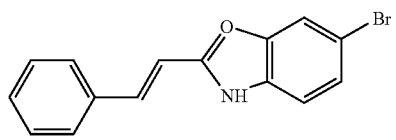
TABLE 7-continued
Ref. 69 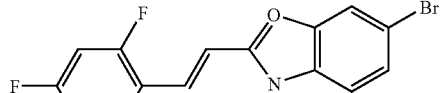
Ref. 70 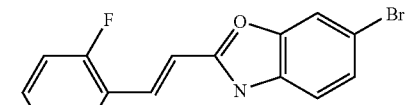
TABLE 8
Ref. 71 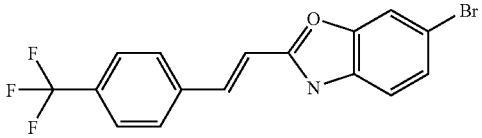
Ref. 72 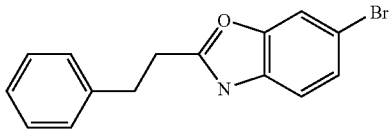
Ref. 73 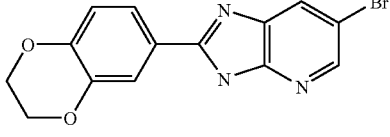
Ref. 74 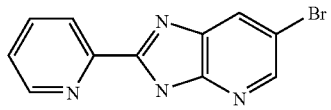
Ref. 75 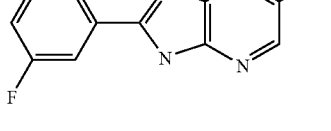
Ref. 76 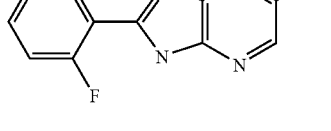
Ref. 77 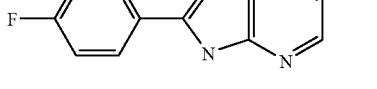
Ref. 78 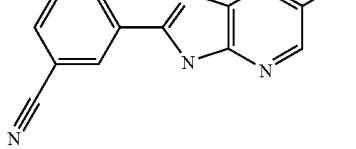

TABLE 8-continued
| Ref. 79 | 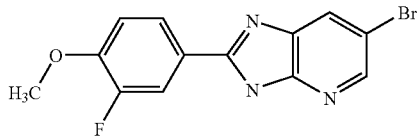 |
| Ref. 80 | 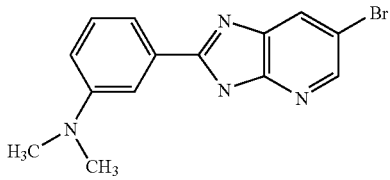 |
TABLE 9
| Ref. 81 | 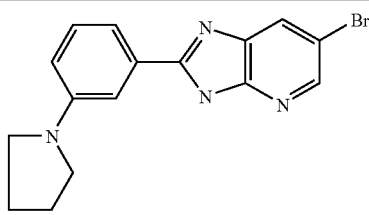 |
| Ref. 82 | 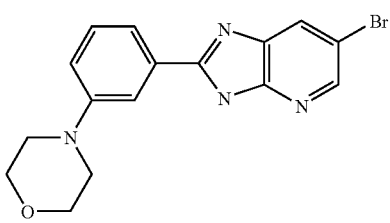 |
| Ref. 83 | 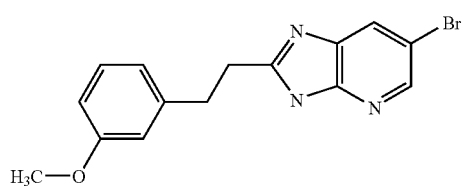 |
| Ref. 84 | 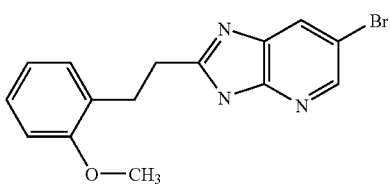 |
| Ref. 85 | 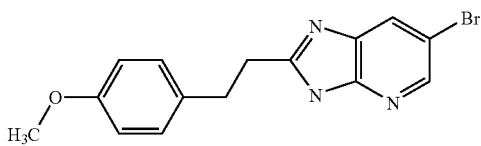 |
| Ref. 86 | 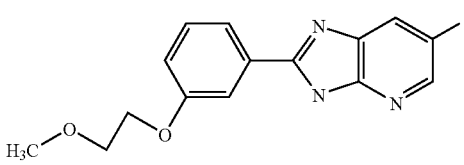 |
TABLE 9-continued
| Ref. 87 | 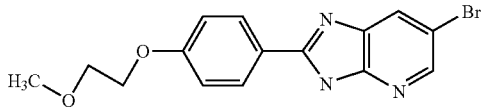 |
| Ref. 88 | 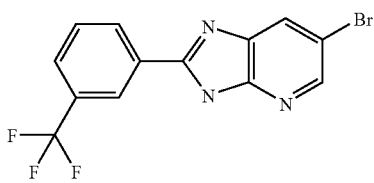 |
| Ref. 89 | 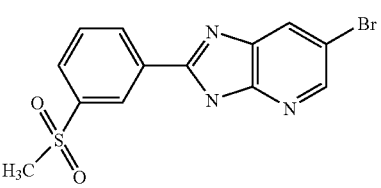 |
| Ref. 90 | 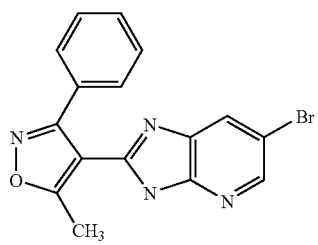 |
TABLE 10
| Ref. 91 | 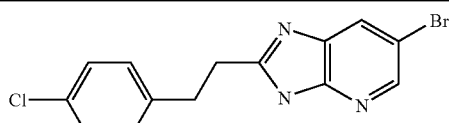 |
| Ref. 92 | 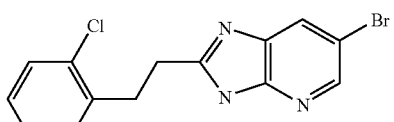 |
| Ref. 93 | 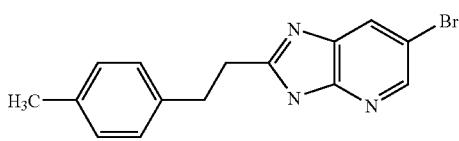 |
| Ref. 94 | 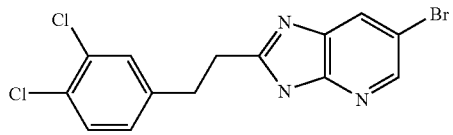 |
| Ref. 95 | 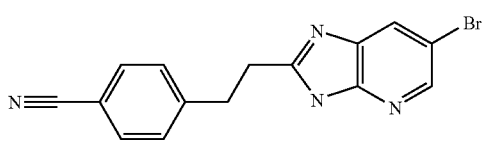 |

TABLE 10-continued
Ref. 96 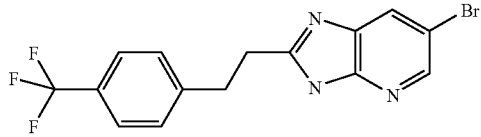
Ref. 97 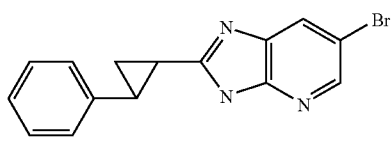
Ref. 98 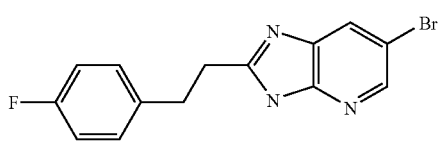
Ref. 99 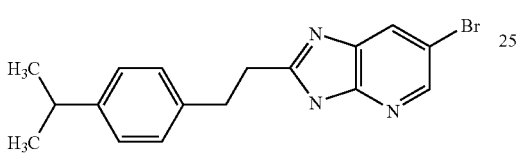
Ref. 100 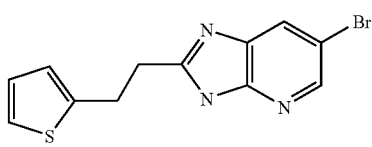
TABLE 11
Ref. 101 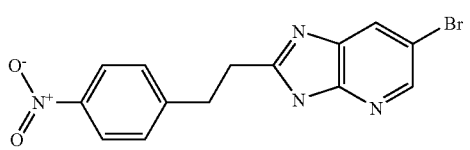
Ref. 102 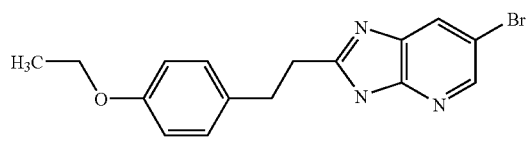
Ref. 103 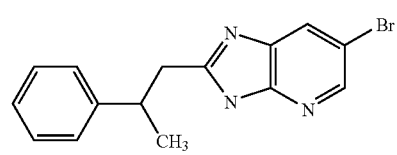
Ref. 104 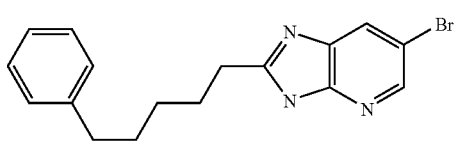
TABLE 11-continued
Ref. 105 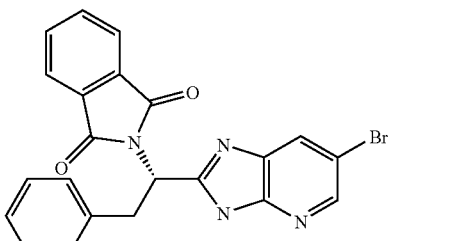
Ref. 106 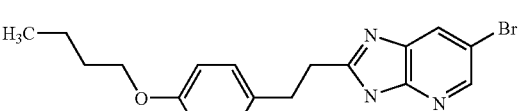
Ref. 107 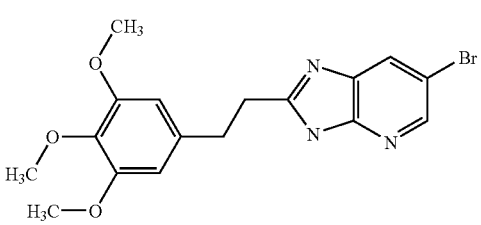
Ref. 108 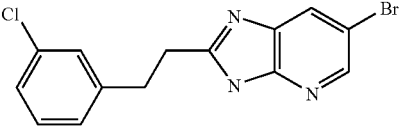
Ref. 109 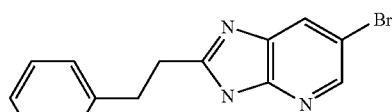
Ref. 110 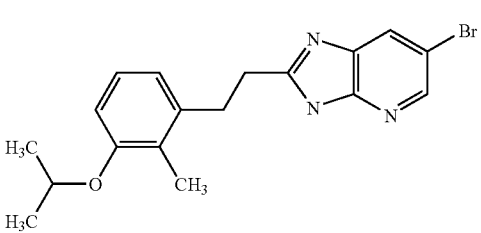
TABLE 12
Ref. 111 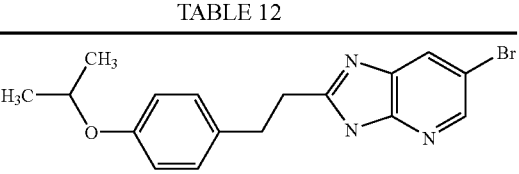

TABLE 12-continued
| Ref. 112 | 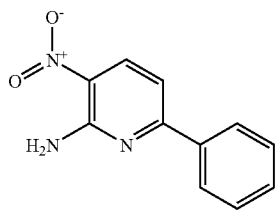 |
| --- | --- |
| Ref. 113 | 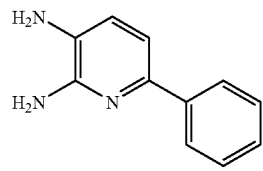 |
| Ref. 114 | 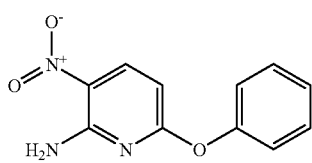 |
| Ref. 115 | 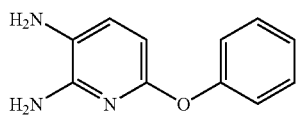 |
| Ex. 1 | 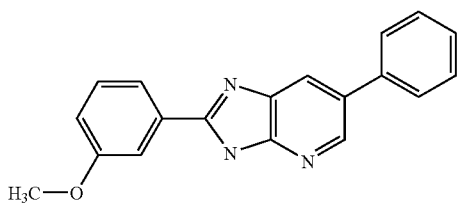 |
| Ex. 2 | 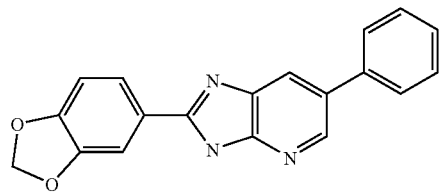 |
| Ex. 3 | 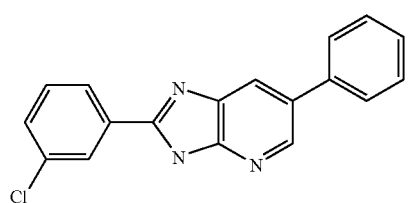 |
| Ex. 4 | 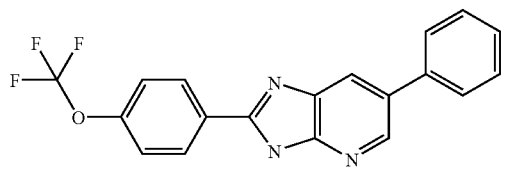 |
TABLE 12-continued
| Ex. 5 | 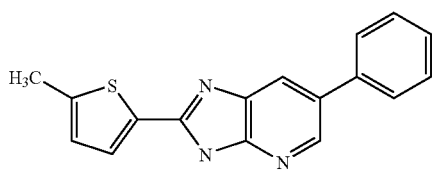 |
| --- | --- |
TABLE 13
| Ex. 6 | 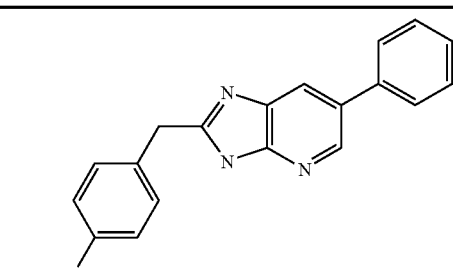 |
| --- | --- |
| Ex. 7 | 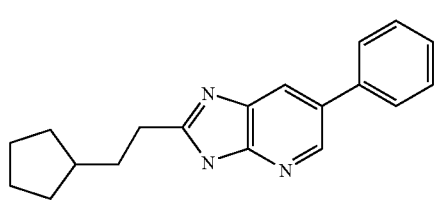 |
| Ex. 8 | 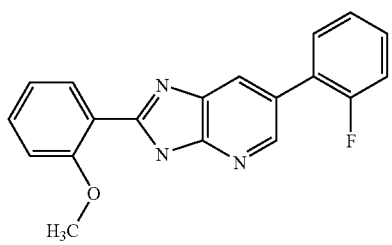 |
| Ex. 9 | 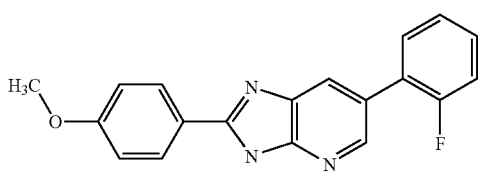 |
| Ex. 10 | 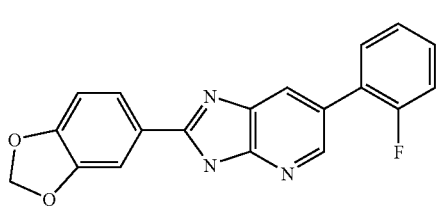 |
| Ex. 11 | 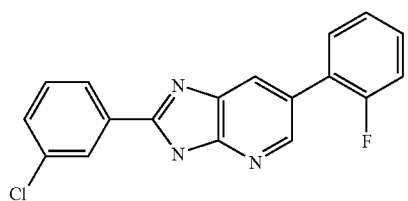 |

TABLE 13-continued
Ex. 12
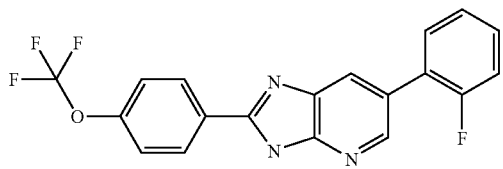
Ex. 13
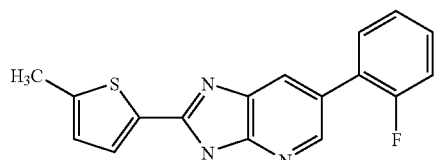
Ex. 14
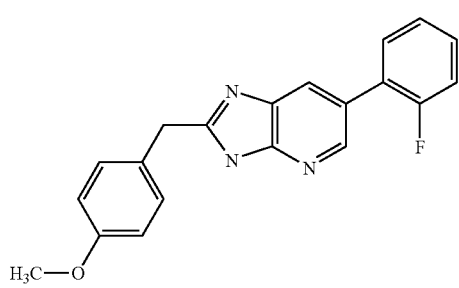
Ex. 15
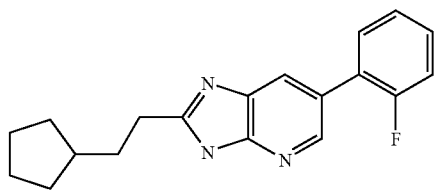
TABLE 14
Ex. 16
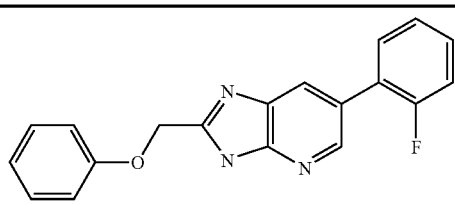
Ex. 17
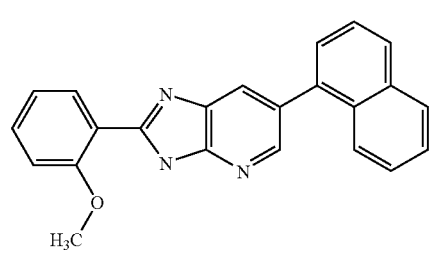
Ex. 18
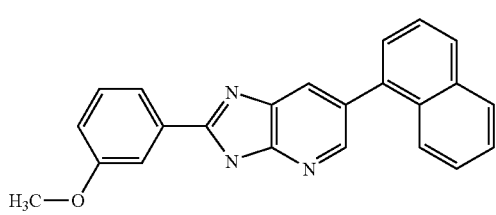
TABLE 14-continued
Ex. 19
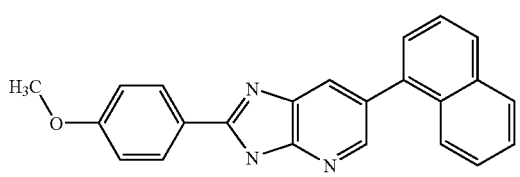
Ex. 20
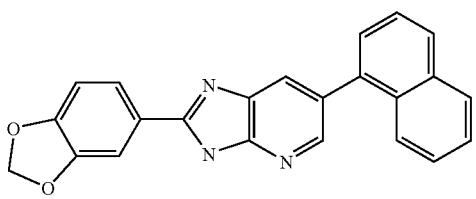
Ex. 21
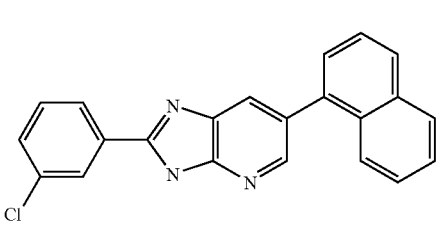
Ex. 22
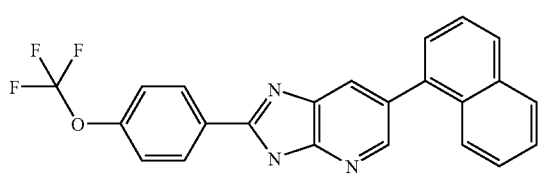
Ex. 23
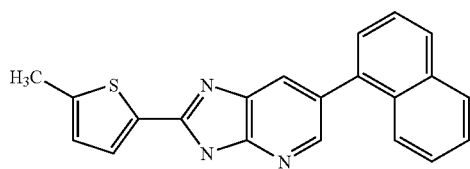
Ex. 24
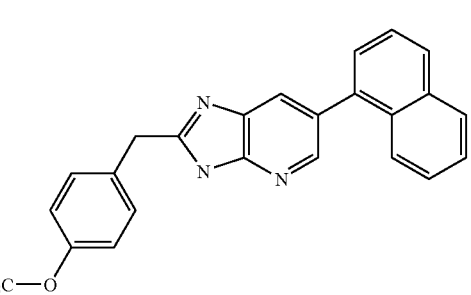
Ex. 25
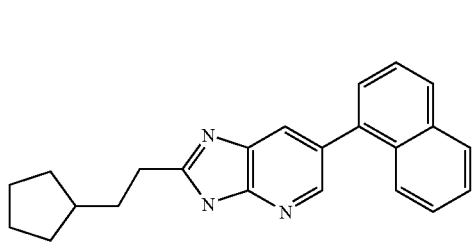

TABLE 15
Ex. 26 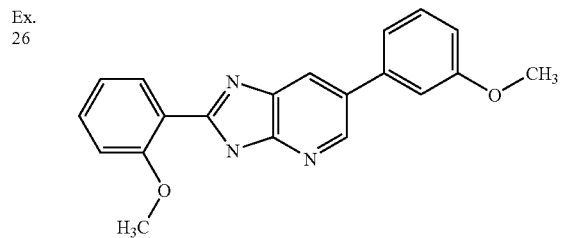
Ex. 27 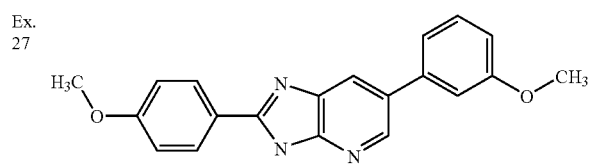
Ex. 28 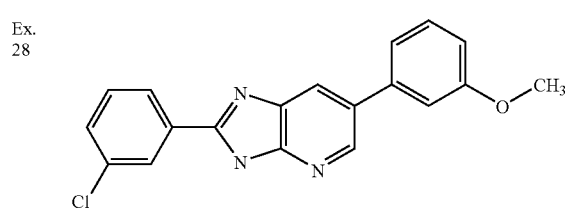
Ex. 29 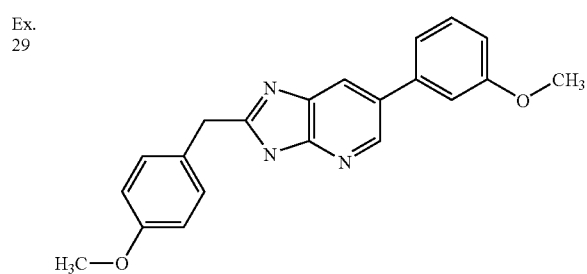
Ex. 30 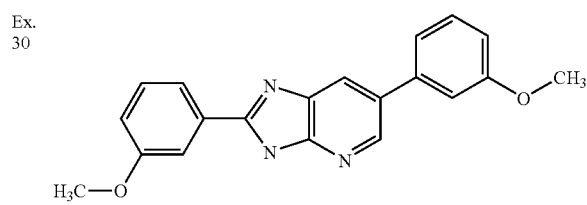
Ex. 31 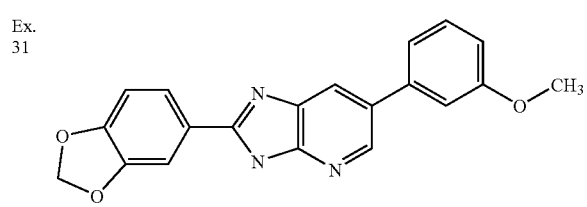
Ex. 32 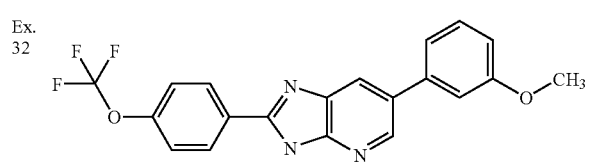
TABLE 15-continued
Ex. 33 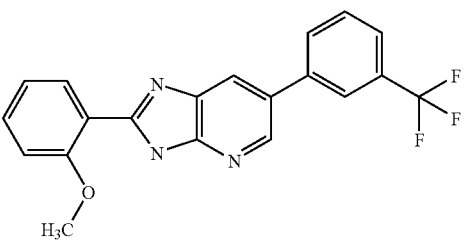
Ex. 34
Ex. 35 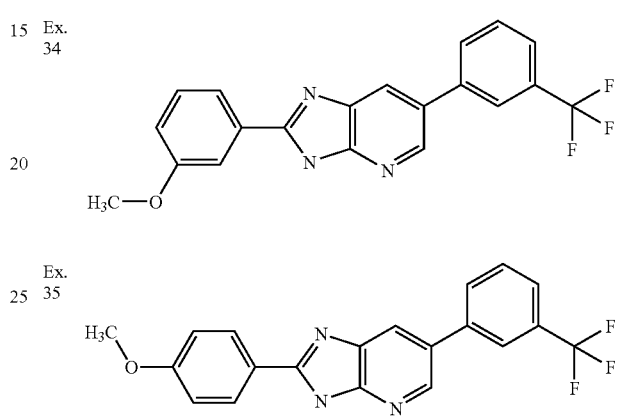
TABLE 16
Ex. 36 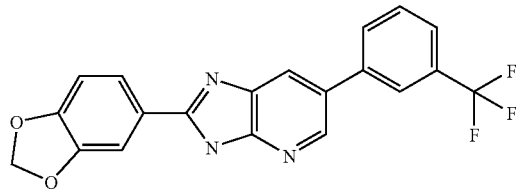
Ex. 37 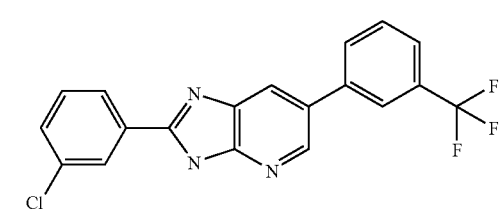
Ex. 38 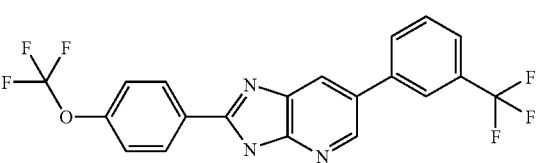
Ex. 39 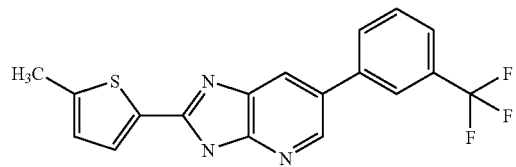

TABLE 16-continued
Ex. 40
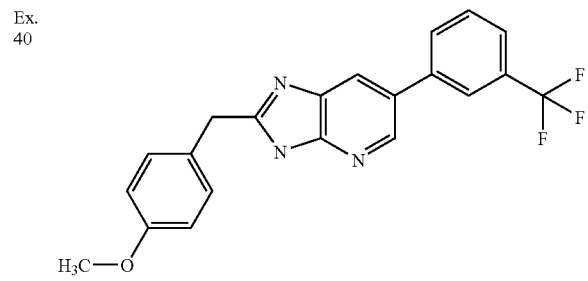
Ex. 41
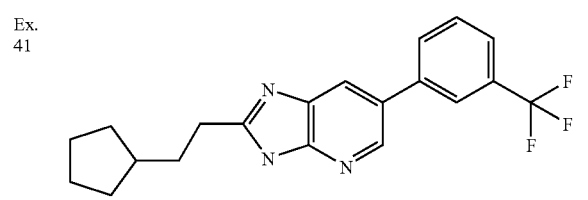
Ex. 42
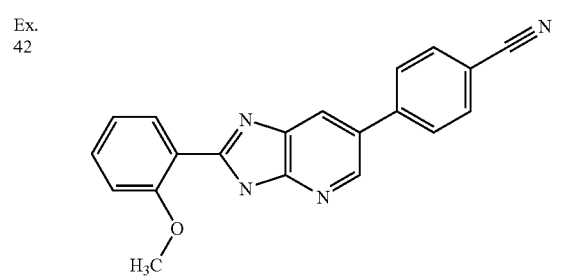
Ex. 43
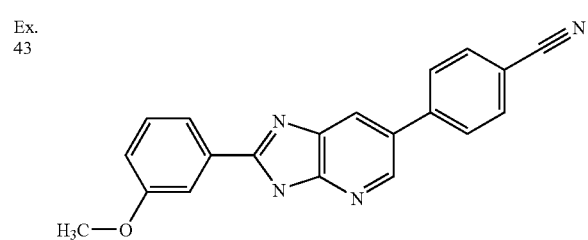
Ex. 44
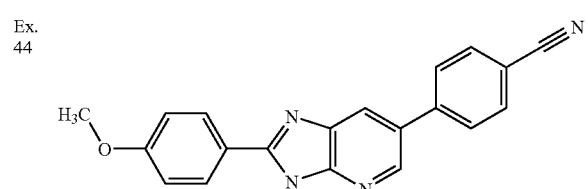
Ex. 45
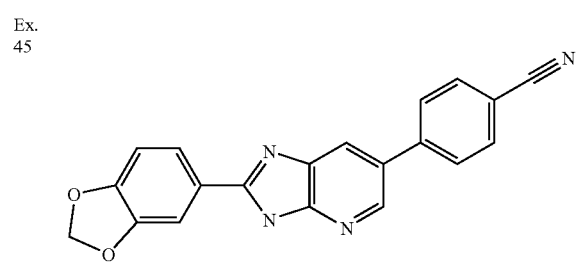
TABLE 17
Ex. 46
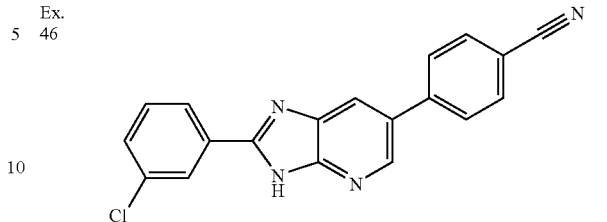
Ex. 47
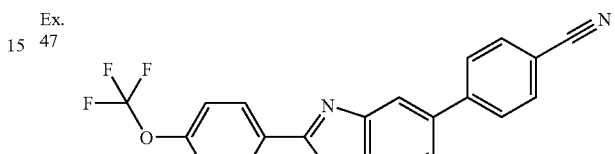
Ex. 48
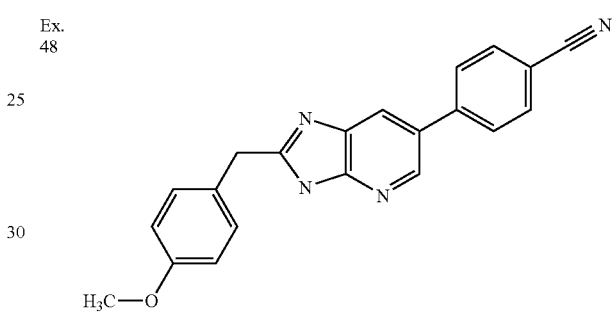
Ex. 49
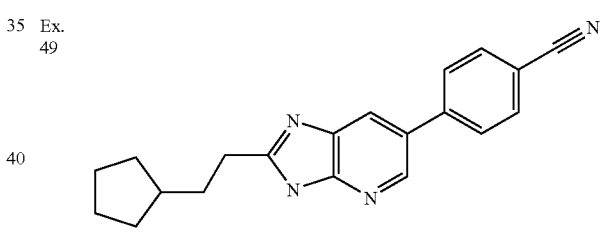
Ex. 50
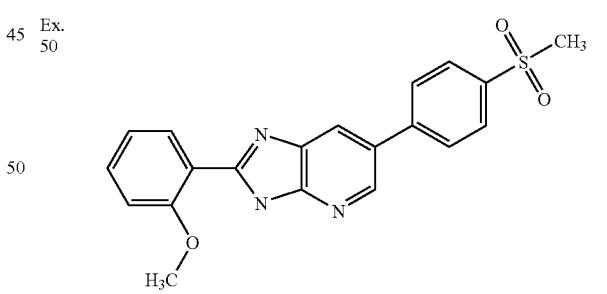
Ex. 51
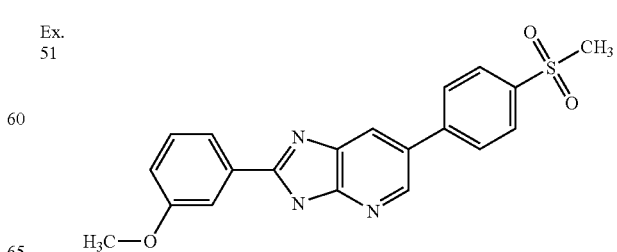

TABLE 17-continued
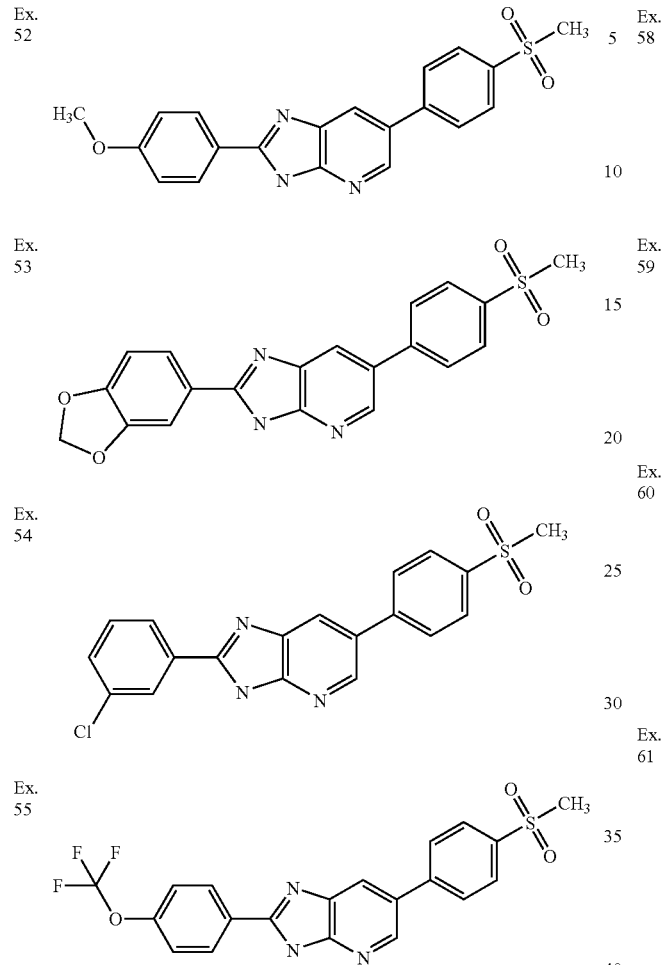
TABLE 18
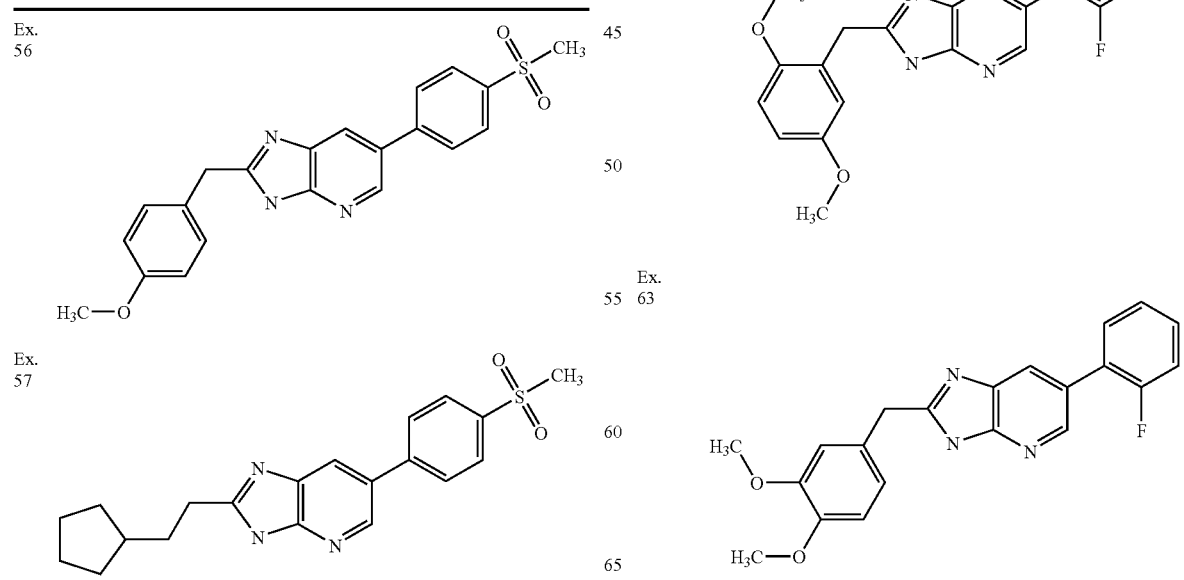
TABLE 18-continued
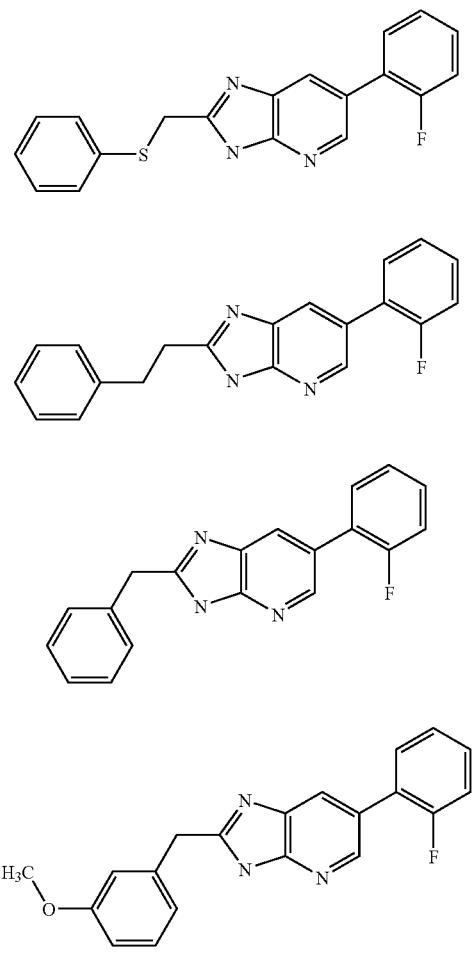

TABLE 18-continued
| Ex. 64 | 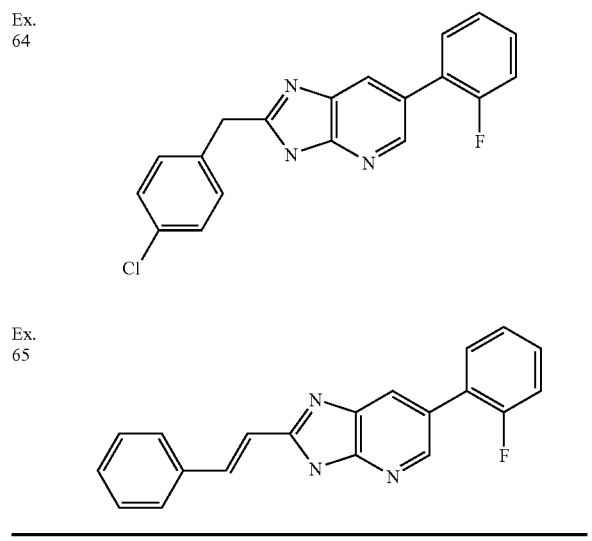 |
| Ex. 65 | |
TABLE 19
| Ex. 66 | 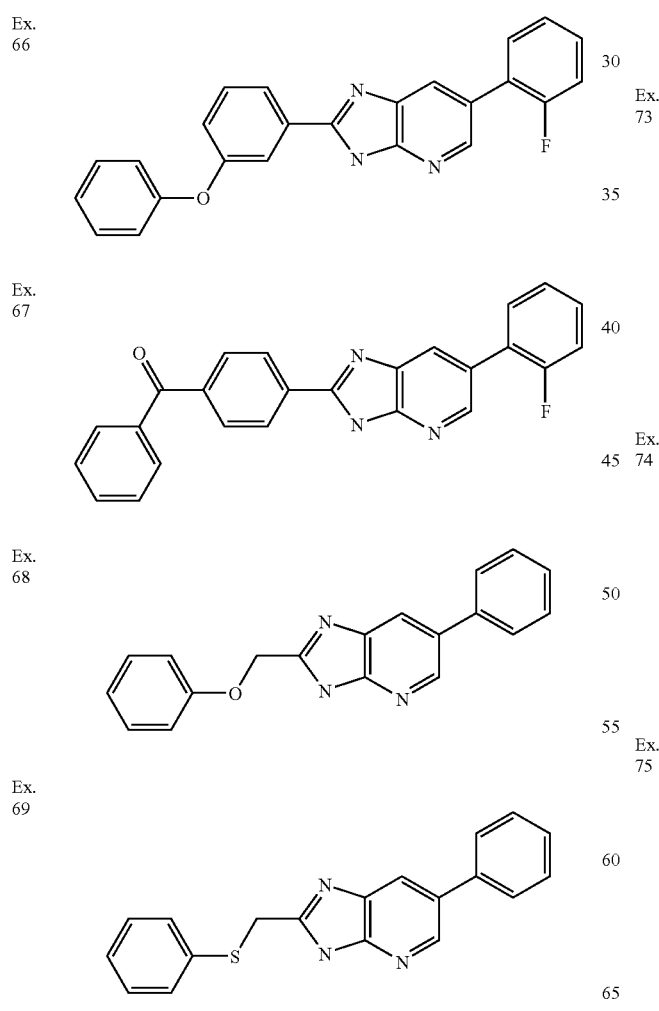 |
| Ex. 67 | |
| Ex. 68 | |
| Ex. 69 | |
TABLE 19-continued
| Ex. 70 | 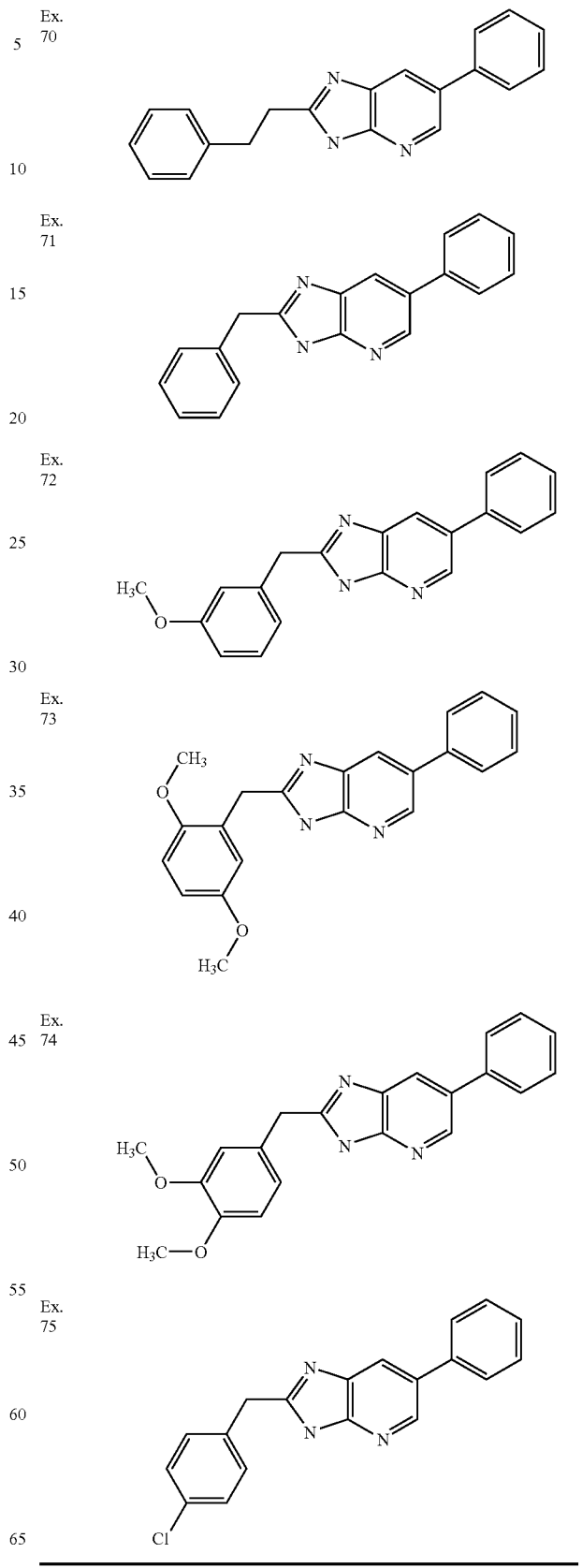 |
| Ex. 71 | |
| Ex. 72 | |
| Ex. 73 | |
| Ex. 74 | |
| Ex. 75 | |

TABLE 20
Ex. 76
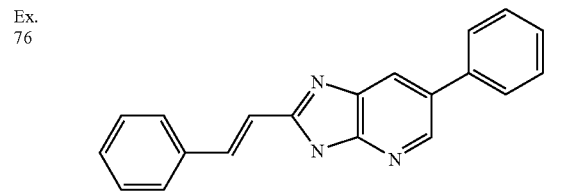
Ex. 77
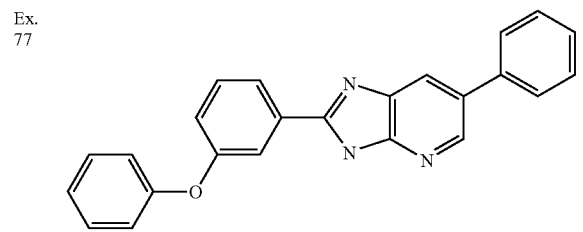
Ex. 78
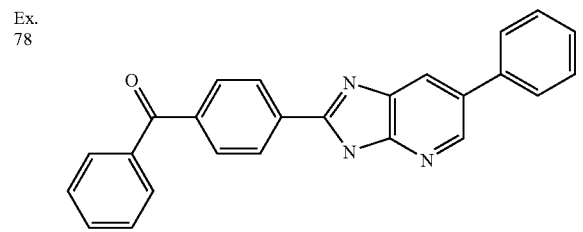
Ex. 79
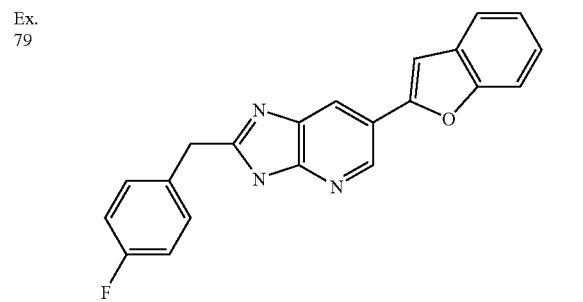
Ex. 80
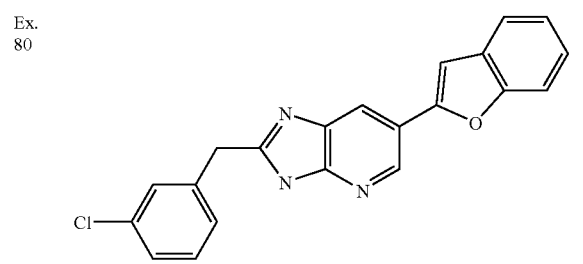
Ex. 81
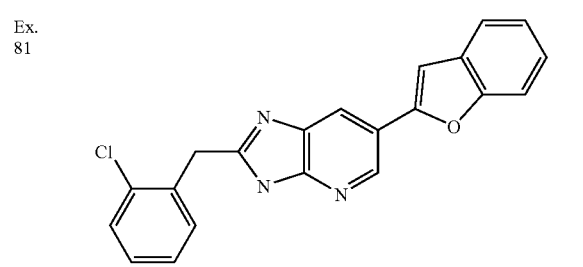
TABLE 20-continued
Ex. 82
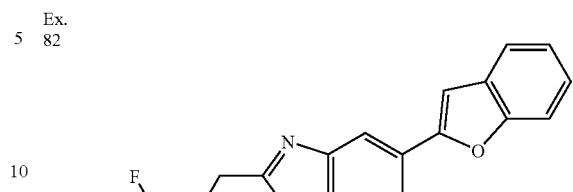
Ex. 83
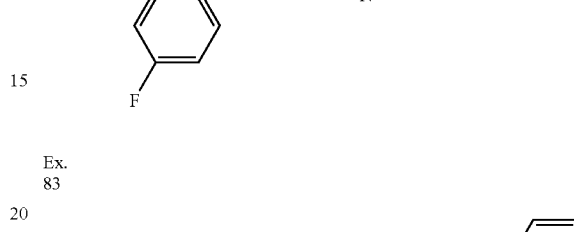
Ex. 84
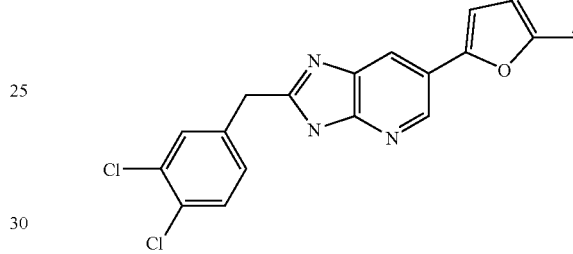
Ex. 85
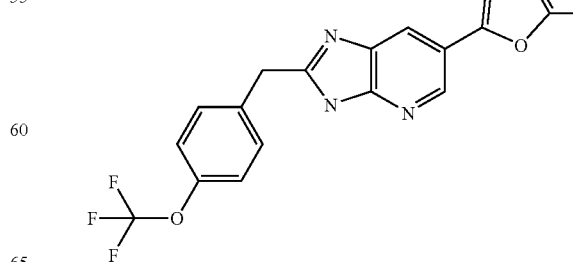

TABLE 21
Ex. 86
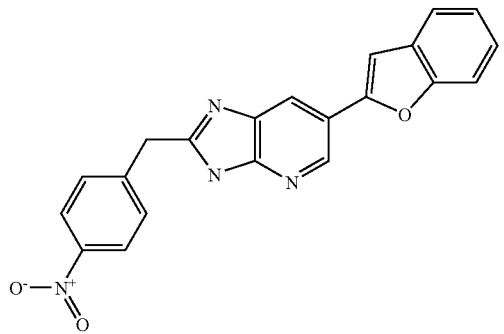
Ex. 87
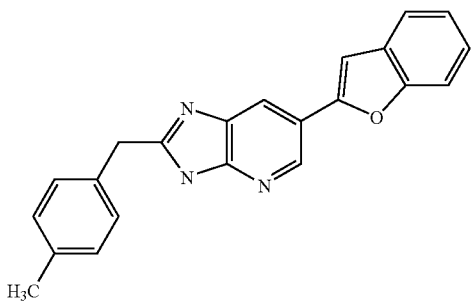
Ex. 88
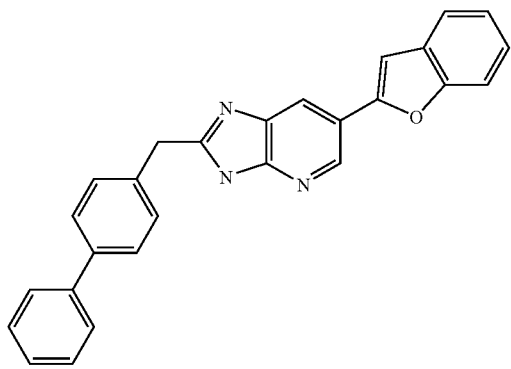
Ex. 89
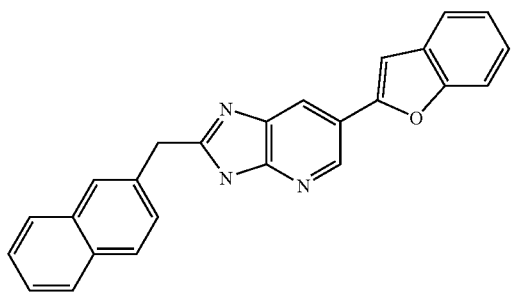
Ex. 90
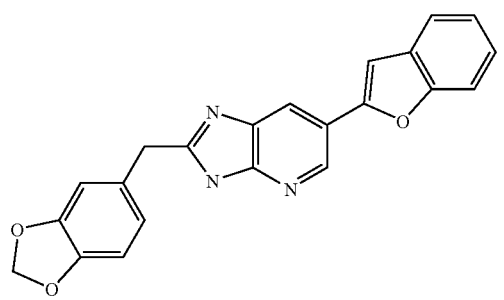
TABLE 21-continued
Ex. 91
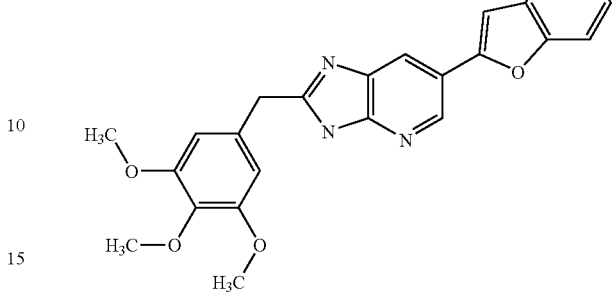
Ex. 92
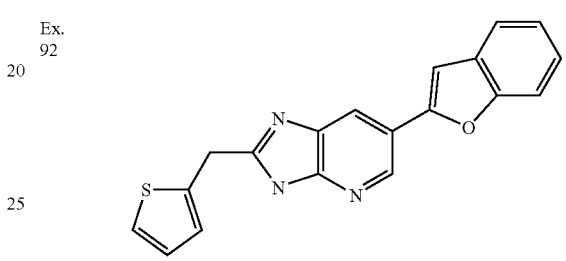
Ex. 93
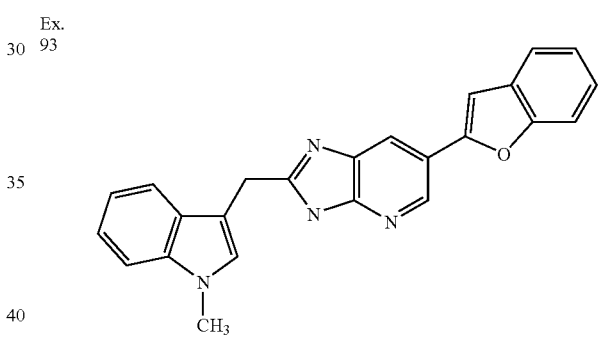
Ex. 94
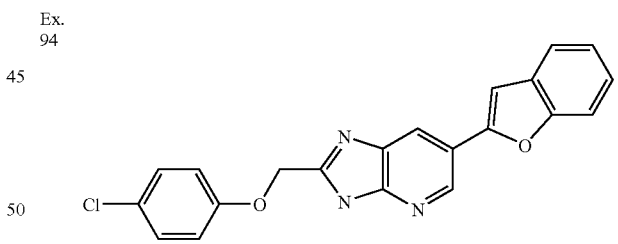
Ex. 95
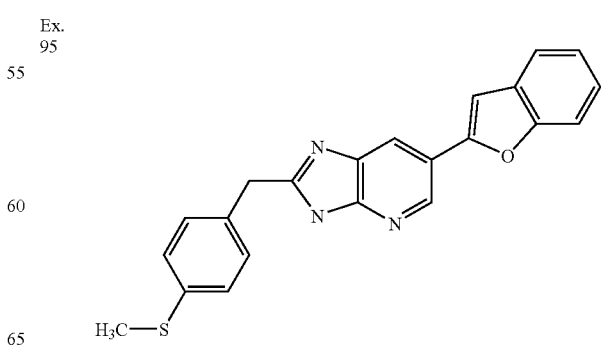

TABLE 22
Ex. 96
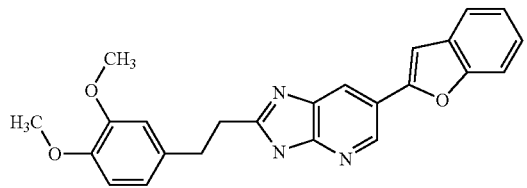
Ex. 97
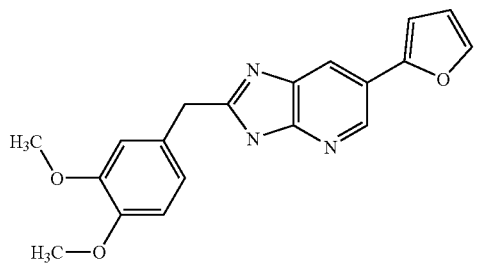
Ex. 98
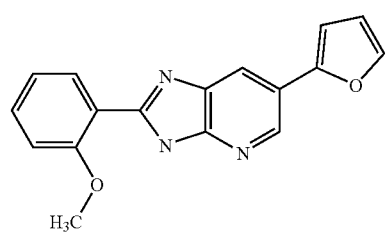
Ex. 99
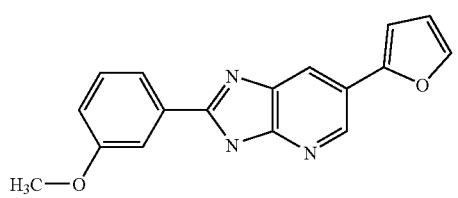
Ex. 100
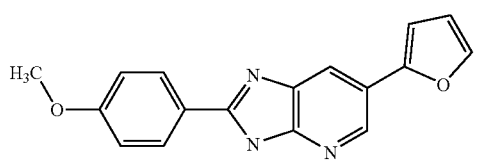
Ex. 101
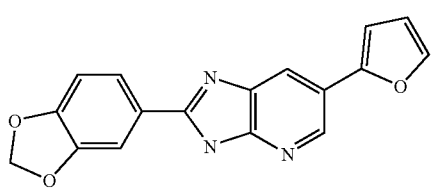
Ex. 102
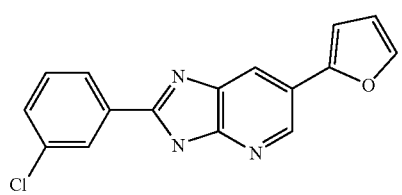
Ex. 103
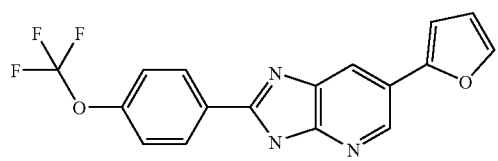
TABLE 22-continued
Ex. 104
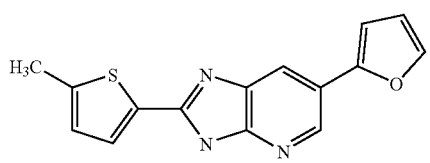
Ex. 105
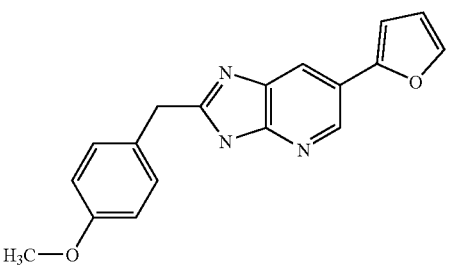
TABLE 23
Ex. 106
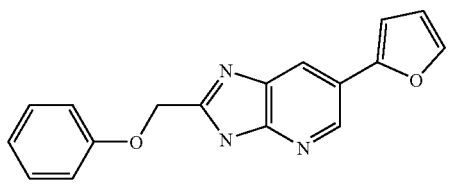
Ex. 107
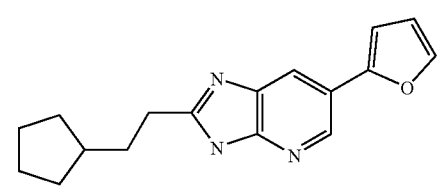
Ex. 108
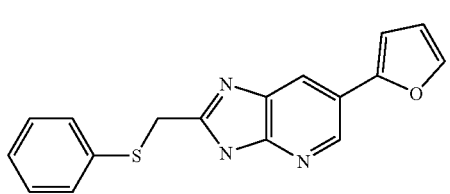
Ex. 109
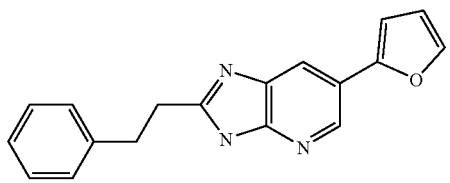
Ex. 110
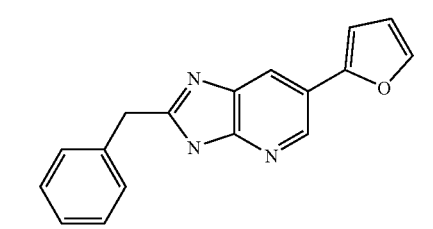

TABLE 23-continued
Ex. 111
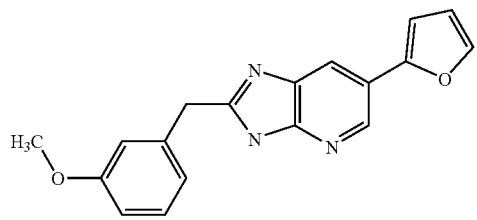
Ex. 112
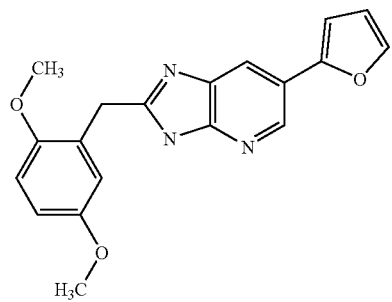
Ex. 113
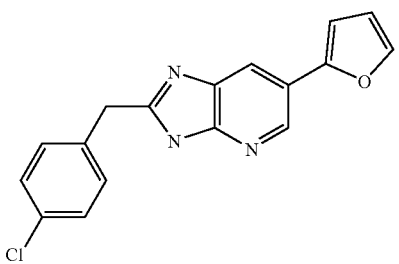
Ex. 114
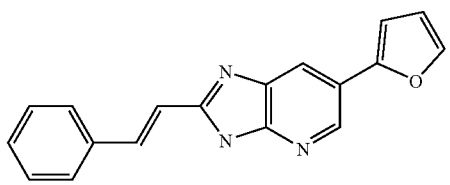
Ex. 115
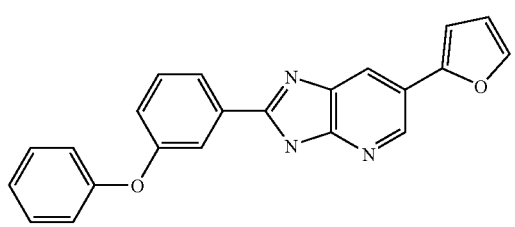
TABLE 24
Ex. 116
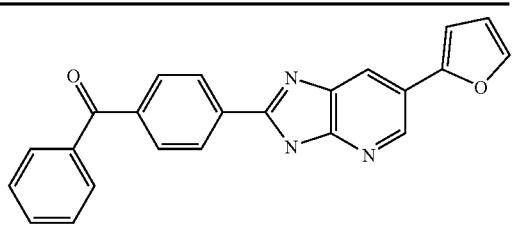
TABLE 24-continued
Ex. 117
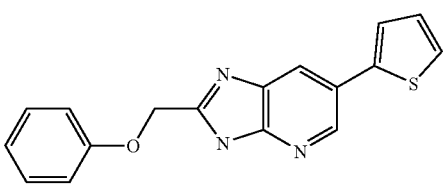
Ex. 118
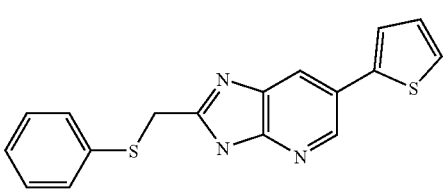
Ex. 119
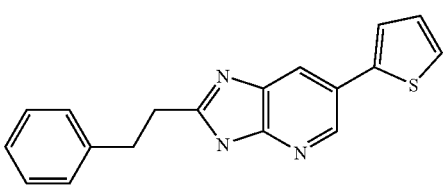
Ex. 120
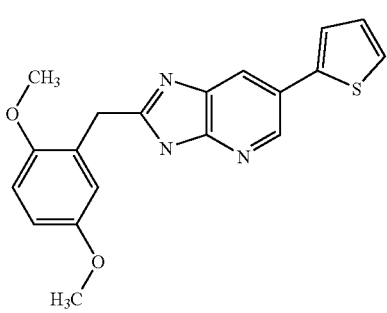
Ex. 121
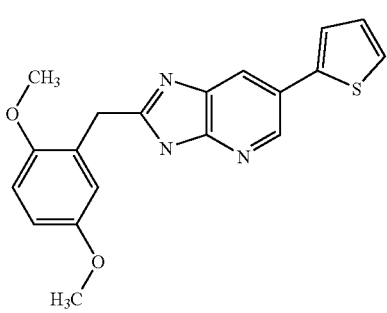
Ex. 122
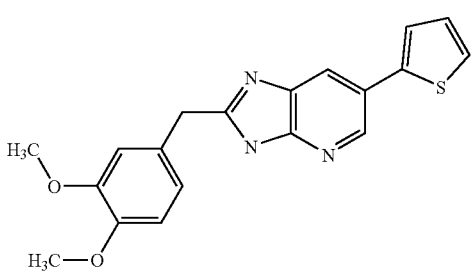

TABLE 24-continued
Ex. 123
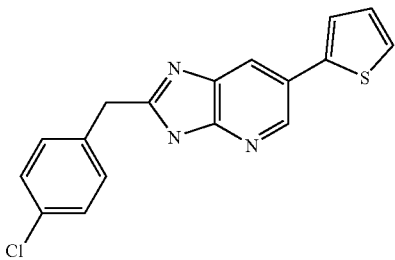
Ex. 124
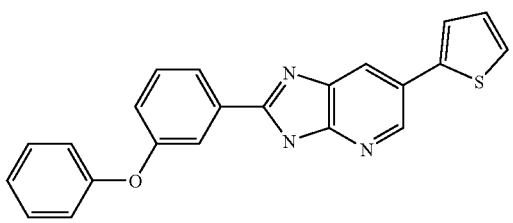
Ex. 125
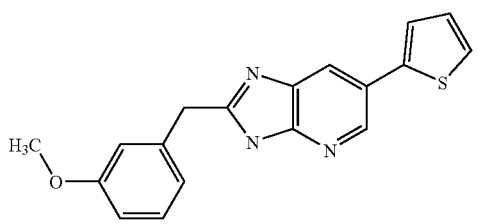
TABLE 25
Ex. 126
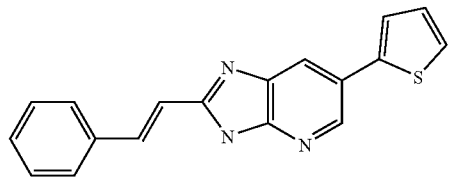
Ex. 127
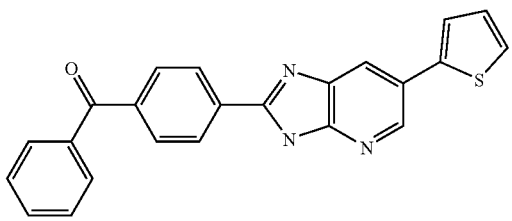
Ex. 128
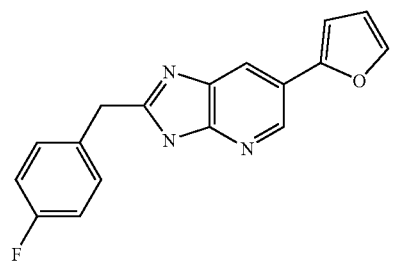
TABLE 25-continued
Ex. 129
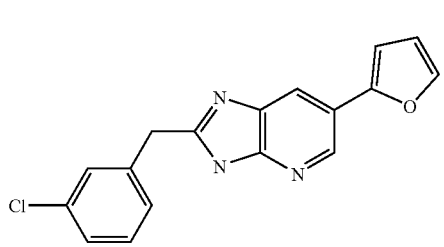
Ex. 130
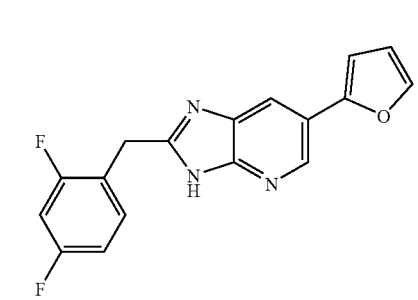
Ex. 131
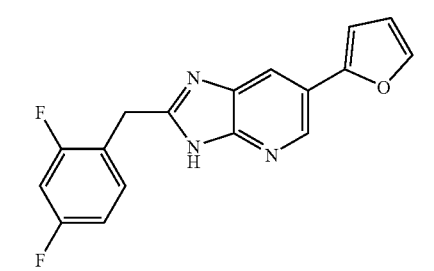
Ex. 132
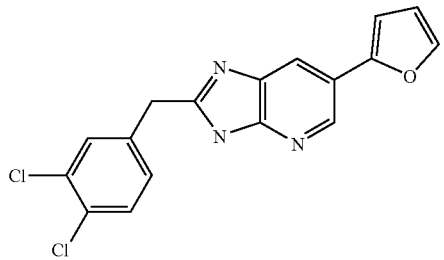
Ex. 133
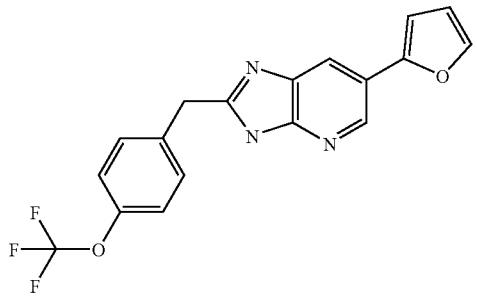

TABLE 25-continued
Ex. 134
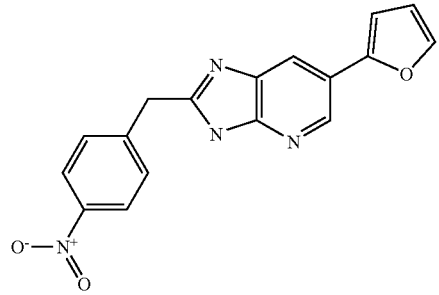
Ex. 135
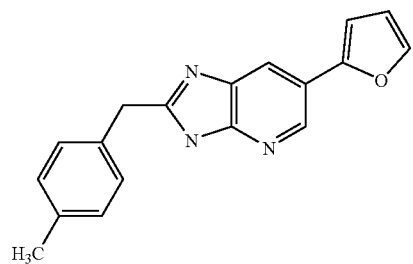
TABLE 26
Ex. 136
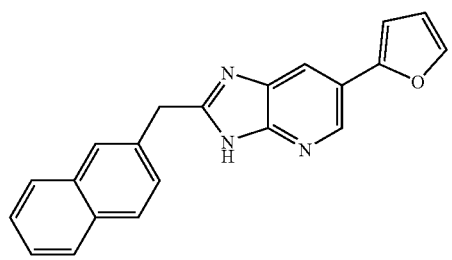
Ex. 137
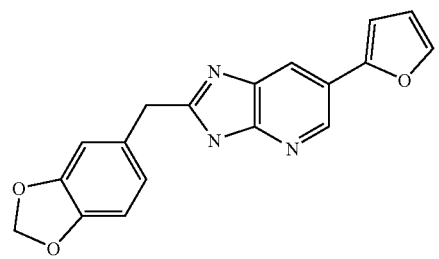
Ex. 138
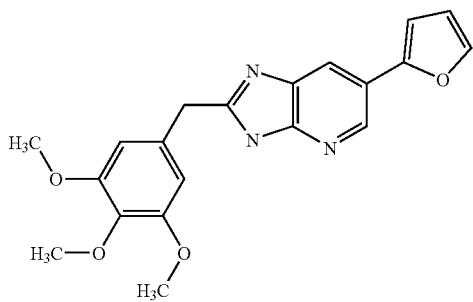
TABLE 26-continued
Ex. 139
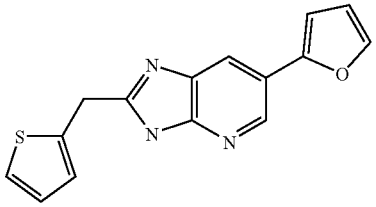
Ex. 140
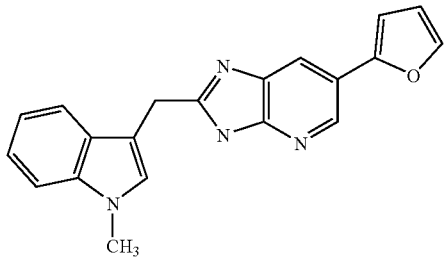
Ex. 141
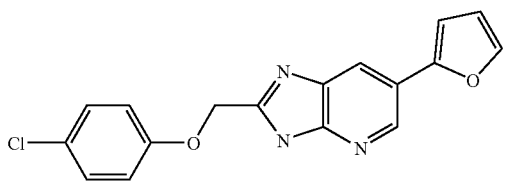
Ex. 142
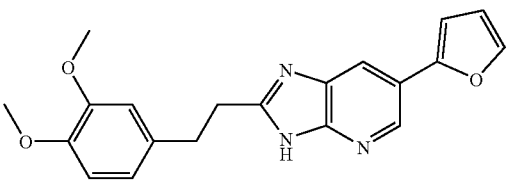
Ex. 143
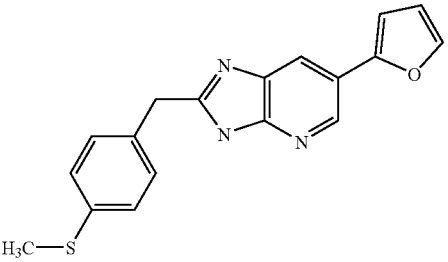
Ex. 144
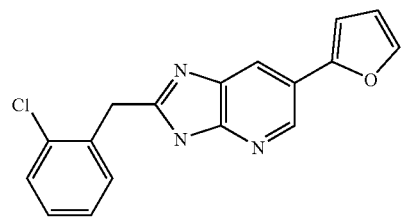

TABLE 26-continued
Ex. 145
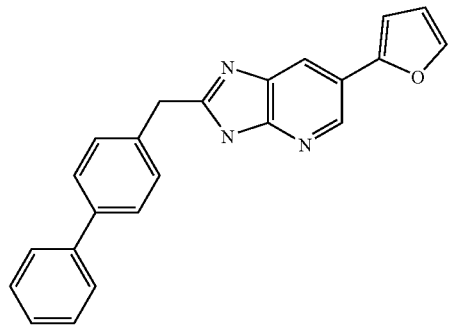
TABLE 27
Ex. 146
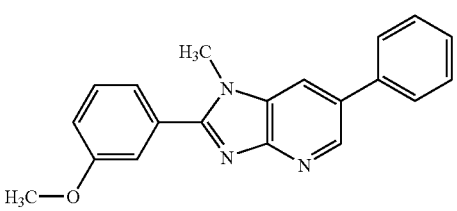
Ex. 147
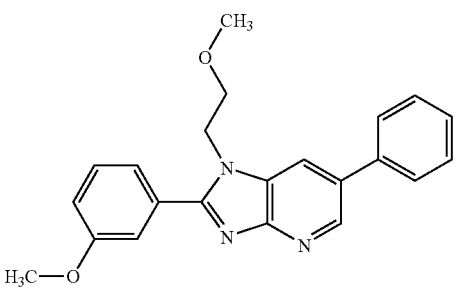
Ex. 148
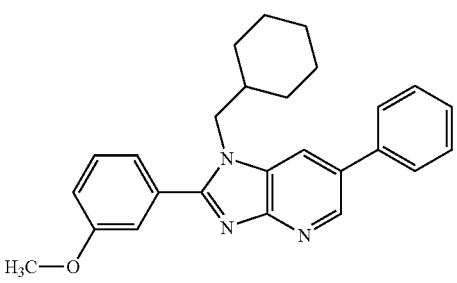
Ex. 149
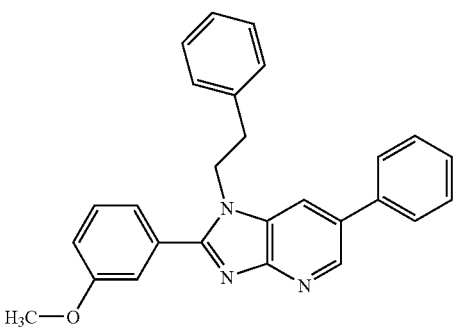
TABLE 27-continued
Ex. 150
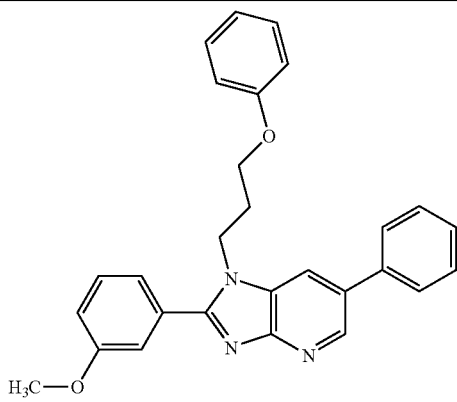
Ex. 151
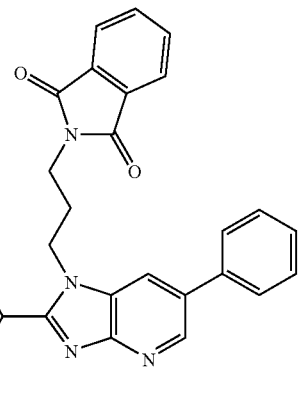
Ex. 152
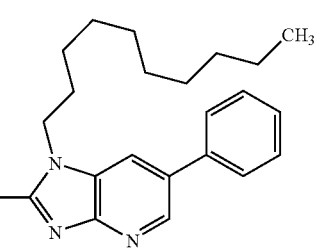
Ex. 153
Ex. 154

TABLE 27-continued
Ex. 155
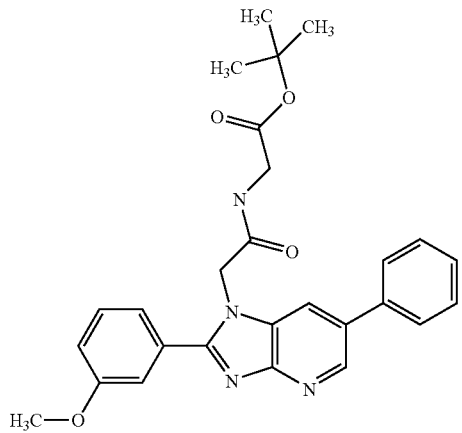
TABLE 28
Ex. 156
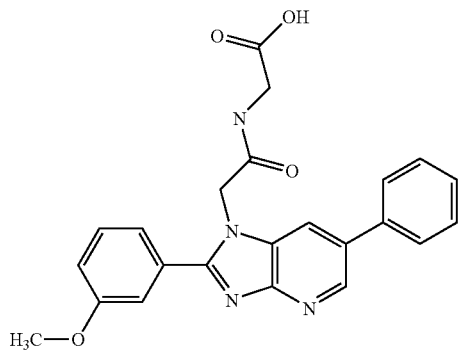
Ex. 157
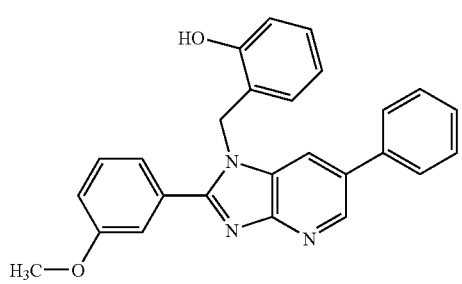
Ex. 158
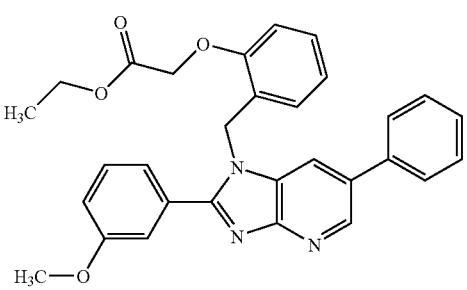
TABLE 28-continued
Ex. 159
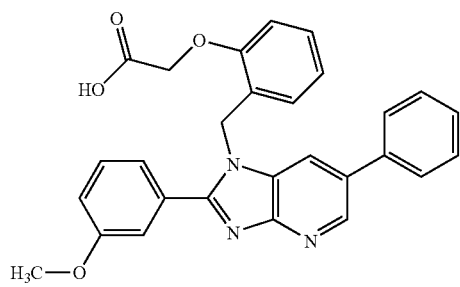
Ex. 160
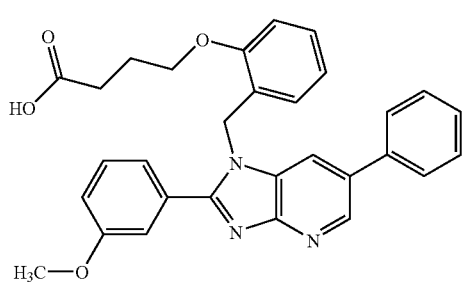
Ex. 161
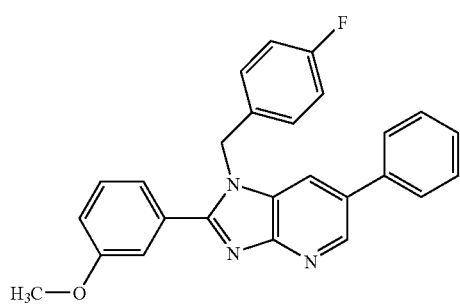
Ex. 162
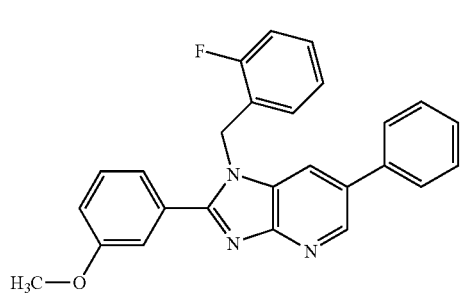
Ex. 163
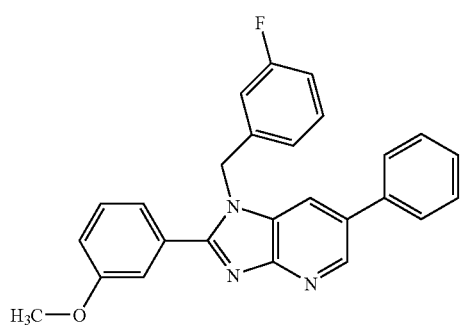

| TABLE 28-continued | TABLE 29-continued |
|---|---|
| Ex. 164 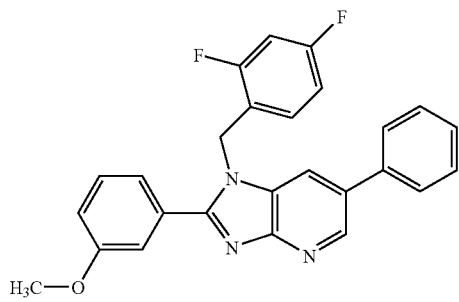 | Ex. 169 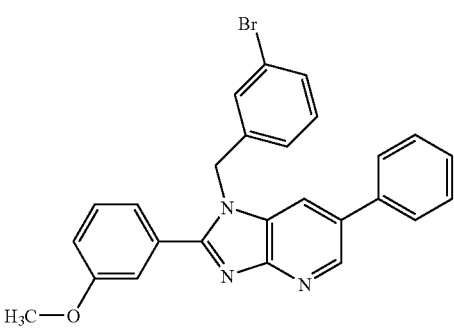 |
| Ex. 165 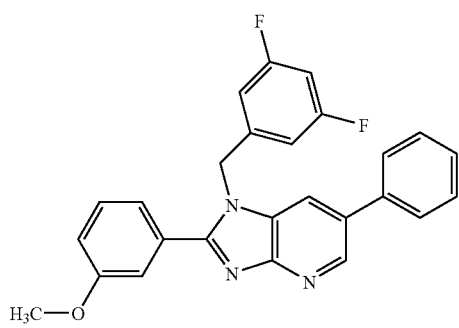 | Ex. 170 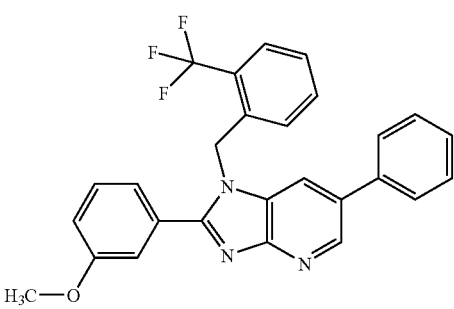 |
| TABLE 29 | |
| Ex. 166 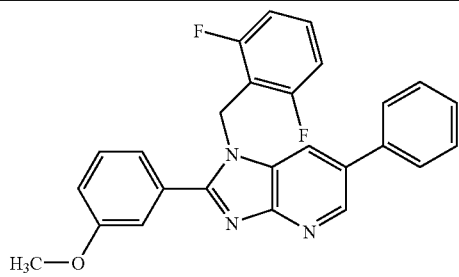 | Ex. 171 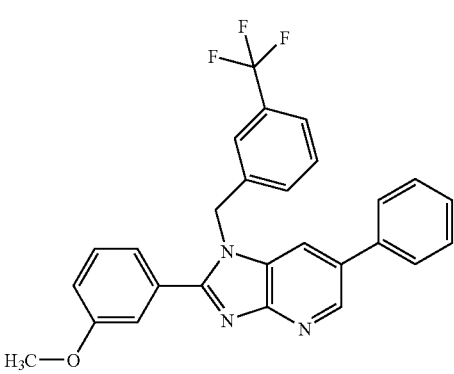 |
| Ex. 167 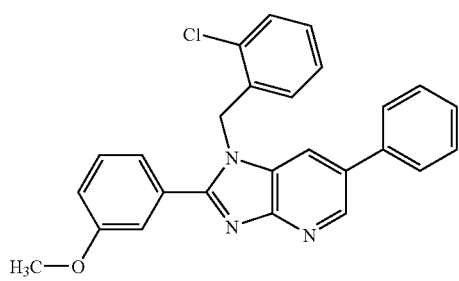 | |
| Ex. 168 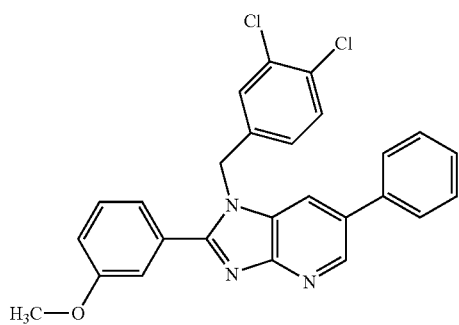 | Ex. 172 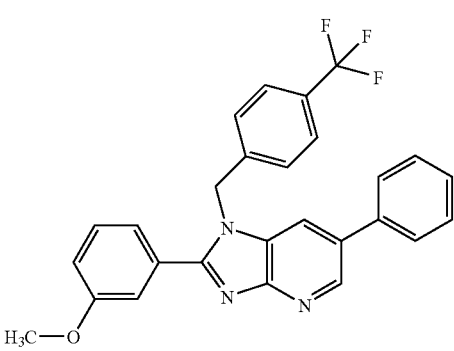 |

TABLE 29-continued
Ex. 173
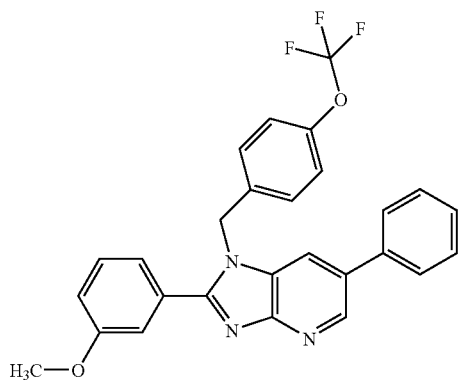
Ex. 174
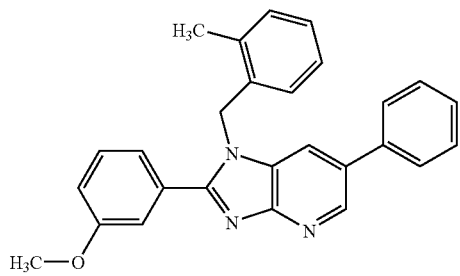
Ex. 175
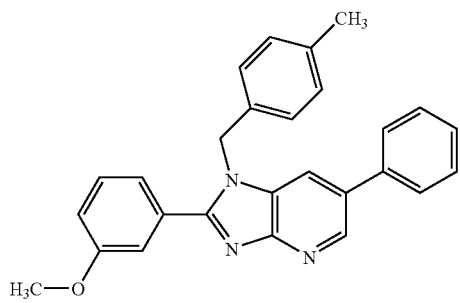
TABLE 30
Ex. 176
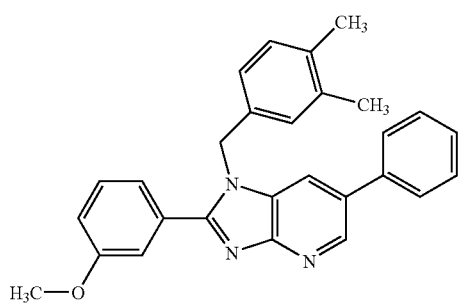
TABLE 30-continued
Ex. 177
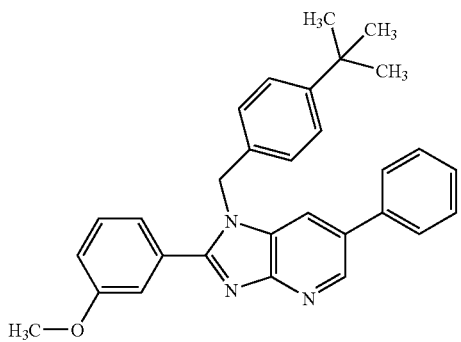
Ex. 178
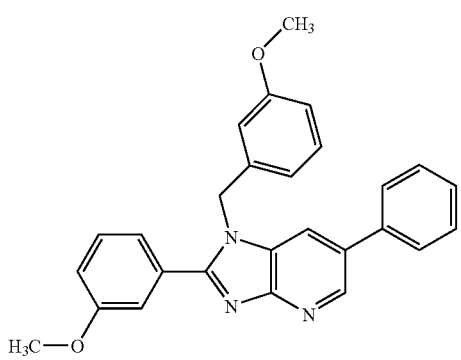
Ex. 179
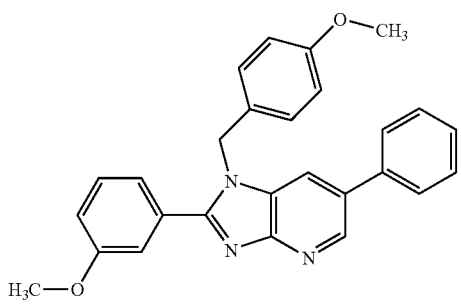
Ex. 180
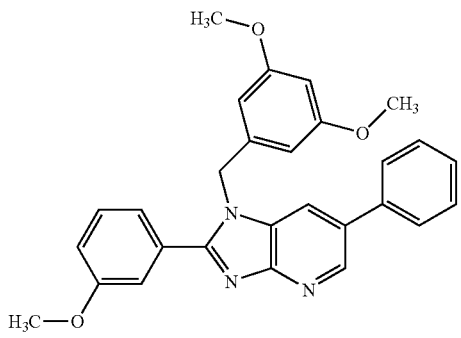

TABLE 30-continued
Ex. 181 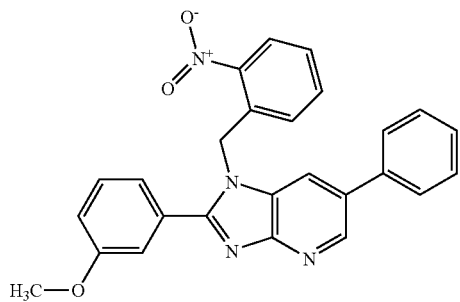
Ex. 182 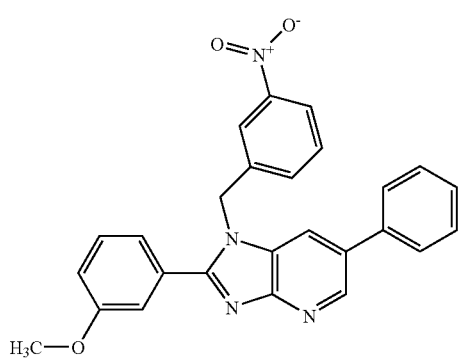
Ex. 183 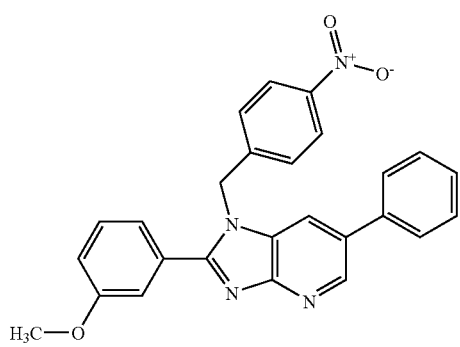
Ex. 184 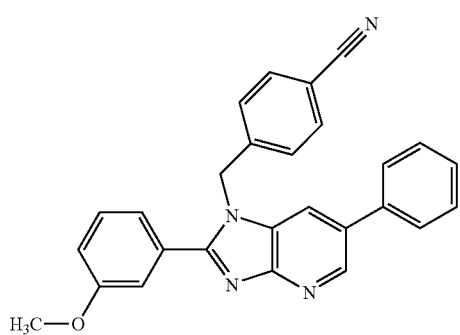
TABLE 30-continued
Ex. 185 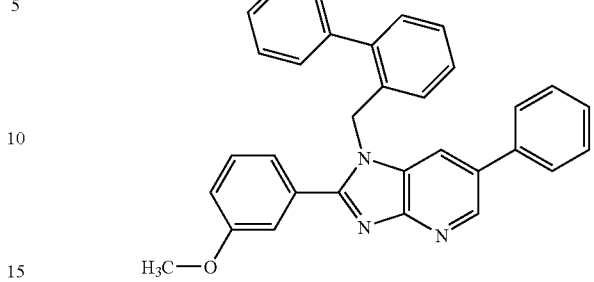
TABLE 31
Ex. 186 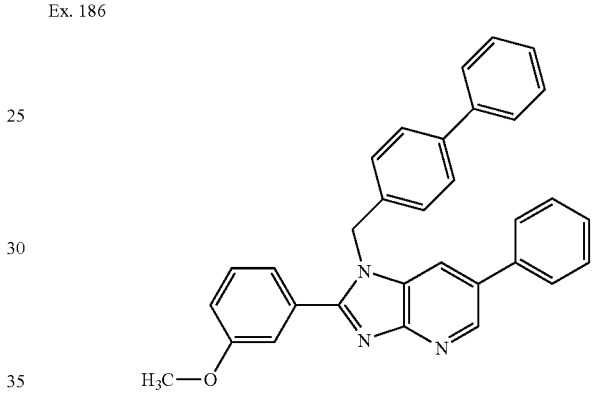
Ex. 187 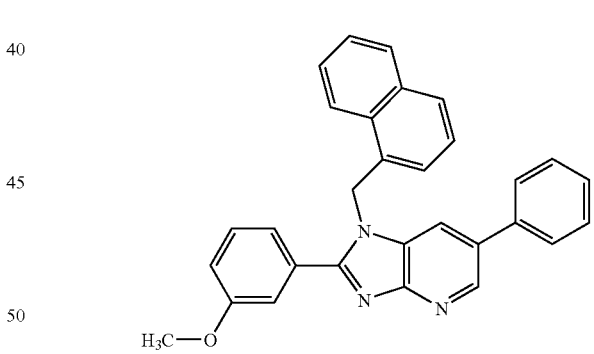
Ex. 188 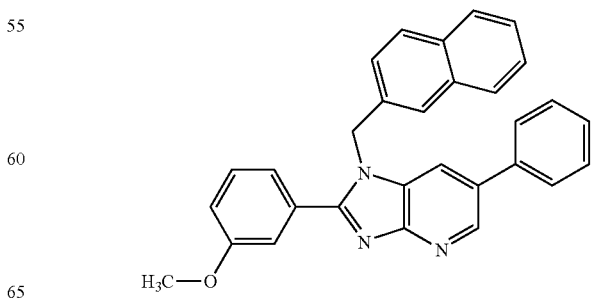

TABLE 31-continued
Ex. 189
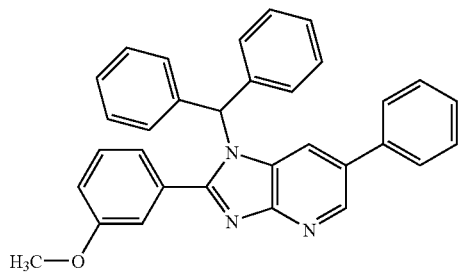
Ex. 190
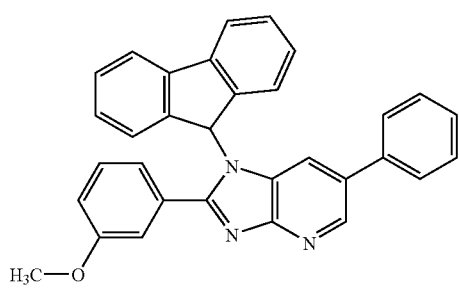
Ex. 191
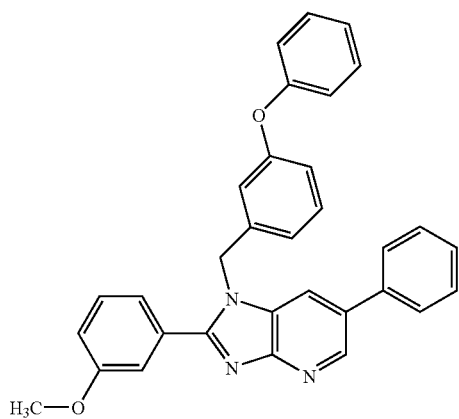
Ex. 192
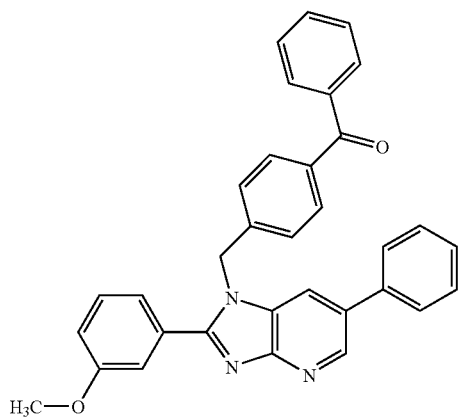
TABLE 31-continued
Ex. 193
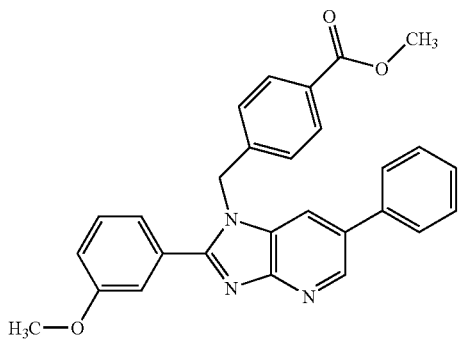
Ex. 194
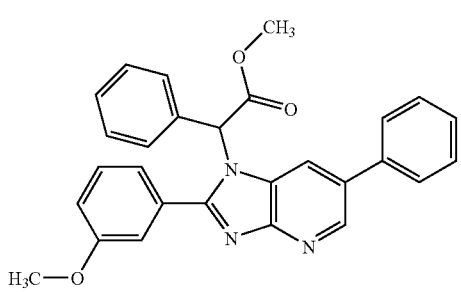
Ex. 195
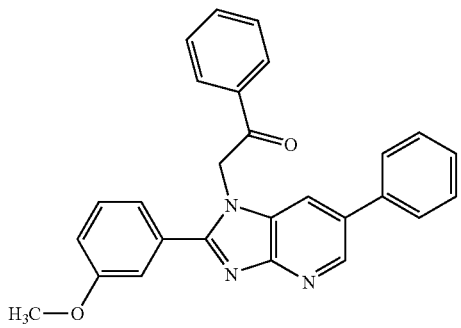
TABLE 32
Ex. 196
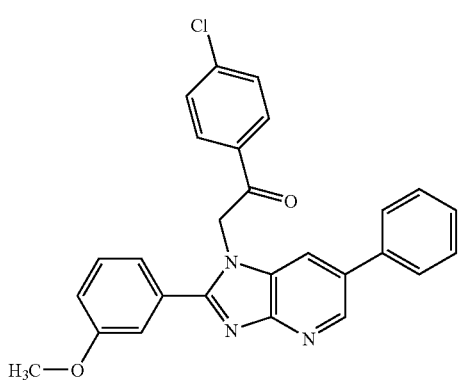

TABLE 32-continued
Ex. 197
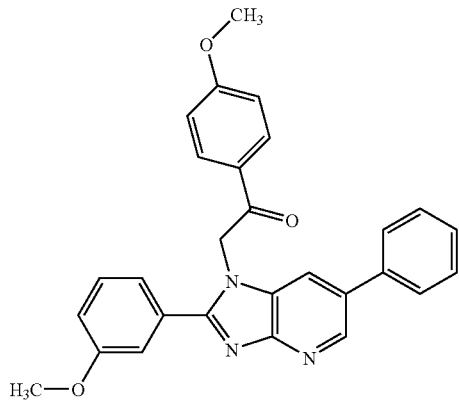
Ex. 198
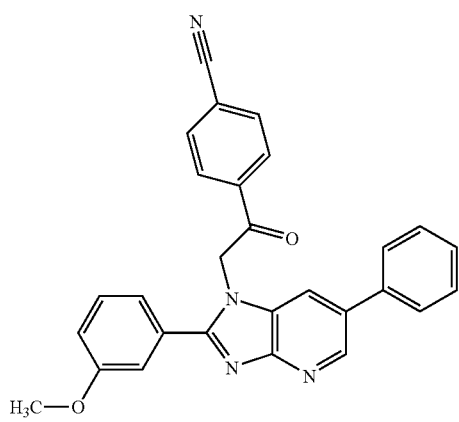
Ex. 199
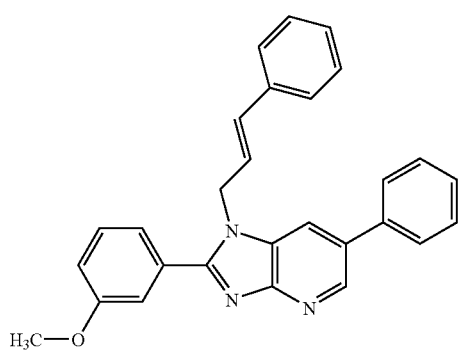
Ex. 200
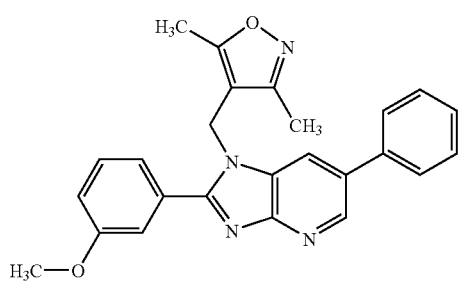
TABLE 32-continued
Ex. 201
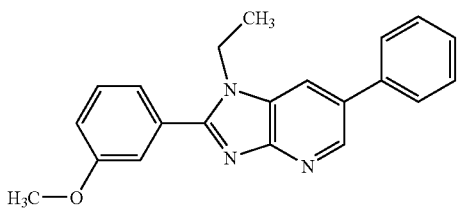
Ex. 202
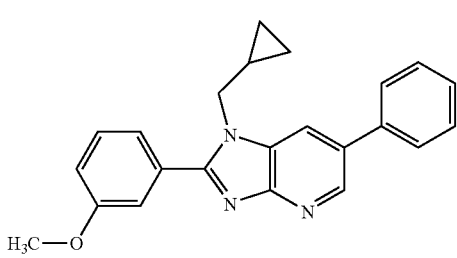
Ex. 203
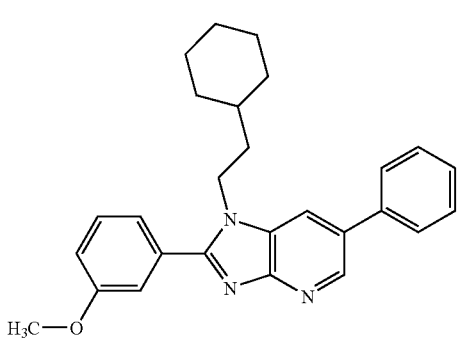
Ex. 204
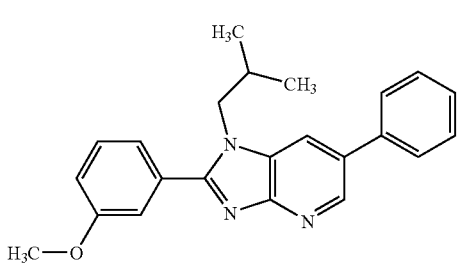
Ex. 205
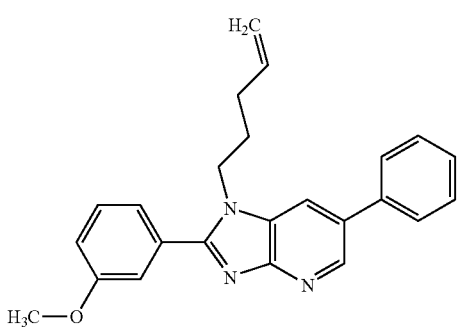

TABLE 33
Ex. 206
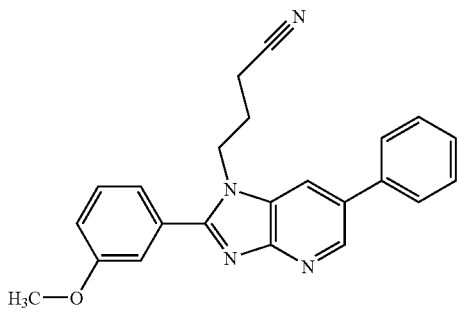
Ex. 207
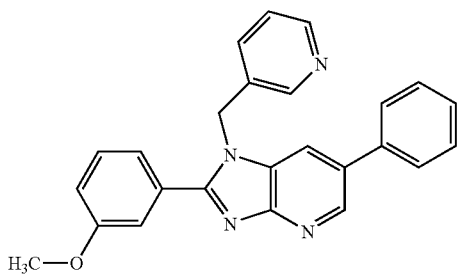
Ex. 208
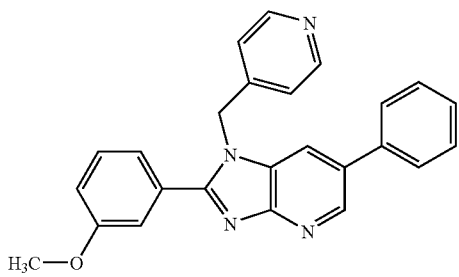
Ex. 209
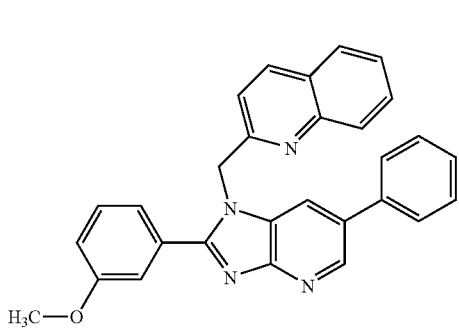
Ex. 210
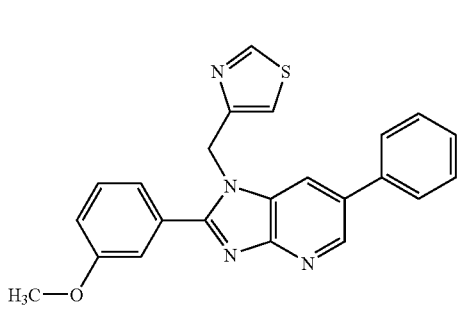
TABLE 33-continued
Ex. 211
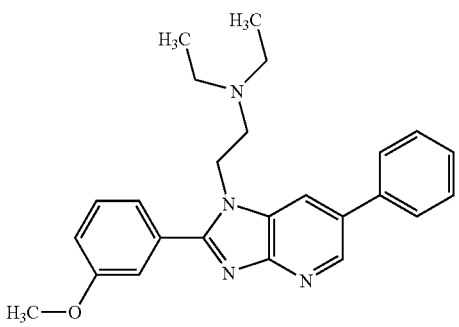
Ex. 212
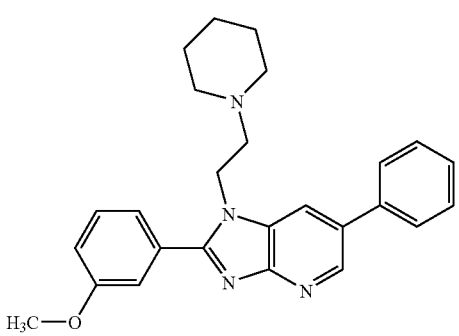
Ex. 213
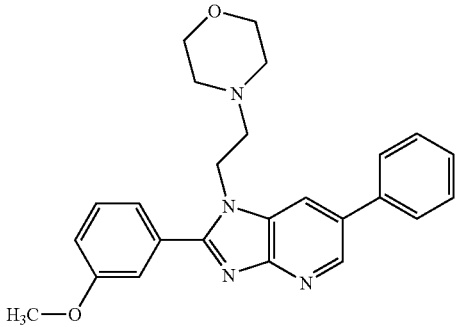
Ex. 214
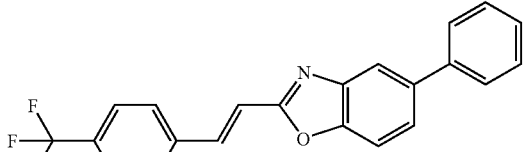
Ex. 215
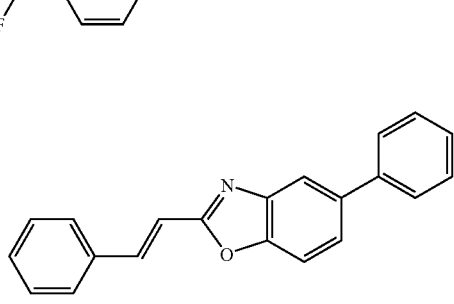

TABLE 34
Ex. 216 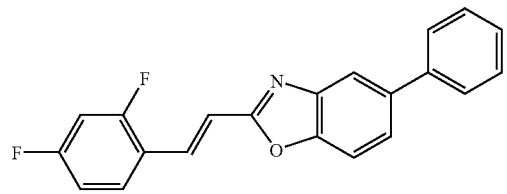
Ex. 217 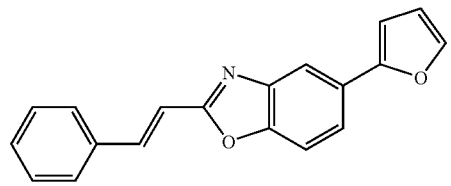
Ex. 218 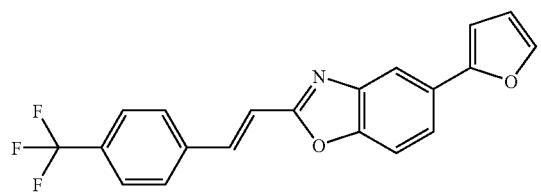
Ex. 219 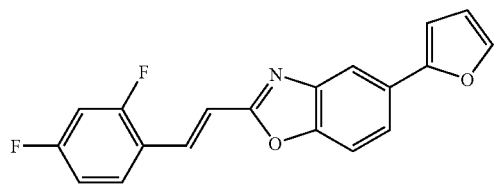
Ex. 220 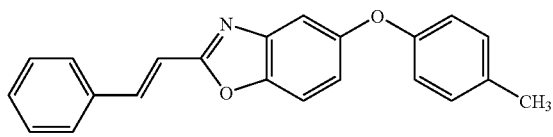
Ex. 221 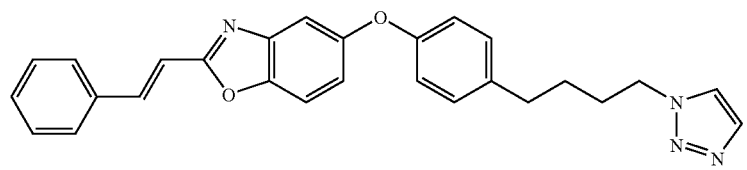
Ex. 222 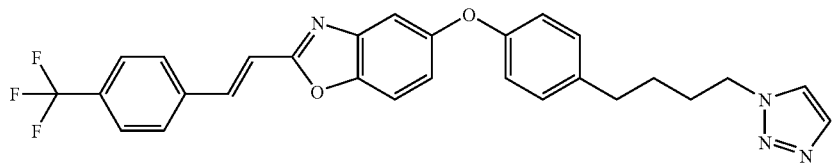
Ex. 223 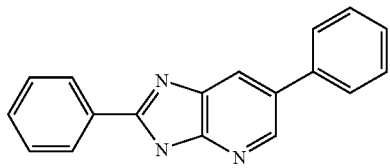

TABLE 34-continued
Ex. 224
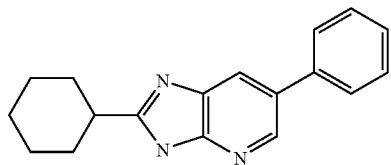
Ex. 225
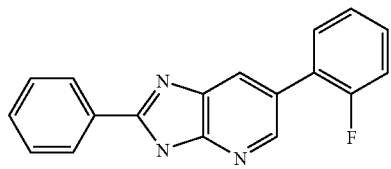
TABLE 35
Ex. 226
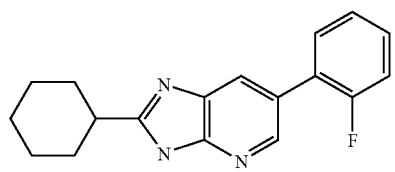
Ex. 227
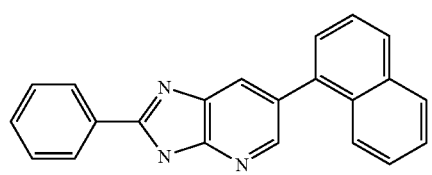
Ex. 228
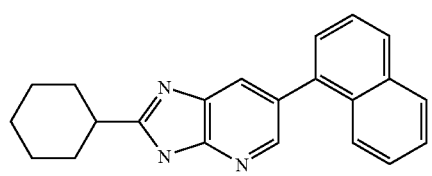
Ex. 229
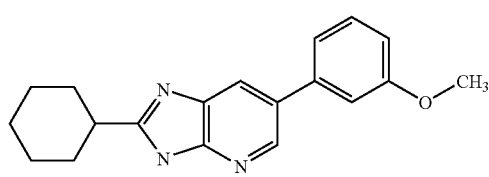
Ex. 230
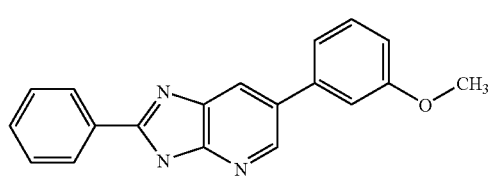
Ex. 231
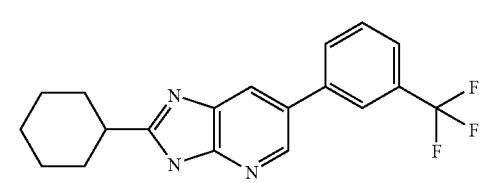
TABLE 35-continued
Ex. 232
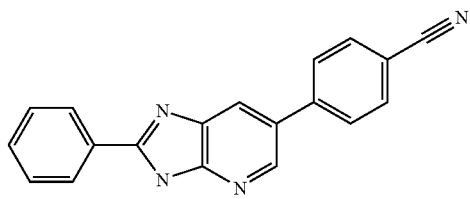
Ex. 233
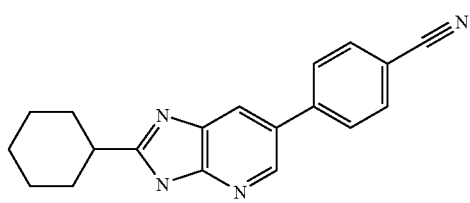
Ex. 234
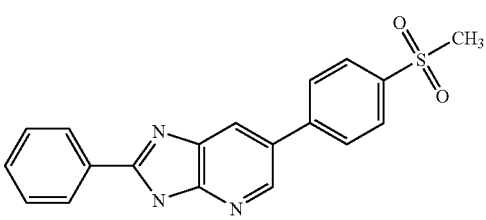
Ex. 235
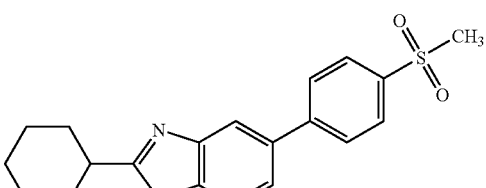
TABLE 36
Ex. 236
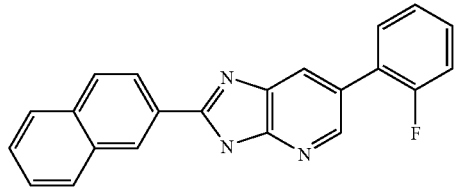

TABLE 36-continued
Ex. 237 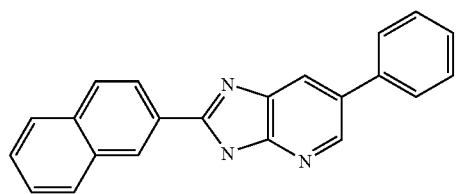
Ex. 238 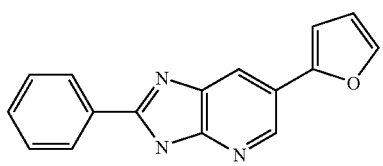
Ex. 239 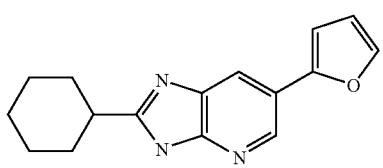
Ex. 240 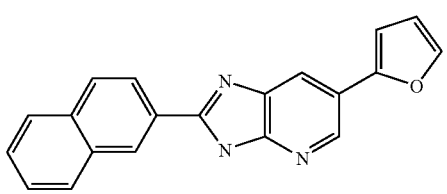
Ex. 241 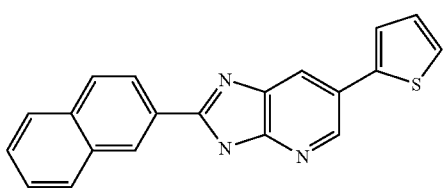
Ex. 242 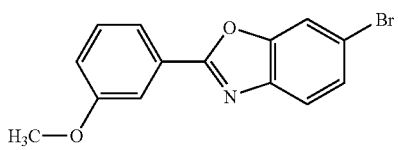
Ex. 243 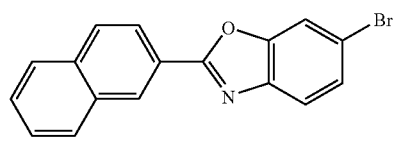
Ex. 244 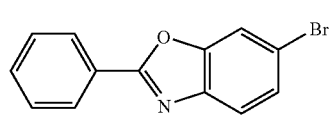
Ex. 245 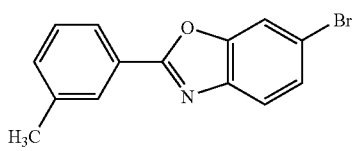
TABLE 37
Ex. 246 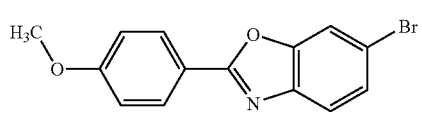
Ex. 247 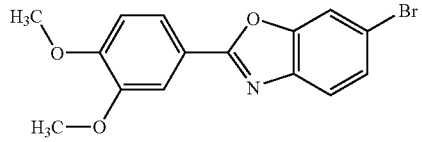
Ex. 248 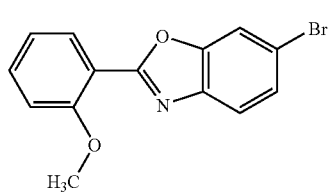
Ex. 249 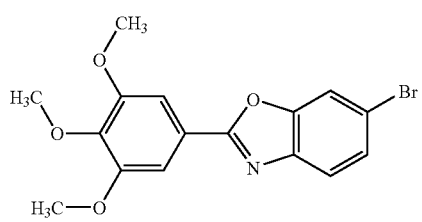
Ex. 250 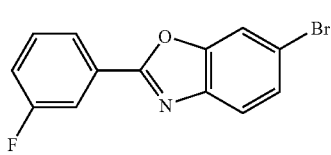
Ex. 251 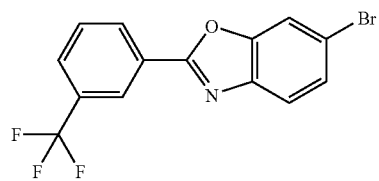
Ex. 252 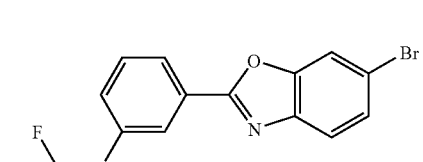
Ex. 253 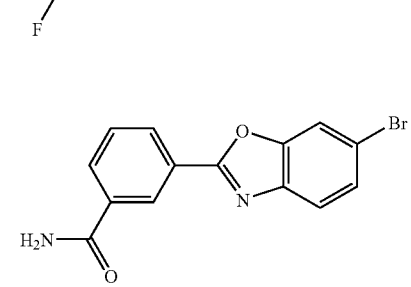

TABLE 37-continued
Ex. 254 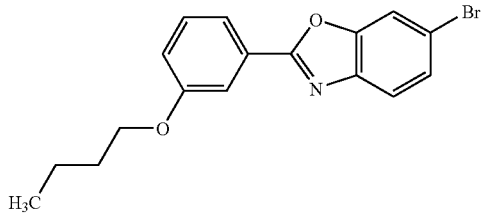
Ex. 255 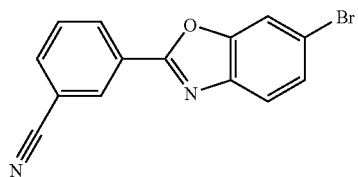
TABLE 38
Ex. 256 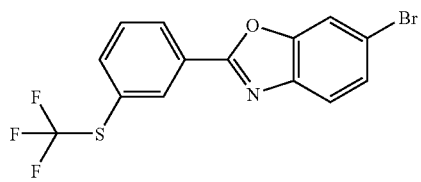
Ex. 257 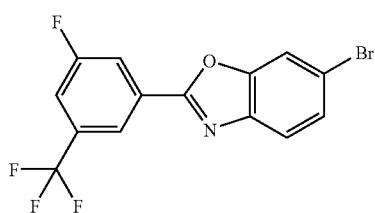
Ex. 258 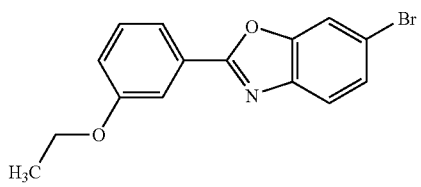
Ex. 259 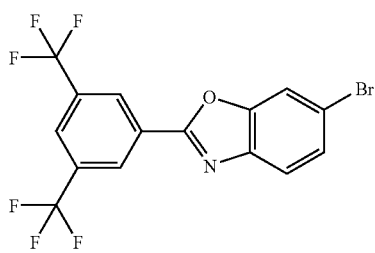
Ex. 260 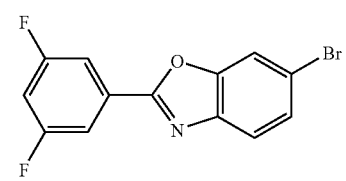
TABLE 38-continued
Ex. 261 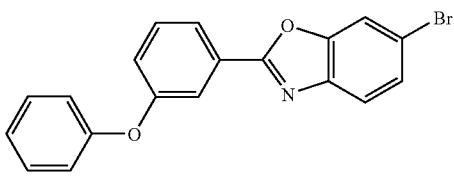
Ex. 262 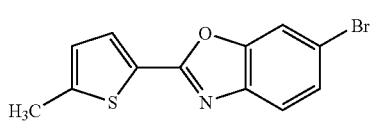
Ex. 263 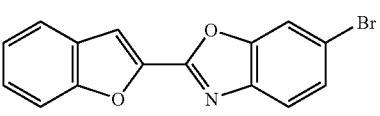
Ex. 264 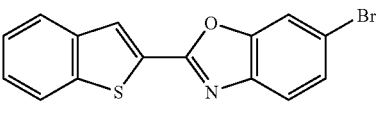
Ex. 265 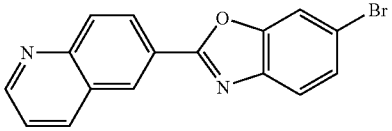
TABLE 39
Ex. 266 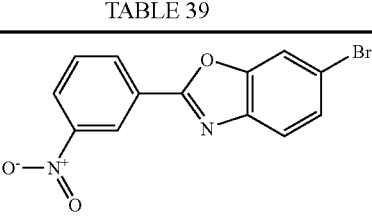
Ex. 267 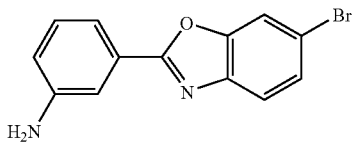
Ex. 268 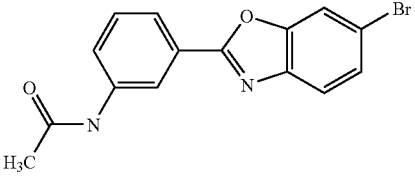
Ex. 269 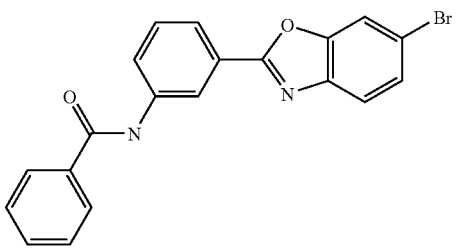

TABLE 39-continued
Ex. 270 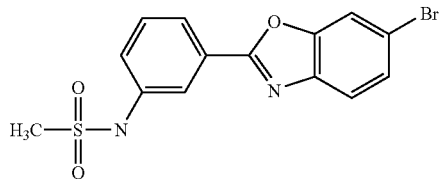
Ex. 271 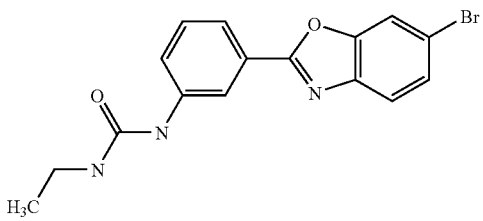
Ex. 272 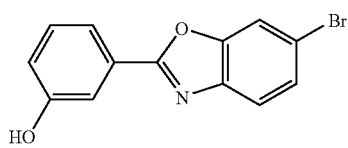
Ex. 273 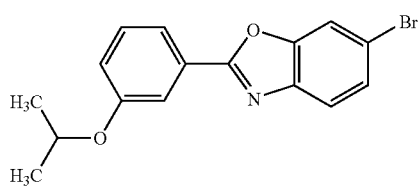
Ex. 274 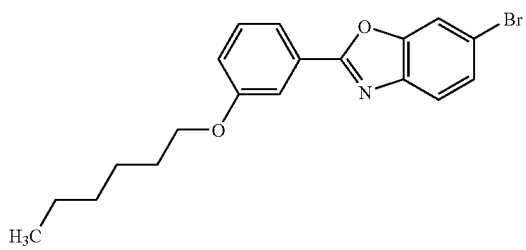
Ex. 275 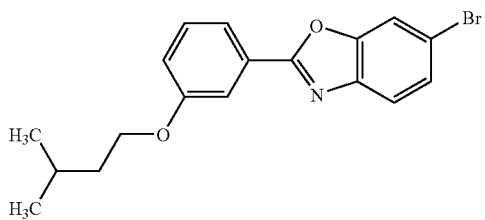
TABLE 40
Ex. 276 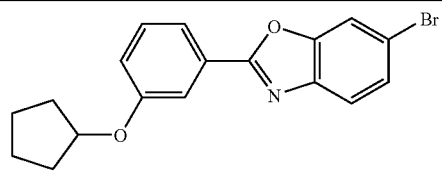
TABLE 40-continued
Ex. 277 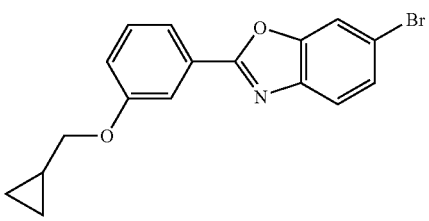
Ex. 278 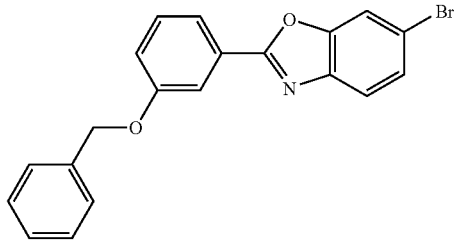
Ex. 279 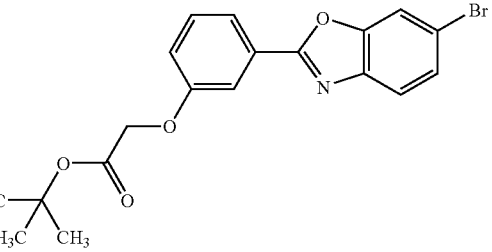
Ex. 280 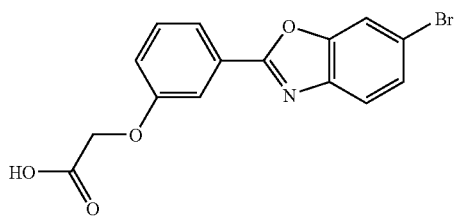
Ex. 281 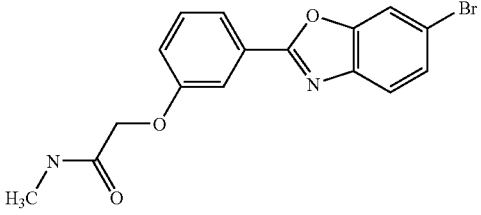
Ex. 282 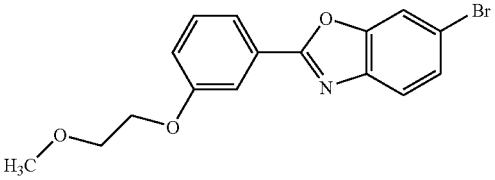
Ex. 283 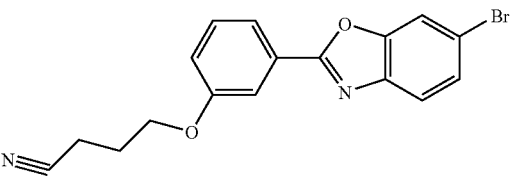

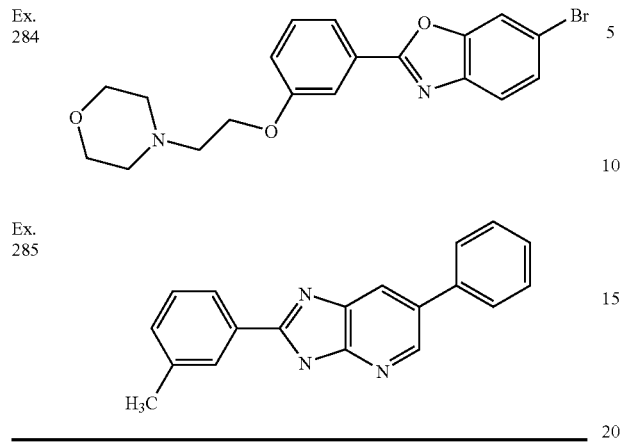
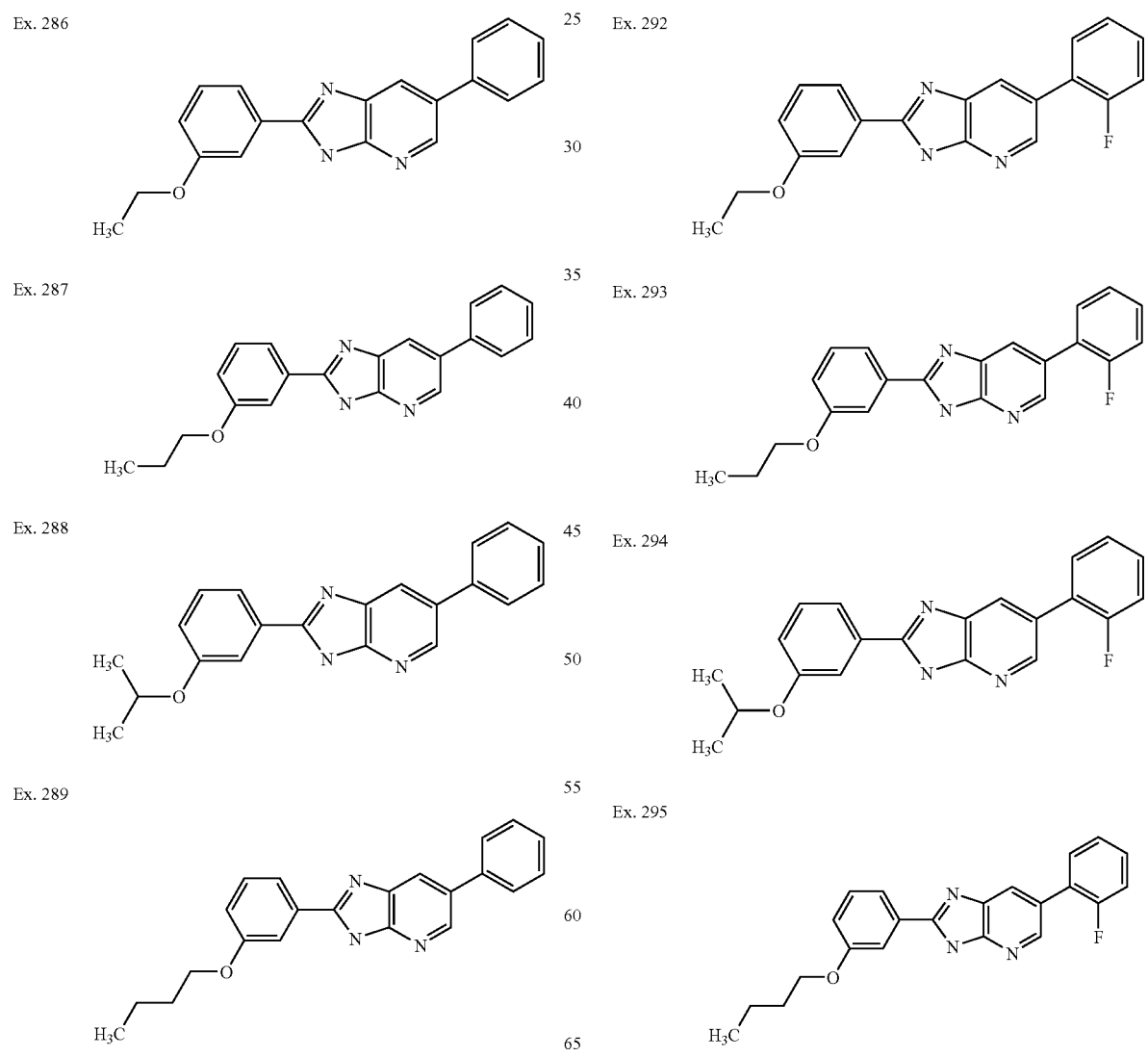

TABLE 42
Ex. 296 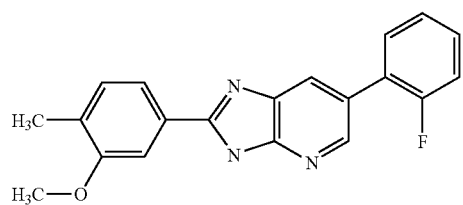
Ex. 297 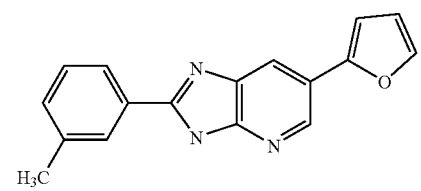
Ex. 298 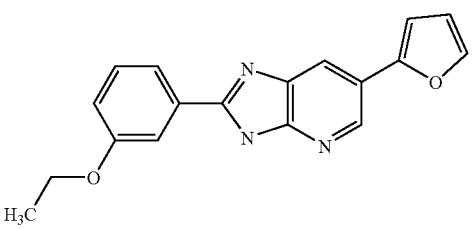
Ex. 299 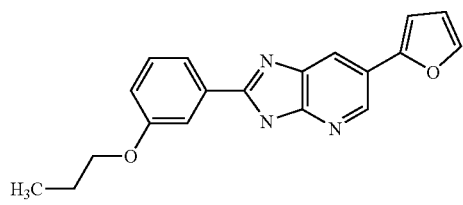
Ex. 300 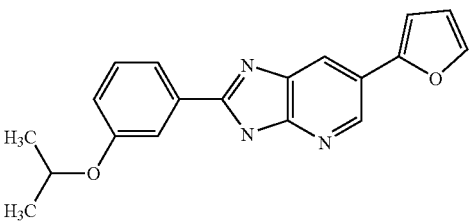
Ex. 301 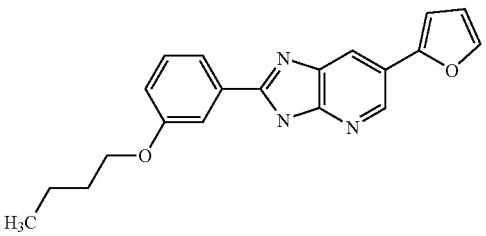
Ex. 302 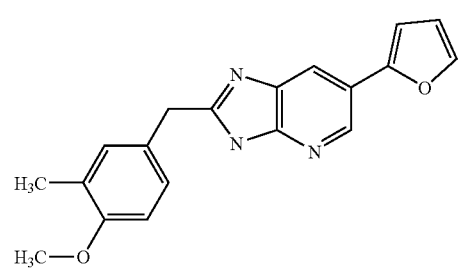
TABLE 42-continued
Ex. 303 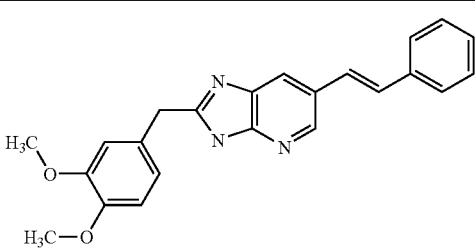
Ex. 304 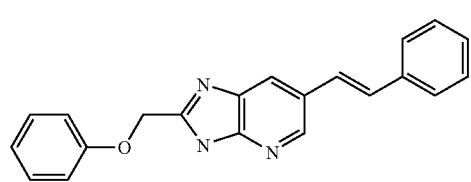
Ex. 305 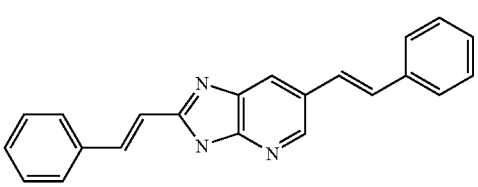
TABLE 43
Ex. 306 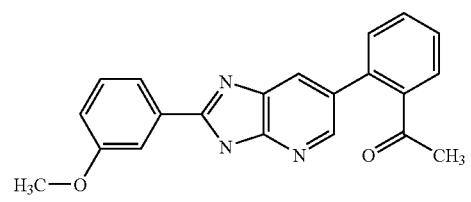
Ex. 307 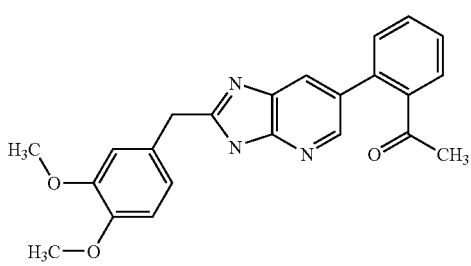
Ex. 308 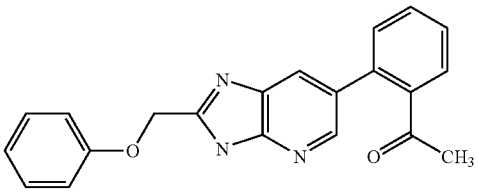
Ex. 309 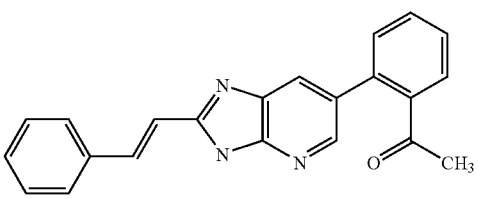

TABLE 43-continued
Ex. 310
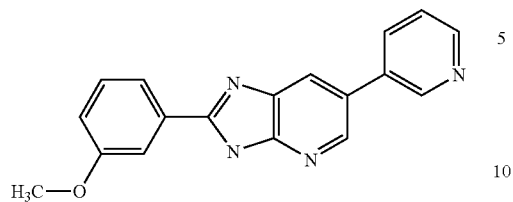
Ex. 311
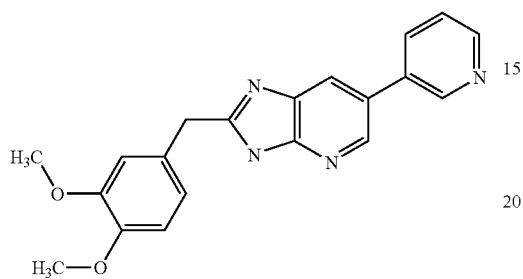
Ex. 312
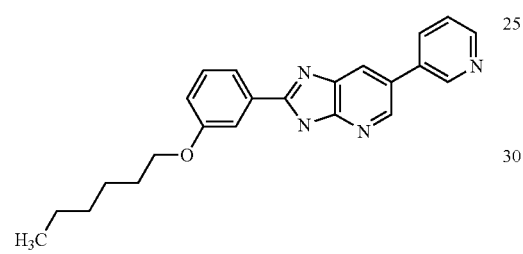
Ex. 313
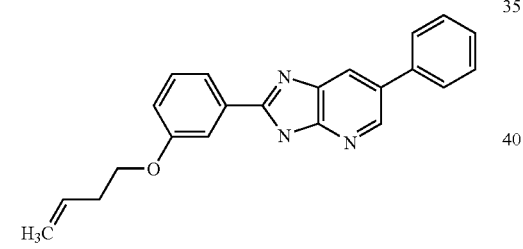
Ex. 314
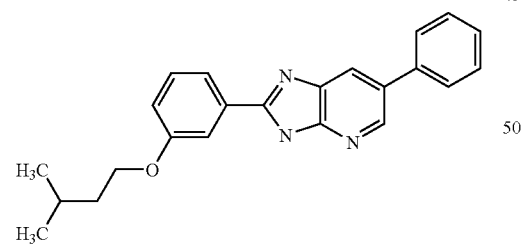
Ex. 315
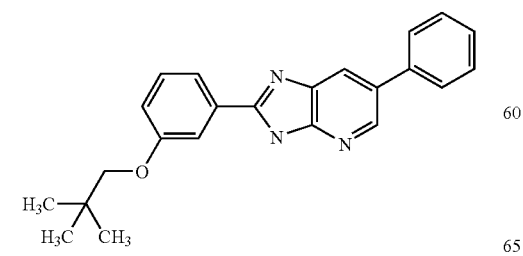
TABLE 44
Ex. 316
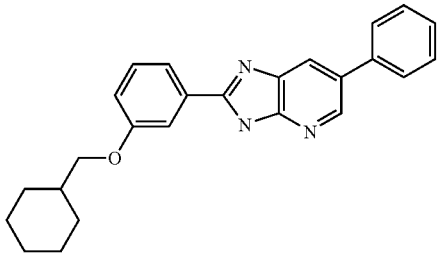
Ex. 317
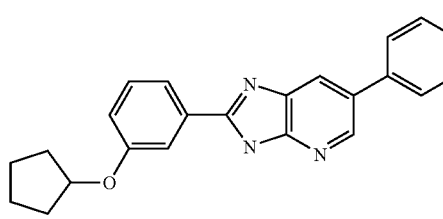
Ex. 318
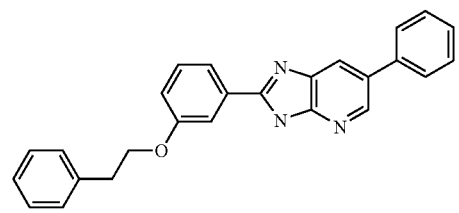
Ex. 319
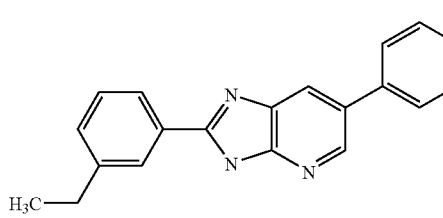
Ex. 320
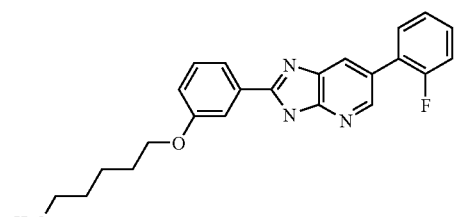
Ex. 321
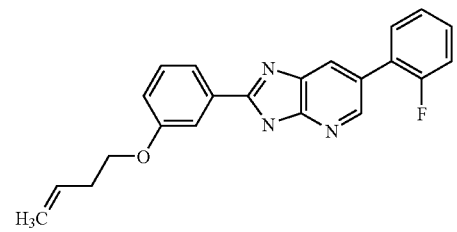
Ex. 322
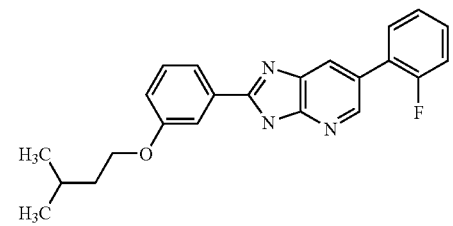

TABLE 44-continued
Ex. 323
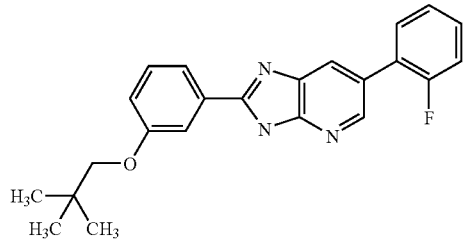
Ex. 324
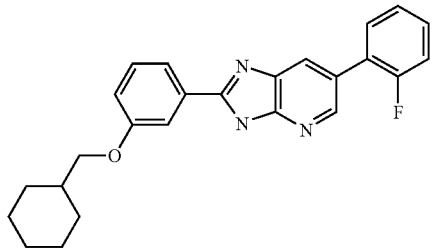
Ex. 325
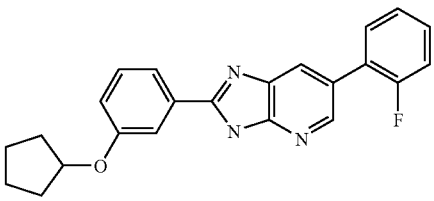
TABLE 45
Ex. 326
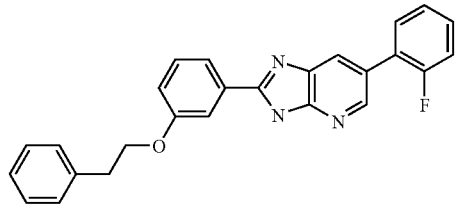
Ex. 327
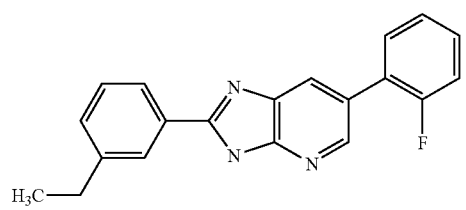
Ex. 328
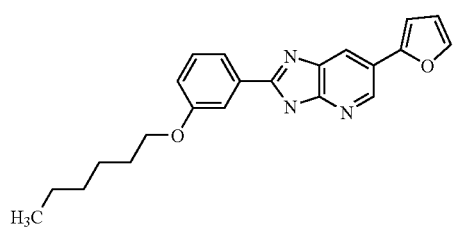
TABLE 45-continued
Ex. 329
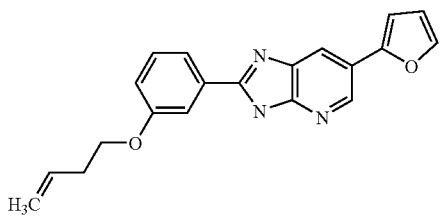
Ex. 330
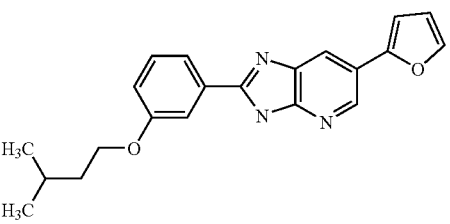
Ex. 331
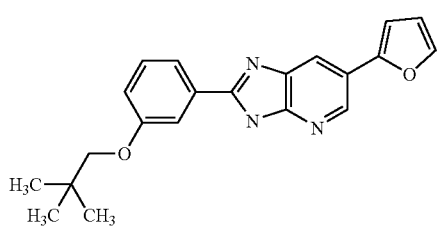
Ex. 332
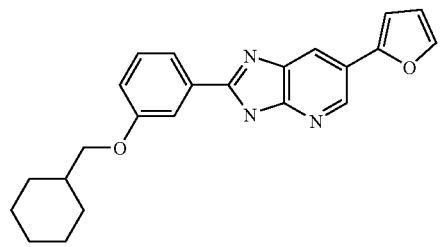
Ex. 333
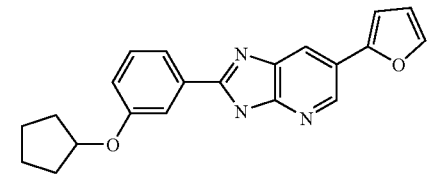
Ex. 334
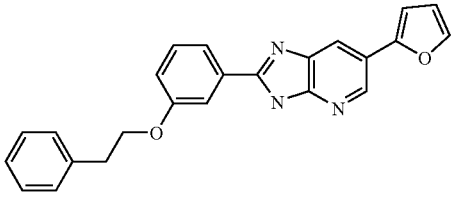
Ex. 335
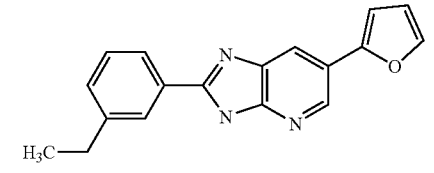

TABLE 46
Ex. 336 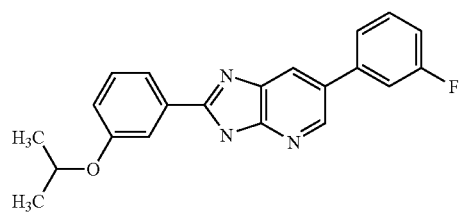
Ex. 337 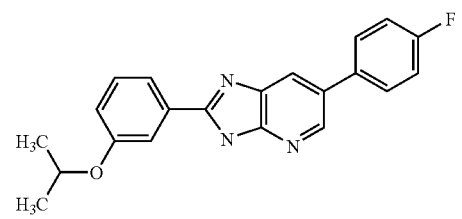
Ex. 338 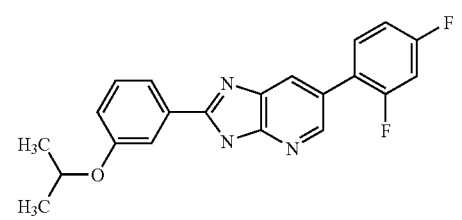
Ex. 339 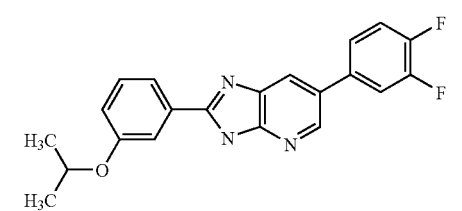
Ex. 340 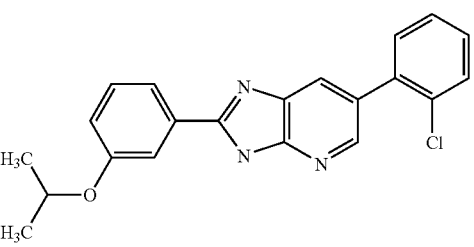
Ex. 341 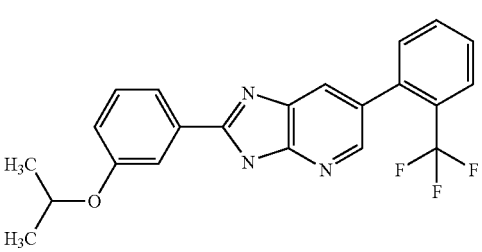
Ex. 342 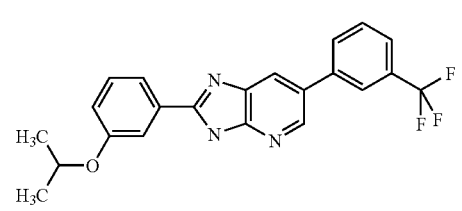
TABLE 46-continued
Ex. 343 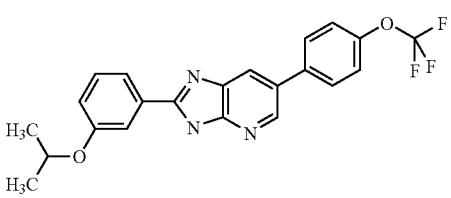
Ex. 344 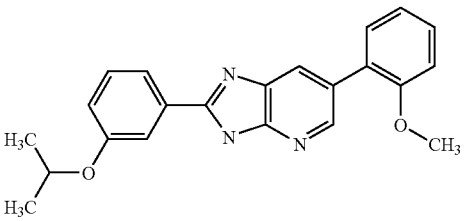
Ex. 345 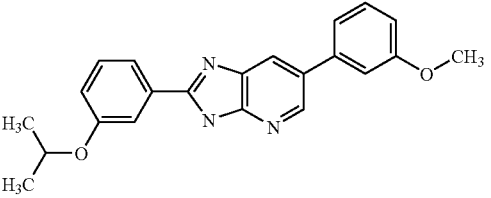
TABLE 47
Ex. 346 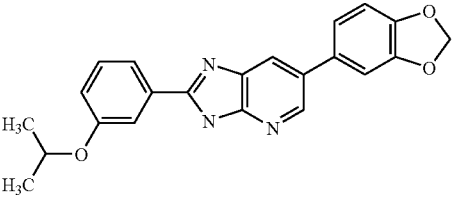
Ex. 347 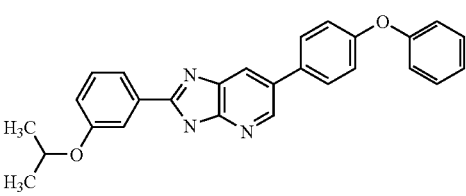
Ex. 348 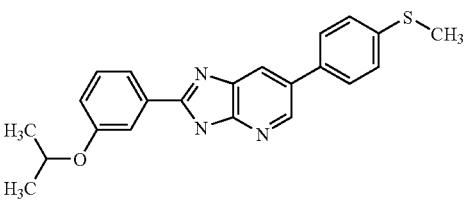
Ex. 349 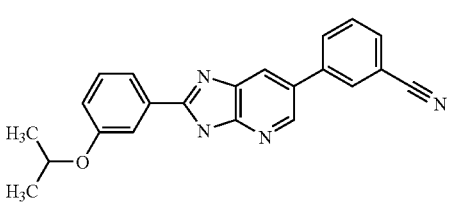

TABLE 47-continued
Ex. 350 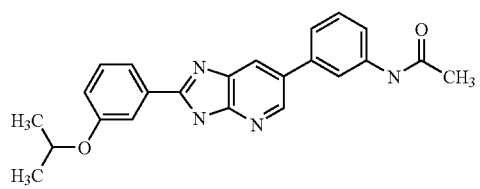
Ex. 351 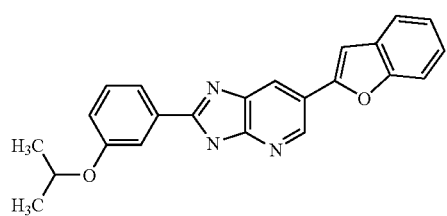
Ex. 352 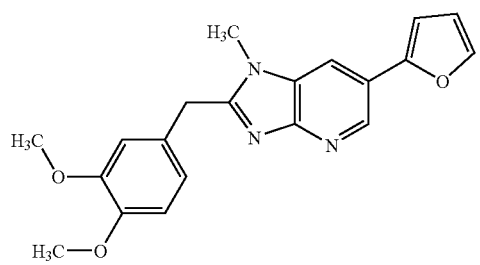
Ex. 353 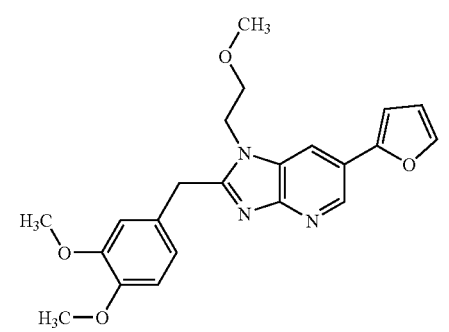
Ex. 354 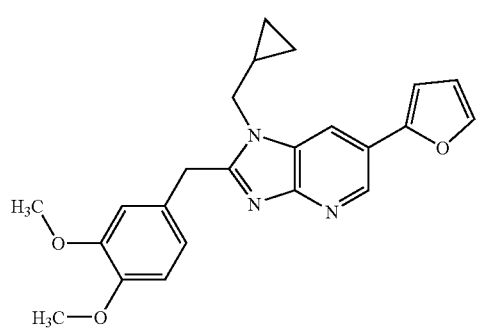
TABLE 47-continued
Ex. 355 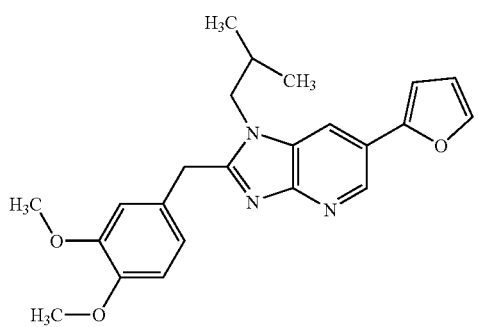
TABLE 48
Ex. 356 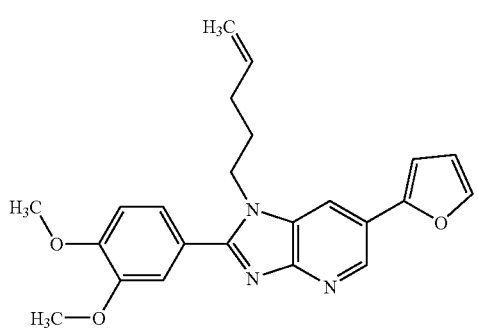
Ex. 357 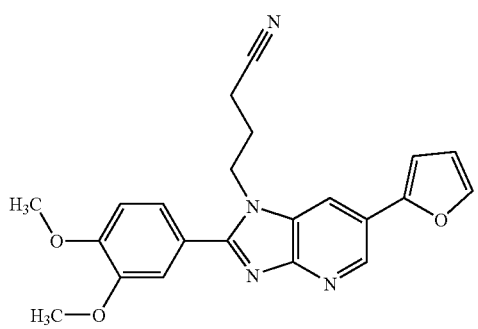
Ex. 358 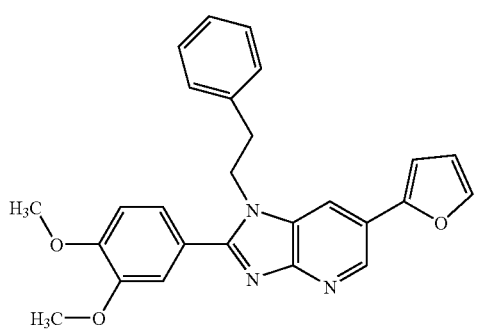

TABLE 48-continued
Ex. 359 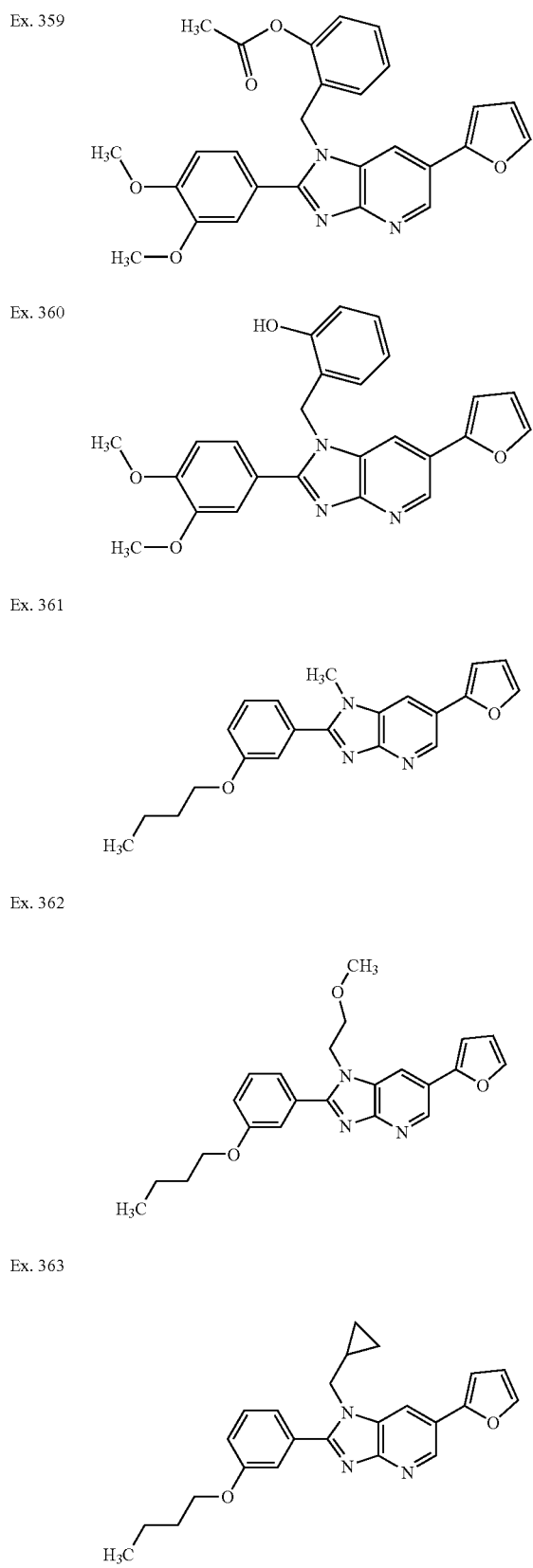
Ex. 360
Ex. 361
Ex. 362
Ex. 363
TABLE 48-continued
Ex. 364 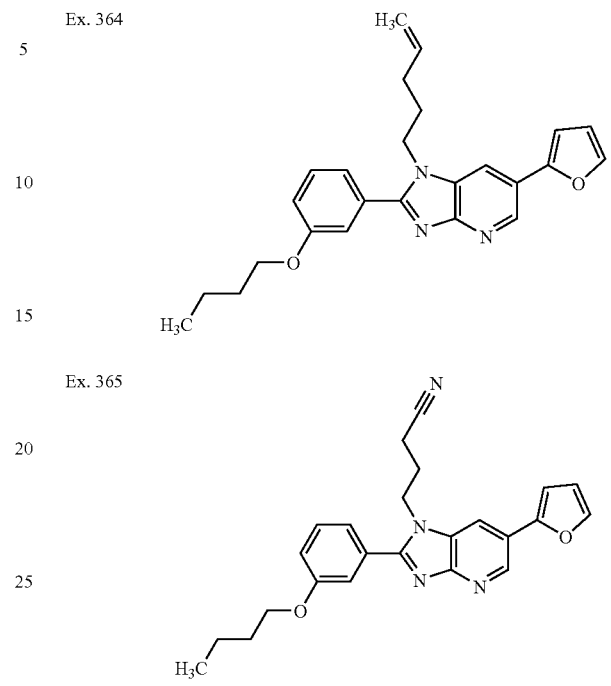
Ex. 365
TABLE 49
Ex. 366 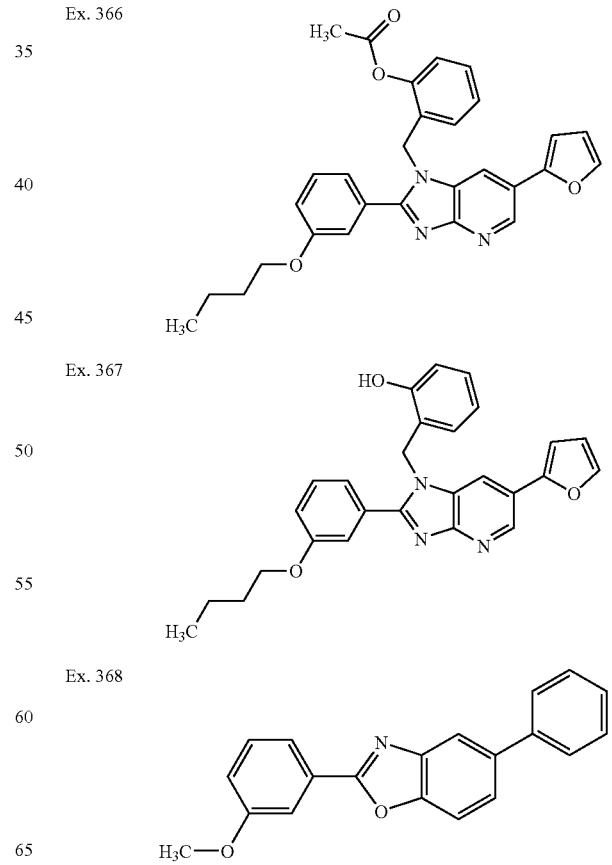
Ex. 367
Ex. 368

TABLE 49-continued
Ex. 369
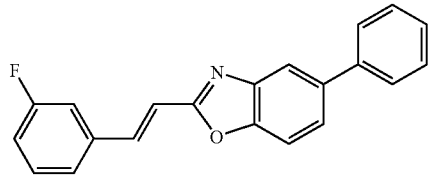
Ex. 370
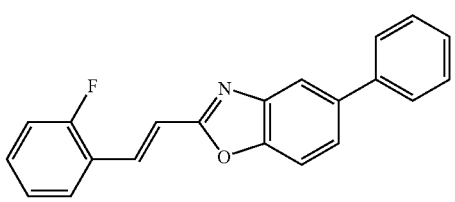
Ex. 371
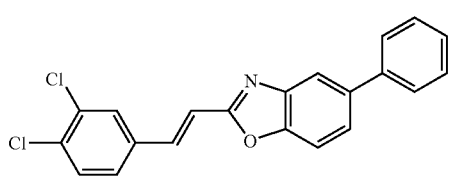
Ex. 372
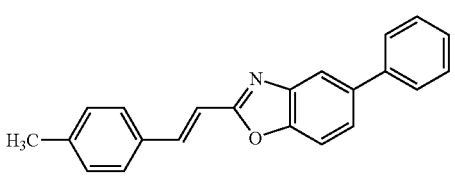
Ex. 373
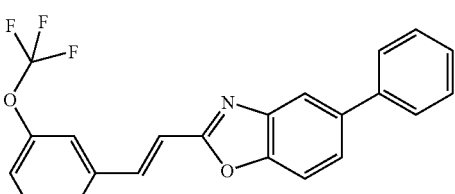
Ex. 374
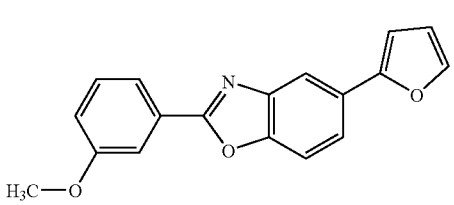
Ex. 375
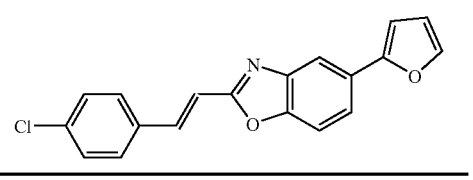
TABLE 50
Ex. 376
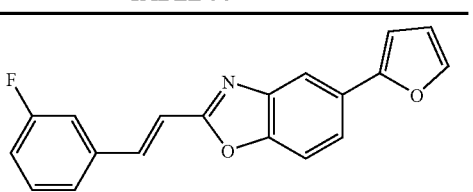
TABLE 50-continued
Ex. 377
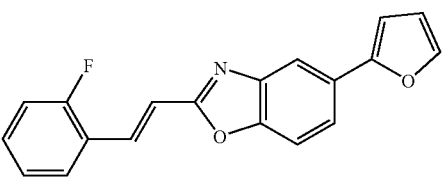
Ex. 378
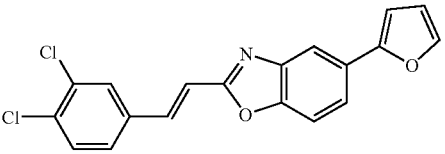
Ex. 379
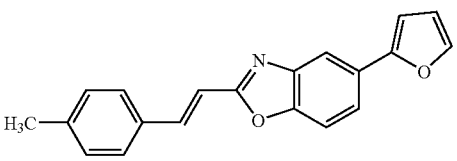
Ex. 380
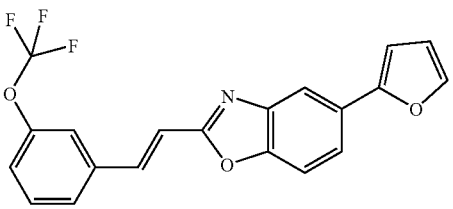
Ex. 381
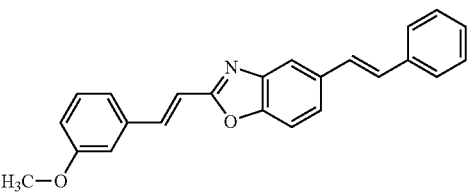
Ex. 382
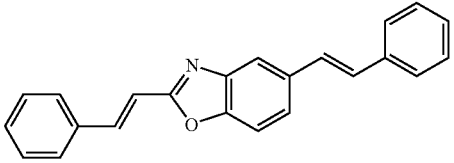
Ex. 383
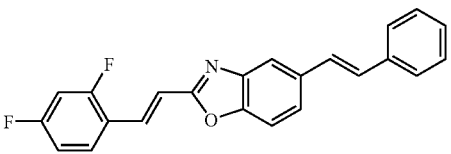
Ex. 384
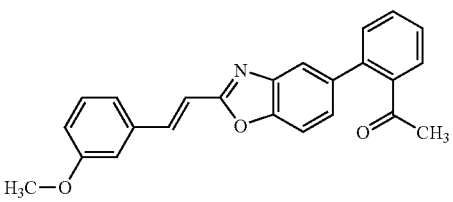

TABLE 50-continued
Ex. 385
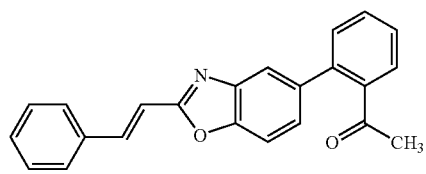
TABLE 51
Ex. 386
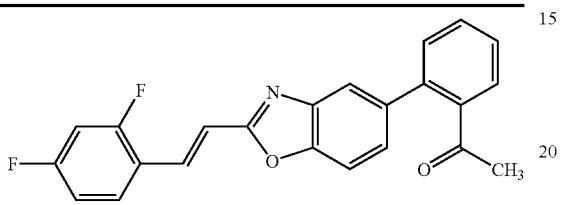
Ex. 387
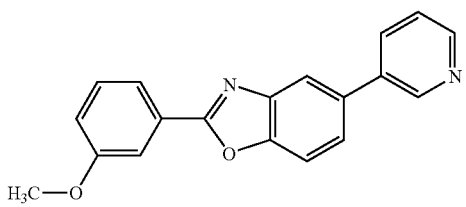
Ex. 388
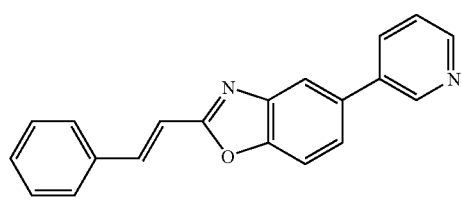
Ex. 389
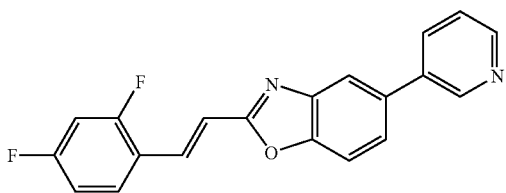
Ex. 390
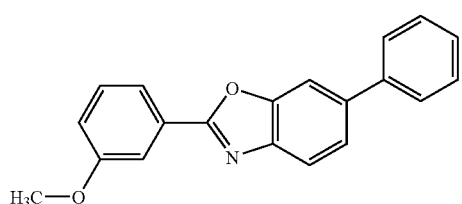
Ex. 391
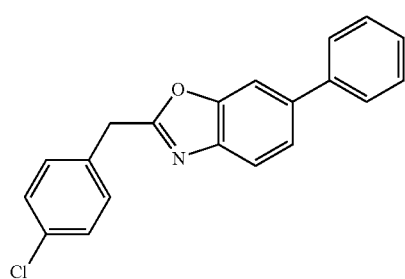
TABLE 51-continued
Ex. 392
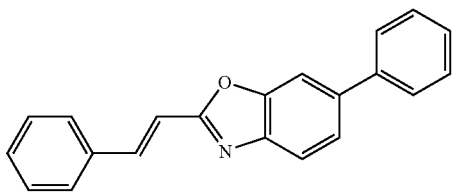
Ex. 393
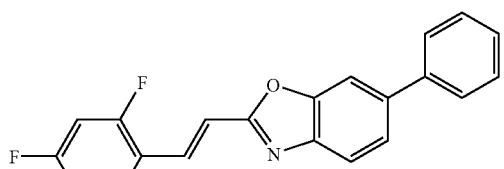
Ex. 394
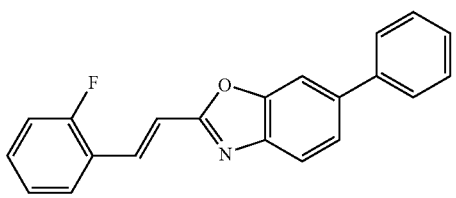
Ex. 395
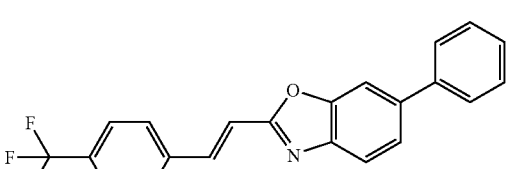
TABLE 52
Ex. 396
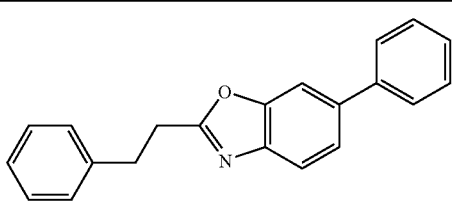
Ex. 397
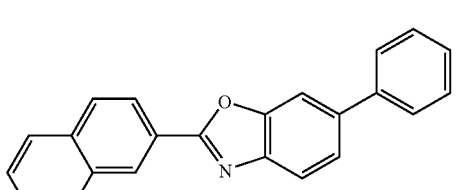
Ex. 398
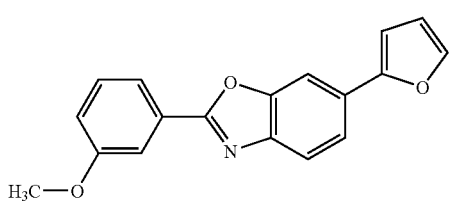

TABLE 52-continued
Ex. 399
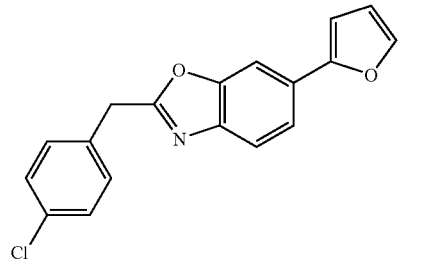
Ex. 400
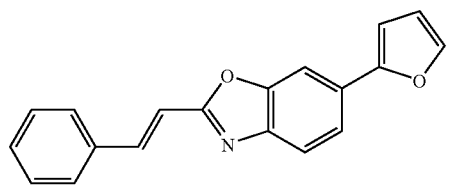
Ex. 401
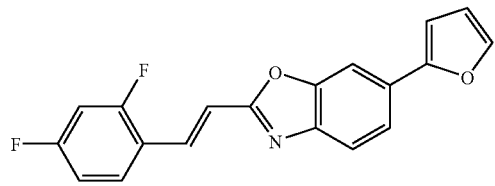
Ex. 402
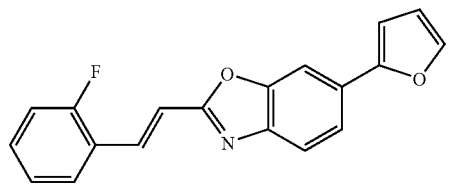
Ex. 403
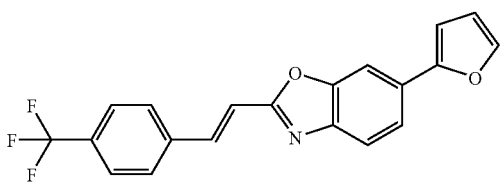
Ex. 404
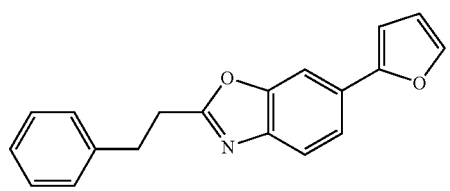
Ex. 405
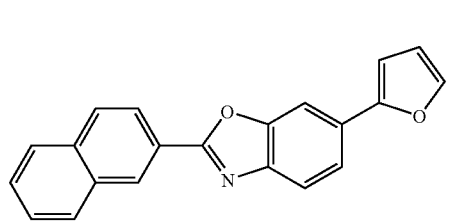
TABLE 53
Ex. 406
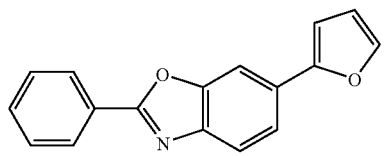
Ex. 407
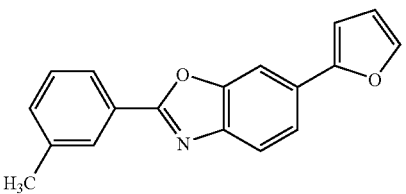
Ex. 408
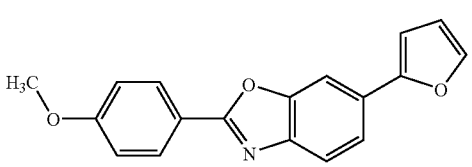
Ex. 409
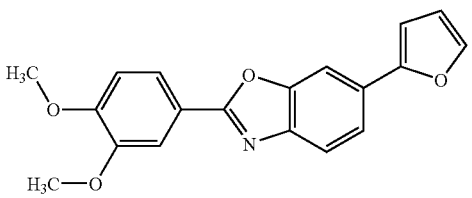
Ex. 410
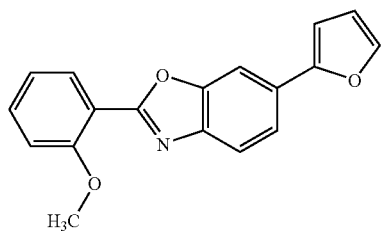
Ex. 411
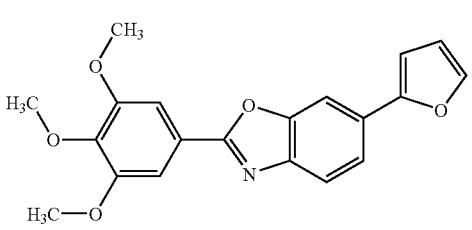
Ex. 412
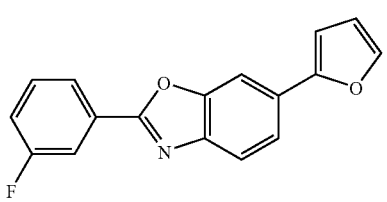

TABLE 53-continued
Ex. 413
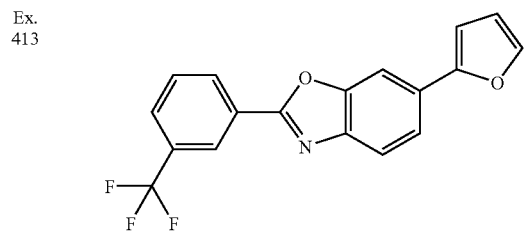
Ex. 414
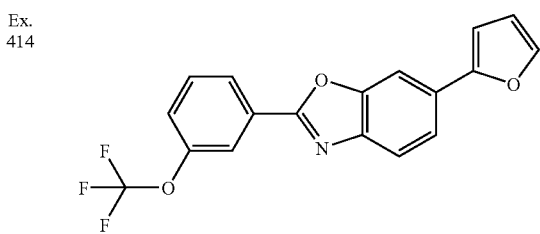
Ex. 415
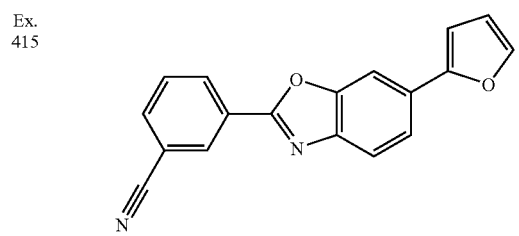
TABLE 54
Ex. 416
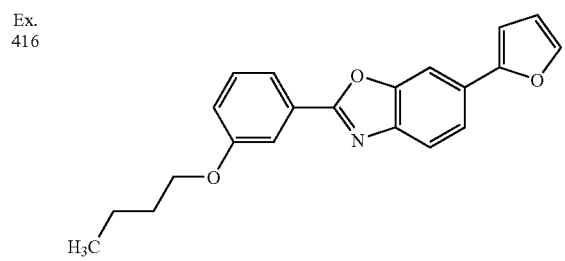
Ex. 417
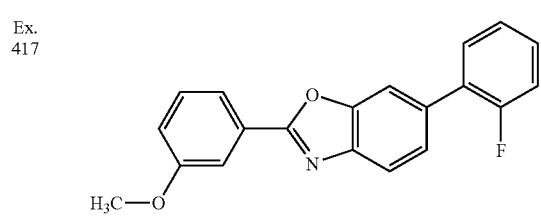
Ex. 418
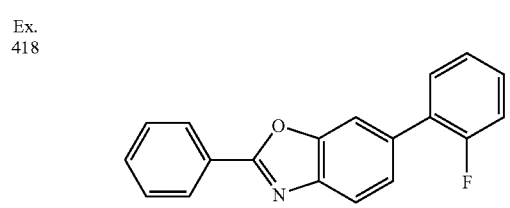
TABLE 54-continued
Ex. 419
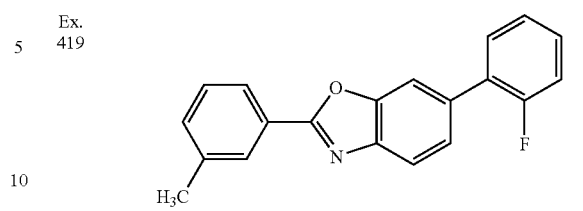
Ex. 420
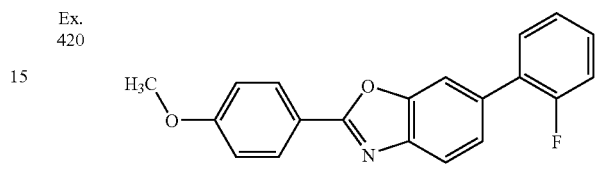
Ex. 421
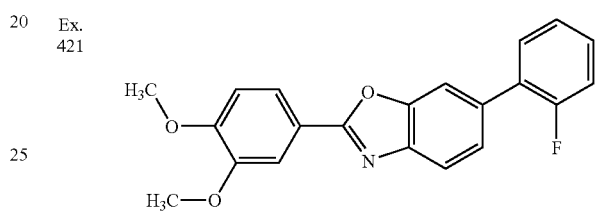
Ex. 422
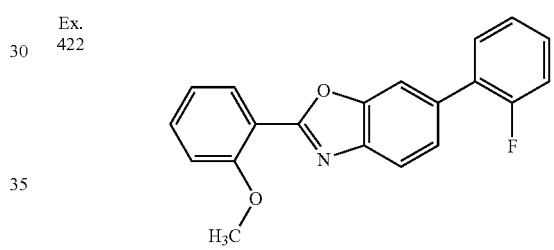
Ex. 423
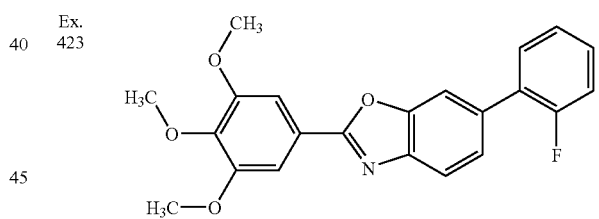
Ex. 424
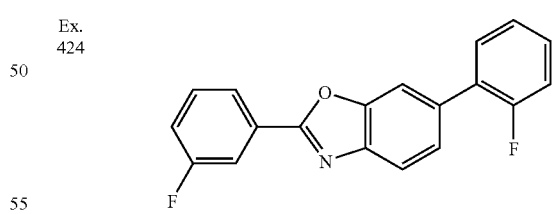
Ex. 425
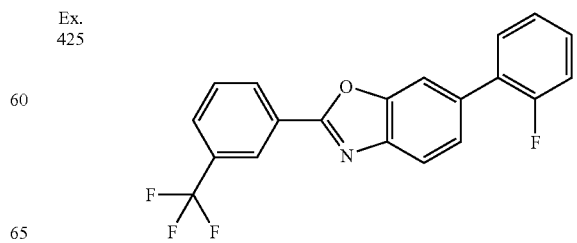

TABLE 55
Ex. 426
Ex. 427
Ex. 428
Ex. 429
Ex. 430
Ex. 431
Ex. 432
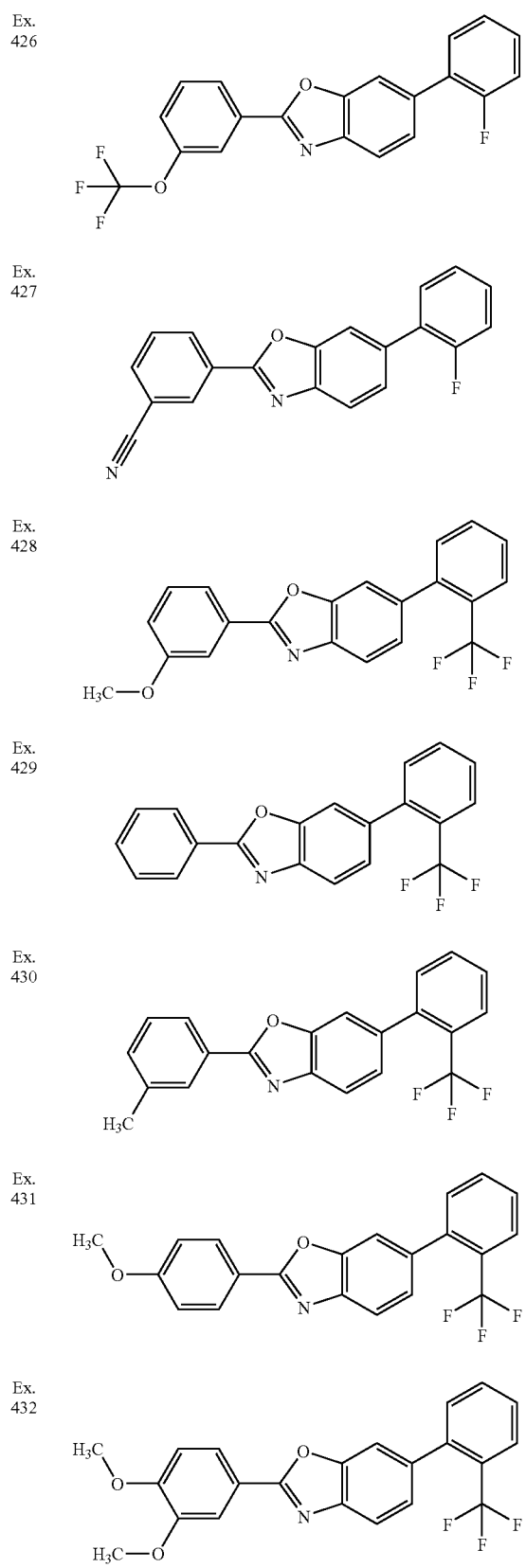
TABLE 55-continued
Ex. 433
Ex. 434
Ex. 435
TABLE 56
Ex. 436
Ex. 437
Ex. 438
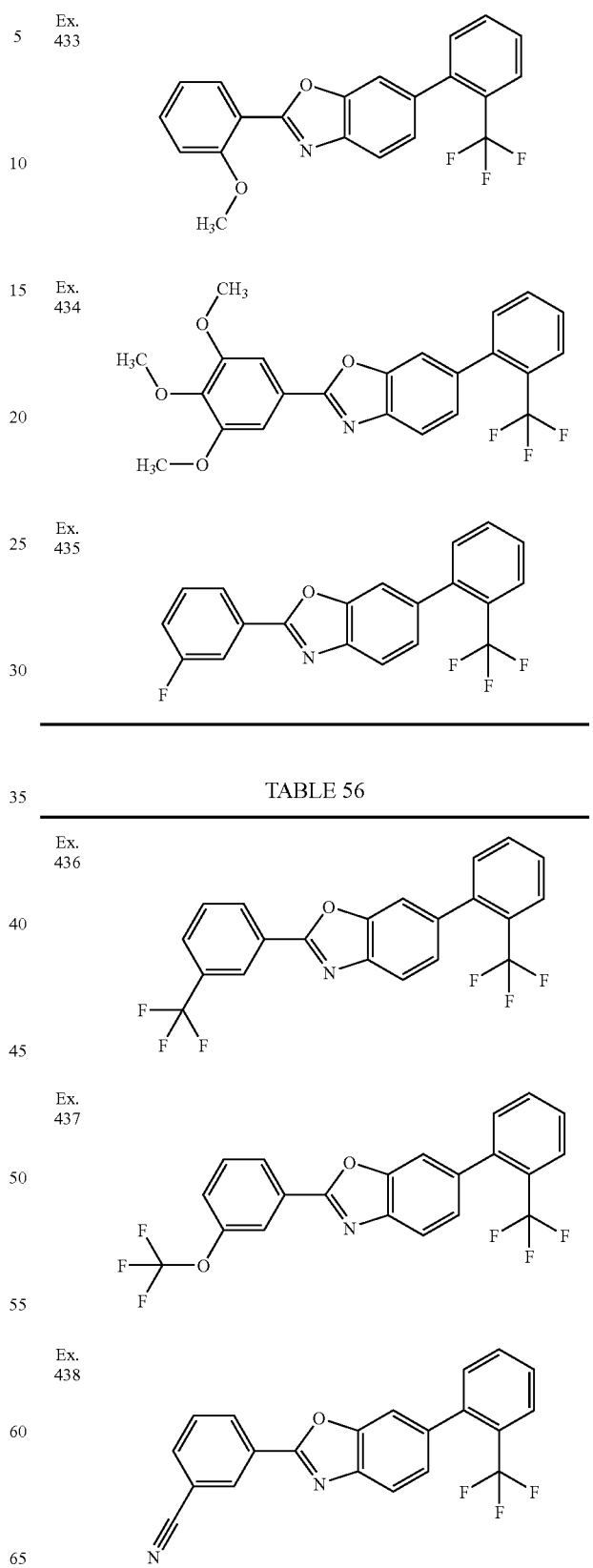

TABLE 56-continued
Ex. 439
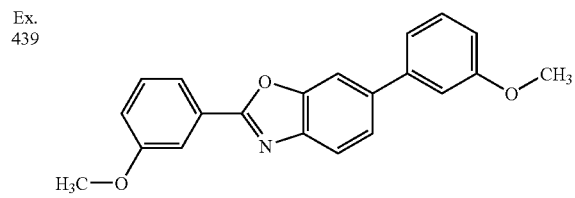
Ex. 440
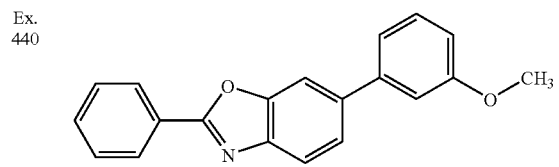
Ex. 441
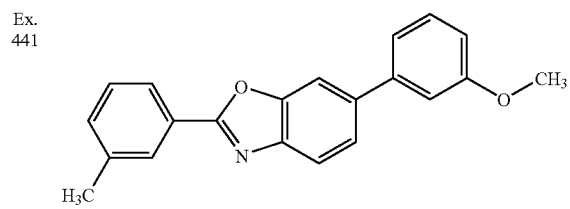
Ex. 442
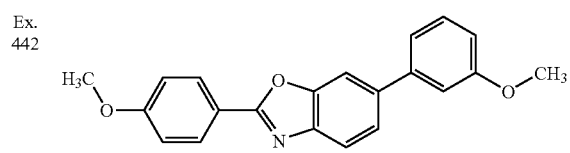
Ex. 443
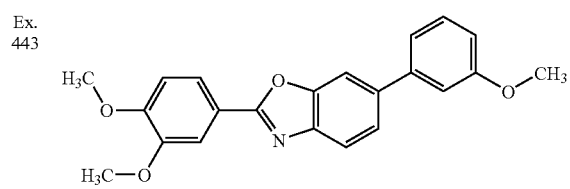
Ex. 444
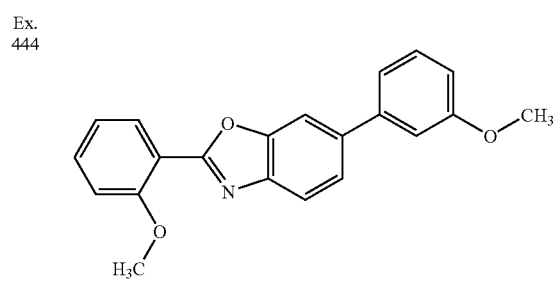
Ex. 445
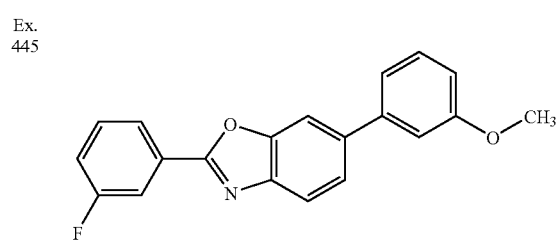
TABLE 57
Ex. 446
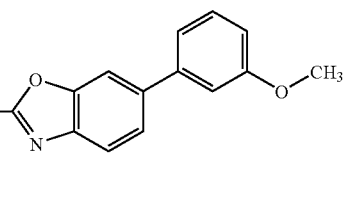
Ex. 447
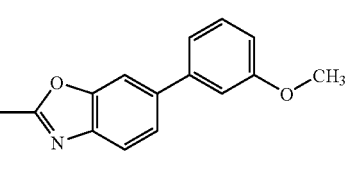
Ex. 448
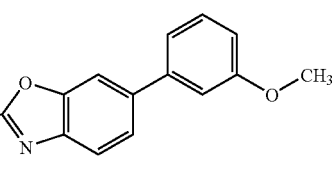
Ex. 449
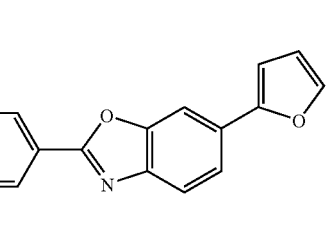
Ex. 450
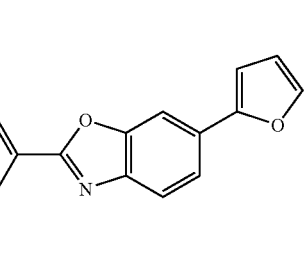
Ex. 451
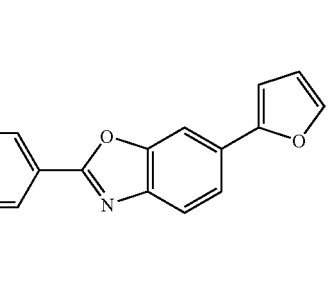

TABLE 57-continued
Ex. 452
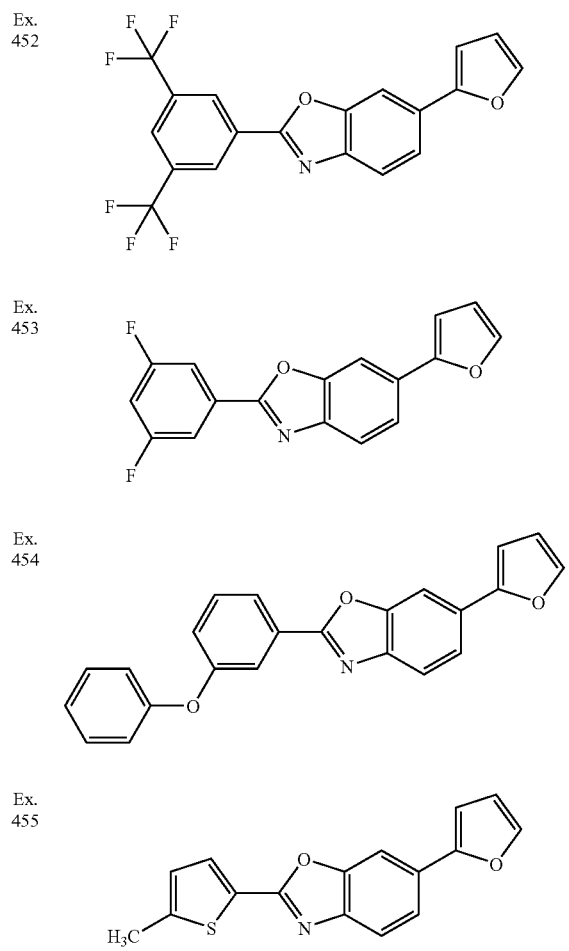
Ex. 453
Ex. 454
Ex. 455
TABLE 58
Ex. 456
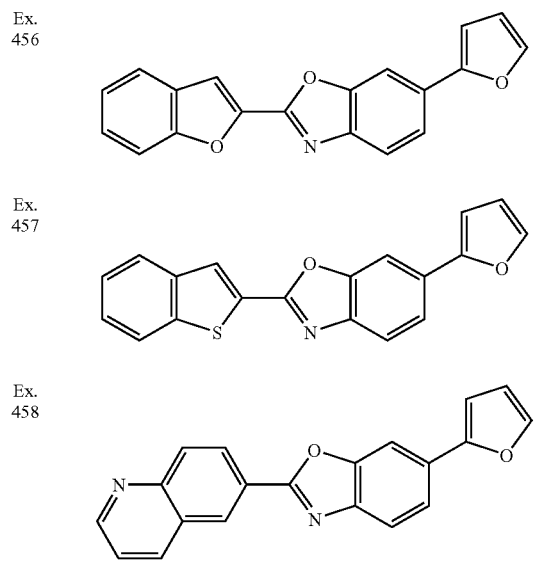
Ex. 457
Ex. 458
TABLE 58-continued
Ex. 459
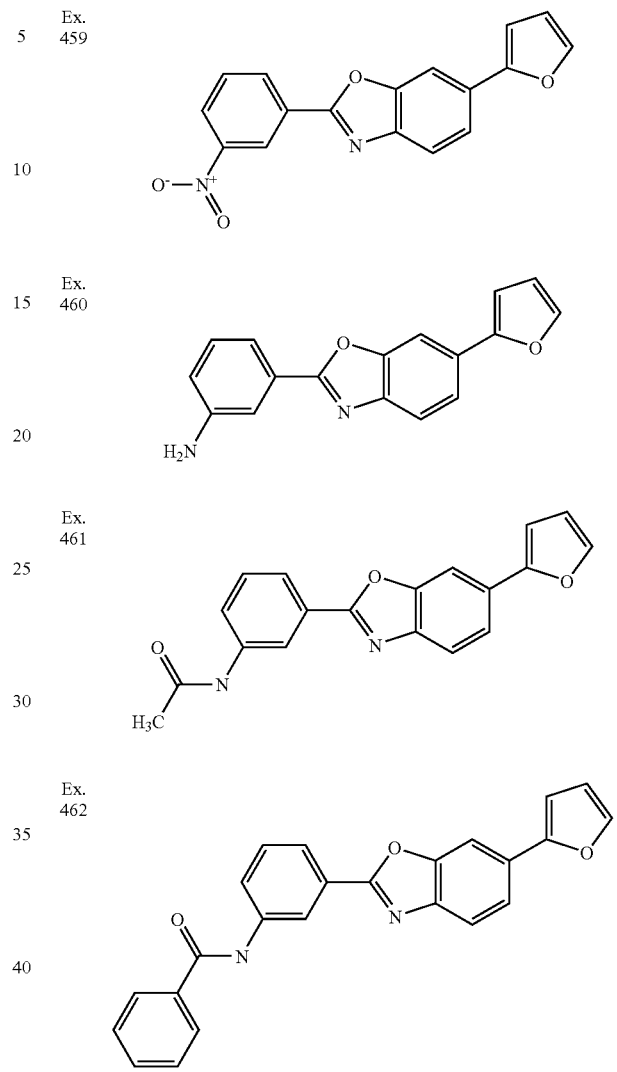
Ex. 460
Ex. 461
Ex. 462
Ex. 463
Ex. 464

TABLE 58-continued
Ex. 465
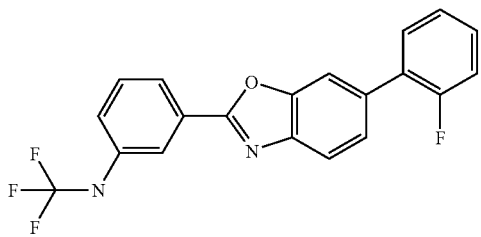
TABLE 59
Ex. 466
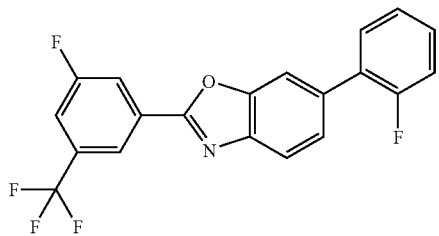
Ex. 467
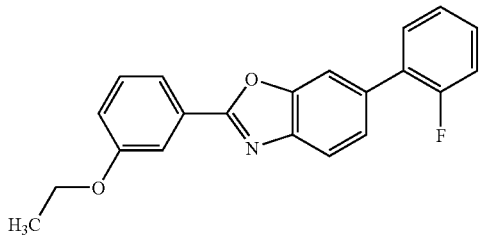
Ex. 468
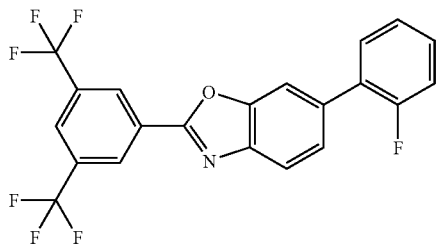
Ex. 469
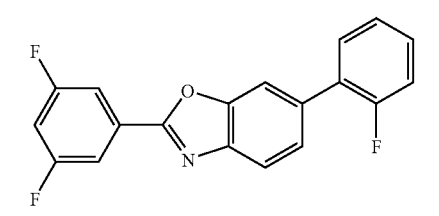
Ex. 470
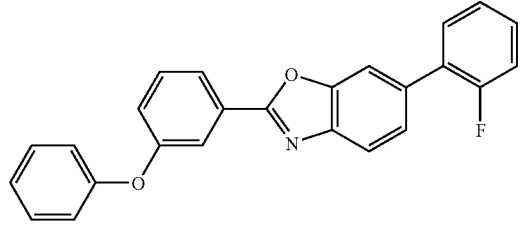
TABLE 59-continued
Ex. 471
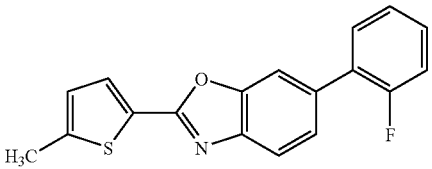
Ex. 472
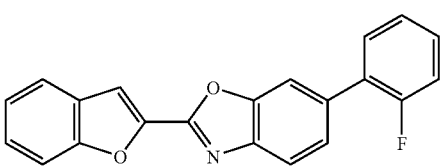
Ex. 473
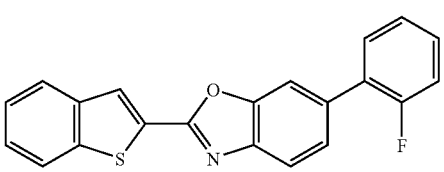
Ex. 474
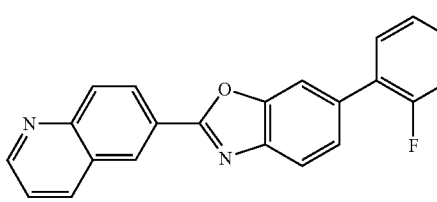
Ex. 475
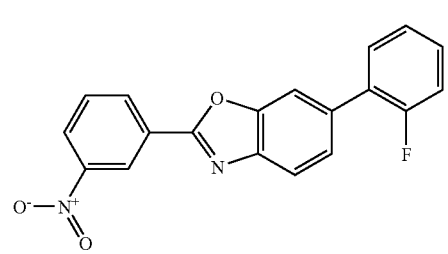
TABLE 60
Ex. 476
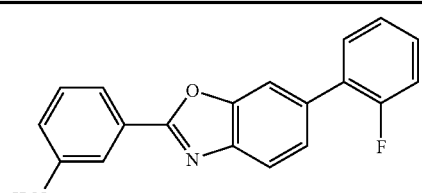
Ex. 477
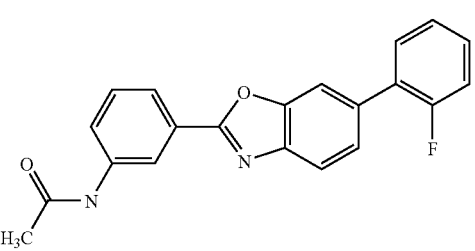

TABLE 60-continued
Ex. 478 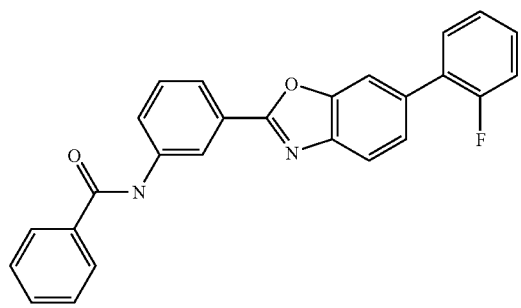
Ex. 479 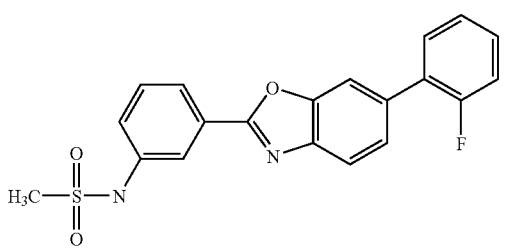
Ex. 480 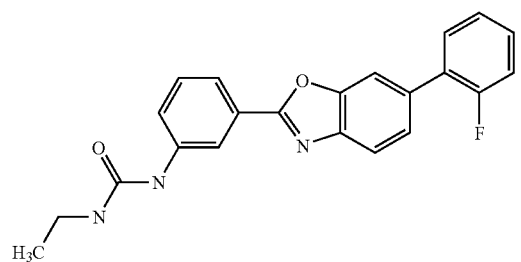
Ex. 481 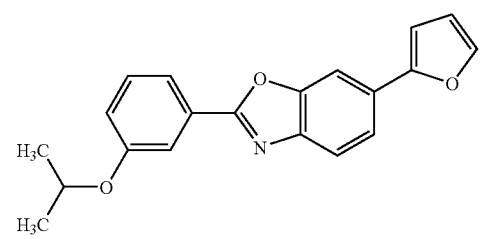
Ex. 482 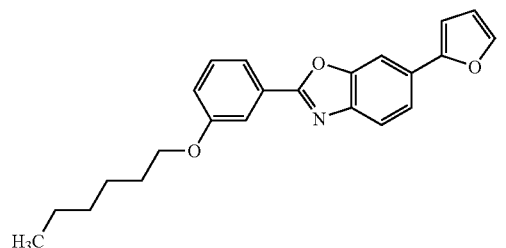
Ex. 483 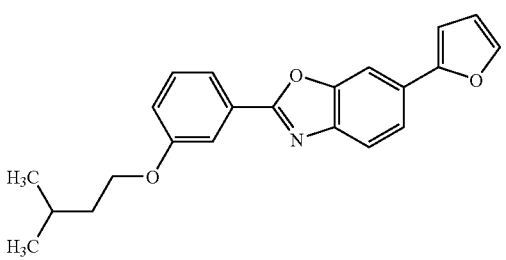
TABLE 60-continued
Ex. 484 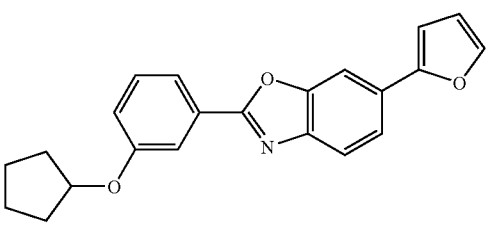
Ex. 485 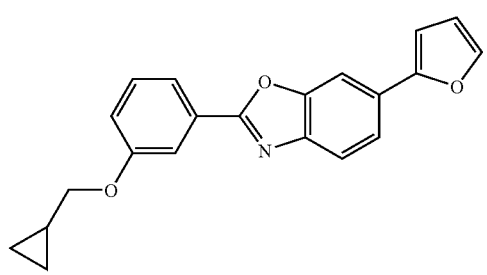
TABLE 61
Ex. 486 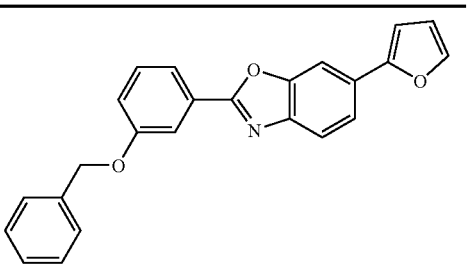
Ex. 487 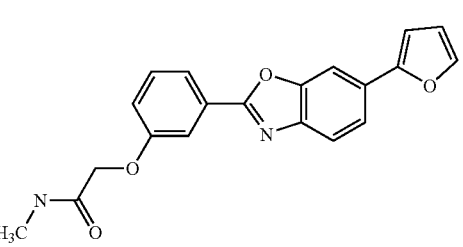
Ex. 488 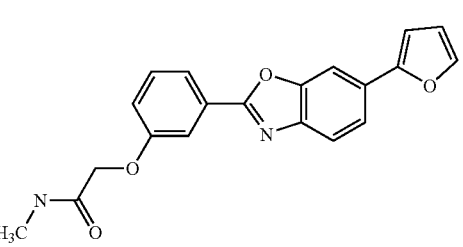
Ex. 489 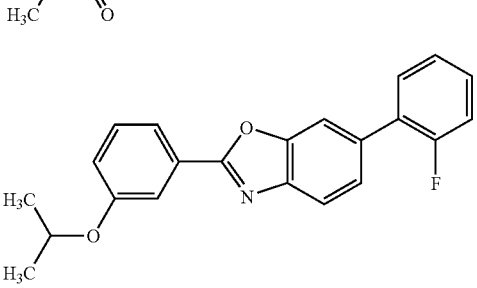

TABLE 61-continued
Ex. 490
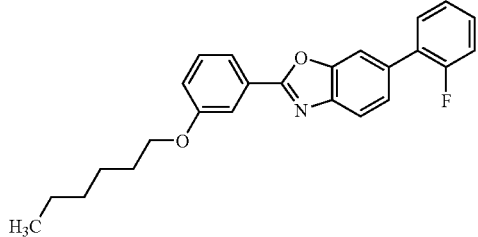
Ex. 491
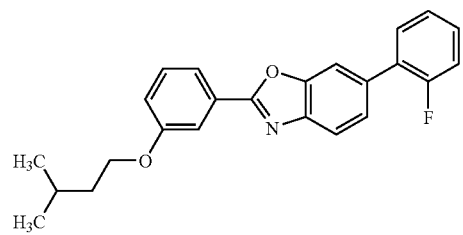
Ex. 492
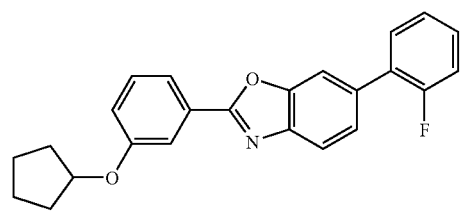
Ex. 493
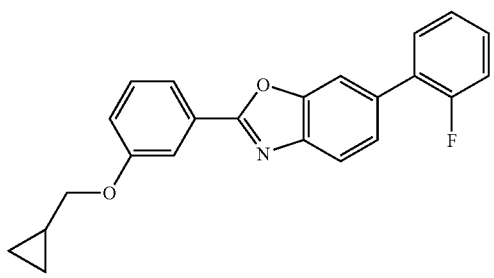
Ex. 494
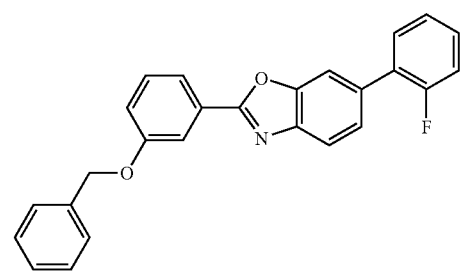
Ex. 495
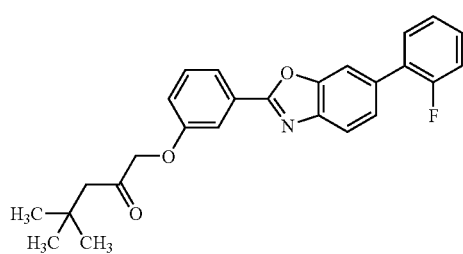
TABLE 62
Ex. 496
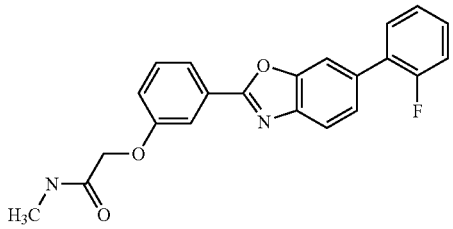
Ex. 497
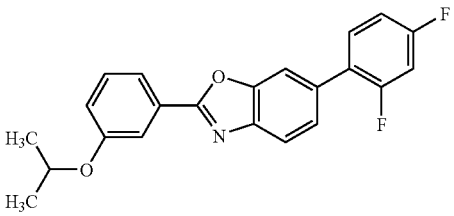
Ex. 498
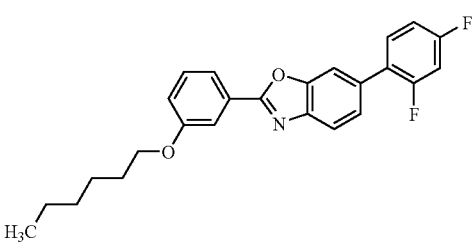
Ex. 499
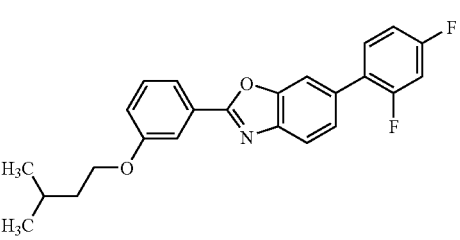
Ex. 500
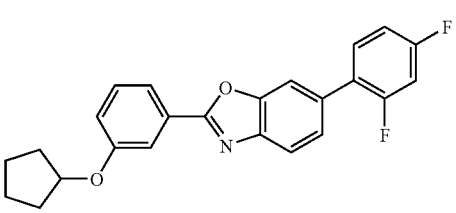
Ex. 501
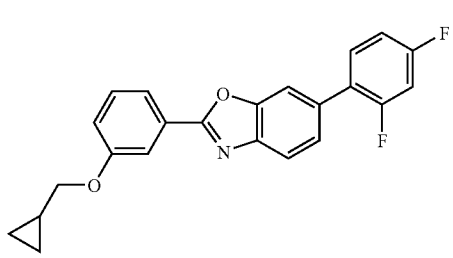

TABLE 62-continued
Ex. 502 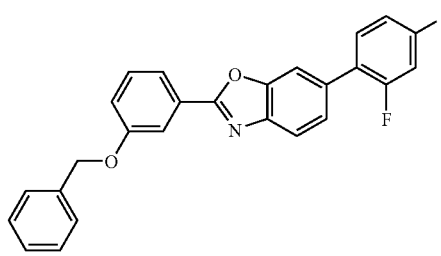
Ex. 503 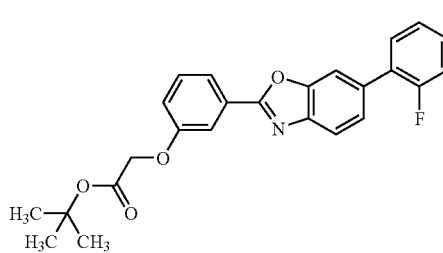
Ex. 504 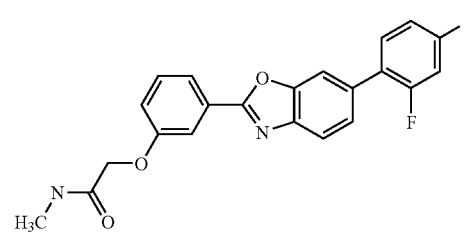
Ex. 505 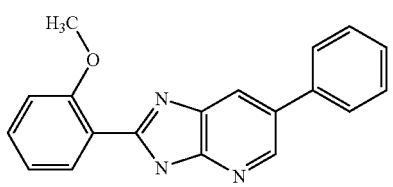
TABLE 63
Ex. 506 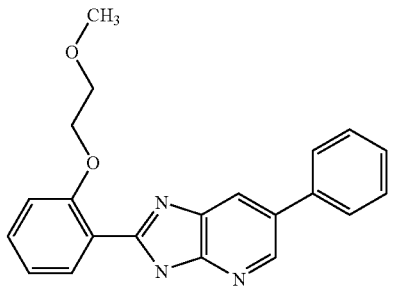
Ex. 507 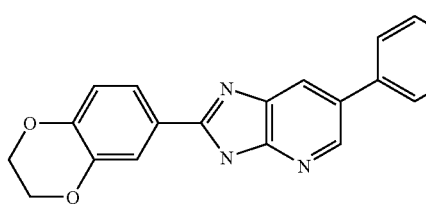
TABLE 63-continued
Ex. 508 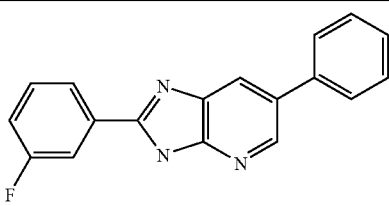
Ex. 509 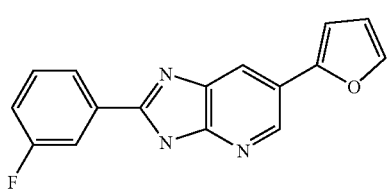
Ex. 510 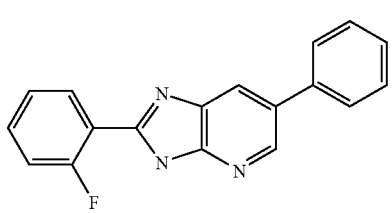
Ex. 511 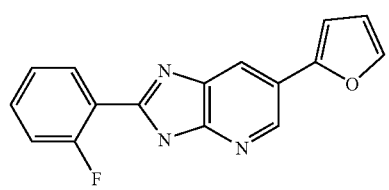
Ex. 512 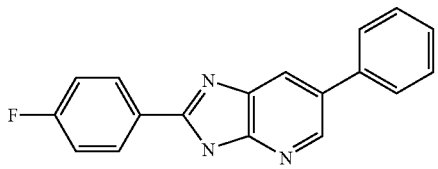
Ex. 513 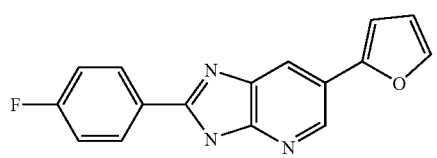
Ex. 514 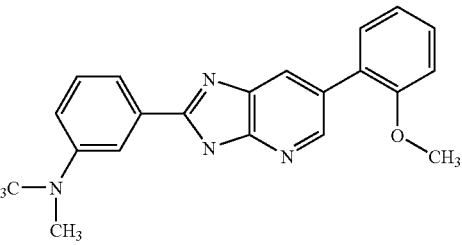
Ex. 515 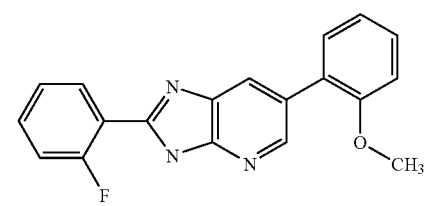

TABLE 64
Ex. 516
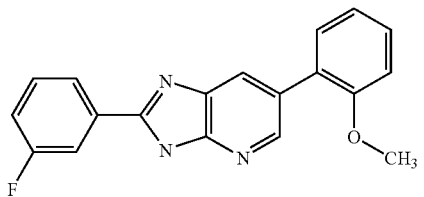
Ex. 517
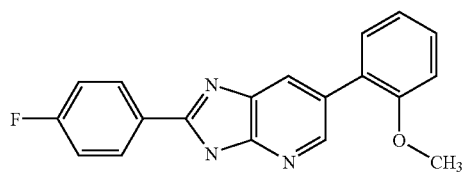
Ex. 518
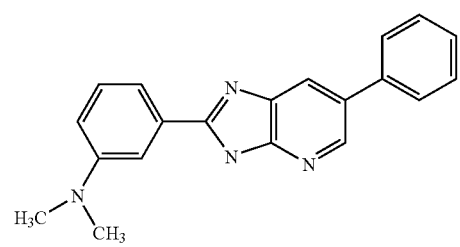
Ex. 519
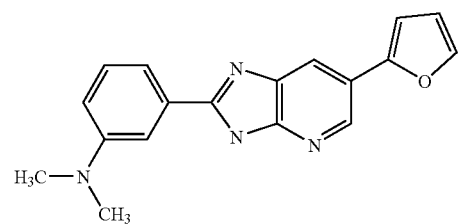
Ex. 520
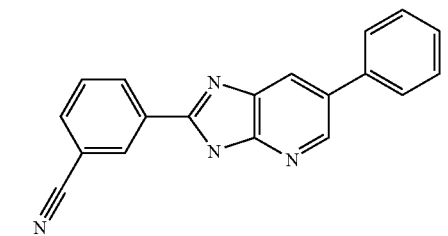
Ex. 521
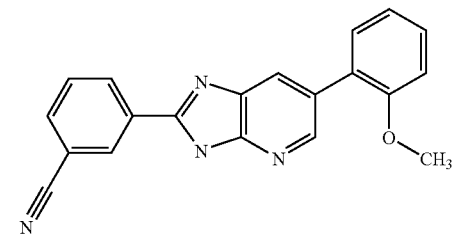
Ex. 522
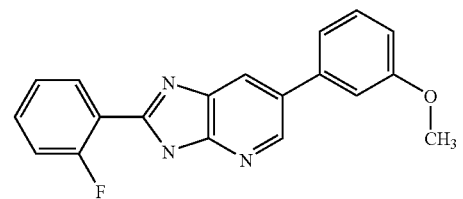
TABLE 64-continued
Ex. 523
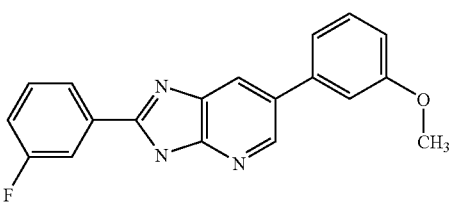
Ex. 524
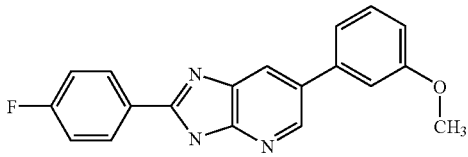
Ex. 525
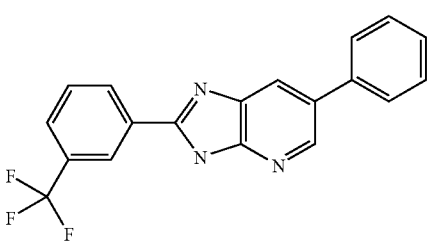
TABLE 65
Ex. 526
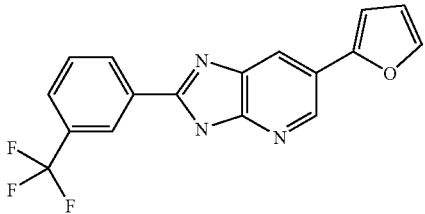
Ex. 527
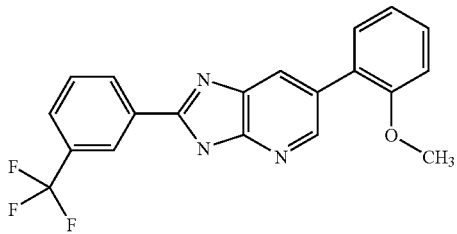
Ex. 528
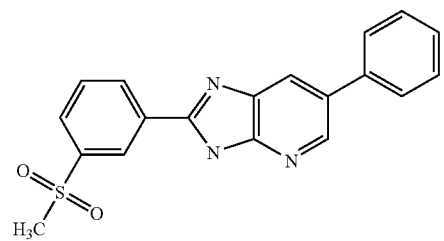

TABLE 65-continued
Ex. 529
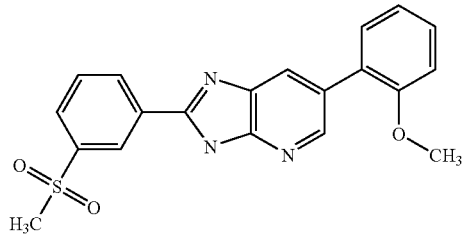
Ex. 530
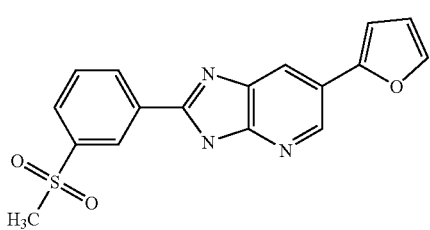
Ex. 531
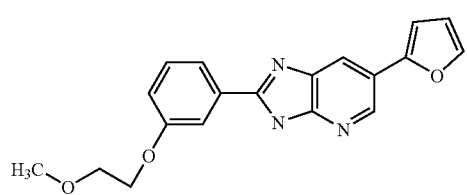
Ex. 532
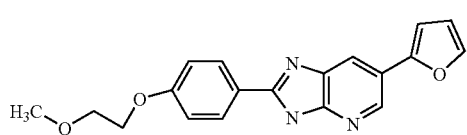
Ex. 533
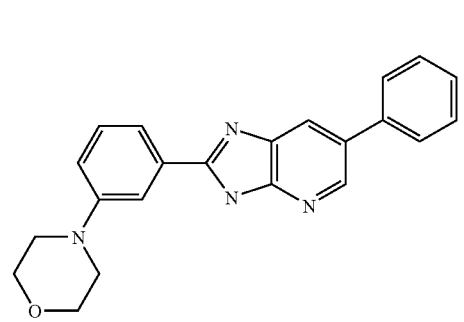
Ex. 534
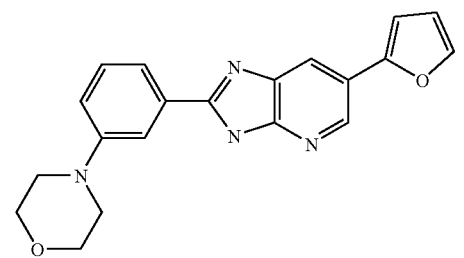
TABLE 65-continued
Ex. 535
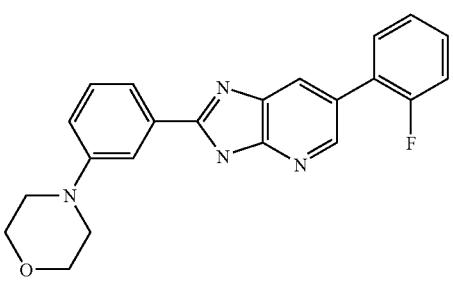
TABLE 66
Ex. 536
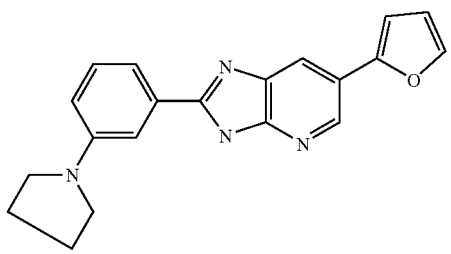
Ex. 537
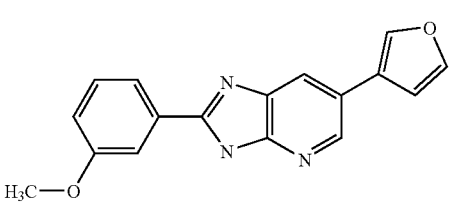
Ex. 538
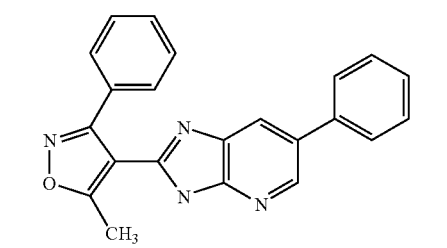
Ex. 539
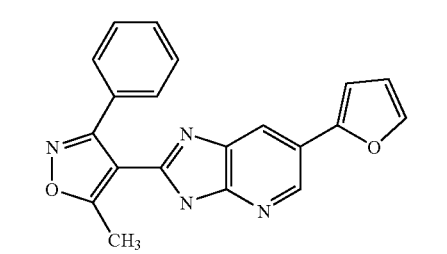
Ex. 540
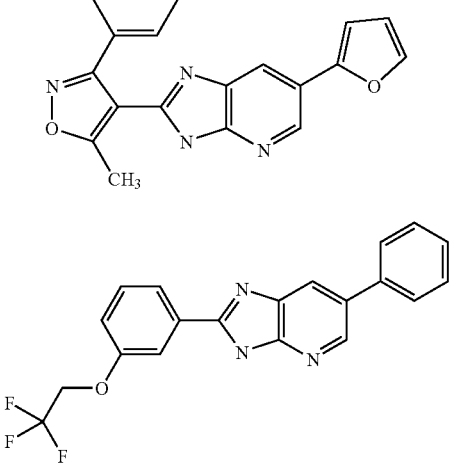

TABLE 66-continued
Ex. 541
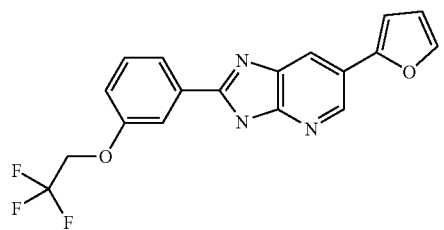
Ex. 542
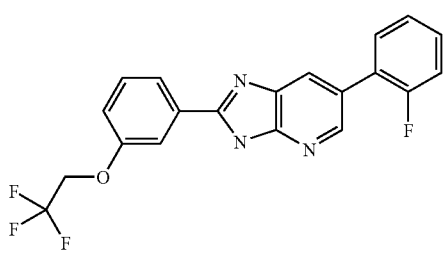
Ex. 543
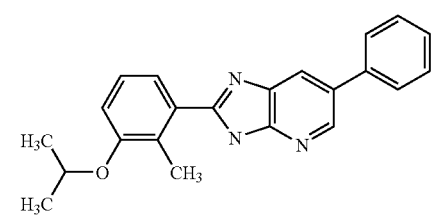
Ex. 544
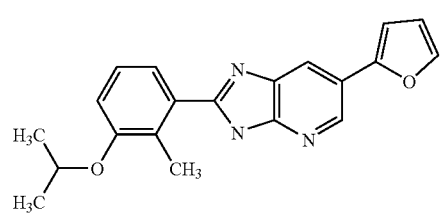
Ex. 545
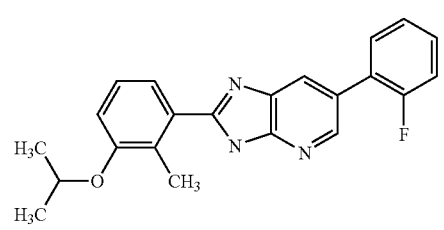
TABLE 67
Ex. 546
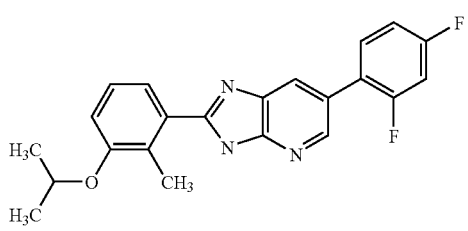
TABLE 67-continued
Ex. 547
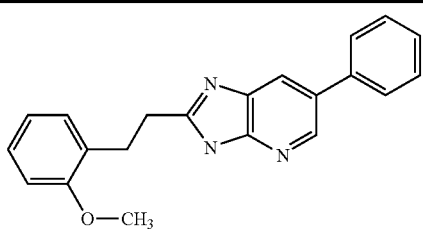
Ex. 548
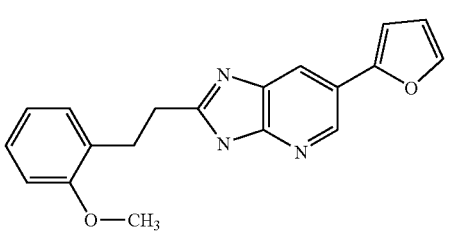
Ex. 549
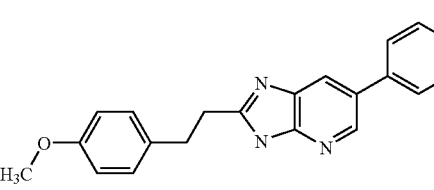
Ex. 550
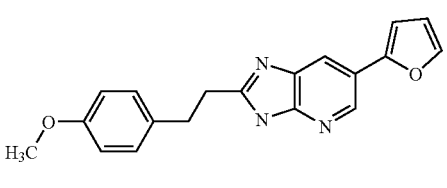
Ex. 551
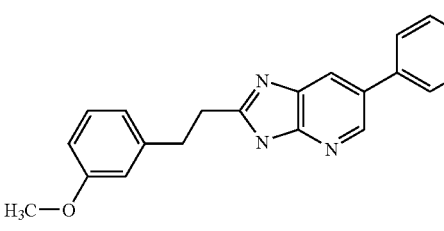
Ex. 552
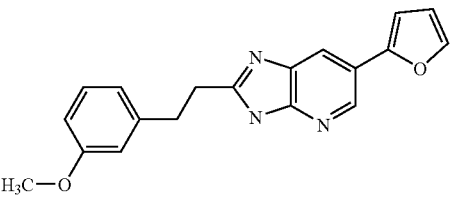
Ex. 553
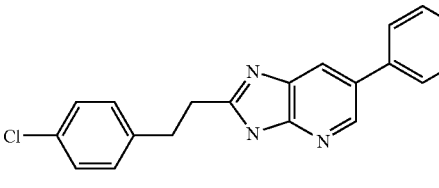
Ex. 554
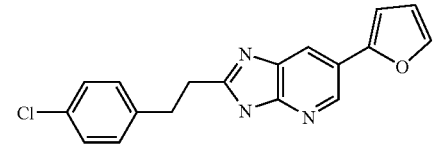

TABLE 67-continued
Ex. 555 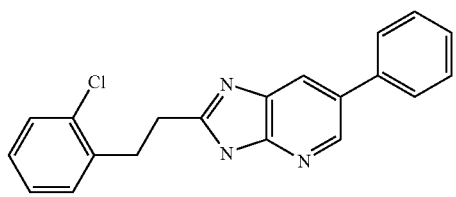
TABLE 68
Ex. 556 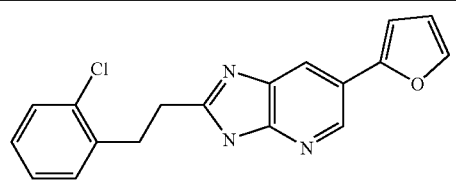
Ex. 557 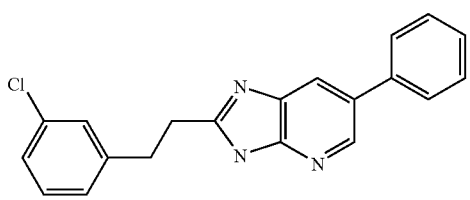
Ex. 558 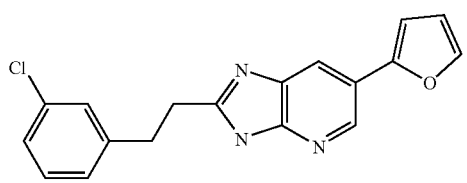
Ex. 559 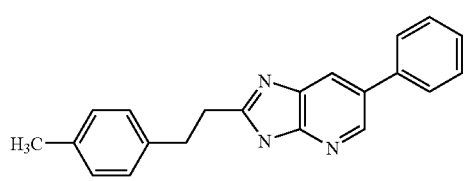
Ex. 560 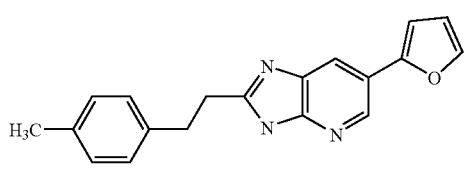
Ex. 561 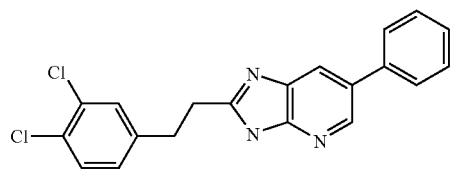
Ex. 562 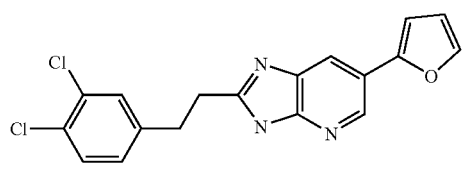
TABLE 68-continued
Ex. 563 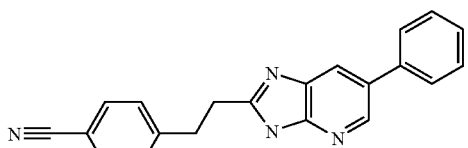
Ex. 564 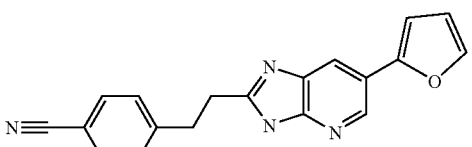
Ex. 565 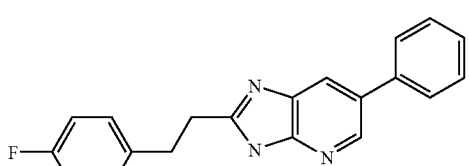
TABLE 69
Ex. 566 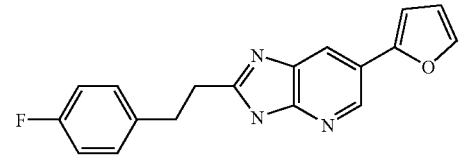
Ex. 567 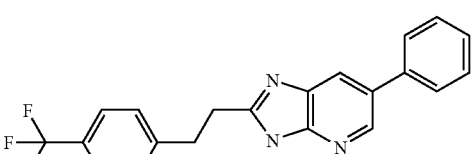
Ex. 568 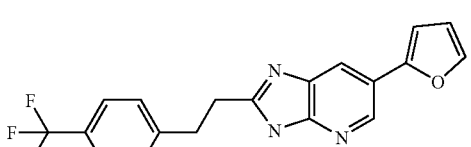
Ex. 569 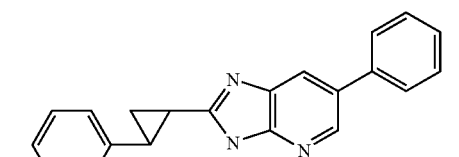
Ex. 570 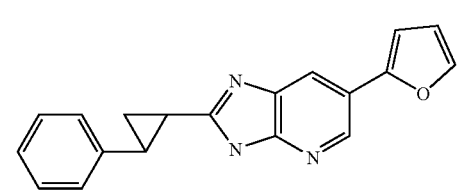

TABLE 69-continued
Ex. 571 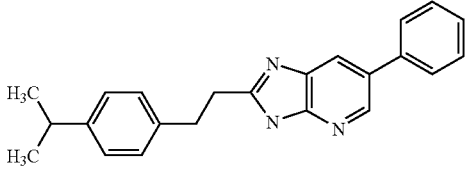
Ex. 572 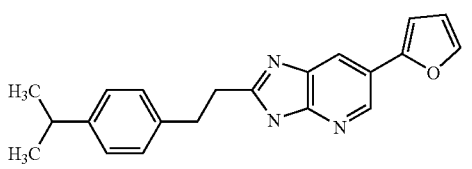
Ex. 573 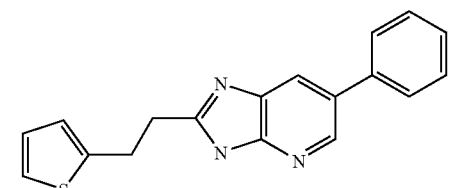
Ex. 574 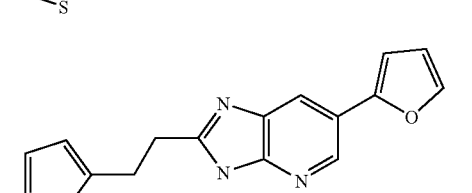
Ex. 575 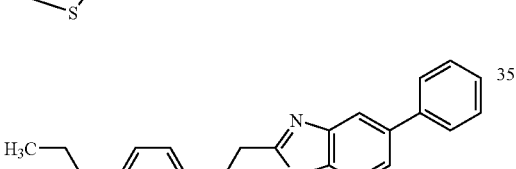
TABLE 70
Ex. 576 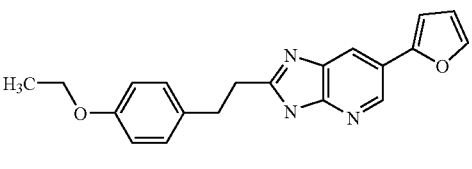
Ex. 577 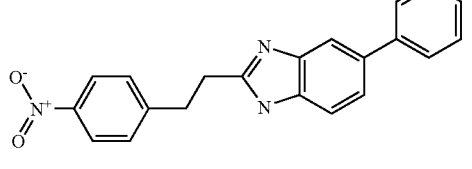
Ex. 578 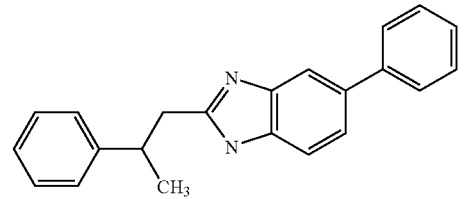
TABLE 70-continued
Ex. 579 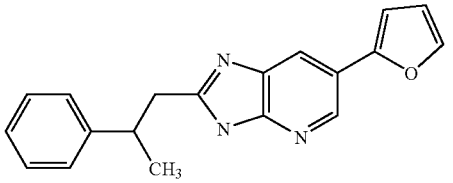
Ex. 580 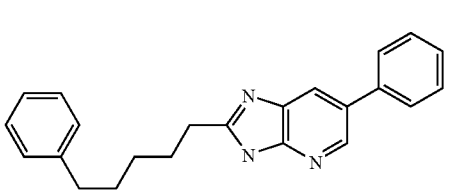
Ex. 581 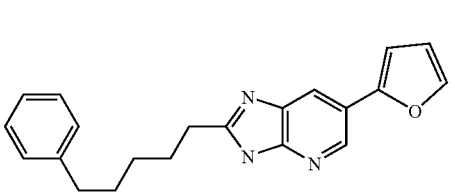
Ex. 582 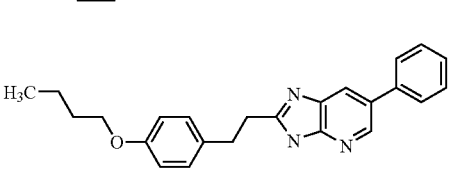
Ex. 583 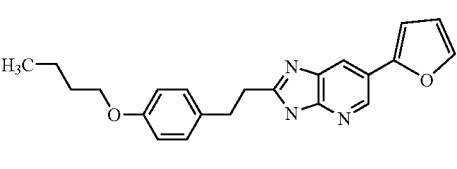
Ex. 584 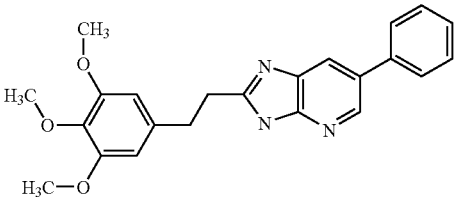
Ex. 585
TABLE 71
Ex. 586 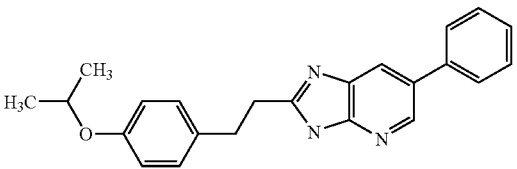

TABLE 71-continued
Ex. 587 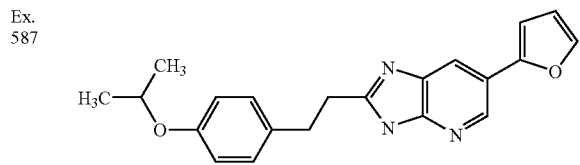
Ex. 588 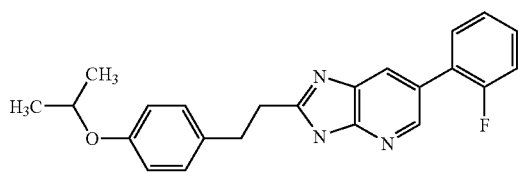
Ex. 589 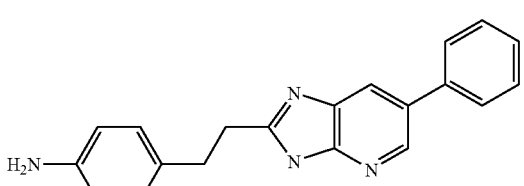
Ex. 590 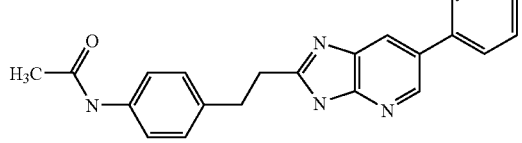
Ex. 591 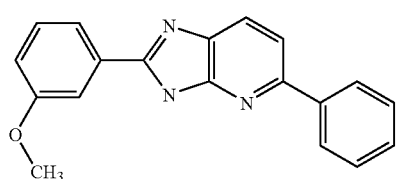
Ex. 592 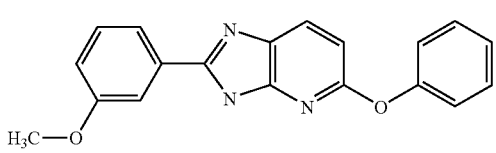
Ex. 593 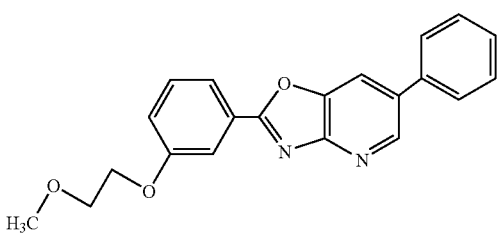
Ex. 594 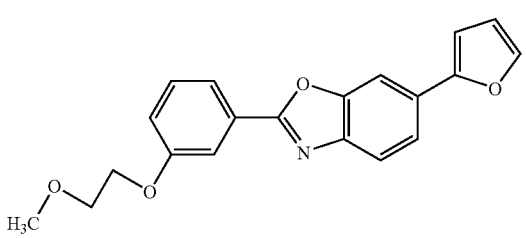
TABLE 71-continued
Ex. 595 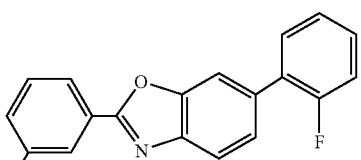
TABLE 72
Ex. 596 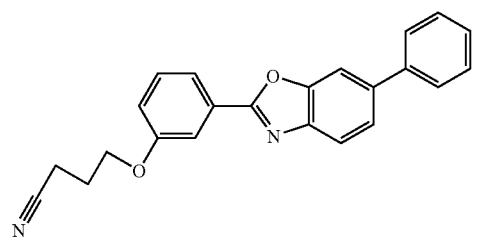
Ex. 597 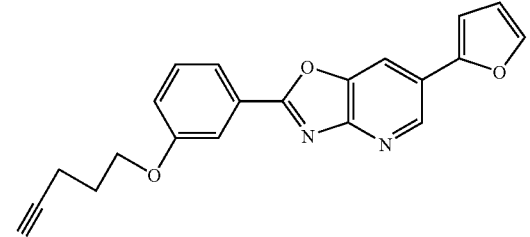
Ex. 598 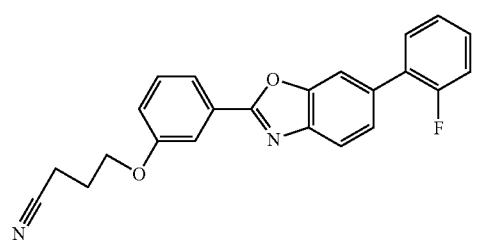
Ex. 599 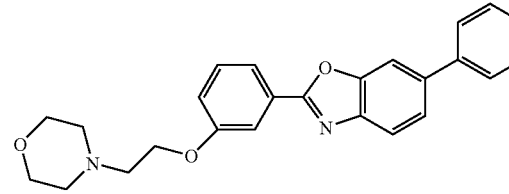
Ex. 600 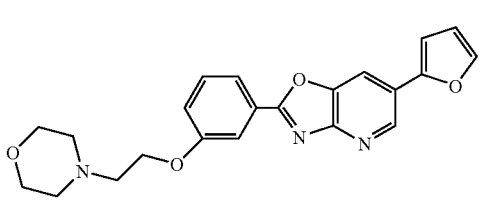

TABLE 72-continued

Ex. 601

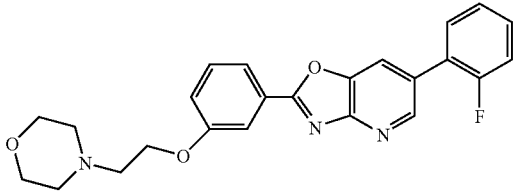

Preparation Example 1

Dose Per Capsule

| | |
|---|---|
| (1) Compound obtained in Example 1 | 10.0 mg |
| (2) Lactose | 90.0 mg |
| (3) Microcrystalline cellulose | 70.0 mg |
| (4) Magnesium stearate | 10.0 mg |

The aforementioned (1), (2) and (3) and 5.0 mg of (4) are mixed together and granulated, and then the remaining 5.0 mg of (4) is added, and the entire mass is filled into gelatin capsules

Preparation Example 2

Dose Per Tablet

| | |
|---|---|
| (1) Compound obtained in Example 1 | 10.0 mg |
| (2) Lactose | 60.0 mg |
| (3) Corn starch | 35.0 mg |
| (4) Gelatin | 3.0 mg |
| (5) Magnesium stearate | 2.0 mg |

A mixture of 10.0 mg of the compound obtained in Example 1, 60.0 mg of lactose, and 35.0 mg of corn starch is granulated through a 1 mm-mesh sieve using 0.03 ml of a 10% by weight aqueous solution of gelatin (3.0 mg of gelatin), after which the granules are dried at 40° C. and filtered again. The granules obtained are mixed with 2.0 mg of magnesium stearate and compressed. The core tablets obtained are coated with a sugar coat comprising a suspension of sucrose, titanium dioxide, talc, and gum arabic and polished with beeswax to yield sugar-coated tablets.

Preparation Example 3

Dose Per Tablet

| | |
|---|---|
| (1) Compound obtained in Example 1 | 10.0 mg |
| (2) Lactose | 70.0 mg |
| (3) Corn starch | 50.0 mg |
| (4) Solubilized starch | 7.0 mg |
| (5) Magnesium stearate | 3.0 mg |

10.0 mg of the compound obtained in Example 1 and 3.0 mg of magnesium stearate are granulated using 0.07 ml of an aqueous solution of solubilized starch (7.0 mg of solubilized starch), after which these granules are dried and mixed with 70.0 mg of lactose and 50.0 mg of corn starch. This mixture is compressed to yield tablets.

Reference Preparation Example 1

Dose Per Tablet

| | |
|---|---|
| (1) Leuprorelin acetate | 10.0 mg |
| (2) Lactose | 70.0 mg |
| (3) Corn starch | 50.0 mg |
| (4) Solubilized starch | 7.0 mg |
| (5) Magnesium stearate | 3.0 mg |

10.0 mg of leuprorelin acetate and 3.0 mg of magnesium stearate are granulated using 0.07 ml of an aqueous solution of solubilized starch (7.0 mg of solubilized starch), after which these granules are dried and mixed with 70.0 mg of lactose and 50.0 mg of corn starch. This mixture is compressed to yield tablets.

Preparation Example 4

A preparation obtained with Preparation Examples 1 to 3 is combined with the preparation obtained with Reference Preparation Example 1.

Test Example 1

Selective Cancer Cell Proliferation Inhibitory Activity

100 μl of a suspension of HER2-expressing SK-BR-3 human breast cancer cells or 100 μl of BT-474 (2,000 cells) or 100 μl (4,000 cells) of a suspension of normal human cell fibroblast MRC-5 was sown in a 96-well microplate and cultured at 37° C. in a 5% carbonic acid gas incubator. On the following day, 100 μl of a solution of the test compound which had previously been diluted 2-fold, was added and the mixture was incubated for 3 or 5 days. The cells were fixed and washed with 5% glutaraldehyde solution and further fixed with 10% trichloroacetic acid solution, after which a 0.4% (W/V) SRB 0.4% (W/V) solution (dissolved in 1% acetic acid) was added to stain the cell protein. After the pigment solution was removed and the plate was washed with 1% acetic acid solution, 100 μl of extract (10 mM tris buffer solution) was added to extract the pigment; absorbance was measured at an absorption wavelength of 550 nm to quantify the amount of cells as protein content.

Taking the absorbance for the control group, which received no test compound solution, as 100% the ratio of the absorbance for each treatment group was determined, and the compound concentration required to achieve 50% suppression of the residual cell content relative to the control ($IC_{50}$ value) was calculated.

The results are shown in Table 73. The compound of the present invention was thus shown to suppress the proliferation of cells of the human breast cancer cell lines SK-BR-3 and BT-474. On the other hand, inhibitory activity against a normal cell was not detected.

It was determined that the compound of the present invention is a substance which selectively and strongly inhibits proliferation of tumor cells, especially HER2-expressing cancer cells.

TABLE 73

Cell proliferation suppression test

| Compound | Cell proliferation inhibition (IC$_{50}$; µM) | | |
|---|---|---|---|
| | SK-BR-3 | BT-474 | MRC-5 |
| Compound of Example 1 | 0.12 | 0.28 | >25 |
| Compound of Example 97 | 0.94 | 0.49 | >25 |
| Compound of Example 113 | 0.22 | 0.25 | 25 |
| Compound of Example 157 | 0.23 | 0.19 | >25 |
| Compound of Example 202 | 0.55 | 1.1 | 21 |
| Compound of Example 219 | 0.14 | 0.83 | >25 |

Test Example 2

Antitumor Test

1×10$^7$ BT-474 human cancer cells were suspended in Matrigel solution, and the suspension was subcutaneously transplanted to a nude BALB/c female mouse (5 weeks old). In order to enhance the take ratio of the tumor, an estrogen preparation was intramuscularly administered to a hind leg at plantation and 7 days after transplantation.

14 days after transplantation, mice in which it was found that the tumor had taken, were selected and divided into 5-membered groups. A Gelucire solution (0.3 or 1 mg/ml) of the compound of the present invention was orally administered at a dosage of 10 ml/kg, twice each day, for 14 days. During the first day and the last day that the administration was carried out, the tumor diameter was measured, and the tumor volume was calculated using the formula: tumor volume=major axis x minor axis x minor axis x(1/2). The T/C (%) was calculated as the ratio of the value obtained by subtracting the tumor volume on the last day of administration from the tumor volume on the first day of administration for the control group (to which only Gelucire was administered) and the value obtained by subtracting the tumor volume on the last day of administration from the tumor volume on the first day of administration for the treatment group.

The results are shown in Table 74. The compound of the present invention exhibited significant, dose-related suppression of tumor proliferation in a nude mouse model in which HER2-expressing human cancer cell strain BT-474 had been transplanted. There was no observed reduction in the body weight of the mice during the test period due to the administration of the compound of the present invention.

TABLE 74

Antitumor effect on nude mouse model implanted with human cancer cells

| Compound | T/C(%) | |
|---|---|---|
| | 3 mg/kg | 10 mg/kg |
| Compound of Example 1 | 58* | 31** |

(*P < 0.05, **P < 0.01, Dunnet test)

Test Example 3

Suppression of Tyrosine-phosphorylation of Human Breast Cancer Cell Receptors

500 µl of a suspension of BT-474 human breast cancer cells (300,000 cells) was sown into a 24-well plate, and cultured at 37° C. in the presence of 5% carbon dioxide. On the following day, 500 µl of a solution of the test compound, which had previously been diluted 4-fold, was added. After 2 hours, an extract was added to stop the reaction, and the protein was extracted. This protein was subjected to protein electrophoresis to fractionate it, and the protein in the gel electrophoresis was transferred to a nylon filter. This filter was reacted with an anti-phosphotyrosine antibody, and the reaction product was fluorescently labeled and measured using image-analysis equipment. Taking as 100% the amount of phosphorylation of the HER2 tyrosine in the control group, the ratio of the amount of phosphorylation of the HER2 tyrosine in each group receiving a solution of the test compound at each concentration was determined, and the test compound concentration required to achieve 50% suppression of phosphorylation of HER2 tyrosine (IC$_{50}$ value) was calculated.

Industrial Applicability

Since compound (V) of the present invention, a salt thereof or a prodrug thereof possesses tyrosine kinase-inhibiting activity and is of low toxicity, it can be used to prevent or treat tyrosine kinase-dependent diseases in mammals. Tyrosine kinase-dependent diseases include diseases characterized by increased cell proliferation due to abnormal tyrosine kinase enzyme activity. Furthermore, compound (V) of the present invention or a salt thereof or a prodrug thereof specifically inhibits tyrosine kinase and is therefore also useful as a therapeutic agent for suppressing the growth of HER2-expressing cancer, or a preventive agent for preventing the transition of hormone-dependent cancer to hormone-independent cancer.

Similarly, a HER2 protein inhibitor containing compound of the present invention, a salt thereof or a prodrug thereof, which is the pharmaceutical preparation of the present invention shown in formula (I), is useful as a therapeutic agent for suppressing the growth of HER2-expressing cancer, or a preventive agent for preventing the transition of hormone-dependent cancer to hormone-independent cancer.

The present application is based on Japanese Application No. 2001-359753, and the whole content of the Japanese application is contained in the present application.

The invention claimed is:

1. A compound represented by the formula (VII'):

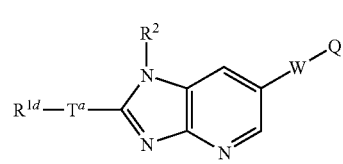

wherein, $R^{1d}$ is a $C_{6-10}$ aryl group which may have 1-3 substituents selected from the substituent group B mentioned below, a $C_{3-8}$ cycloalkyl group which may have 1-3 substituents selected from the substituent group B mentioned below or a heterocyclic group which may have 1-5 substituents selected from the substituent group A mentioned below;

$T^a$ is a single bond, a $C_{1-6}$ alkyl group, —CH$_2$O—, —OCH$_2$—, —CH$_2$S—, —SCH$_2$—, —CH$_2$—CH$_2$— or —CH=CH—;

$R^2$ is a hydrogen atom, a $C_{1-6}$ alkyl group which may have 1-3 substituents selected from the substituent group B mentioned below, a $C_{6-10}$ aryl group which may have 1-3 substituents selected from the substituent group B mentioned below or a $C_{3-8}$ cycloalkyl group which may have 1-3 substituents selected from the substituent group B mentioned below;

W is a single bond;

Q is a $C_{6-10}$ aryl group which may have 1-3 substituents selected from the substituent group B mentioned below or an aromatic heterocyclic group which may have 1-5 substituents selected from the substituent group C mentioned below; or a salt thereof, wherein substituent group A consists of:
(i) a $C_{1-6}$ alkyl group which may have 1-3 substituents selected from the substituent group B mentioned below,
(ii) a $C_{2-6}$ alkenyl group which may have 1-3 substituents selected from the substituent group B mentioned below,
(iii) a $C_{2-6}$ alkynyl group which may have 1-3 substituents selected from the substituent group B mentioned below,
(iv) a $C_{6-14}$ aryl group which may have 1-3 substituents selected from the substituent group B mentioned below,
(v) a $C_{7-11}$ aralkyl group which may have 1-3 substituents selected from the substituent group B mentioned below,
(vi) a $C_{3-7}$ cycloalkyl group which may have 1-3 substituents selected from the substituent group B mentioned below,
(vii) a $C_{3-7}$ cycloalkenyl group which may have 1-3 substituents selected from the substituent group B mentioned below,
(viii) a heterocyclic group which may have 1-5 substituents selected from the substituent group C mentioned below,
(ix) an amino group which may have 1 or 2 substituents selected from the substituent group D mentioned below, a $C_{1-6}$ alkylimidoyl, a $C_{1-6}$ alkoxyimidoyl, a $C_{1-6}$ alkylthioimidoyl and amidino, and 2 of the substituents may combine together with a nitrogen atom to form a cyclic amino group,
(x) an imidoyl group which may have 1 or 2 substituents selected from the substituent group D mentioned below,
(xi) an amidino group which may have 1-3 substituents selected from the substituent group D mentioned below,
(xii) a hydroxyl group which may have a substituent selected from the substituent group D mentioned below,
(xiii) a thiol group which may have a substituent selected from the substituent group D mentioned below,
(xiv) a $C_{1-6}$ alkylsulfinyl group which may have 1-3 substituents selected from the substituent group B mentioned below,
(xv) a carboxyl group which may be esterified or amidated,
(xvi) a thiocarbamoyl group which may have 1 or 2 substituents selected from the substituent group E mentioned below,
(xvii) a sulfamoyl group which may have 1 or 2 substituents selected from the substituent group E mentioned below,
(xviii) a halogen atom,
(xix) a cyano group,
(xx) an isocyano group,
(xxi) a cyanate group,
(xxii) an isocyanate group,
(xxiii) a thiocyanate group,
(xxiv) an isothiocyanate group,
(xxv) a nitro group,
(xxvi) a nitroso group,
(xxvii) an acyl group derived from sulphonic acid,
(xxviii) an acyl group derived from a carboxylic acid, and
(xxix) an oxo group;

substituent group B consists of:
(i) a nitro group,
(ii) a carboxyl group,
(iii) a $C_{1-6}$ alkoxy group,
(iv) a halogen atom,
(v) a $C_{1-6}$ alkyl group,
(vi) a $C_{2-6}$ alkenyl group,
(vii) a $C_{2-6}$ alkynyl group,
(viii) an amino group which may have 1 or 2 substituents selected from the substituent group D mentioned below, a $C_{1-6}$ alkylimidoyl, a $C_{1-6}$ alkoxyimidoyl, a $C_{1-6}$ alkylthioimidoyl and amidino, and 2 of the substituents may combine together with a nitrogen atom to form a cyclic amino group,
(ix) a hydroxyl group which may have a substituent selected from the substituent group D mentioned below,
(x) a cyano group,
(xi) an amidino group which may have 1-3 substituents selected from the substituent group D mentioned below,
(xii) a carboxy group,
(xiii) a $C_{1-6}$ alkoxycarbonyl group,
(xiii) a carbamoyl group which may be substituted by a $C_{1-6}$ alkyl group which may further be substituted by a 5- or 6-membered aromatic monocyclic heterocyclic group or an acyl group, and
(xiv) an alicyclic hydrocarbon group which may contain 1 or more hetero atoms as a ring-constituting atom;

substituent group C consists of:
(i) a $C_{1-6}$ alkyl group,
(ii) a $C_{2-6}$ alkenyl group,
(iii) a $C_{2-6}$ alkynyl group,
(iv) an acyl group,
(v) an amino group which may have 1 or 2 substituents selected from the substituent group D mentioned below, a $C_{1-6}$ alkylimidoyl, a $C_{1-6}$ alkoxyimidoyl, a $C_{1-6}$ alkylthioimidoyl and amidino, and 2 of the substituents may combine together with a nitrogen atom to form a cyclic amino group,
(vi) a hydroxyl group which may have a substituent selected from the substituent group D mentioned below,
(vii) a halogen atom,
(viii) an imidoyl group which may have 1 or 2 substituents selected from the substituent group D mentioned below, and
(ix) an amidino group which may have 1-3 substituents selected from the substituent group D mentioned below;

substituent group D consists of:
(i) a $C_{1-6}$ alkyl group which may have substituents selected from the group consisting of a halogen atom, a $C_{1-6}$ alkoxy group which may be halogenated and a $C_{7-11}$ alkyl-aryl group,
(ii) an acyl group,
(iii) benzoyl,
(iv) a $C_{1-6}$ alkylsulfonyl,
(v) benzensulfonyl, (vi) a $C_{1-6}$ alkoxycarbonyl group which may be halogenated, (vii) a $C_{1-6}$ alkoxycarbonyl group which may be substituted by phenyl, (viii) a $C_{6-10}$ aryl group, (ix) a $C_{7-10}$ aralkyl group, (x) a $C_{8-10}$ arylalkenyl, and (xi) a heterocyclic group; and substituent group E consists of:

(i) a $C_{1-6}$ alkyl, (ii) a $C_{2-6}$ alkenyl, (iii) a $C_{3-6}$ cycloalkyl, (iv) a $C_{6-10}$ aryl, (v) a $C_{7-10}$ aralkyl, (vi) a $C_{8-10}$ aryl alkenyl, and (vii) a heterocyclic group.

2. A compound represented by the formula (IX'):

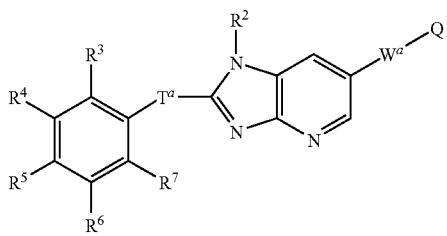

wherein, $R^3$, $R^4$, $R^5$, $R^6$ and $R^7$ are the same or different, and each is a hydrogen atom, a halogen atom, OH, CN, $NO_2$, $NH_2$, NHCOR, NHCONHR, $NHSO_2R$, $SO_2R$, COOH, COOR, CONHR, $CONH_2$, $CF_3$, $CF_3O$, a $C_{1-6}$ alkyl group, a $C_{1-6}$ alkoxy group, a $C_{1-6}$ alkoxy-carbonyl group or a $C_{1-4}$ alkylenedioxy group which is formed by a combination of two neighboring groups;

R is a $C_{1-6}$ alkyl group, a $C_{3-8}$ cycloalkyl group or a $C_{6-10}$ aryl group;

$T^a$ is a single bond, a $C_{1-6}$ alkyl group, —$CH_2O$—, —$OCH_2$—, —$CH_2S$—, —$SCH_2$—, —$CH_2$—$CH_2$— or —CH=CH—;

$R^2$ is a hydrogen atom, a $C_{1-6}$ alkyl group which may have 1-3 substituents selected from the substituent group B as defined in claim 1, a $C_{6-10}$ aryl group which may have 1-3 substituents selected from the substituent group B as defined in claim 1, or a $C_{3-8}$ cycloalkyl group which may have 1-3 substituents selected from the substituent group B as defined in claim 1;

$W^a$ is a single bond;

Q is a $C_{6-10}$ aryl group which may have 1-3 substituents selected from the substituent group B as defined in claim 1 or an aromatic heterocyclic group which may have 1-5 substituents selected from the substituent group C as defined in claim 1; or a salt thereof.

3. The compound as claimed in claim 2, wherein $T^a$ is a single bond; or a salt thereof.

4. The compound as claimed in claim 2, wherein $R^4$ and $R^6$ are each a group other than a hydrogen atom; or a salt thereof.

5. A compound represented by the formula (XI'):

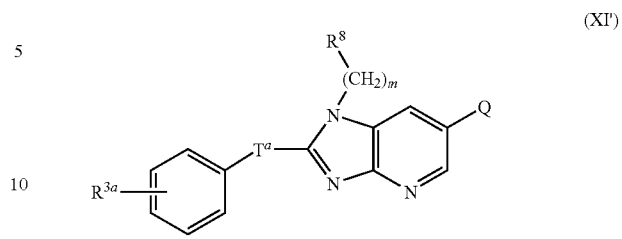

wherein, $R^{3a}$ is a hydrogen atom, a halogen atom, OH, CN, $NO_2$, $NH_2$, NHCOR, NHCONHR, $NHSO_2R$, $SO_2R$, COOH, COOR, CONHR, $CONH_2$, $CF_3$, $CF_3O$, a $C_{1-6}$ alkyl group, a $C_{1-6}$ alkoxy group or a $C_{1-6}$ alkoxy-carbonyl group;

R is a $C_{1-6}$ alkyl group, a $C_{3-8}$ cycloalkyl group or a $C_{6-10}$ aryl group;

$T^a$ is a single bond, a $C_{1-6}$ alkyl group, —$CH_2O$—, —$OCH_2$—, —$CH_2S$—, —$SCH_2$—, —$CH_2$—$CH_2$— or —CH=CH—, m is an integer from 1 to 3;

$R^8$ is a $C_{6-10}$ aryl group which may have 1-3 substituents selected from the substituent group B as defined in claim 1, a $C_{3-8}$cycloalkyl group which may have 1-3 substituents selected from the substituent group B as defined in claim 1 or a heterocyclic group which may have 1-5 substituents selected from the substituent group A as defined in claim 1;

Q is a $C_{6-10}$ aryl group which may have 1-3 substituents selected from the substituent group B as defined in claim 1 or an aromatic heterocyclic group which may have 1-5 substituents selected from the substituent group C as defined in claim 1 or a salt thereof.

6. The compound as claimed in claim 1, wherein Q is a $C_{6-10}$ aryl group which has substituent(s), and the substituent(s) in the $C_{6-10}$ aryl group which has substituent(s) are 1 to 3 substituents selected from a halogen atom, a $C_{1-6}$ alkyl group and a cyano group; or a salt thereof.

7. The compound as claimed in claim 2, wherein Q is a $C_{6-10}$ aryl group which has substituent(s), and the substituent(s) in the $C_{6-10}$ aryl group which has substituent(s) are 1 to 3 substituents selected from a halogen atom, a $C_{1-6}$ alkyl group and a cyano group; or a salt thereof.

8. The compound as claimed in claim 5, wherein Q is a $C_{6-10}$ aryl group which has the 1-3 substituents, and the substituents in the $C_{6-10}$ aryl group which has substituent(s) are 1 to 3 substituents selected from a halogen atom, a $C_{1-6}$ alkyl group and a cyano group; or a salt thereof.

9. A pharmaceutical composition containing the compound shown in claim 1 and a pharmaceutically acceptable carrier, excipient or diluent.

10. A pharmaceutical composition containing the compound shown in claim 2 and a pharmaceutically acceptable carrier, excipient or diluent.

11. A pharmaceutical composition containing the compound shown in claim 5 and a pharmaceutically acceptable carrier, excipient or diluent.

12. The pharmaceutical composition as claimed in claim 9, which contains the compound in an amount suitable for treating breast cancer.

13. The pharmaceutical composition as claimed in claim 10, which contains the compound in an amount suitable for treating breast cancer.

14. The pharmaceutical composition as claimed in claim 11, which contains the compound in an amount suitable for treating breast cancer.

15. The compound as claimed in claim 1, wherein Q is a phenyl group, a naphthyl group, a furyl group, a thienyl group or a benzofuryl group, each of which may have 1-3 halogen atoms; or a salt thereof.

16. The compound as claimed in claim 2, wherein Q is a phenyl group, a naphthyl group, a furyl group, a thienyl group or a benzofuryl group, each of which may have 1-3 halogen atoms; or a salt thereof.

17. The compound as claimed in claim 5, wherein Q is a phenyl group, a naphthyl group, a furyl group, a thienyl group or a benzofuryl group, each of which may have 1-3 halogen atoms; or a salt thereof.

* * * * *

UNITED STATES PATENT AND TRADEMARK OFFICE
CERTIFICATE OF CORRECTION

PATENT NO. : 7,622,479 B2 Page 1 of 1
APPLICATION NO. : 10/498461
DATED : November 24, 2009
INVENTOR(S) : Oda et al.

It is certified that error appears in the above-identified patent and that said Letters Patent is hereby corrected as shown below:

On the Title Page:
Item (87) PCT Pub. No.: "WO03/415929" should read --WO03/045929--

Signed and Sealed this

Twenty-fourth Day of August, 2010

David J. Kappos
*Director of the United States Patent and Trademark Office*